US012649782B2

(12) United States Patent
Chowdhury et al.

(10) Patent No.: US 12,649,782 B2
(45) Date of Patent: Jun. 9, 2026

(54) IMMUNOCYTOKINES FOR TREATMENT OF AUTOIMMUNE AND INFLAMMATORY CONDITIONS

(71) Applicant: Horizon Therapeutics Ireland DAC, Dublin (IE)

(72) Inventors: Partha S. Chowdhury, Gaithersburg, MD (US); Yong Jun Liu, Gaithersburg, MD (US); Shino Hanabuchi, Clarksburg, MD (US); Nazzareno Dimasi, Waltham, MA (US)

(73) Assignee: Horizon Therapeutics Ireland DAC, Dublin (IE)

( * ) Notice: Subject to any disclaimer, the term of this patent is extended or adjusted under 35 U.S.C. 154(b) by 673 days.

(21) Appl. No.: 18/017,005

(22) PCT Filed: Jul. 20, 2021

(86) PCT No.: PCT/US2021/042331
§ 371 (c)(1),
(2) Date: Jan. 19, 2023

(87) PCT Pub. No.: WO2022/020324
PCT Pub. Date: Jan. 27, 2022

(65) Prior Publication Data
US 2023/0279092 A1      Sep. 7, 2023

Related U.S. Application Data

(60) Provisional application No. 63/053,949, filed on Jul. 20, 2020.

(51) Int. Cl.
C07K 16/24          (2006.01)
A61P 37/06          (2006.01)
C07K 14/54          (2006.01)

(52) U.S. Cl.
CPC ............ C07K 16/241 (2013.01); A61P 37/06 (2018.01); C07K 14/5428 (2013.01); C07K 2317/76 (2013.01); C07K 2319/30 (2013.01)

(58) Field of Classification Search
CPC .......................... C07K 16/241; C07K 14/5428
See application file for complete search history.

(56) References Cited

U.S. PATENT DOCUMENTS

| | | | |
|---|---|---|---|
| 4,683,195 A | 7/1987 | Mullis et al. |
| 4,873,192 A | 10/1989 | Kunkel |
| 5,116,964 A | 5/1992 | Capon et al. |
| 5,223,409 A | 6/1993 | Ladner et al. |
| 5,225,538 A | 7/1993 | Capon et al. |
| 5,225,539 A | 7/1993 | Winter |
| 5,403,484 A | 4/1995 | Ladner et al. |
| 5,427,908 A | 6/1995 | Dower et al. |
| 5,516,637 A | 5/1996 | Huang et al. |
| 5,571,698 A | 11/1996 | Ladner et al. |
| 5,580,717 A | 12/1996 | Dower et al. |
| 5,585,089 A | 12/1996 | Queen et al. |
| 5,658,727 A | 8/1997 | Barbas et al. |
| 5,693,761 A | 12/1997 | Queen et al. |
| 5,693,762 A | 12/1997 | Queen et al. |
| 5,698,426 A | 12/1997 | Huse |
| 5,733,743 A | 3/1998 | Johnson et al. |
| 5,750,753 A | 5/1998 | Kimae et al. |
| 5,780,225 A | 7/1998 | Wigler et al. |
| 5,821,047 A | 10/1998 | Garrard et al. |
| 5,859,205 A | 1/1999 | Adair et al. |
| 5,885,793 A | 3/1999 | Griffiths et al. |
| 5,939,598 A | 8/1999 | Kucherlapati et al. |
| 5,969,108 A | 10/1999 | McCafferty et al. |
| 6,172,197 B1 | 1/2001 | McCafferty et al. |
| 6,180,370 B1 | 1/2001 | Queen et al. |
| 6,300,064 B1 | 10/2001 | Knappik et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,653,068 B2 | 11/2003 | Frisch et al. |
| 6,706,484 B1 | 3/2004 | Knappik et al. |
| 6,737,056 B1 | 5/2004 | Presta |
| 7,264,963 B1 | 9/2007 | Knappik et al. |
| 2004/0132101 A1 | 7/2004 | Lazar et al. |
| 2016/0340413 A1 | 11/2016 | Duerner et al. |

FOREIGN PATENT DOCUMENTS

| | | |
|---|---|---|
| TW | 201418283 A | 5/2014 |
| WO | WO-9002809 A1 | 3/1990 |
| WO | WO-9110737 A1 | 7/1991 |
| WO | WO-9201047 A1 | 1/1992 |
| WO | WO-9218319 A1 | 10/1992 |
| WO | WO-9311236 A1 | 6/1993 |
| WO | WO-9515982 A2 | 6/1995 |
| WO | WO-9520401 A1 | 8/1995 |
| WO | WO-0127160 A1 | 4/2001 |
| WO | WO-2011068896 A1 | 6/2011 |
| WO | 2015114150 A1 | 8/2015 |

OTHER PUBLICATIONS

Ames, R. S., et al., "Conversion of murine Fabs isolated from a combinatorial phage display library to full length immunoglobulins," Journal of Immunological Methods, Aug. 18, 1995, 184(2), pp. 177-186.

Brinkmann, U., et al., "Phage display of disulfide-stabilized Fv fragments," Journal of Immunological Methods, May 11, 1995, 182(1), pp. 41-50.

Burton, Dennis R., et al. "Human antibodies from combinatorial libraries", Advances in Immunology, vol. 57, Jan. 1994, pp. 191-280.

Butler J.E., "The Amplified ELISA: Principles of and Applications for the Comparative Quantitation of Class and Subclass Antibodies and the Distribution of Antibodies and Antigens in Biochemical Separates," Methods in Enzymology, 1981, vol. 73, Part B, pp. 482-523.

(Continued)

*Primary Examiner* — Prema M Mertz

(57)          ABSTRACT

The present disclosure is directed to fusion proteins comprising a Tumor Necrosis Factor α (TNFα) binding protein and an interleukin-10 (IL-10) molecule, methods of making the fusion proteins, and methods of treating or preventing autoimmune and inflammatory conditions using the fusion proteins.

15 Claims, 30 Drawing Sheets

Specification includes a Sequence Listing.

(56)         References Cited

OTHER PUBLICATIONS

Chothia, C. et al., "Canonical Structures for the Hypervariable Regions of Immunoglobins", Journal of Molecular Biology, Aug. 1987, vol. 196, No. 4, pp. 901-917.
Cockett et al., "High level expression of tissue inhibitor of metalloproteinases in Chinese hamster ovary cells using glutamine synthetase gene amplification," Bio/Technology, 8:2, Jul. 1990, pp. 662-667.
Colbere-Garapin F., et al., "A New Dominant Hybrid Selective Marker for Higher Eukaryotic Cells," Journal of Molecular Biology, Jul. 25, 1981, vol. 150 (1), pp. 1-14.
Cordiali-Fei P., et al., "Immunologic Biomarkers For Clinical And Therapeutic Management Of Psoriasis," Mediators Inflammation, Oct. 2014, vol. 2014, Article 236060, Abstract, 12 Pages.
Dayhoff M.O., et al., "A model of Evolutionary Change in Proteins", Chapter 22 in Atlas of Protein Sequence and Structure, National Biomedical Research Foundation, Washington DC, 1978, vol. 5 (3), pp. 345-352.
Foecking M.K., et al., "Powerful and Versatile Enhancer-Promoter Unit for Mammalian Expression Vectors," Gene, Jan. 1986, vol. 45, No. 1, pp. 101-105.
Gentz R., et al., "Bioassay for Trans-Activation Using Purified Human Immunodeficiency Virus Tat-Encoded Protein: Trans-Activation Requires mRNA Synthesis," Proceedings of the National Academy of Sciences of the United States of America, Feb. 1989, vol. 86, pp. 821-824.
Hamers-Casterman, C. et al., "Naturally occurring antibodies devoid of light chains," Nature, vol. 363, No. 6428, Jun. 1993, pp. 446-448.
Hoogenboorn and Winter, "By-passing Immunisation Human Antibodies from Synthetic Repertoires of Germline VH Gene Segments Rearranged in Vitro," Journal of Molecular Biology, 227(2), Sep. 1992, pp. 381-388.
Inaki and Lee, "B cells as therapeutic targets in SLE," Nature Reviews Rheumatology, Jun. 2010, 6(6), pp. 326-337.
Inouye S., et al., "Up-Promoter Mutations in the Lpp Gene of Escherichia coli," Nucleic Acids Research, May 10, 1985, vol. 13, No. 9, pp. 3101-3110.
International Preliminary Report on Patentability for International Application No. PCT/US2021/042331 dated Feb. 2, 2023, 7 pages.
International Search Report and Written Opinion for International Application No. PCT/US2021/042331, mailed Nov. 15, 2021, 10 pages.
Jones et al., "Replacing the complementary-determining regions in a human antibody with those from a mouse," Nature, vol. 321, May 1986, pp. 522-525.
Jones E.W., "Proteinase mutants of Saccharomyces cerevisiae1," Genetics 85, Jan. 1977, pp. 23-33.
Ketileborough, C. A., et al., "Isolation of tumor cell-specific single-chain Fv from immunized mice using phage-antibody libraries and the re-construction of whole antibodies from these antibody fragments", European Journal of Immunology, Apr. 1994, 24(4), pp. 952-958.
Kim K-N., et al., "Viral IL-10 and Soluble TNF Receptor Act Synergistically to Inhibit Collagen-Induced Arthritis Following Adenovirus-Mediated Gene Transfer," Journal of Immunology, Feb. 1, 2000, vol. 164, No. 3, pp. 1576-1581.
Kingsman A.J., et al., "Replication In Saccharomyces Cerevisiae of Plasmid pBR313 Carrying DNA from the Yeast Trpl Region," Gene, Oct. 1979, vol. 7, No. 2, pp. 141-152.
Kunkel et al., "Rapid and efficient site-specific mutagenesis without phenotypic selection," Methods in Enzymology, vol. 154, (1987), pp. 367-382.
Kunkel T.A., "Rapid And Efficient Site-specific Mutagenesis Without Phenotypic Selection," Proceedings of the National Academy of Sciences USA, Jan. 1985, vol. 82(2), pp. 488-492.
Kütemeier et al., "Assembly of Humanized antibody genes from synthetic oligonucleotides using a single-round PCR," BioTechniques, vol. 17, No. 2, Aug. 1994, pp. 242-246.
Lefranc, MP. et al., "IMGT unique numbering for immunoglobulin and T cell receptor variable domains and Ig superfamily V-like domains," Developmental & Comparative Immunology, Jan. 2003, 27(1), pp. 55-77.
Lonberg and Huszar, "Human Antibodies from Transgenic Mice," International Reviews of Immunology, Jan. 1995, 13(1), pp. 65-93.
Lowy I., et al., "Isolation Of Transforming Dna: Cloning The Hamster Aprt Gene," Cell, Dec. 1980, vol. 22 (3), pp. 817-823.
Marks et al., "By-passing Immunization Human Antibodies from V-gene Libraries Displayed on Phage," Journal of Molecular Biology, vol. 222, Dec. 1992, pp. 581-597.
Morgan R.A., et al., "Human Gene Therapy," Annual Review of Biochemistry, Jul. 1993, vol. 62, pp. 191-217.
Mulligan R.C., et al., "Selection for Animal Cells that Express the Escherichia coli Gene Coding for Xanthine-Guanine Phosphoribosyltransferase," Proceedings of the National Academy of Sciences of the United States of America, Apr. 1981, vol. 78, No. 4, pp. 2072-2076.
Mulligan R.C., "The Basic Science of Gene Therapy," Science, May 14, 1993, vol. 260, No. 5110, pp. 926-932.
Nakamura, Y., et al., "Codon usage tabulated from the international DNA sequence databases: status for the year 2000," Nucleic Acids Research, vol. 28, No. 1, 292, Jan. 2000, pp. 1-3 (supplementary material attached).
O'Hare K., et al., "Transformation of Mouse Fibroblasts to Methotrexate Resistance by a Recombinant Plasmid Expressing a Prokaryotic Dihydrofolate Reductase," Proceedings of the National Academy of Sciences of the United States of America, Mar. 1981, vol. 78 (3), pp. 1527-1531.
Persic, L., et al., "An integrated vector system for the eukaryotic expression of antibodies or their fragments after selection from phage display libraries," Gene, Mar. 10, 1997, 187(1), pp. 9-18.
Presta, L.G., "Antibody engineering," Current Opinion In Structural Biology, 2(4), Aug. 1992, pp. 593-596.
Quah, B.J. and Parish C.R., "The use of carboxyfluorescein diacetate succinimidyl ester (CFSE) to monitor lymphocyte proliferation," Journal of Visualized Experiments, 44:e2259, Oct. 2010,pp. 1-4.
Quah, BJ, et al., "Monitoring lymphocyte prolification in vitro and in vivo with the intracellular fluorescent dye carboxyfluorescein diacetate succinimidyl ester," Nature Protocols, vol. 2, No. 9, Sep. 2007, pp. 2049-2056.
Rattan S.I.S., et al., "Protein Synthesis, Posttranslational Modifications, and Aging," Annals of the New York Academy of Sciences, Nov. 1992, vol. 663, pp. 48-62.
Riechmann et al., "Reshaping human antibodies for therapy," Nature, vol. 332, Mar. 1988, pp. 323-327.
Rothe C., et al., "The Human Combinatorial Antibody Library HuCAL GOLD Combines Diversification of All Six CDRs According to the Natural Immune System with a Novel Display Method for Efficient Selection of High-Affinity Antibodies," Journal of Molecular Biology, Feb. 29, 2008, vol. 376, No. 4, pp. 1182-1200, DOI:0. 1016/j.jmb.2007.12018.
Roux K.H., et al., "Comparisons of the Ability of Human IgG3 Hinge Mutants, IgM, IgE, and IgA2, to Form Small Immune Complexes: A Role for Flexibility and Geometry," The Journal of Immunology, Oct. 1998, vol. 161, pp. 4083-4090, Retrieved from URL: http://www.jimmunol.org/content/161/8/4083.
Ruther et al., "Easy identification of cDNA clones," The EMBO Journal, vol. 2, No. 10, Oct. 1983, pp. 1791-1794.
Santerre et al., "Expression of prokaryotic genes for hygromycin B and G418 resistance as dominant-selection markers in mouse L cells," Gene 30(1-3), Oct. 1984, pp. 147-156.
Seifter S., et al., "Analysis for Protein Modifications and Nonprotein Cofactors," Methods in Enzymology, Jan. 1990, vol. 182, pp. 626-646.
Sheets M.D., et al., "Efficient Construction of a Large Nonimmune Phage Antibody Library: The Production of High-Affinity Human Single-Chain Antibodies to Protein Antigens," Proceedings of the National Academy of Sciences, USA, May 26, 1998, vol. 95 (11), pp. 6157-6162.
Smith, T.F. and Waterman, M.S., "Comparison of biosequences," Advances in Applied Mathematics 2(4), Dec. 1981, pp. 482-489.
Stinchcomb D.T., et al., "Isolation and Characterisation of a Yeast Chromosomal Replicator," Nature, Nov. 1, 1979, vol. 282, pp. 39-43.

(56)            References Cited

OTHER PUBLICATIONS

Szybalska, E.H. and Szybalska, W., "Genetics of human cell lines, IV. DNA-mediated heritable transformation of a biochemical trait," Proceedings of the National Academy of Sciences, 48(12), Dec. 1962, pp. 2026-2034.

Thorpe P.E., et al., "The Preparation and Cytotoxic Properties of Antibody-Toxin Conjugates," Immunological Reviews, Feb. 1982, vol. 62, pp. 119-158.

Tolstoshev P., "Gene Therapy, Concepts, Current Trials and Future Directions," Annual Review of Pharmacology and Toxicology, Apr. 1993, vol. 33, pp. 573-596, Retrieved from URL: www.annualreviews.org.

Tschemper et al., "Sequence of a yeast DNA fragment containing a chromosomal replicator and the TRP1 gene," Gene 10(2), Jul. 1980, pp. 157-166.

Van Heeke G., et al., "Expression of Human Asparagine Synthetase in *Escherichia coli*," Journal of Biological Chemistry, Apr. 5, 1989, vol. 264, No. 10, pp. 5503-5509.

Vaughan et al., "Human antibodies with sub-nanomolar affinities isolated from a large non-immunized phage display library," Nature Biotechnology, Mar. 1996, 14(3), pp. 309-314.

Verhoeyen, M., et al., "Reshaping human antibodies: grafting an antilysozyme activity", Science, Mar. 1988, 239(4847), pp. 1534-1536.

Voller et al., "Enzyme immunoassays with special reference to ELISA techniques," Journal of Clinical Pathology, 31(6), Jun. 1978, pp. 507-520.

Wigler et al., "Transformation of mammalian cells with an amplifiable dominant-acting gene," Proceedings of the National Academy and Sciences, vol. 77, No. 6, Jun. 1980, pp. 3567-3570.

Wigler M., et al., "Transfer Of Purified Herpes Virus Thymidine Kinase Gene To Cultured Mouse Cells," Cell, May 1977, vol. 11, pp. 223-232.

Wilson et al., "The structure of an antigenic determinant in a protein," Cell, vol. 37, Jul. 1984, pp. 767-778.

Wu G.Y., et al., "Delivery Systems for Gene Therapy," Biotherapy, Jan. 1991, vol. 3, pp. 87-95.

Zdanov et al., "Crystal structure of interleukin-10 reveals the functional dimer with an unexpected topological similarity to interferon γ," Structure 3, Jun. 1995, pp. 591-601.

Anti TNFα.IL10

◆ Anti-TNFα variant fused to IL10 at HC C-terminus

1.End of CH3:SPGK_Linker_IL10 ( K fusion)
2.End of CH3:SPGA_Linker_IL10 (A fusion)

IL10
YTQKSLSLSPGKSSSSGSSSSGSSSSGSSSSGSSGGQTQSENSCTHFPGNLPNMLRDLRDAF (SEQ ID NO: 42)

CH3

K-fusion
Monomer 88%
Loss: ~ 45%

A-fusion
Monomer 99%
Loss: ~ 0%

Expression level ~ 25 μg/ml

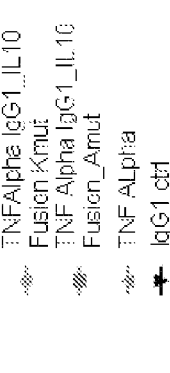
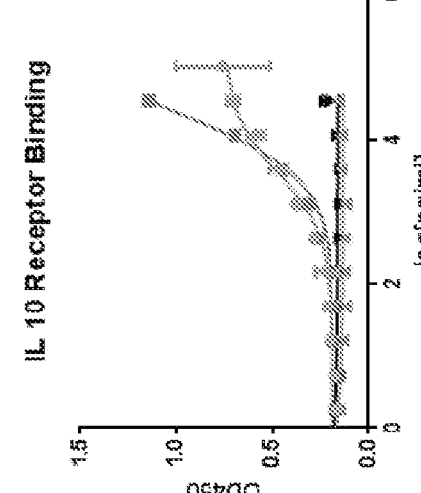
FIG. 2B
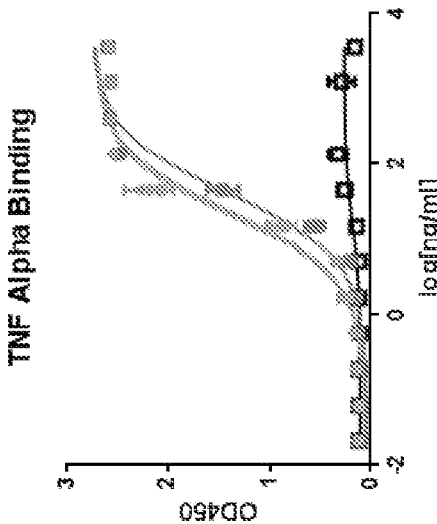
FIG. 2A

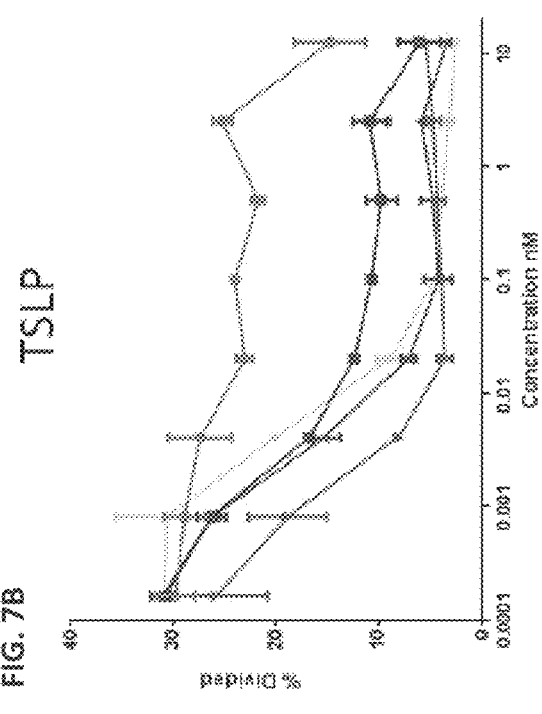
FIG. 7B
TSLP
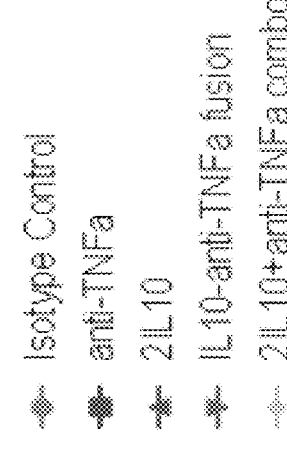
Isotype Control
anti-TNFa
2iL10
IL10-anti-TNFa fusion
2iL10+anti-TNFa combo
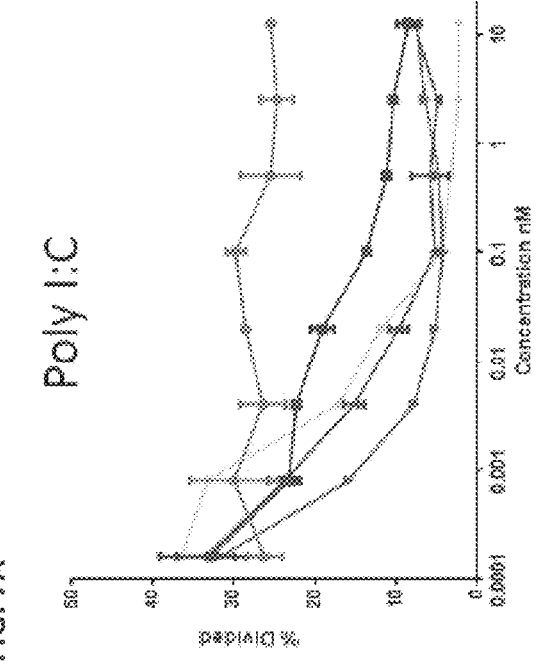
FIG. 7A
Poly I:C
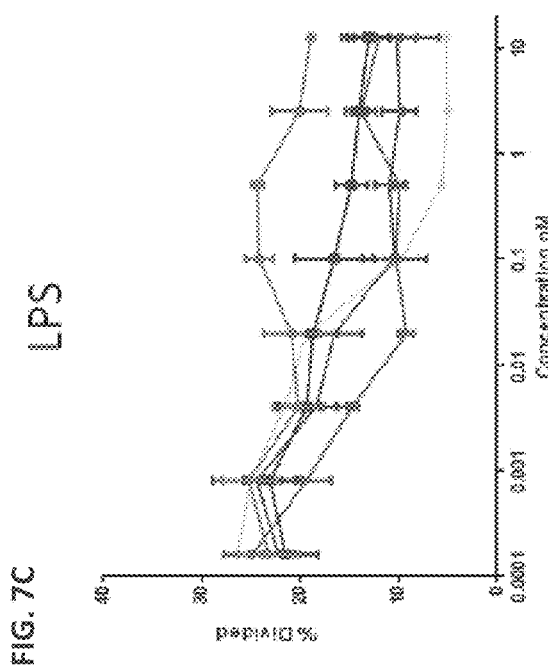
FIG. 7C
LPS

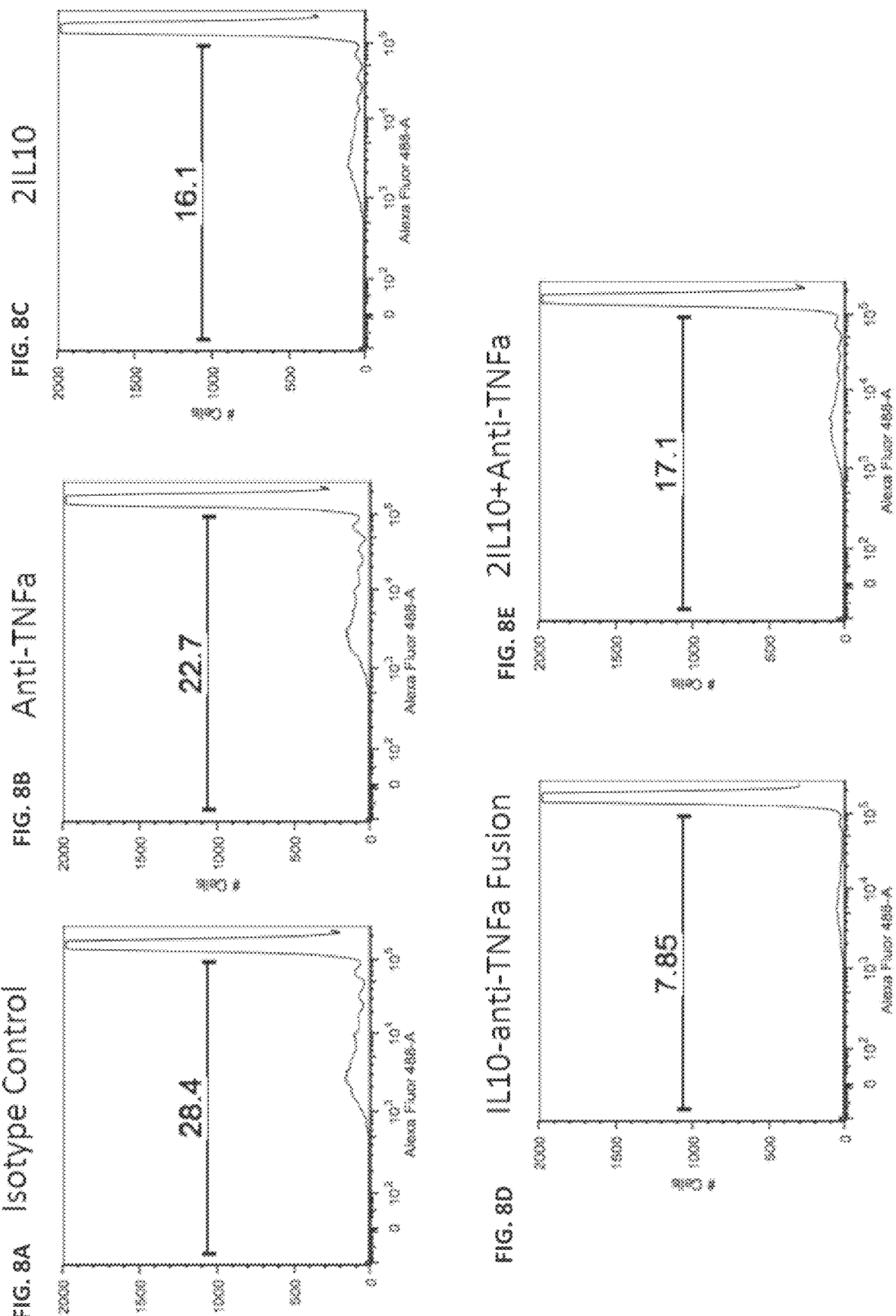
FIG. 8A  Isotype Control
FIG. 8B  Anti-TNFa
FIG. 8C  2iL10
FIG. 8D  IL10-anti-TNFa Fusion
FIG. 8E  2iL10+Anti-TNFa

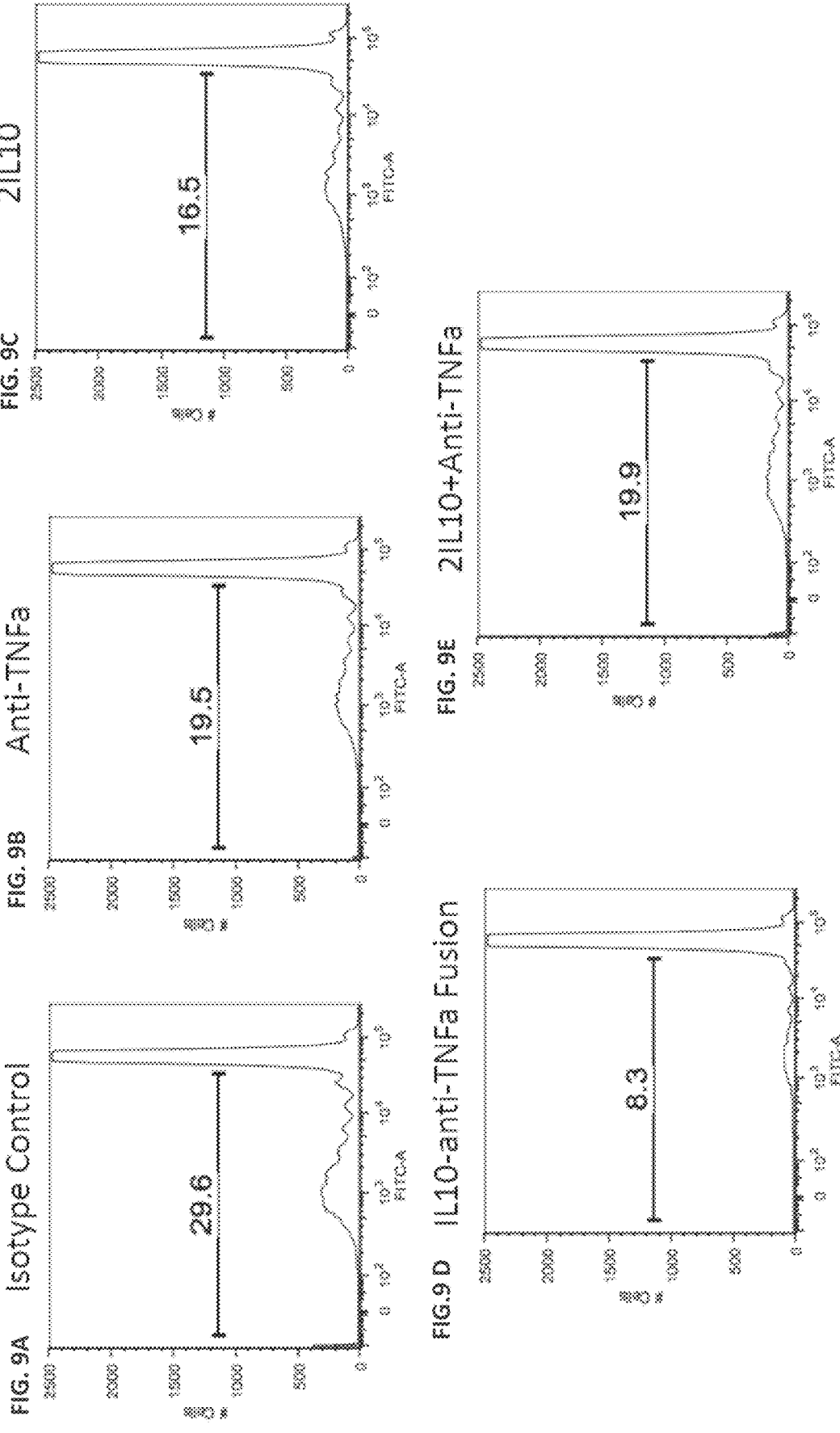

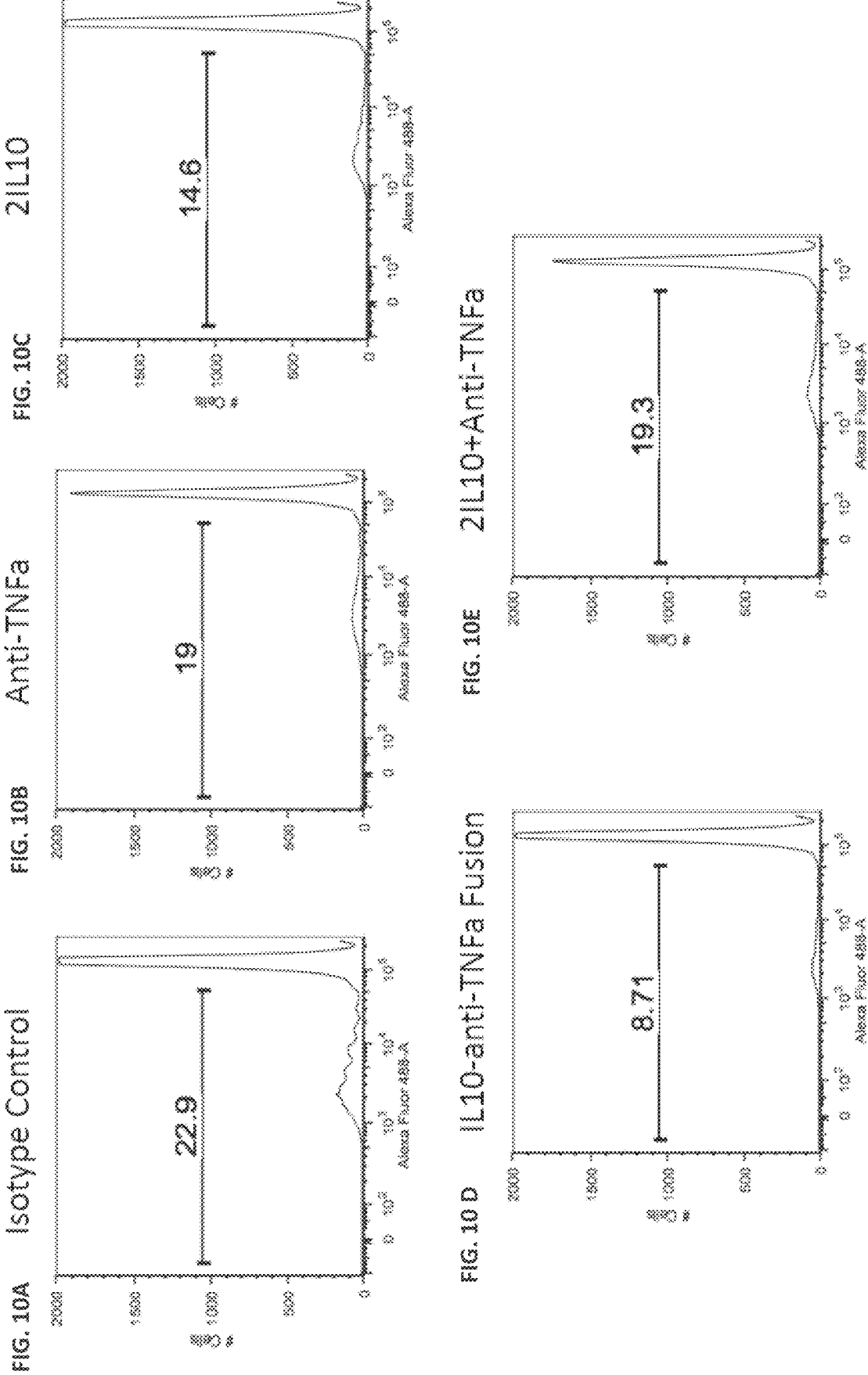

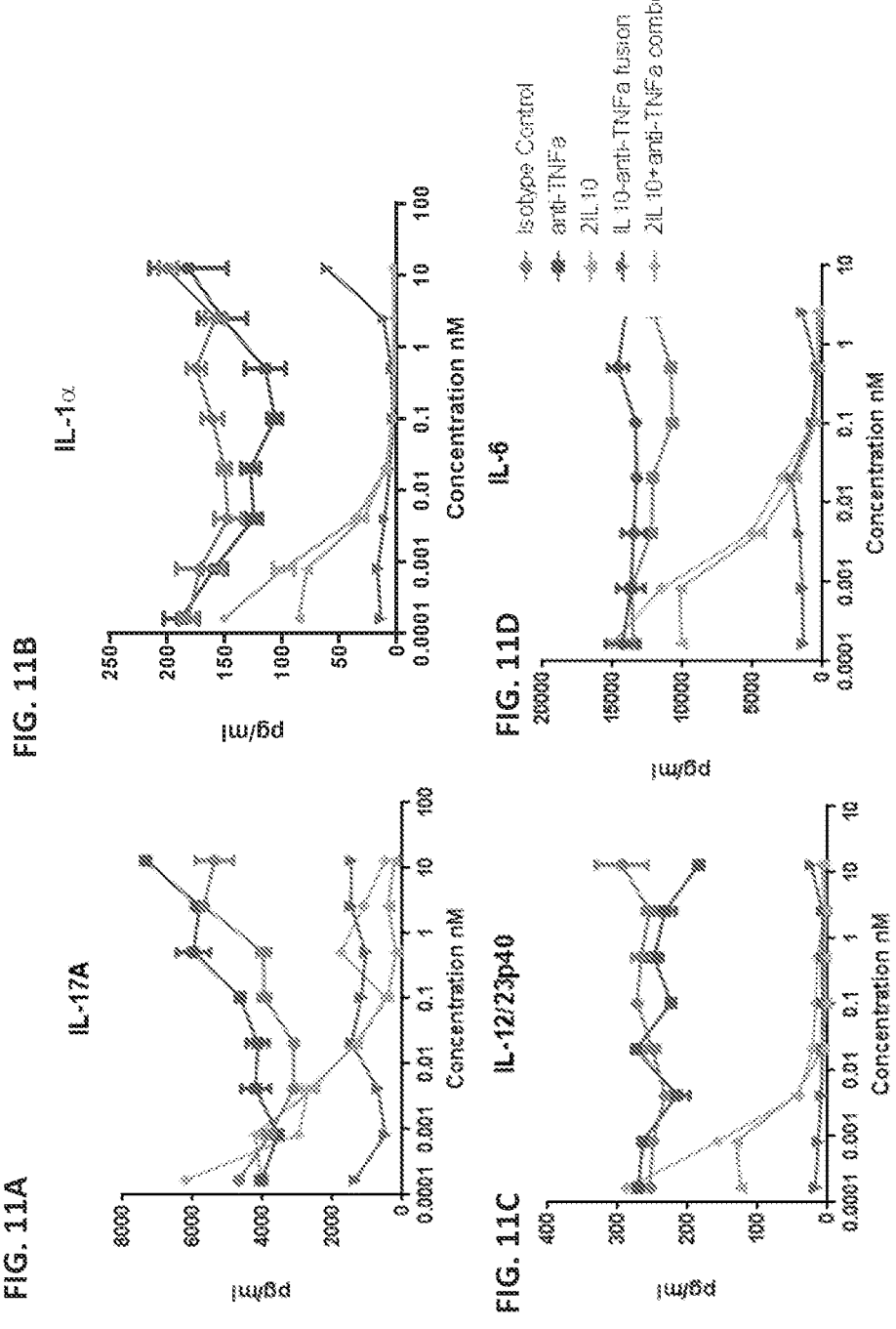

IL-5

IL-13

Isotype Control
anti-TNFa
2IL10
IL10-anti-TNFa fusion
2IL10+anti-TNFa combo

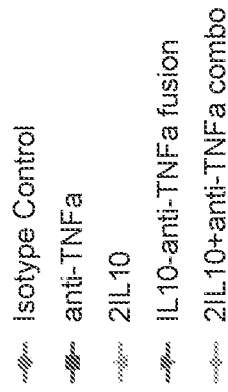
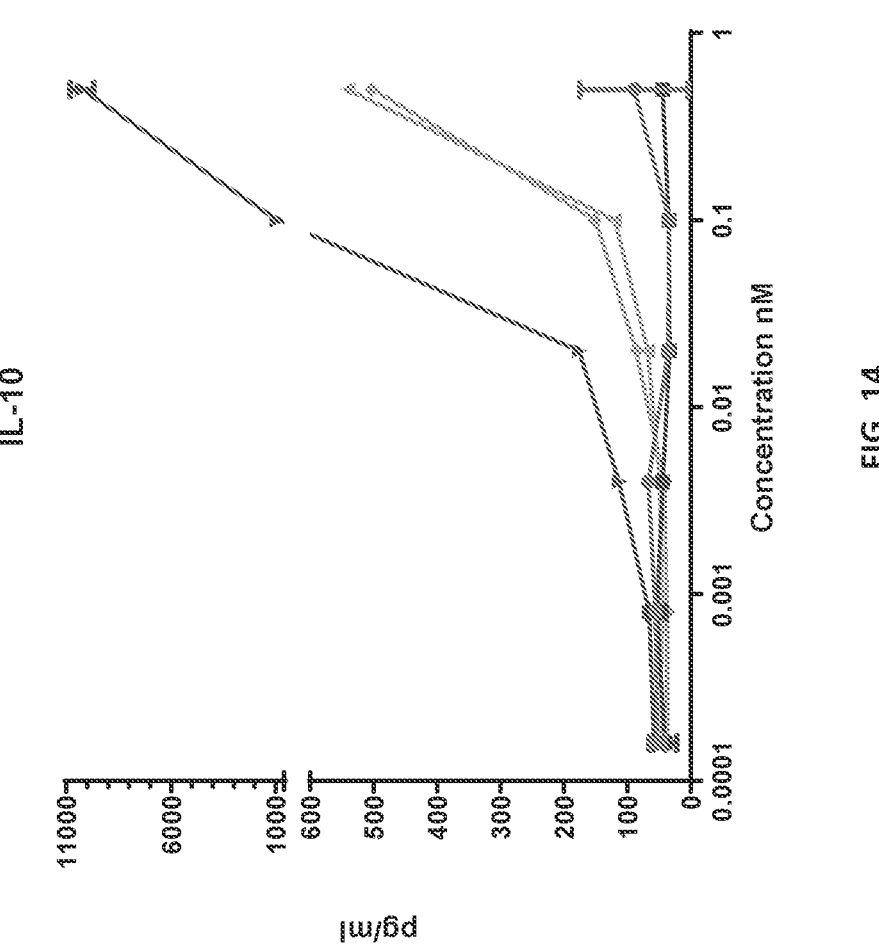
FIG. 14

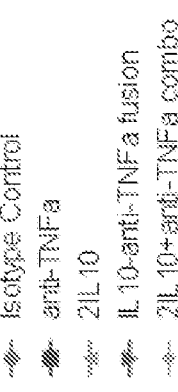
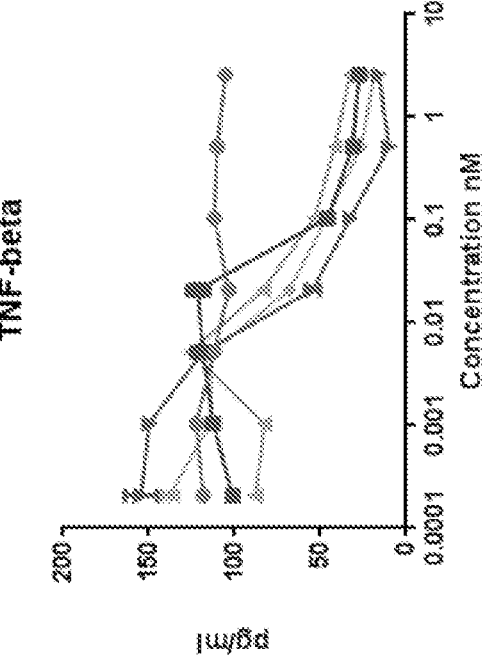
FIG. 15

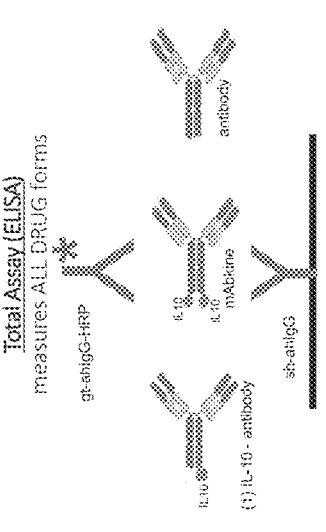
FIG. 16A
FIG. 16B
FIG. 16C
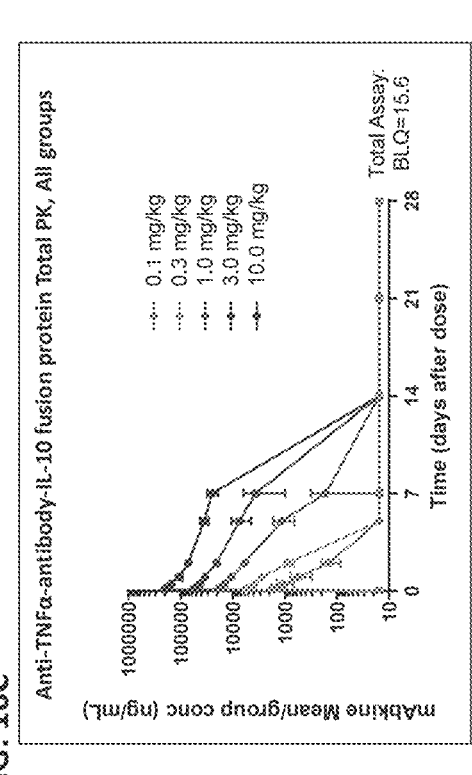
FIG. 16D

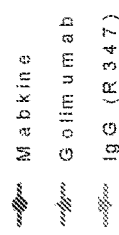
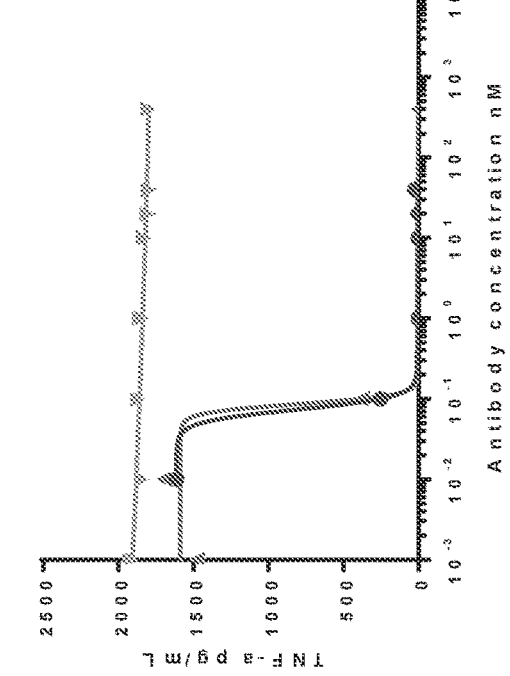
FIG. 17B
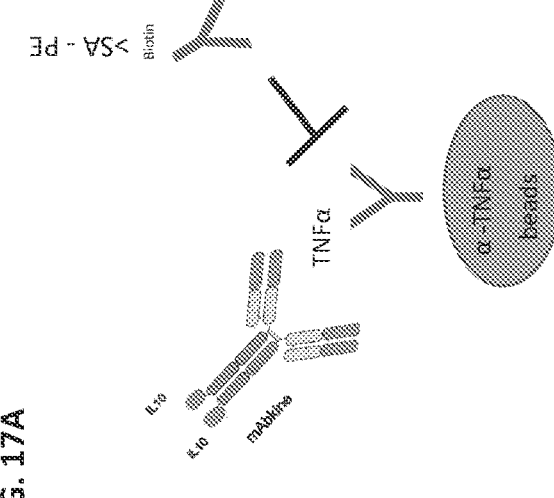
FIG. 17A
TNF-α is a Target Engagement Readout for the anti-TNF moiety of mAbkine Golimumab Single 3 mg/kg SC dose:

| | |
|---|---|
| Cmax (µg/mL) | 22.9%±8.95 |
| tmax (day) | 3.00 (2.00 to 7.00) |
| AUC (µg.day/mL) | 181.79±70.79 |
| t½ (day) | 1.08 (0.45 to 1.65) |
| CL/F (mL/day/kg) | 19.84±10.16 |
| Vss/F (mL/kg) | 27.46±21.55 |

Single 10 mg/kg SC dose:

| | |
|---|---|
| Cmax (µg/mL) | 54.36±16.13 |
| tmax (day) | 2.26±0.79 |
| AUC (µg.day/mL) | 571.60±229.50 |
| t½ (day) | 0.46±0.14 |
| CL/F (mL/day/kg) | 20.74±9.70 |
| Vss/F (mL/kg) | NA | anti-TNFα-antibody-IL-10 fusion protein PK Parameters (intact)

| Dose (mg/kg) | Terminal t½ (days) | $AUC_{last}$ (µg/mL·day) | $C_{max}$ (µg/mL) | CL (mL/day/kg) |
|---|---|---|---|---|
| 0.1 | 0.447 ±0.101 (n=3) | 1.66 ±0.679 (n=3) | 2.15 ±0.415 (n=3) | 62.7 ±26.1 (n=3) |
| 0.3 | 0.735 ±0.164 (n=3) | 7.57 ±0.297 (n=3) | 7.58 ±0.427 (n=3) | 33.8 ±2.77 (n=3) |
| 1 | 0.838 ±0.255 (n=2) | 41.1 ±16.8 (n=2) | 26.7 ±8.51 (n=2) | 25.7 ±6.73 (n=2) |
| 3 | 1.98 ±0.763 (n=3) | 125 ±16.6 (n=3) | 58.5 ±6.96 (n=3) | 22.5 ±4.23 (n=3) |
| 10 | 3.23 ±0.342 (n=3) | 538 ±18.8 (n=3) | 235 ±10.6 (n=3) | 14.9 ±1.2 (n=3) |

Golimumab Drug Approval Package; Pharmacology Review, www.fda.gov. Accessed Apr 29, 2019 (www.accessdata.fda.gov/drugsatfda_docs/nda/2009/125289s000TOC.cfm)

FIG. 18

In-vivo

Single dose mAbkine in cyno monkeys

Collect blood
at time points of PD assessment

Ex-vivo

LPS Stimulation
24 h at 37°C (whole blood ±LPS)

Collect plasma

Measure cytokines
(TNF-a, IL1b, IL-6)
3-plex Luminex assay

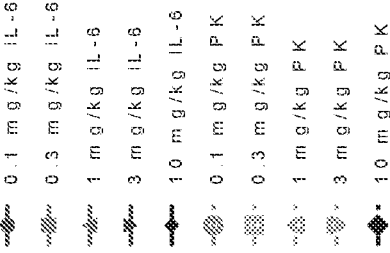
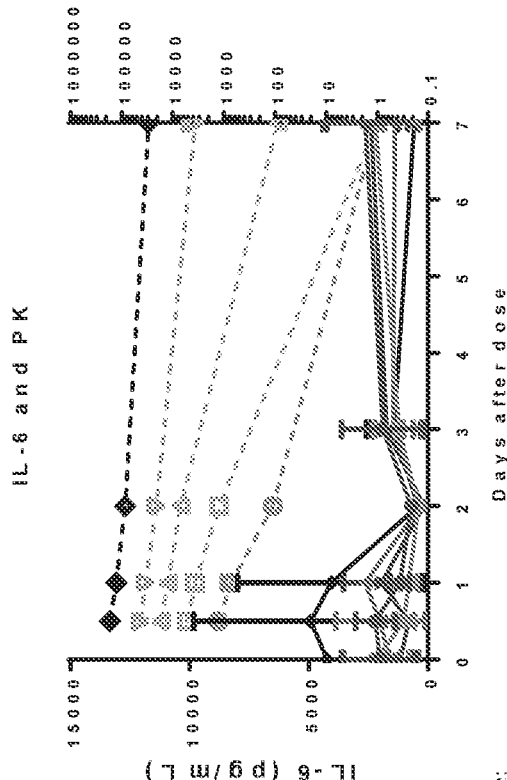
FIG. 22

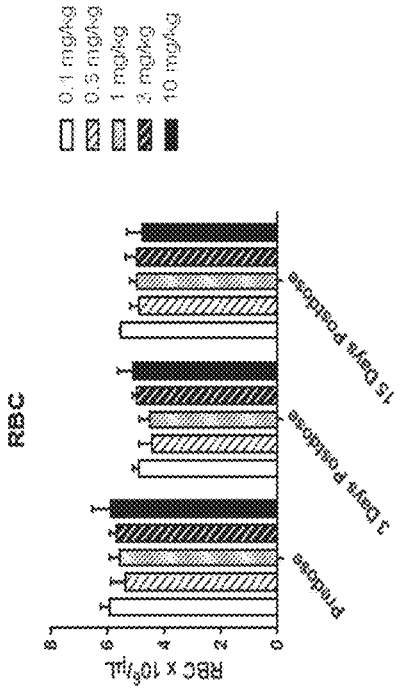

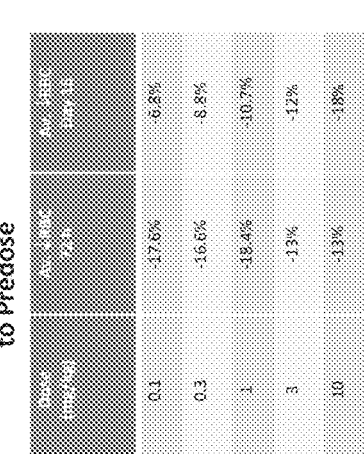

↓RBC observed in ALL monkeys ~72 h postdose

• Ranged between ~ 6%-19% (in individual animals )

• Postdose treatment values within historical control range for majority of treated animals

• 2 weeks post dose a trend towards recovery was observed at doses ≤ 1 mg/kg with more persistent reduction in RBC noted at doses ≥ 3 mg/kg

• Not toxicologically significant up to 10 mg/kg

• Possibility of procedural effect (eg: impacted by frequent blood sampling) cannot be excluded

FIG. 24

% Change HGB Relative to Predose

| | 6.5 h | 72 h | 15 d |
|---|---|---|---|
| 0.1 | -6% | -7% | -3% |
| 0.3 | -18% | -12% | |
| 1 | -20% | -12% | |
| 3 | -13% | -15% | |
| 10 | -13% | -21% | |

- Post dosing decreases in HGB in ALL monkeys ~72 h postdose
- Decreases in HGB between 7-21%; in 4 monkeys ~ 20%
- Slight anemia (HGB < 11.8 g/dL) present in all but 1 monkey correlated with decrease in RBC and HCT
- MCV values relatively unchanged; normocytic anemia
- Persisted at doses > 0.1 mg/kg up to 2 weeks post dosing

- Post dosing increase in RETIC in ALL monkeys 15 days postdose
- Relatively unchanged reticulocytes at 72 h with increases up to 9.8-fold by Day 15 in individual monkeys
- Consistent with a compensatory response to normocytic anemia

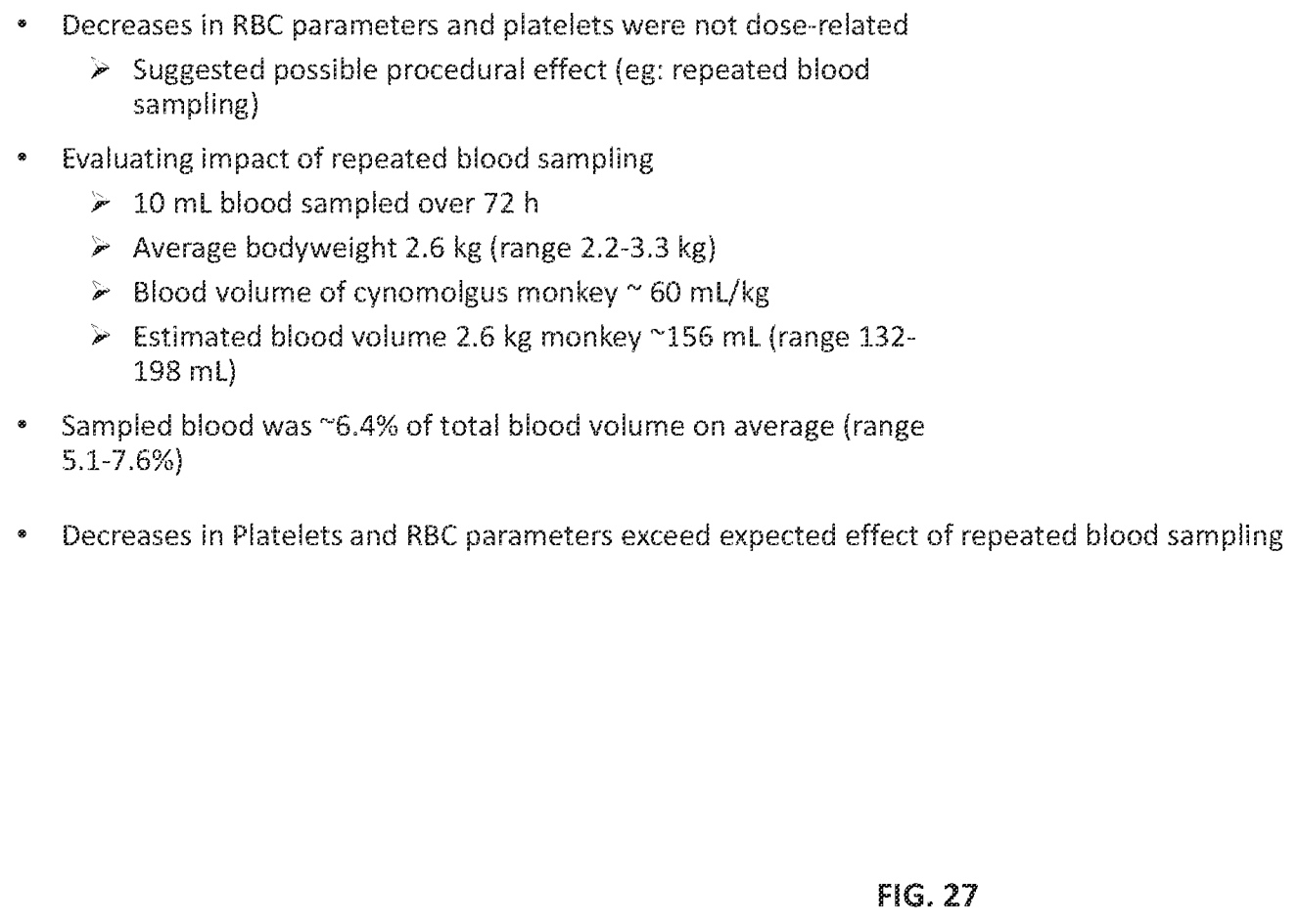

- Decreases in RBC parameters and platelets were not dose-related
  - ⋗ Suggested possible procedural effect (eg: repeated blood sampling)

- Evaluating impact of repeated blood sampling
  - ⋗ 10 mL blood sampled over 72 h
  - ⋗ Average bodyweight 2.6 kg (range 2.2-3.3 kg)
  - ⋗ Blood volume of cynomolgus monkey ~ 60 mL/kg
  - ⋗ Estimated blood volume 2.6 kg monkey ~156 mL (range 132-198 mL)

- Sampled blood was ~6.4% of total blood volume on average (range 5.1-7.6%)

- Decreases in Platelets and RBC parameters exceed expected effect of repeated blood sampling

FIG. 27

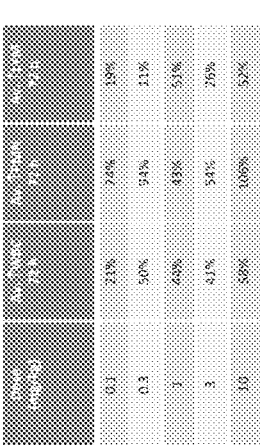
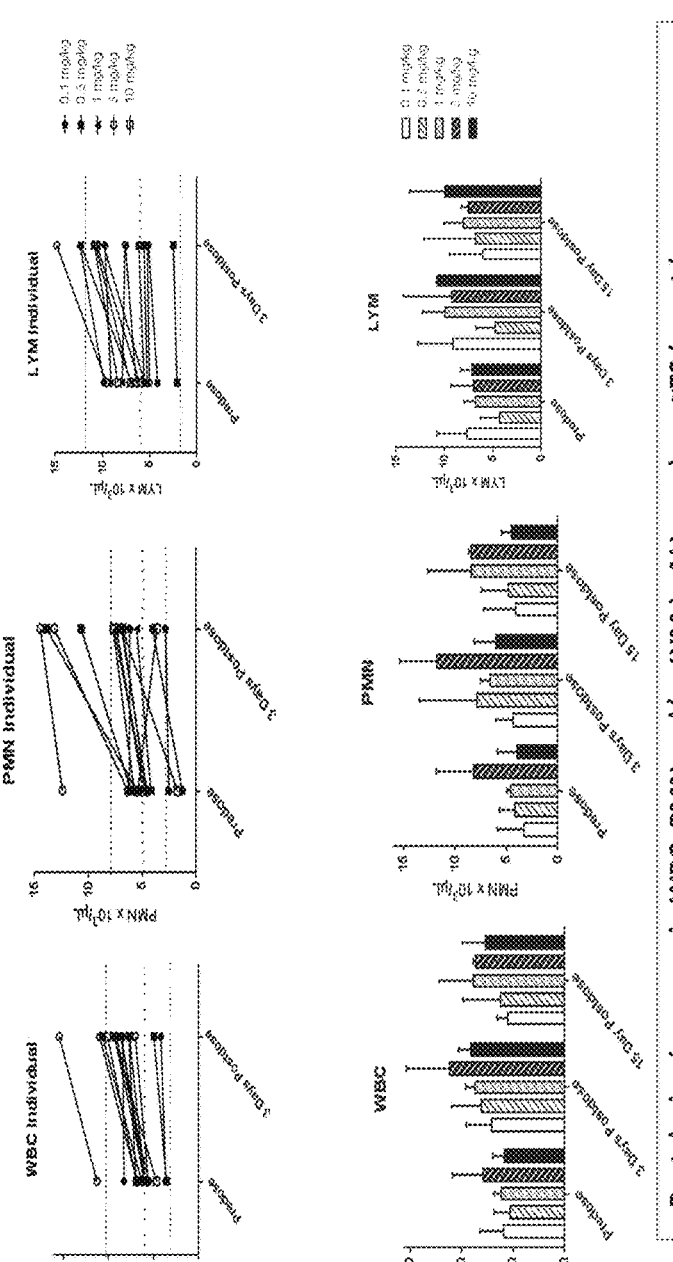
FIG. 28

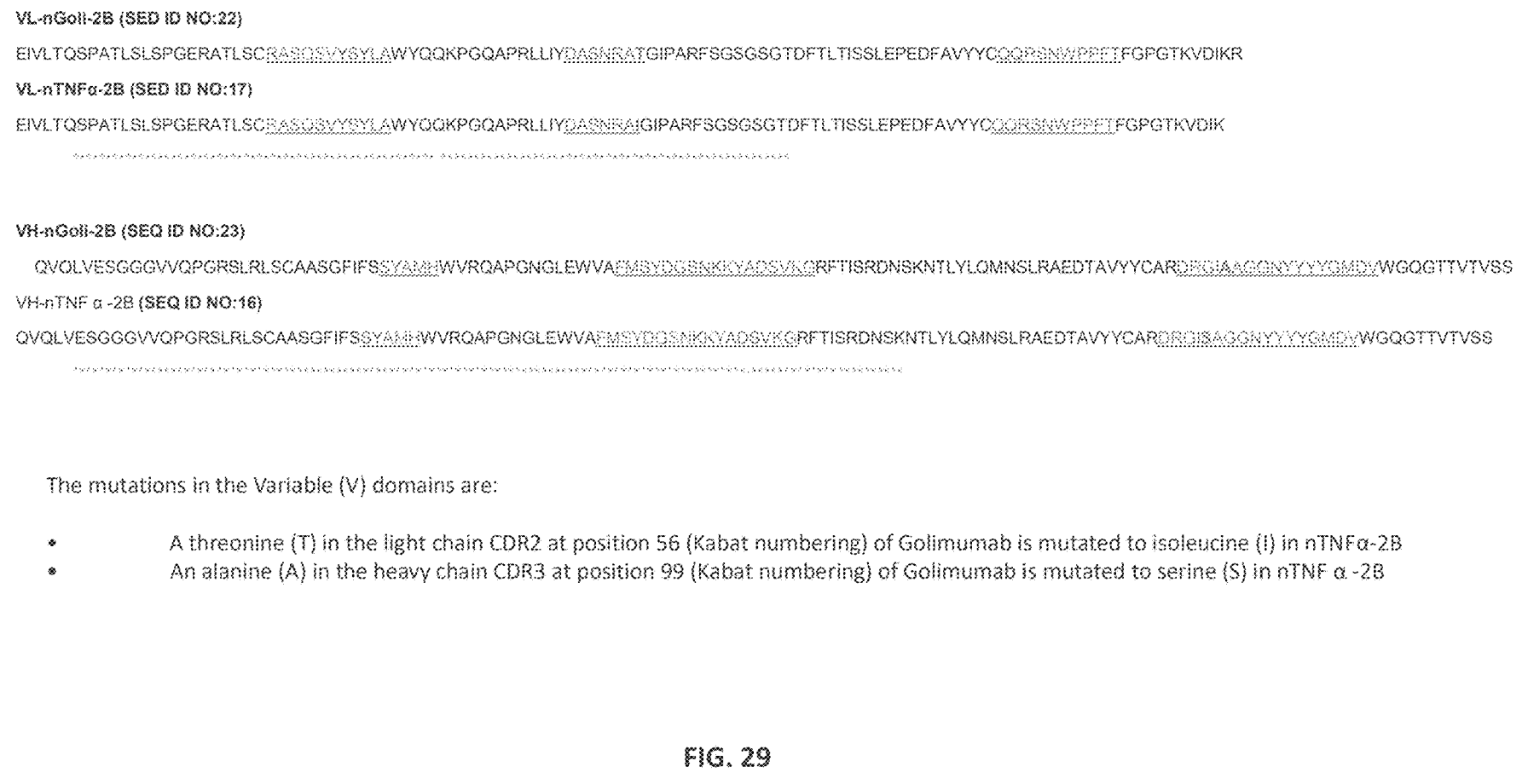

VL-nGoli-2B (SEQ ID NO:22)

EIVLTQSPATLSLSPGERATLSCRASQSVGSYLAWYQQKPGQAPRLLIYDASNRATGIPARFSGSGSGTDFTLTISSLEPEDFAVYYCQQRSNWPPEFGPGTKVDIKR

VL-nTNFα-2B (SEQ ID NO:17)

EIVLTQSPATLSLSPGERATLSCRASQSVGSYLAWYQQKPGQAPRLLIYDASNRAIGIPARFSGSGSGTDFTLTISSLEPEDFAVYYCQQRSNWPPEFGPGTKVDIK

VH-nGoli-2B (SEQ ID NO:23)

QVQLVESGGGVVQPGRSLRLSCAASGFIFSSYAMHWVRQAPGNGLEWVARFTISRDNSKNTLYLQMNSLRAEDTAVYYCARDRGIADDYYYGMDVWGQGTTVTVSS

VH-nTNFα-2B (SEQ ID NO:18)

QVQLVESGGGVVQPGRSLRLSCAASGFIFSSYAMHWVRQAPGNGLEWVARFTISRDNSKNTLYLQMNSLRAEDTAVYYCAPDRGIAGKYYYGMDVWGQGTTVTVSS

The mutations in the Variable (V) domains are:

- A threonine (T) in the light chain CDR2 at position 56 (Kabat numbering) of Golimumab is mutated to isoleucine (I) in nTNFα-2B
- An alanine (A) in the heavy chain CDR3 at position 99 (Kabat numbering) of Golimumab is mutated to serine (S) in nTNF α -2B

FIG. 29

Human IL-10 (SEQ ID NO:1)

PGQGTQSENSCTHFPGNLPNMLRDLRDAFSRVKTFFQMKDQLDNLLLKESLLEDFKGYLGCQALSEMIQFYLEEVMPQAENQDPDIKAHVNSLGEN
LKTLRLRLRRCHRFLPCENKSKAVEQVKNAFNKLQEKGIYKAMSEFDIFINYIEAYMTMKIRN

SEQUENCE LISTING

<160> NUMBER OF SEQ ID NOS: 42

<210> SEQ ID NO 1
<211> LENGTH: 159
<212> TYPE: PRT
<213> ORGANISM: Homo sapiens

<400> SEQUENCE: 1

```
Pro Gly Gln Gly Thr Gln Ser Glu Asn Ser Cys Thr His Phe Pro Gly
1               5                   10                  15

Asn Leu Pro Asn Met Leu Arg Asp Leu Arg Asp Ala Phe Ser Arg Val
            20                  25                  30

Lys Thr Phe Phe Gln Met Lys Asp Gln Leu Asp Asn Leu Leu Leu Lys
        35                  40                  45

Glu Ser Leu Leu Glu Asp Phe Lys Gly Tyr Leu Gly Cys Gln Ala Leu
    50                  55                  60

Ser Glu Met Ile Gln Phe Tyr Leu Glu Glu Val Met Pro Gln Ala Glu
65                  70                  75                  80

Asn Gln Asp Pro Asp Ile Lys Ala His Val Asn Ser Leu Gly Glu Asn
            85                  90                  95

Leu Lys Thr Leu Arg Leu Arg Leu Arg Arg Cys His Arg Phe Leu Pro
            100                 105                 110

Cys Glu Asn Lys Ser Lys Ala Val Glu Gln Val Lys Asn Ala Phe Asn
            115                 120                 125

Lys Leu Gln Glu Lys Gly Ile Tyr Lys Ala Met Ser Glu Phe Asp Ile
    130                 135                 140

Phe Ile Asn Tyr Ile Glu Ala Tyr Met Thr Met Lys Ile Arg Asn
145                 150                 155
```

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

```
Gly Gly Gly Gly Ser Ser
1               5
```

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

```
Gly Gly Gly Gly Ser Gly Gly Gly Gly Ser Ser
1               5                   10
```

<210> SEQ ID NO 4
<211> LENGTH: 631
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

-continued

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
            35                  40                  45

Ala Phe Met Ser Tyr Asp Gly Ser Asn Lys Lys Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ser Ala Gly Gly Asn Tyr Tyr Tyr Tyr Gly
            100                 105                 110

Met Asp Val Trp Gly Gln Gly Thr Thr Val Thr Val Ser Ser Ala Ser
            115                 120                 125

Thr Lys Gly Pro Ser Val Phe Pro Leu Ala Pro Ser Ser Lys Ser Thr
            130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
            355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
```

-continued

```
              420               425               430
Ser Cys Ser Val Met His Glu Ala Leu His Asn His Tyr Thr Gln Lys
        435               440               445

Ser Leu Ser Leu Ser Pro Gly Lys Gly Gly Gly Ser Gly Gly Gly
    450               455               460

Gly Ser Gly Gly Gly Gly Ser Ser Pro Gly Gln Gly Thr Gln Ser Glu
465               470               475               480

Asn Ser Cys Thr His Phe Pro Gly Asn Leu Pro Asn Met Leu Arg Asp
            485               490               495

Leu Arg Asp Ala Phe Ser Arg Val Lys Thr Phe Phe Gln Met Lys Asp
        500               505               510

Gln Leu Asp Asn Leu Leu Leu Lys Glu Ser Leu Leu Glu Asp Phe Lys
        515               520               525

Gly Tyr Leu Gly Cys Gln Ala Leu Ser Glu Met Ile Gln Phe Tyr Leu
        530               535               540

Glu Glu Val Met Pro Gln Ala Glu Asn Gln Asp Pro Asp Ile Lys Ala
545               550               555               560

His Val Asn Ser Leu Gly Glu Asn Leu Lys Thr Leu Arg Leu Arg Leu
            565               570               575

Arg Arg Cys His Arg Phe Leu Pro Cys Glu Asn Lys Ser Lys Ala Val
            580               585               590

Glu Gln Val Lys Asn Ala Phe Asn Lys Leu Gln Glu Lys Gly Ile Tyr
            595               600               605

Lys Ala Met Ser Glu Phe Asp Ile Phe Ile Asn Tyr Ile Glu Ala Tyr
        610               615               620

Met Thr Met Lys Ile Arg Asn
625               630

<210> SEQ ID NO 5
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Glu Ser Gly Gly Gly Val Val Gln Pro Gly Arg
1               5               10               15

Ser Leu Arg Leu Ser Cys Ala Ala Ser Gly Phe Ile Phe Ser Ser Tyr
            20               25               30

Ala Met His Trp Val Arg Gln Ala Pro Gly Asn Gly Leu Glu Trp Val
        35               40               45

Ala Phe Met Ser Tyr Asp Gly Ser Asn Lys Lys Tyr Ala Asp Ser Val
        50               55               60

Lys Gly Arg Phe Thr Ile Ser Arg Asp Asn Ser Lys Asn Thr Leu Tyr
65               70               75               80

Leu Gln Met Asn Ser Leu Arg Ala Glu Asp Thr Ala Val Tyr Tyr Cys
            85               90               95

Ala Arg Asp Arg Gly Ile Ser Ala Gly Gly Asn Tyr Tyr Tyr Tyr Gly
            100               105               110

Met Asp Val Trp Gly Gln Gly Thr Thr Val Thr Val Ser Ser Ala Ser
        115               120               125

Thr Lys Gly Pro Ser Val Phe Pro Leu Ala Pro Ser Ser Lys Ser Thr
        130               135               140
```

```
Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Ser Leu Gly Thr Gln Thr Tyr Ile
                195                 200                 205

Cys Asn Val Asn His Lys Pro Ser Asn Thr Lys Val Asp Lys Arg Val
        210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
                275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Glu Glu Met Thr
                355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
        435                 440                 445

Ser Leu Ser Leu Ser Pro Gly Lys
    450                 455
```

```
<210> SEQ ID NO 6
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6
```

```
Glu Ile Val Leu Thr Gln Ser Pro Ala Thr Leu Ser Leu Ser Pro Gly
1                   5                   10                  15

Glu Arg Ala Thr Leu Ser Cys Arg Ala Ser Gln Ser Val Tyr Ser Tyr
                20                  25                  30

Leu Ala Trp Tyr Gln Gln Lys Pro Gly Gln Ala Pro Arg Leu Leu Ile
                35                  40                  45
```

```
Tyr Asp Ala Ser Asn Arg Ala Ile Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Arg Thr Val Ala
                100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Tyr Ala Met His
1               5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Met Ser Tyr Asp Gly Ser Asn Lys Lys Tyr Ala Asp Ser Val Lys
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Arg Gly Ile Ser Ala Gly Gly Asn Tyr Tyr Tyr Gly Met Asp
1               5                   10                  15

Val
```

-continued

```
<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ala Ser Gln Ser Val Tyr Ser Tyr Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Ala Ser Asn Arg Ala Ile
1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Gln Arg Ser Asn Trp Pro Pro Phe Thr
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Ser Ser Ser Gly Ser Ser Ser Ser Gly Ser Ser Ser Ser Gly
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Gly Gly Ser Gly Gly Gly Gly Ser Gly Gly Gly Gly Ser Ser
1               5                   10                  15

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 15

Gly Gly Gly Gly Ser Gly Gly Gly Gly Ser Gly Gly Gly Gly Ser Gly
1               5                   10                  15

Gly Gly Gly Ser Ser
            20

<210> SEQ ID NO 16
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ser Ala Gly Gly Asn Tyr Tyr Tyr Tyr Gly
            100                 105                 110

Met Asp Val Trp Gly Gln Gly Thr Thr Val Thr Val Ser Ser
        115                 120                 125

<210> SEQ ID NO 17
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Ile Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Arg
            100                 105

<210> SEQ ID NO 18
<211> LENGTH: 645

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gaaatcgtgc tgacccagag ccccgccacc ctgtctctga gccctggcga gagagccacc          60
ctgagctgca gagccagcca gagcgtgtac tcctacctgg cttggtatca gcagaagccc         120
ggccaggccc ccagactgct gatctacgac gccagcaacc gggccatcgg catccctgcc         180
agattttctg gcagcggcag cggcaccgac ttcaccctga ccatcagcag cctggaaccc         240
gaggacttcg ccgtgtacta ctgccagcag cggagcaact ggcccccctt caccttcggc         300
cctggcacca agtggacat caagcgtacg gtggctgcac catctgtctt catcttcccg          360
ccatctgatg agcagttgaa atctggaact gcctctgttg tgtgcctgct gaataacttc         420
tatcccagag aggccaaagt acagtggaag gtggataacg ccctccaatc gggtaactcc         480
caggagagtg tcacagagca ggacagcaag gacagcacct acagcctcag cagcaccctg         540
acgctgagca aagcagacta cgagaaacac aaagtctacg cctgcgaagt cacccatcag         600
ggcctgagct cgcccgtcac aaagagcttc aacaggggag agtgt                         645

<210> SEQ ID NO 19
<211> LENGTH: 1875
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
caggtgcagc tggtggaaag cggcggaggc gtggtgcagc ccggcagaag cctgagactg          60
agctgcgctg ccagcggctt catcttcagc agctacgcca tgcactgggt ccgccaggcc         120
cctggcaacg gactggaatg ggtggccttc atgagctacg acggcagcaa caagaagtac         180
gccgacagcg tgaagggccg gttcaccatc agccgggaca acagcaagaa caccctgtac         240
ctgcagatga acagcctgcg ggctgaggac accgccgtgt actactgcgc cagagaccga         300
ggcatcagtg ctggcggcaa ctactactac tacggcatgg acgtgtgggg ccagggcacc         360
accgtgaccg tgtctagcgc gtcgaccaag ggcccatccg tcttccccct ggcaccctcc         420
tccaagagca cctctggggg cacagcggcc ctgggctgcc tggtcaagga ctacttcccc         480
gaaccggtga cggtgtcctg gaactcaggc gctctgacca cggccgtgca caccttcccg         540
gctgtcctac agtcctcagg actctactcc ctcagcagcg tggtgaccgt gccctccagc         600
agcttgggca cccagaccta catctgcaac gtgaatcaca agcccagcaa caccaaggtg         660
gacaagagag ttgagcccaa atcttgtgac aaaactcaca catgcccacc gtgcccagca         720
cctgaactcc tggggggacc gtcagtcttc ctcttccccc caaaacccaa ggacaccctc         780
atgatctccc ggacccctga ggtcacatgc gtggtggtgg acgtgagcca cgaagaccct         840
gaggtcaagt tcaactggta cgtggacggc gtggaggtgc ataatgccaa gacaaagccg         900
cgggaggagc agtacaacag cacgtaccgt gtggtcagcg tcctcaccgt cctgcaccag         960
gactggctga atggcaagga gtacaagtgc aaggtctcca acaaagccct cccagccccc        1020
atcgagaaaa ccatctccaa agccaaaggg cagccccgag aaccacaggt ctacaccctg        1080
cccccatccc gggaggagat gaccaagaac caggtcagcc tgacctgcct ggtcaaaggc        1140

-continued

```
ttctatccca gcgacatcgc cgtggagtgg gagagcaatg ggcagccgga gaacaactac    1200
aagaccacgc ctcccgtgct ggactccgac ggctccttct tcctctatag caagctcacc    1260
gtggacaaga gcaggtggca gcaggggaac gtcttctcat gctccgtgat gcatgaggct    1320
ctgcacaacc actacacgca gaagagctta agcctgtctc cgggtaaagg aggaggagga    1380
agcggaggag gaggaagccc aggccagggc acccagtctg agaacagctg cacccacttc    1440
ccaggcaacc tgcctaacat gcttcgagat ctccgagatg ccttcagcag agtgaagact    1500
ttctttcaaa tgaaggatca gctggacaac ttgttgttaa aggagtcctt gctggaggac    1560
tttaagggtt acctgggttg ccaagccttg tctgagatga tccagttttta cctggaggag    1620 gtgatgcccc aagctgagaa ccaagaccca gacatcaagg cgcatgtgaa ctccctgggg    1680
gagaacctga gaccctcag gctgaggcta cggcgctgtc atcgatttct tccctgtgaa    1740
aacaagagca aggccgtgga gcaggtgaag aatgccttta ataagctcca agagaaaggc    1800
atctacaaag ccatgagtga gtttgacatc ttcatcaact acatagaagc ctacatgaca    1860
atgaagatac gaaac                                                       1875
```

<210> SEQ ID NO 20
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

-continued

<210> SEQ ID NO 21
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Arg Val
        210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
            355                 360                 365

```
Lys Asn Gln Val Ser Leu Thr Cys Leu Val Lys Gly Phe Tyr Pro Ser
    370             375             380

Asp Ile Ala Val Glu Trp Glu Ser Asn Gly Gln Pro Glu Asn Asn Tyr
385             390             395             400

Lys Thr Thr Pro Pro Val Leu Asp Ser Asp Gly Ser Phe Phe Leu Tyr
            405             410             415

Ser Lys Leu Thr Val Asp Lys Ser Arg Trp Gln Gln Gly Asn Val Phe
            420             425             430

Ser Cys Ser Val Met His Glu Ala Leu His Asn His Tyr Thr Gln Lys
        435             440             445

Ser Leu Ser Leu Ser Pro Gly Lys
    450             455
```

```
<210> SEQ ID NO 22
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Ile Val Leu Thr Gln Ser Pro Ala Thr Leu Ser Leu Ser Pro Gly
1               5               10              15

Glu Arg Ala Thr Leu Ser Cys Arg Ala Ser Gln Ser Val Tyr Ser Tyr
            20              25              30

Leu Ala Trp Tyr Gln Gln Lys Pro Gly Gln Ala Pro Arg Leu Leu Ile
        35              40              45

Tyr Asp Ala Ser Asn Arg Ala Thr Gly Ile Pro Ala Arg Phe Ser Gly
    50              55              60

Ser Gly Ser Gly Thr Asp Phe Thr Leu Thr Ile Ser Ser Leu Glu Pro
65              70              75              80

Glu Asp Phe Ala Val Tyr Tyr Cys Gln Gln Arg Ser Asn Trp Pro Pro
            85              90              95

Phe Thr Phe Gly Pro Gly Thr Lys Val Asp Ile Lys Arg
            100             105
```

```
<210> SEQ ID NO 23
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Glu Ser Gly Gly Gly Val Val Gln Pro Gly Arg
1               5               10              15

Ser Leu Arg Leu Ser Cys Ala Ala Ser Gly Phe Ile Phe Ser Ser Tyr
            20              25              30

Ala Met His Trp Val Arg Gln Ala Pro Gly Asn Gly Leu Glu Trp Val
        35              40              45

Ala Phe Met Ser Tyr Asp Gly Ser Asn Lys Lys Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95
```

-continued

```
Ala Arg Asp Arg Gly Ile Ala Ala Gly Gly Asn Tyr Tyr Tyr Gly
            100                 105                 110

Met Asp Val Trp Gly Gln Gly Thr Thr Val Thr Val Ser Ser
        115                 120                 125

<210> SEQ ID NO 24
<211> LENGTH: 631
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
            35                  40                  45

Ala Phe Met Ser Tyr Asp Gly Ser Asn Lys Lys Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ser Ala Gly Gly Asn Tyr Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
```

-continued

```
              325              330              335
Leu Pro Ala Pro Ile Glu Lys Thr Ile Ser Lys Ala Lys Gly Gln Pro
          340              345              350
Arg Glu Pro Gln Val Tyr Thr Leu Pro Pro Ser Arg Glu Glu Met Thr
          355              360              365
Lys Asn Gln Val Ser Leu Thr Cys Leu Val Lys Gly Phe Tyr Pro Ser
    370              375              380
Asp Ile Ala Val Glu Trp Glu Ser Asn Gly Gln Pro Glu Asn Asn Tyr
385              390              395              400
Lys Thr Thr Pro Pro Val Leu Asp Ser Asp Gly Ser Phe Phe Leu Tyr
              405              410              415
Ser Lys Leu Thr Val Asp Lys Ser Arg Trp Gln Gln Gly Asn Val Phe
          420              425              430
Ser Cys Ser Val Met His Glu Ala Leu His Asn His Tyr Thr Gln Lys
          435              440              445
Ser Leu Ser Leu Ser Pro Gly Ala Gly Gly Gly Ser Gly Gly Gly
          450              455              460
Gly Ser Gly Gly Gly Gly Ser Ser Pro Gly Gln Gly Thr Gln Ser Glu
465              470              475              480
Asn Ser Cys Thr His Phe Pro Gly Asn Leu Pro Asn Met Leu Arg Asp
              485              490              495
Leu Arg Asp Ala Phe Ser Arg Val Lys Thr Phe Phe Gln Met Lys Asp
          500              505              510
Gln Leu Asp Asn Leu Leu Leu Lys Glu Ser Leu Leu Glu Asp Phe Lys
          515              520              525
Gly Tyr Leu Gly Cys Gln Ala Leu Ser Glu Met Ile Gln Phe Tyr Leu
          530              535              540
Glu Glu Val Met Pro Gln Ala Glu Asn Gln Asp Pro Asp Ile Lys Ala
545              550              555              560
His Val Asn Ser Leu Gly Glu Asn Leu Lys Thr Leu Arg Leu Arg Leu
              565              570              575
Arg Arg Cys His Arg Phe Leu Pro Cys Glu Asn Lys Ser Lys Ala Val
          580              585              590
Glu Gln Val Lys Asn Ala Phe Asn Lys Leu Gln Glu Lys Gly Ile Tyr
          595              600              605
Lys Ala Met Ser Glu Phe Asp Ile Phe Ile Asn Tyr Ile Glu Ala Tyr
          610              615              620
Met Thr Met Lys Ile Arg Asn
625              630
```

```
<210> SEQ ID NO 25
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Pro Gly Gln Gly Thr Gln Ser Glu Asn Ser Cys Thr His Phe Pro Gly
1               5               10              15
Asn Leu Pro Asn Met Leu Arg Asp Leu Arg Asp Ala Phe Ser Arg Val
          20              25              30
Lys Thr Phe Phe Gln Met Lys Asp Gln Leu Asp Asn Leu Leu Leu Lys
          35              40              45
```

Glu Ser Leu Leu Glu Asp Phe Lys Gly Tyr Leu Gly Cys Gln Ala Leu
    50                  55                  60

Ser Glu Met Ile Gln Phe Tyr Leu Glu Glu Val Met Pro Gln Ala Glu
65                  70                  75                  80

Asn Gln Asp Pro Asp Ile Lys Ala His Val Asn Ser Leu Gly Glu Asn
                85                  90                  95

Leu Lys Thr Leu Arg Leu Arg Leu Arg Arg Cys His Arg Phe Leu Pro
            100                 105                 110

Cys Glu Asn Lys Ser Lys Ala Val Glu Gln Val Lys
        115                 120

<210> SEQ ID NO 26
<211> LENGTH: 595
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ser Ala Gly Gly Asn Tyr Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

```
Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Glu Glu Met Thr
                355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
    435                 440                 445

Ser Leu Ser Leu Ser Pro Gly Lys Gly Gly Gly Ser Gly Gly Gly
    450                 455                 460

Gly Ser Gly Gly Gly Gly Ser Pro Gly Gln Gly Thr Gln Ser Glu Asn
465                 470                 475                 480

Ser Cys Thr His Phe Pro Gly Asn Leu Pro Asn Met Leu Arg Asp Leu
                485                 490                 495

Arg Asp Ala Phe Ser Arg Val Lys Thr Phe Phe Gln Met Lys Asp Gln
                500                 505                 510

Leu Asp Asn Leu Leu Leu Lys Glu Ser Leu Leu Glu Asp Phe Lys Gly
                515                 520                 525

Tyr Leu Gly Cys Gln Ala Leu Ser Glu Met Ile Gln Phe Tyr Leu Glu
    530                 535                 540

Glu Val Met Pro Gln Ala Glu Asn Gln Asp Pro Asp Ile Lys Ala His
545                 550                 555                 560

Val Asn Ser Leu Gly Glu Asn Leu Lys Thr Leu Arg Leu Arg Leu Arg
                565                 570                 575

Arg Cys His Arg Phe Leu Pro Cys Glu Asn Lys Ser Lys Ala Val Glu
                580                 585                 590

Gln Val Lys
        595
```

```
<210> SEQ ID NO 27
<211> LENGTH: 595
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
                20                  25                  30

Ala Met His Trp Val Arg Gln Ala Pro Gly Asn Gly Leu Glu Trp Val
```

```
              35                        40                        45
Ala Phe Met Ser Tyr Asp Gly Ser Asn Lys Lys Tyr Ala Asp Ser Val
      50                        55                        60

Lys Gly Arg Phe Thr Ile Ser Arg Asp Asn Ser Lys Asn Thr Leu Tyr
65                        70                        75                        80

Leu Gln Met Asn Ser Leu Arg Ala Glu Asp Thr Ala Val Tyr Tyr Cys
                  85                        90                        95

Ala Arg Asp Arg Gly Ile Ser Ala Gly Gly Asn Tyr Tyr Tyr Tyr Gly
                  100                       105                       110

Met Asp Val Trp Gly Gln Gly Thr Thr Val Thr Val Ser Ser Ala Ser
                  115                       120                       125

Thr Lys Gly Pro Ser Val Phe Pro Leu Ala Pro Ser Ser Lys Ser Thr
      130                       135                       140

Ser Gly Gly Thr Ala Ala Leu Gly Cys Leu Val Lys Asp Tyr Phe Pro
145                       150                       155                       160

Glu Pro Val Thr Val Ser Trp Asn Ser Gly Ala Leu Thr Ser Gly Val
                  165                       170                       175

His Thr Phe Pro Ala Val Leu Gln Ser Ser Gly Leu Tyr Ser Leu Ser
                  180                       185                       190

Ser Val Val Thr Val Pro Ser Ser Ser Leu Gly Thr Gln Thr Tyr Ile
                  195                       200                       205

Cys Asn Val Asn His Lys Pro Ser Asn Thr Lys Val Asp Lys Arg Val
      210                       215                       220

Glu Pro Lys Ser Cys Asp Lys Thr His Thr Cys Pro Pro Cys Pro Ala
225                       230                       235                       240

Pro Glu Leu Leu Gly Gly Pro Ser Val Phe Leu Phe Pro Pro Lys Pro
                  245                       250                       255

Lys Asp Thr Leu Met Ile Ser Arg Thr Pro Glu Val Thr Cys Val Val
                  260                       265                       270

Val Asp Val Ser His Glu Asp Pro Glu Val Lys Phe Asn Trp Tyr Val
                  275                       280                       285

Asp Gly Val Glu Val His Asn Ala Lys Thr Lys Pro Arg Glu Glu Gln
      290                       295                       300

Tyr Asn Ser Thr Tyr Arg Val Val Ser Val Leu Thr Val Leu His Gln
305                       310                       315                       320

Asp Trp Leu Asn Gly Lys Glu Tyr Lys Cys Lys Val Ser Asn Lys Ala
                  325                       330                       335

Leu Pro Ala Pro Ile Glu Lys Thr Ile Ser Lys Ala Lys Gly Gln Pro
                  340                       345                       350

Arg Glu Pro Gln Val Tyr Thr Leu Pro Pro Ser Arg Glu Glu Met Thr
                  355                       360                       365

Lys Asn Gln Val Ser Leu Thr Cys Leu Val Lys Gly Phe Tyr Pro Ser
      370                       375                       380

Asp Ile Ala Val Glu Trp Glu Ser Asn Gly Gln Pro Glu Asn Asn Tyr
385                       390                       395                       400

Lys Thr Thr Pro Pro Val Leu Asp Ser Asp Gly Ser Phe Phe Leu Tyr
                  405                       410                       415

Ser Lys Leu Thr Val Asp Lys Ser Arg Trp Gln Gln Gly Asn Val Phe
                  420                       425                       430

Ser Cys Ser Val Met His Glu Ala Leu His Asn His Tyr Thr Gln Lys
                  435                       440                       445

Ser Leu Ser Leu Ser Pro Gly Ala Gly Gly Gly Ser Gly Gly Gly
      450                       455                       460
```

```
Gly Ser Gly Gly Gly Gly Ser Pro Gly Gln Gly Thr Gln Ser Glu Asn
465                 470                 475                 480

Ser Cys Thr His Phe Pro Gly Asn Leu Pro Asn Met Leu Arg Asp Leu
                485                 490                 495

Arg Asp Ala Phe Ser Arg Val Lys Thr Phe Phe Gln Met Lys Asp Gln
            500                 505                 510

Leu Asp Asn Leu Leu Leu Lys Glu Ser Leu Leu Glu Asp Phe Lys Gly
            515                 520                 525

Tyr Leu Gly Cys Gln Ala Leu Ser Glu Met Ile Gln Phe Tyr Leu Glu
        530                 535                 540

Glu Val Met Pro Gln Ala Glu Asn Gln Asp Pro Asp Ile Lys Ala His
545                 550                 555                 560

Val Asn Ser Leu Gly Glu Asn Leu Lys Thr Leu Arg Leu Arg Leu Arg
                565                 570                 575

Arg Cys His Arg Phe Leu Pro Cys Glu Asn Lys Ser Lys Ala Val Glu
            580                 585                 590

Gln Val Lys
        595
```

```
<210> SEQ ID NO 28
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gagattgtgc tgacccagtc tcctgccaca ctgtctttga ccctggcga  gagagctacc      60 ctgtcctgta gagcctctca gtccgtgtac tcctacctgg cctggtatca gcagaagcct     120
ggacaggctc cccggctgct gatctacgat gcctctaaca gagccatcgg catccccgcc     180
agattctccg gatctggctc tggcacagac tttaccctga ccatctccag cctggaacct     240
gaggacttcg ccgtgtacta ctgccagcag cggtctaact ggcctccttt caccttggga     300
cccggcacca aggtggacat caagagaaca gtggccgctc cttccgtgtt catcttccca     360
ccttccgacg agcagctgaa gtctggcacc gcttctgtcg tgtgcctgct gaacaacttc     420
taccctcggg aagccaaggt gcagtggaaa gtggataacg ccctgcagtc cggcaactcc     480
caagagtctg tgaccgagca ggactccaag acagcacct  acagcctgtc ctccacactg     540
accctgtcca aggccgacta cgagaagcac aaggtgtacg cctgcgaagt gacccatcag     600
ggcctgtcta gccctgtgac caagtctttc aaccggggcg agtgc               645
```

```
<210> SEQ ID NO 29
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
```

```
              35                    40                    45
Ala Phe Met Ser Tyr Asp Gly Ser Asn Lys Lys Tyr Ala Asp Ser Val
    50                    55                    60

Lys Gly Arg Phe Thr Ile Ser Arg Asp Asn Ser Lys Asn Thr Leu Tyr
65                    70                    75                    80

Leu Gln Met Asn Ser Leu Arg Ala Glu Asp Thr Ala Val Tyr Tyr Cys
                85                    90                    95

Ala Arg Asp Arg Gly Ile Ser Ala Gly Gly Asn Tyr Tyr Tyr Tyr Gly
            100                   105                   110

Met Asp Val Trp Gly Gln Gly Thr Thr Val Thr Val Ser Ser Ala Ser
            115                   120                   125

Thr Lys Gly Pro Ser Val Phe Pro Leu Ala Pro Ser Ser Lys Ser Thr
    130                   135                   140

Ser Gly Gly Thr Ala Ala Leu Gly Cys Leu Val Lys Asp Tyr Phe Pro
145                   150                   155                   160

Glu Pro Val Thr Val Ser Trp Asn Ser Gly Ala Leu Thr Ser Gly Val
                165                   170                   175

His Thr Phe Pro Ala Val Leu Gln Ser Ser Gly Leu Tyr Ser Leu Ser
            180                   185                   190

Ser Val Val Thr Val Pro Ser Ser Ser Leu Gly Thr Gln Thr Tyr Ile
            195                   200                   205

Cys Asn Val Asn His Lys Pro Ser Asn Thr Lys Val Asp Lys Arg Val
    210                   215                   220

Glu Pro Lys Ser Cys Asp Lys Thr His Thr Cys Pro Pro Cys Pro Ala
225                   230                   235                   240

Pro Glu Leu Leu Gly Gly Pro Ser Val Phe Leu Phe Pro Pro Lys Pro
                245                   250                   255

Lys Asp Thr Leu Met Ile Ser Arg Thr Pro Glu Val Thr Cys Val Val
            260                   265                   270

Val Asp Val Ser His Glu Asp Pro Glu Val Lys Phe Asn Trp Tyr Val
            275                   280                   285

Asp Gly Val Glu Val His Asn Ala Lys Thr Lys Pro Arg Glu Glu Gln
    290                   295                   300

Tyr Asn Ser Thr Tyr Arg Val Val Ser Val Leu Thr Val Leu His Gln
305                   310                   315                   320

Asp Trp Leu Asn Gly Lys Glu Tyr Lys Cys Lys Val Ser Asn Lys Ala
                325                   330                   335

Leu Pro Ala Pro Ile Glu Lys Thr Ile Ser Lys Ala Lys Gly Gln Pro
            340                   345                   350

Arg Glu Pro Gln Val Tyr Thr Leu Pro Pro Ser Arg Glu Glu Met Thr
            355                   360                   365

Lys Asn Gln Val Ser Leu Thr Cys Leu Val Lys Gly Phe Tyr Pro Ser
    370                   375                   380

Asp Ile Ala Val Glu Trp Glu Ser Asn Gly Gln Pro Glu Asn Asn Tyr
385                   390                   395                   400

Lys Thr Thr Pro Pro Val Leu Asp Ser Asp Gly Ser Phe Phe Leu Tyr
                405                   410                   415

Ser Lys Leu Thr Val Asp Lys Ser Arg Trp Gln Gln Gly Asn Val Phe
            420                   425                   430

Ser Cys Ser Val Met His Glu Ala Leu His Asn His Tyr Thr Gln Lys
            435                   440                   445

Ser Leu Ser Leu Ser Pro Gly Ala
    450                   455
```

-continued

```
<210> SEQ ID NO 30
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asn Ala Phe Asn Lys Leu Gln Glu Lys Gly Ile Tyr Lys Ala Met Ser
1               5                   10                  15

Glu Phe Asp Ile Phe Ile Asn Tyr Ile Glu Ala Tyr Met Thr Met Lys
            20                  25                  30

Ile Arg Asn
        35

<210> SEQ ID NO 31
<211> LENGTH: 1893
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
caggtgcagc tggtggaaag cggcggaggc gtggtgcagc ccggcagaag cctgagactg      60
agctgcgctg ccagcggctt catcttcagc agctacgcca tgcactgggt ccgccaggcc     120
cctggcaacg gactggaatg ggtggccttc atgagctacg acggcagcaa caagaagtac     180
gccgacagcg tgaagggccg gttcaccatc agccgggaca cagcaagaa caccctgtac      240 ctgcagatga acagcctgcg ggctgaggac accgccgtgt actactgcgc cagagaccga     300
ggcatcagtg ctggcggcaa ctactactac tacggcatgg acgtgtgggg ccagggcacc     360
accgtgaccg tgtctagcgc gtcgaccaag ggcccatccg tcttcccct ggcaccctcc       420 tccaagagca cctctggggg cacagcggcc ctgggctgcc tggtcaagga ctacttcccc     480
gaaccggtga cggtgtcctg gaactcaggc gctctgacca cgggcgtgca caccttcccg     540
gctgtcctac agtcctcagg actctactcc ctcagcagcg tggtgaccgt gccctccagc     600
agcttgggca cccagaccta catctgcaac gtgaatcaca agcccagcaa caccaaggtg     660
gacaagagag ttgagcccaa atcttgtgac aaaactcaca catgcccacc gtgcccagca     720
cctgaactcc tggggggacc gtcagtcttc ctcttcccc caaaacccaa ggacaccctc      780
atgatctccc ggacccctga ggtcacatgc gtggtggtgg acgtgagcca cgaagaccct     840
gaggtcaagt tcaactggta cgtggacggc gtggaggtgc ataatgccaa gacaaagccg     900
cgggaggagc agtacaacag cacgtaccgt gtggtcagcg tcctcaccgt cctgcaccag     960
gactggctga atggcaagga gtacaagtgc aaggtctcca acaaagccct cccagccccc    1020
atcgagaaaa ccatctccaa agccaaaggg cagccccgag aaccacaggt ctacaccctg    1080
cccccatccc gggaggagat gaccaagaac caggtcagcc tgacctgcct ggtcaaaggc    1140
ttctatccca gcgacatcgc cgtggagtgg gagagcaatg ggcagccgga gaacaactac    1200
aagaccacgc ctcccgtgct ggactccgac ggctccttct tcctctatag caagctcacc    1260
gtggacaaga gcaggtggca gcaggggaac gtcttctcat gctccgtgat gcatgaggct    1320
ctgcacaacc actacacgca gaagagctta agcctgtctc cgggtgcagg aggcggcggt    1380
tcaggcggag gtggctctgg cggtggcgga agtagcccag ccagggcac ccagtctgag     1440
```

-continued

```
aacagctgca cccacttccc aggcaacctg cctaacatgc ttcgagatct ccgagatgcc    1500
ttcagcagag tgaagacttt ctttcaaatg aaggatcagc tggacaactt gttgttaaag    1560
gagtccttgc tggaggactt taagggttac ctgggttgcc aagccttgtc tgagatgatc    1620
cagttttacc tggaggaggt gatgccccaa gctgagaacc aagacccaga catcaaggcg    1680
catgtgaact ccctggggga gaacctgaag accctcaggc tgaggctacg gcgctgtcat    1740
cgatttcttc cctgtgaaaa caagagcaag gccgtggagc aggtgaagaa tgcctttaat    1800
aagctccaag agaaaggcat ctacaaagcc atgagtgagt ttgacatctt catcaactac    1860
atagaagcct acatgacaat gaagatacga aac                                 1893
```

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Gly Gly Gly Ser
1               5

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gly Gly Gly Ser Gly Gly Gly Gly Ser
1               5                   10

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Gly Gly Gly Ser Gly Gly Gly Gly Ser Gly Gly Gly Gly Ser
1               5                   10                  15

<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Gly Gly Ser Gly Gly Gly Gly Ser Gly Gly Gly Gly Ser Gly
1               5                   10                  15

Gly Gly Gly Ser
            20

<210> SEQ ID NO 36
<211> LENGTH: 630
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ser Ala Gly Gly Asn Tyr Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380
```

-continued

```
Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys Gly Gly Gly Ser Gly Gly Gly
    450                 455                 460

Gly Ser Gly Gly Gly Gly Ser Pro Gly Gln Gly Thr Gln Ser Glu Asn
465                 470                 475                 480

Ser Cys Thr His Phe Pro Gly Asn Leu Pro Asn Met Leu Arg Asp Leu
                485                 490                 495

Arg Asp Ala Phe Ser Arg Val Lys Thr Phe Phe Gln Met Lys Asp Gln
            500                 505                 510

Leu Asp Asn Leu Leu Leu Lys Glu Ser Leu Leu Glu Asp Phe Lys Gly
        515                 520                 525

Tyr Leu Gly Cys Gln Ala Leu Ser Glu Met Ile Gln Phe Tyr Leu Glu
    530                 535                 540

Glu Val Met Pro Gln Ala Glu Asn Gln Asp Pro Asp Ile Lys Ala His
545                 550                 555                 560

Val Asn Ser Leu Gly Glu Asn Leu Lys Thr Leu Arg Leu Arg Leu Arg
                565                 570                 575

Arg Cys His Arg Phe Leu Pro Cys Glu Asn Lys Ser Lys Ala Val Glu
            580                 585                 590

Gln Val Lys Asn Ala Phe Asn Lys Leu Gln Glu Lys Gly Ile Tyr Lys
        595                 600                 605

Ala Met Ser Glu Phe Asp Ile Phe Ile Asn Tyr Ile Glu Ala Tyr Met
    610                 615                 620

Thr Met Lys Ile Arg Asn
625                 630
```

```
<210> SEQ ID NO 37
<211> LENGTH: 630
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37
```

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ser Ala Gly Gly Asn Tyr Tyr Tyr Tyr Gly
```

```
           100              105              110

Met Asp Val Trp Gly Gln Gly Thr Thr Val Thr Val Ser Ser Ala Ser
        115              120              125

Thr Lys Gly Pro Ser Val Phe Pro Leu Ala Pro Ser Ser Lys Ser Thr
    130              135              140

Ser Gly Gly Thr Ala Ala Leu Gly Cys Leu Val Lys Asp Tyr Phe Pro
145              150              155              160

Glu Pro Val Thr Val Ser Trp Asn Ser Gly Ala Leu Thr Ser Gly Val
            165              170              175

His Thr Phe Pro Ala Val Leu Gln Ser Ser Gly Leu Tyr Ser Leu Ser
            180              185              190

Ser Val Val Thr Val Pro Ser Ser Ser Leu Gly Thr Gln Thr Tyr Ile
        195              200              205

Cys Asn Val Asn His Lys Pro Ser Asn Thr Lys Val Asp Lys Arg Val
    210              215              220

Glu Pro Lys Ser Cys Asp Lys Thr His Thr Cys Pro Pro Cys Pro Ala
225              230              235              240

Pro Glu Leu Leu Gly Gly Pro Ser Val Phe Leu Phe Pro Pro Lys Pro
            245              250              255

Lys Asp Thr Leu Met Ile Ser Arg Thr Pro Glu Val Thr Cys Val Val
            260              265              270

Val Asp Val Ser His Glu Asp Pro Glu Val Lys Phe Asn Trp Tyr Val
            275              280              285

Asp Gly Val Glu Val His Asn Ala Lys Thr Lys Pro Arg Glu Glu Gln
        290              295              300

Tyr Asn Ser Thr Tyr Arg Val Val Ser Val Leu Thr Val Leu His Gln
305              310              315              320

Asp Trp Leu Asn Gly Lys Glu Tyr Lys Cys Lys Val Ser Asn Lys Ala
            325              330              335

Leu Pro Ala Pro Ile Glu Lys Thr Ile Ser Lys Ala Lys Gly Gln Pro
            340              345              350

Arg Glu Pro Gln Val Tyr Thr Leu Pro Pro Ser Arg Glu Glu Met Thr
            355              360              365

Lys Asn Gln Val Ser Leu Thr Cys Leu Val Lys Gly Phe Tyr Pro Ser
    370              375              380

Asp Ile Ala Val Glu Trp Glu Ser Asn Gly Gln Pro Glu Asn Asn Tyr
385              390              395              400

Lys Thr Thr Pro Pro Val Leu Asp Ser Asp Gly Ser Phe Phe Leu Tyr
            405              410              415

Ser Lys Leu Thr Val Asp Lys Ser Arg Trp Gln Gln Gly Asn Val Phe
            420              425              430

Ser Cys Ser Val Met His Glu Ala Leu His Asn His Tyr Thr Gln Lys
        435              440              445

Ser Leu Ser Leu Ser Pro Gly Ala Gly Gly Gly Ser Gly Gly Gly
    450              455              460

Gly Ser Gly Gly Gly Gly Ser Pro Gly Gln Gly Thr Gln Ser Glu Asn
465              470              475              480

Ser Cys Thr His Phe Pro Gly Asn Leu Pro Asn Met Leu Arg Asp Leu
            485              490              495

Arg Asp Ala Phe Ser Arg Val Lys Thr Phe Phe Gln Met Lys Asp Gln
            500              505              510

Leu Asp Asn Leu Leu Leu Lys Glu Ser Leu Leu Glu Asp Phe Lys Gly
        515              520              525
```

-continued

```
Tyr Leu Gly Cys Gln Ala Leu Ser Glu Met Ile Gln Phe Tyr Leu Glu
    530                 535                 540

Glu Val Met Pro Gln Ala Glu Asn Gln Asp Pro Asp Ile Lys Ala His
545                 550                 555                 560

Val Asn Ser Leu Gly Glu Asn Leu Lys Thr Leu Arg Leu Arg Leu Arg
                565                 570                 575

Arg Cys His Arg Phe Leu Pro Cys Glu Asn Lys Ser Lys Ala Val Glu
            580                 585                 590

Gln Val Lys Asn Ala Phe Asn Lys Leu Gln Glu Lys Gly Ile Tyr Lys
        595                 600                 605

Ala Met Ser Glu Phe Asp Ile Phe Ile Asn Tyr Ile Glu Ala Tyr Met
    610                 615                 620

Thr Met Lys Ile Arg Asn
625                 630

<210> SEQ ID NO 38
<211> LENGTH: 1890
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
caggttcagc tggttgaatc tggcggcgga gtggtgcagc ctggcagatc tctgagactg      60
tcttgtgccg cctccggctt catcttctcc agctacgcta tgcactgggt ccgacaggcc     120
cctggcaatg gattggagtg ggtcgccttc atgtcctacg acggtccaa caagaaatac      180 gccgactccg tgaagggcag attcaccatc tctcgggaca actccaagaa caccctgtac     240
ctgcagatga actccctgag agccgaggac accgccgtgt actactgcgc tagagacaga     300
ggcatctccg ctggcggcaa ttactactac tacggcatgg acgtgtgggg ccagggcaca     360
acagtgacag tgtcctccgc ttccaccaag ggaccctctg tgtttcctct ggctcctcc      420 agcaagtcta cctctggtgg aacagctgcc ctgggctgcc tggtcaagga ttactttcct     480
gagcctgtga ccgtgtcctg gaactctggc gctctgacat ctggcgtgca cacctttcca     540
gctgtgctgc agtcctccgg cctgtactct ctgtcctctg tcgtgaccgt gccttccagc     600
tctctgggca cccagaccta catctgcaat gtgaaccaca gccttccaa caccaaggtg      660 gacaagagag tggaacccaa gtcctgcgac aagacccaca cctgtcctcc atgtcctgct     720
ccagaactgc tcggcggacc ttccgtgttc ctgtttcctc caaagcctaa ggacaccctg     780
atgatctctc ggacccctga agtgacctgc gtggtggtgg atgtgtctca cgaggatccc     840
gaagtgaagt tcaattggta cgtggacggc gtggaagtgc acaacgccaa gaccaagcct     900
agagaggaac agtacaactc cacctacaga gtggtgtccg tgctgaccgt gctgcaccag     960
gattggctga cggcaaaga gtacaagtgc aaggtgtcca acaaggccct gcctgctcct     1020
atcgaaaaga ccatctccaa ggccaagggc cagcctaggg aaccccaggt ttacaccctg    1080
cctccaagcc gggaagagat gaccaagaac caggtgtccc tgacctgcct cgtgaaggga    1140
ttctacccct ccgatatcgc cgtggaatgg gagtctaatg gccagcctga gaacaactac    1200
aagacaaccc ctcctgtgct ggactccgac ggctcattct tcctgtactc caagctgaca    1260
gtggacaagt ccagatggca gcagggcaac gtgttctcct gctccgtgat gcacgaggcc    1320
ctgcacaatc actacaccca gaagtccctg tctctgtctc tggtgctgg tggcggagga     1380
```

```
tctggcggag gcggatcagg cggtggtggt tctcctggac agggaaccca gtccgagaac    1440
tcctgcacac acttccctgg caacctgcct aacatgctgc gggacctgag agatgccttc    1500
tccagagtga aaacattctt ccagatgaag gatcagctgg acaacctgct gctgaaagag    1560
tccctgctgg aagatttcaa gggctacctg ggctgtcagg ccctgtccga gatgatccag    1620
ttctacctgg aagaagtgat gccccaggcc gagaatcagg accctgatat caaggcccac    1680
gtgaacagcc tgggcgagaa cctgaaaacc ctgcggctga gactgcggcg gtgccacaga    1740
tttctgccct gcgagaacaa gtccaaggcc gtggaacaag tgaagaacgc cttcaacaag    1800
ctgcaagaga agggcatcta caaggctatg tccgagttcg acatcttcat caactacatc    1860
gaggcctaca tgaccatgaa gatccggaac    1890
```

```
<210> SEQ ID NO 39
<211> LENGTH: 625
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ser Ala Gly Gly Asn Tyr Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Arg Val
        210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270
```

-continued

```
Val Asp Val Ser His Glu Asp Pro Glu Val Lys Phe Asn Trp Tyr Val
    275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Glu Glu Met Thr
                355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
                435                 440                 445

Ser Leu Ser Leu Ser Pro Gly Lys Gly Gly Gly Ser Gly Gly Gly
    450                 455                 460

Gly Ser Pro Gly Gln Gly Thr Gln Ser Glu Asn Ser Cys Thr His Phe
465                 470                 475                 480

Pro Gly Asn Leu Pro Asn Met Leu Arg Asp Leu Arg Asp Ala Phe Ser
                485                 490                 495

Arg Val Lys Thr Phe Phe Gln Met Lys Asp Gln Leu Asp Asn Leu Leu
                500                 505                 510

Leu Lys Glu Ser Leu Leu Glu Asp Phe Lys Gly Tyr Leu Gly Cys Gln
                515                 520                 525

Ala Leu Ser Glu Met Ile Gln Phe Tyr Leu Glu Glu Val Met Pro Gln
    530                 535                 540

Ala Glu Asn Gln Asp Pro Asp Ile Lys Ala His Val Asn Ser Leu Gly
545                 550                 555                 560

Glu Asn Leu Lys Thr Leu Arg Leu Arg Leu Arg Arg Cys His Arg Phe
                565                 570                 575

Leu Pro Cys Glu Asn Lys Ser Lys Ala Val Glu Gln Val Lys Asn Ala
                580                 585                 590

Phe Asn Lys Leu Gln Glu Lys Gly Ile Tyr Lys Ala Met Ser Glu Phe
                595                 600                 605

Asp Ile Phe Ile Asn Tyr Ile Glu Ala Tyr Met Thr Met Lys Ile Arg
    610                 615                 620

Asn
625
```

```
<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

-continued

```
<400> SEQUENCE: 40

His His His His His His
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Ser Leu Ser Pro Gly Ala
1               5

<210> SEQ ID NO 42
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Tyr Thr Gln Lys Ser Leu Ser Leu Ser Pro Gly Lys Ser Ser Ser Ser
1               5                   10                  15

Gly Ser Ser Ser Ser Gly Ser Ser Ser Ser Gly Ser Pro Gly Gln Gly
            20                  25                  30

Thr Gln Ser Glu Asn Ser Cys Thr His Phe Pro Gly Asn Leu Pro Asn
        35                  40                  45

Met Leu Arg Asp Leu Arg Asp Ala Phe
    50                  55
```

IMMUNOCYTOKINES FOR TREATMENT OF AUTOIMMUNE AND INFLAMMATORY CONDITIONS

FIELD OF THE DISCLOSURE

The present disclosure relates generally to fusion proteins comprising a Tumor Necrosis Factor α (TNFα) binding protein and an interleukin-10 (IL-10) molecule, methods of preparing the fusion proteins, and methods for treating or preventing autoimmune and inflammatory conditions using the fusion proteins.

INCORPORATION BY CROSS-REFERENCE TO RELATED APPLICATIONS

This application is U.S. National Stage application, filed under U.S.C § 371(c) of International Application No. PCT/US2021/042331, filed Jul. 20, 2021, which claims the benefit of U.S. Provisional Application No. U.S. 63/053,949, filed Jul. 20, 2020, which is hereby incorporated by reference in its entirety.

STATEMENT REGARDING SEQUENCE LISTING

Reference to an Electronic Sequence Listing

The contents of the electronic sequence listing (HOPA_022_02US_SeqList_ST25.txt; Size: 76.919 bytes; and Date of Creation: Jan. 9, 2023) are herein incorporated by reference in its entirety.

BACKGROUND OF THE DISCLOSURE

Cytokines are critical mediators of protective host responses, including defense against microbial invasion and tumorigenesis. However, the production of specific pro-inflammatory cytokines must be tightly regulated and compartmentalized to prevent the overzealous expression of these molecules that can culminate in unabated inflammation and tissue injury. Like all physiological systems, the immune system is kept in harmony by a yin-yang mechanism that operates between the pro-inflammatory and the anti-inflammatory arms of the immune system. These two arms cross talk between themselves, mostly by means of cytokines and their receptors and keep each other at check. Perturbance of the delicate balance and cross talk between the two arms is a fundamental cause of autoimmune and inflammatory diseases which result from either hyperactivity of the pro-inflammatory or hypoactivity of the anti-inflammatory arm or both. Therefore, it is conceivable that restoration of this balance by using cytokine(s) as drugs would be an effective way to treat immunological diseases.

Cytokine production and/or biologic effects can be inhibited by a variety of endogenous molecules, including anti-inflammatory cytokines, e.g., interleukin-10 (IL-10), soluble cytokine receptors, and receptor or ligand antagonist proteins. As a result of its pleiotropic activity, IL-10 has been linked to a broad range of diseases, disorders and conditions, including inflammatory conditions, immune-related disorders, fibrotic disorders and cancer. Clinical and pre-clinical evaluations with IL-10 for a number of such diseases, disorders and conditions have solidified its therapeutic potential.

However, although small scale preliminary studies with topical IL-10 administration for the treatment of autoimmune diseases such as psoriasis has indicated its beneficial effects, this promising cytokine has not lived up to its clinical expectation in many other studies. One of the reasons cited for this failure is that IL-10 alone fails to suppress all the pro-inflammatory mediators involved in chronic inflammation.

Therefore, there is a need in the art to develop new cytokine-based therapies that are effective in treating immunological diseases. The present disclosure addresses this need.

SUMMARY OF THE DISCLOSURE

Applicant hypothesized that fusion of immunosuppressive cytokines, e.g., IL-10, to binding proteins, e.g., antibodies, to immunostimulatory mediators would result in a bifunctional molecule and may be better able to restore the cytokine balance towards a physiological state. This approach is different from other immunocytokines in that the antibody moiety acts not only as a targeting agent but also functions by neutralizing a pro-inflammatory cytokine that is an important cause underlying the disease. This approach increases the therapeutic index of the immunocytokine compared to each of its two components, alone or in combination, because the binding protein will (i) act as a warhead to carry the immunosuppressive cytokine to the pathologic site and (ii) increase the half-life of the immunosuppressive cytokine.

Provided herein is a fusion protein comprising a first and second domain, wherein the first domain comprises a Tumor Necrosis Factor α (TNFα) binding protein, and wherein the second domain comprises interleukin-10 (IL-10). In embodiments, the TNFα binding protein is positioned at an N-terminus of the IL-10. In embodiments, the TNFα binding protein is linked via its C-terminus end to the N-terminus of the IL-10. In embodiments, the TNFα binding protein is directly linked to the IL-10. In embodiments, the TNFα binding protein is linked to the IL-10 via a linker. In embodiments, the IL-10 comprises an amino acid sequence comprising at least 80% identity to a sequence selected from the group consisting of SEQ ID NOs: 1 and 25. In embodiments, the IL-10 comprises an amino acid sequence comprising at least 85%, 90%, 95%, 97%, 98%, 99%, or 100% identity to a sequence selected from the group consisting of SEQ ID NOs: 1 and 25. In embodiments, the IL-10 comprises the sequence of SEQ ID NO: 1. In embodiments, the TNFα binding protein comprises an amino acid sequence comprising at least 80% identity to a sequence selected from the group consisting of SEQ ID NOs: 5 and 29. In embodiments, the TNFα binding protein comprises an amino acid sequence comprising at least 85%, 90%, 95%, 97%, 98%, 99%, or 100% identity to a sequence selected from the group consisting of SEQ ID NOs: 5 and 29. In embodiments, the TNFα binding protein comprises the sequence of SEQ ID NO: 29. In embodiments, the linker comprises an amino acid sequence comprising at least 80% identity to a sequence selected from the group consisting of SEQ ID NOs: 2, 3, 13, 14, 15, 32, 33, 34, and 35. In embodiments, the linker comprises an amino acid sequence comprising at least 85%, 90%, 95%, 97%, 98%, 99%, or 100% identity to a sequence selected from the group consisting of SEQ ID NOs: 2, 3, 13, 14, 15, 32, 33, 34, and 35. In embodiments, the linker comprises the amino acid sequence of SEQ ID NO: 34. In embodiments, the fusion protein comprises an amino acid sequence comprising at least 80% identity to a sequence selected from the group consisting of SEQ ID NOs: 4, 24, 26, 27, 36, 37, and 39. In embodiments, the fusion protein comprises an amino acid sequence comprising at least 85%, 90%, 95%, 97%, 98%, 99%, or 100% identity to a sequence selected from the group consisting of SEQ ID NOs: 4, 24, 26, 27, 36, 37, and 39. In embodiments, the fusion protein comprises the amino acid sequence of SEQ ID NO: 24. In embodiments, the fusion protein comprises the amino acid sequence of SEQ ID NO: 37. In embodiments, the TNFα binding protein binds to the same epitope of TNFα as an antibody comprising a heavy chain variable region ($V_H$) of SEQ ID NO: 16 and a light chain variable region ($V_L$) of SEQ ID NO: 17. In embodiments, the fusion protein competitively inhibits the binding to TNFα of an antibody comprising a $V_H$ of SEQ ID NO: 16 and a $V_L$ of SEQ ID NO: 17. In embodiments, the IL-10 binds to an IL-10 receptor. In embodiments, the IL-10 binds to a cell expressing an IL-10 receptor. In embodiments, the fusion protein consists of the TNFα binding protein and the IL-10. In embodiments, the fusion protein further comprises at least one additional IL-10. In embodiments, the fusion protein comprises two IL-10. In embodiments, the TNFα binding protein is a TNFα binding protein fragment. In embodiments, the IL-10 is an IL-10 fragment.

Provided are also nucleic acids that comprise a sequence that encodes a fusion protein.

Provided are also vectors comprising nucleic acids that comprise a sequence that encodes a fusion protein.

Provided are also host cells comprising nucleic acid(s) or vector(s). In embodiments, a host cell is a bacterial cell. In embodiments, a host cell is a mammalian cell.

Provided are also pharmaceutical compositions comprising (a) a fusion protein; and (b) one or more pharmaceutically acceptable excipients. In embodiments, the pharmaceutical composition is in unit dose form.

Provided are also methods of treating a disease or condition, comprising administering a pharmaceutical composition to a subject in need thereof thereby treating the disease or condition. the administering is sufficient to reduce or eliminate at least one symptom of the disease or condition in the subject in need thereof. In embodiments, a disease or condition comprises inflammation. In embodiments, a disease or condition is autoimmune.

Provided are also methods of treating a subject with an autoimmune disease or inflammatory disease comprising administering to the subject an effective amount a fusion protein; or a pharmaceutical composition provided herein, thereby treating the autoimmune disease or inflammatory disease. In embodiments, the autoimmune disease or inflammatory disease is selected from a group consisting of: Addison's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune pancreatitis, Autoimmune retinopathy, Autoimmune urticarial, Axonal & neuronal neuropathy (AMAN), Baló disease, Behçet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss, Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressier's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Graft vs host disease (GVHD), Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hypogammaglobulinemia, IgA Nephropathy, IgG4-related sclerosing disease, Immune thrombocytopenic purpura (ITP), Inclusion body myositis (IBM), Inflammatory bowel disease (IBD), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multiple sclerosis, Myasthenia gravis, Myositis, Narcolepsy, Neuromyelitis optica, Neutropenia, Non-alcoholic Fatty Liver Disease (NAFLD), Non-alcoholic Steatohepatitis (NASH), Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatic, Polymyositis, Post myocardial infarction syndrome, Post pericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, and Wegener's granulomatosis (or Granulomatosis with Polyangiitis (GPA)). In embodiments, the subject has an inflammatory disease, and wherein the inflammatory disease is NASH.

Provided are also methods of reducing an autoimmune response or inflammatory response in a subject in need thereof comprising administering to the subject in need thereof an effective amount of: a fusion protein; or a pharmaceutical composition described herein.

Provided are also methods of producing a fusion protein, the method comprising: expressing the fusion protein in a host cell; and purifying the fusion protein.

Provided are also methods of isolating a fusion protein, comprising: contacting a host cell with: a nucleic acid; or a vector, thereby transforming the host cell; and purifying the fusion protein encoded by the nucleic acid or the vector, thereby isolating the fusion protein.

Provided are also methods of inhibiting T cell proliferation comprising contacting a peripheral blood mononuclear cell (PBMC) with an effective amount of a fusion protein described herein.

Provided are also methods of inhibiting T cell proliferation in a subject in need thereof comprising administering to the subject in need thereof an effective amount of: a fusion protein; or a pharmaceutical composition, thereby inhibiting the T cell proliferation in the subject in need thereof. In embodiments, the fusion protein shows an increased inhibitory effect on T cell proliferation as compared to: a) at least one molar equivalent of IL-10 (mIL10); b) a TNFα binding protein; or c) codelivery of at least one molar equivalent of IL-10 or a fragment thereof and a TNFα binding protein (mIL10+anti-TNFα). In embodiments, the method comprises c), wherein the increased inhibitory effect comprises at least 10 fold, at least 100 fold, at least 1,000 fold, or at least 10,000 fold increased inhibition on T cell proliferation as compared to the codelivery of the at least one molar equivalent of the mIL10+anti-TNFα.

Provided are also methods of inhibiting production of one or more pro-inflammatory cytokines comprising contacting a cell secreting one or more pro-inflammatory cytokines with an effective amount of a fusion protein provided herein.

Provided are also methods of inhibiting production of one or more pro-inflammatory cytokines in a subject in need thereof comprising administering to the subject in need thereof an effective amount of: a fusion protein; or a pharmaceutical composition, thereby inhibiting production of the one or more pro-inflammatory cytokines in the subject in need thereof. In embodiments, the fusion protein shows an increased inhibitory effect on pro-inflammatory cytokine production as compared to: a) at least one molar equivalent of IL-10 (mIL10); b) a TNFα binding protein; or c) codelivery of at least one molar equivalent of IL-10 and a TNFα binding protein (mIL10+anti-TNFα). In embodiments, the method comprises c), wherein the fusion protein shows an at least 10 fold, at least 100 fold, at least 1,000 fold, or at least 10,000 fold increased inhibitory effect on pro-inflammatory cytokine production as compared to the codelivery of the at least one molar equivalent of the mIL10+anti-TNFα. In embodiments, the one or more pro-inflammatory cytokines are selected from a group consisting of TNFα, IL-17A, IL-12, IL-12/23p40, IL-6, IFN-γ, GM-CSF, and IL-1β. In embodiments, an effective amount of a fusion protein is at least about 0.1 mg/kg of the subject in need thereof. In embodiments, an effective amount of a fusion protein is at least about 0.3 mg/kg of the subject in need thereof. In embodiments, an effective amount of a fusion protein is at least about 1 mg/kg of the subject in need thereof. In embodiments, an effective amount of a fusion protein is at least about 3 mg/kg of the subject in need thereof. In embodiments, an effective amount of a fusion protein is at least about 10 mg/kg of the subject in need thereof.

In various aspects, the disclosure provides fusion proteins comprising a first and second domain, with the first domain comprising a Tumor Necrosis Factor α (TNFα) binding protein and the second domain comprising an interleukin-10 (IL-10) molecule. In certain aspects, the fusion proteins are bifunctional and are capable of inhibiting the production of one or more pro-inflammatory cytokines in a cell.

In other aspects, the disclosure provides a pharmaceutical composition comprising the fusion proteins of the disclosure and one or more pharmaceutically acceptable excipients.

In some aspects, the disclosure provides a method of treating a subject with an autoimmune disease or inflammatory disease comprising administering to the subject an effective amount of the fusion proteins of the disclosure.

In other aspects, the disclosure provides a method of reducing an autoimmune response or inflammatory response in a subject comprising administering to the subject an effective amount of the fusion proteins of the disclosure.

In certain embodiments, the disclosure provides a method of producing the fusion proteins of the disclosure comprising expressing the fusion proteins in a host cell and purifying the fusion proteins.

In certain embodiments, the disclosure provides a method of increasing half-life of an IL-10 protein comprising producing the fusion proteins of the disclosure.

In yet other embodiments, the disclosure provides a method of inhibiting T cell proliferation comprising incubating a peripheral blood mononuclear cell (PBMC) with an effective amount of the fusion proteins of the disclosure.

In still other embodiments, the disclosure provides a method of inhibiting T cell proliferation in a subject comprising administering to the subject an effective amount of the fusion proteins of the disclosure or the pharmaceutical compositions of the disclosure.

In other aspects, the disclosure provides a method of inhibiting production of one or more pro-inflammatory cytokines comprising incubating a cell secreting the one or more pro-inflammatory cytokines with an effective amount of the fusion proteins of the disclosure.

In yet other aspects, the disclosure provides a method of inhibiting production of one or more pro-inflammatory cytokines in a subject comprising administering to the subject an effective amount of the fusion proteins of the disclosure.

Nucleic acids encoding the fusion proteins of the disclosure, vectors comprising such nucleic acids, and host cells comprising such nucleic acids or vectors are also provided.

Unless otherwise defined, all technical and scientific terms used herein have the same meaning as commonly understood by one of ordinary skill in the art to which this disclosure pertains. Although methods and materials similar or equivalent to those described herein can be used in the practice of the present disclosure, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the disclosure will be apparent from and encompassed by the following detailed description and claims.

BRIEF DESCRIPTION OF THE DRAWINGS

The accompanying figures, which are incorporated herein and form a part of the specification, illustrate some, but not the only or exclusive, example embodiments and/or features. It is intended that the embodiments and figures disclosed herein are to be considered illustrative rather than limiting.

FIG. 1A: depicts the K fusion protein construct and the A fusion protein construct (SEQ ID NO: 42). FIG. 1B: depicts purification of the K fusion protein yielding 88% of the protein monomer with a concomitant loss of 45% of the protein. FIG. 1C: depicts purification of the A fusion protein yielding 99% of the protein monomer, with 0% loss. The protein expression level of the A fusion protein construct is about 25 µg/ml.

FIG. 2A shows that both the K fusion protein and the A fusion protein exhibit binding specificity to TNFα. FIG. 2B shows that both the K fusion protein and the A fusion protein exhibit binding specificity to the IL-10 receptor.

FIG. 5A shows results of T cell proliferation when T cells are contacted with isotype control. FIG. 5B shows results of T cell proliferation when T cells are contacted with anti-TNFα. FIG. 5C shows results of T cell proliferation when T cells are contacted with a double IL-10 fusion protein. FIG. 5D shows results of T cell proliferation when T cells are contacted with an IL-10 and anti-TNFα fusion protein. FIG. 5E shows results of T cell proliferation when T cells are contacted with a triple fusion protein having 2 IL-10 proteins and anti-TNFα.

FIG. 6 shows that T cell proliferation is markedly reduced upon treatment with the anti-TNFα-antibody-IL-10 fusion protein. Additionally, the fusion protein shows an increased inhibitory effect on T cell proliferation than an isotype control antibody, molar equivalents of an anti-TNFα antibody, or molar equivalents of IL-10 (2IL10), or the codelivery of molar equivalents of IL-10 molecule and an anti-TNFα antibody (2IL10+anti-TNFα). Especially at very low concentrations (e.g., at 0.0008 nM, and 0.004 nM), the IL-10-anti-TNFα fusion protein had an about 10-fold increased inhibitory effect on T cell proliferation over molar equivalents of IL-10 (2IL10), and an about 10,000-fold increased inhibitory effect on T cell proliferation than the anti-TNFα antibody. Further, surprisingly, the anti-TNFα-antibody-IL-10 fusion protein showed a greater than additive, i.e. synergistic, inhibitory effect on T cell proliferation in comparison to the codelivery of molar equivalents of IL-10 molecule and an anti-TNFα antibody (2IL10+anti-TNFα) over the concentration range of 0.0008 nM to 0.04 nM.

FIG. 7A-FIG. 7C show the effect of increasing concentrations (0.00016 nM, 0.0008 nM, 0.004 nM, 0.02 nM, 0.1 nM, 0.5 nM, 2.5 nM, and 12.5 nM) of the anti-TNFα-antibody-IL-10 fusion protein on T cell proliferation in proinflammatory conditions in an allogenic MLR assay. The anti-TNFα-antibody-IL-10 fusion protein inhibits T cell proliferation in proinflammatory conditions using polyinosinic:polycytidylic acid (poly I:C; 5 μg/mL) (FIG. 7A), thymic stromal lymphopoietin (TSLP; 20 μg/mL) (FIG. 7B), and lipopolysaccharide (LPS; 1 μg/mL) (FIG. 7C). In each case, the fusion protein shows an increased inhibitory effect on T cell proliferation compared to molar equivalents of an anti-TNFα binding protein, or IL-10 (2IL10), or the codelivery of molar equivalents of IL-10 molecule and an anti-TNFα antibody (2IL10+anti-TNFα). Further, at each concentration tested, but especially at very low concentrations (0.0008 nM, and 0.004 nM, and 0.02 nM), the fusion protein had an increased inhibitory effect on T cell proliferation compared to the isotype control antibody, molar equivalents of an anti-TNFα antibody, or IL-10 (2IL10), or the codelivery of molar equivalents of IL-10 molecule and an anti-TNFα antibody (2IL10+anti-TNFα). Unexpectedly, the anti-TNFα-antibody-IL-10 fusion protein showed a greater than additive, i.e. synergistic, inhibitory effect on T cell proliferation in pro-inflammatory conditions in comparison to the codelivery of molar equivalents of IL-10 molecule and an anti-TNFα antibody (2IL10+anti-TNFα) over the concentration range of 0.0008 nM to 0.02 nM.

FIG. 8A-FIG. 8E show the effect of the anti-TNFα-antibody-IL-10 fusion protein on T cell proliferation in proinflammatory conditions using poly I:C (5 μg/mL) stimulation. FIG. 8 shows that the anti-TNFα-antibody-IL-10 fusion protein inhibits poly:IC-stimulated T cell proliferation. Surprisingly, the fusion protein (FIG. 8D) showed a greater than additive, i.e. synergistic, inhibitory effect on T cell proliferation than an isotype control (FIG. 8A), molar equivalents of an anti-TNFα antibody (FIG. 8B), or IL-10 (2IL10) (FIG. 8C), or the codelivery of molar equivalents of IL-10 molecule and an anti-TNFα binding protein (2IL10+anti-TNFα) (FIG. 8E).

FIG. 9A-FIG. 9E show that the anti-TNFα-antibody-IL-10 fusion protein inhibits TSLP-stimulated T cell proliferation more effectively than an isotype control (FIG. 9A), molar equivalents of anti-TNFα antibody (FIG. 9B), or molar equivalents of IL-10 (2IL10) (FIG. 9C). Surprisingly, the fusion protein (FIG. 9D) shows a greater than additive, i.e. synergistic, inhibitory effect on T cell proliferation than the codelivery of molar equivalents of IL-10 molecule and an anti-TNFα binding protein (2IL10+anti-TNFα) (FIG. 9E).

FIG. 10A-FIG. 10E show that the anti-TNFα-antibody-IL-10 fusion protein inhibits LPS-stimulated T cell proliferation more effectively than an isotype control (FIG. 10A), molar equivalents of anti-TNFα antibody (FIG. 10B), or molar equivalents of IL-10 (2IL10) (FIG. 10C). Surprisingly, the fusion protein (FIG. 10D) shows a greater than additive, i.e. synergistic, inhibitory effect on T cell proliferation than the codelivery of molar equivalents of IL-10 molecule and an anti-TNFα binding protein (2IL10+anti-TNFα) (FIG. 10E).

FIG. 11A-FIG. 11D show the effect of increasing concentrations (0.00016 nM, 0.0008 nM, 0.004 nM, 0.02 nM, 0.1 nM, 0.5 nM, 2.5 nM, and 12.5 nM) of the anti-TNFα-antibody-IL-10 fusion protein on the production of Th1-type and Th17-type pro-inflammatory cytokines using an allogenic MLR assay. FIG. 11 shows that the anti-TNFα-antibody-IL-10 fusion protein markedly inhibits production of pro-inflammatory cytokine IL-17A (FIG. 11A); IL-1α (FIG. 11B); IL-12/23p40 (FIG. 11C); and IL-6 (FIG. 11D). The fusion protein unexpectedly shows a greater than additive, i.e. synergistic, inhibitory effect on pro-inflammatory cytokine production compared to the codelivery of molar equivalents of IL-10 molecule and an anti-TNFα antibody (2IL10+anti-TNFα).

FIG. 12 shows that the anti-TNFα-antibody-IL-10 fusion protein markedly inhibits production of pro-inflammatory cytokine IL-1β (FIG. 12A); IFN-γ (FIG. 12B); TNFα (FIG. 12C); and GM-CSF (FIG. 12D). The fusion protein unexpectedly shows a greater than additive, i.e. synergistic, inhibitory effect on T cell proliferation compared to the codelivery of molar equivalents of IL-10 molecule and an anti-TNFα antibody (2IL10+anti-TNFα).

FIG. 14 shows the effect of the anti-TNFα-antibody-IL-10 fusion protein on the stability of the IL-10 moiety at protein concentrations of 0.00016 nM, 0.0008 nM, 0.004 nM, 0.02 nM, 0.1 nM, 0.5 nM, 2.5 nM, and 12.5 nM using an MLR allogenic assay. FIG. 14 shows that the IL-10 moiety on the anti-TNFα-antibody-IL-10 fusion protein is more stable than recombinant IL-10 alone.

FIG. 15 shows the activity of the anti-TNFα moiety of the anti-TNFα-antibody-IL-10 fusion protein at protein concentrations of 0.00016 nM, 0.0008 nM, 0.004 nM, 0.02 nM, 0.1 nM, 0.5 nM, 2.5 nM, and 12.5 nM on TNFβ production. FIG. 15 shows that there is no difference between the activity of the anti-TNFα-antibody-IL-10 fusion protein and an anti-TNFα antibody as measured by TNFβ production.

FIG. 16A-FIG. 16D show the stability of the IL-10 moiety following a single intravenous dose of the anti-TNFα-antibody-IL-10 fusion protein in 15 cynomolgus monkeys. Following administration of the fusion protein, blood from each cynomolgus monkey was collected at day 1 through day 28 and the presence of total and intact forms of the anti-TNFα-antibody-IL-10 fusion protein in the circulation was measured. ELISA was performed to measure all forms of the anti-TNFα-antibody-IL-10 fusion protein in circulation (FIG. 16A). ECL and MSD assays were performed to measure only the intact form of the anti-TNFα-antibody-IL-10 fusion protein in the circulation (FIG. 16B). Both assays showed that the total form (FIG. 16C) and intact form (FIG. 16D) of the anti-TNFα-antibody-IL-10 fusion protein persists in serum for several days (up to a maximum of 14 days) following a single intravenous dose. Therefore, the half-life of IL-10 increased from several hours to several days in the fusion protein (see, e.g., Rosemblum et al. Regul Toxicol Pharmacol., 2002, February; 35(1):56-71, which is incorporated by reference in its entirety).

FIG. 17A-FIG. 17B show results of a competition assay (FIG. 17A) in which the TNFα binding activity of the anti-TNFα-antibody-IL-10 fusion protein (mAbkine) was compared to a reference anti-TNFα-antibody (Golimumab) to determine if the anti-TNFα activity of the TNFα binding moiety in the anti-TNFα-antibody-IL-10 fusion protein was affected by IL-10 fusion. As shown in FIG. 17B, the anti-TNFα activity of the TNFα binding moiety in the anti-TNFα-antibody-IL-10 fusion protein is not affected by IL-10 fusion.

FIG. 18 shows that the fusion of IL-10 to the TNFα binding moiety does not adversely impact the half-life or clearance of the anti-TNFα-antibody-IL-10 fusion protein.

FIG. 22 shows additional results of the pharmacodynamic assay to study the role of the anti-TNFα-antibody-IL-10 fusion protein in an ex-vivo LPS-stimulated cytokine production in cynomolgus monkey whole blood. IL-10 dependent suppression of LPS induced IL-6 production following treatment with the anti-TNFα-antibody-IL-10 fusion protein was observed (FIG. 22, solid lines). The inhibition of IL-6 production was maximal at day 2 after dosing. However, no evident dose-dependency was observed for the inhibition of IL-6 production (FIG. 22, compare solid lines to dotted lines).

FIG. 24 shows the changes in hematology parameters (RBC) following intravenous administration of the anti-TNFα-antibody-IL-10 fusion protein in cynomolgus monkeys. Reversible decreases in RBC parameters following single intravenous injection of the anti-TNFα-antibody-IL-10 fusion protein at all doses ranging from 0.1 mg/kg to 10 mg/kg. The decrease in RBC was observed in all monkeys ~72 hours post-dose. The decrease in RBC ranged between ~6%-19% in individual animals. 2 weeks post-dose, a trend towards recovery was observed at doses≤1 mg/kg, with more persistent reduction in RBC noted at doses≥3 mg/kg. The decrease in RBC was not toxicologically significant up to doses of 10 mg/kg.

FIG. 27 shows the evaluation of the impact of repeated blood sampling on the observed effects of the anti-TNFα-antibody-IL-10 fusion protein on platelets and RBC parameters in cynomolgus monkeys. In the study, 10 mL blood was sampled over 72 hours. Based on an average bodyweight and blood volume of a cynomolgus monkey, the amount of blood sampled was calculated as a percentage of the average total blood volume of the cynomolgus monkeys. The decreases in platelets, RBCs, and HGB in the monkeys (FIG. 23-25) in animals treated with various doses of the fusion protein were compared to this theoretically calculated parameter. The decreases in platelets RBCs and HGB parameters exceed the expected effect of repeated blood sampling.

FIG. 28 shows the effect of the anti-TNFα-antibody-IL-10 fusion protein at all doses ranging from 0.1 mg/kg to 10 mg/kg on WBC parameters in cynomolgus monkeys. Post dosing increases in WBC, PMN and/or LYM were observed in all monkeys ~72 hours post-dose. Increases in PMN primarily drove increases in WBC at 72 hours. A trend to baseline values was observed 2 weeks post dosing.

FIG. 29 shows the variable domain alignment between Golimumab and anti-TNFα antibody. The CDRs are underlined. Substitutions in amino acid are depicted in bold. In the $V_L$-CDR2, a Threonine (T) residue is substituted with an Isoleucine (I) residue. In the $V_H$-CDR3, an Alanine (A) residue is substituted with a Serine (S) residue.

DETAILED DESCRIPTION OF THE DISCLOSURE

Definitions

Figures 1A, 1B, 1C:
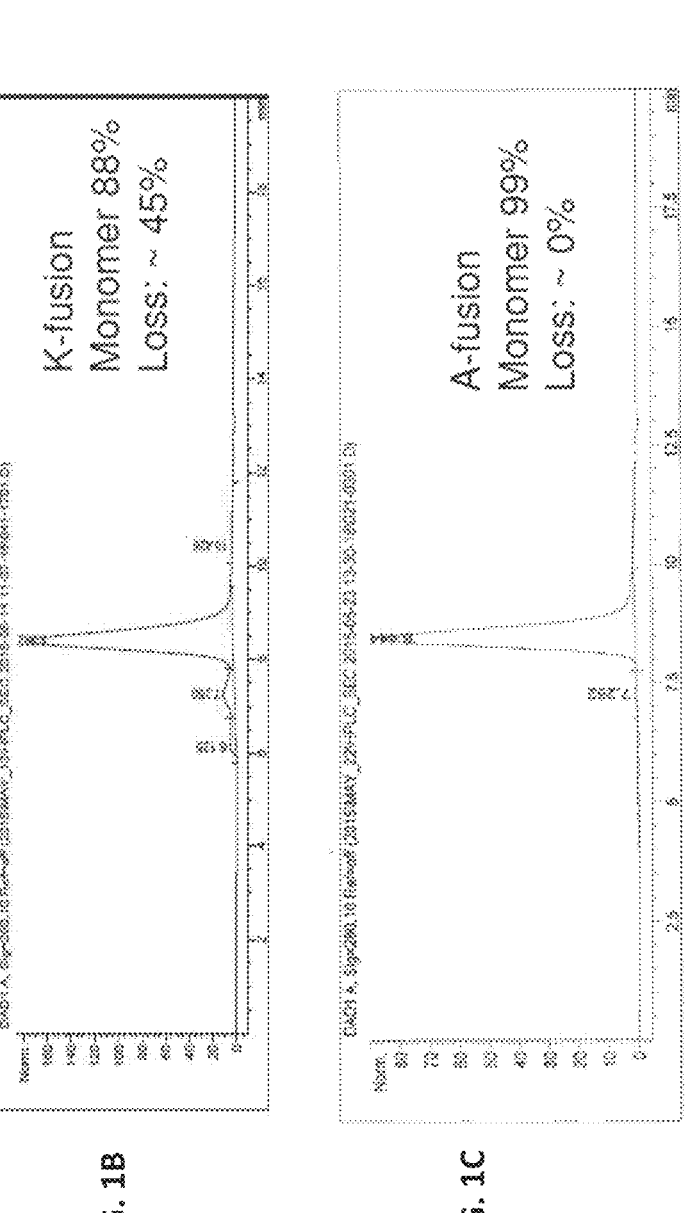
FIG. 1A-FIG. 1C illustrate the purification of different anti-TNFα. IL10 fusion protein constructs.
Figure 3:
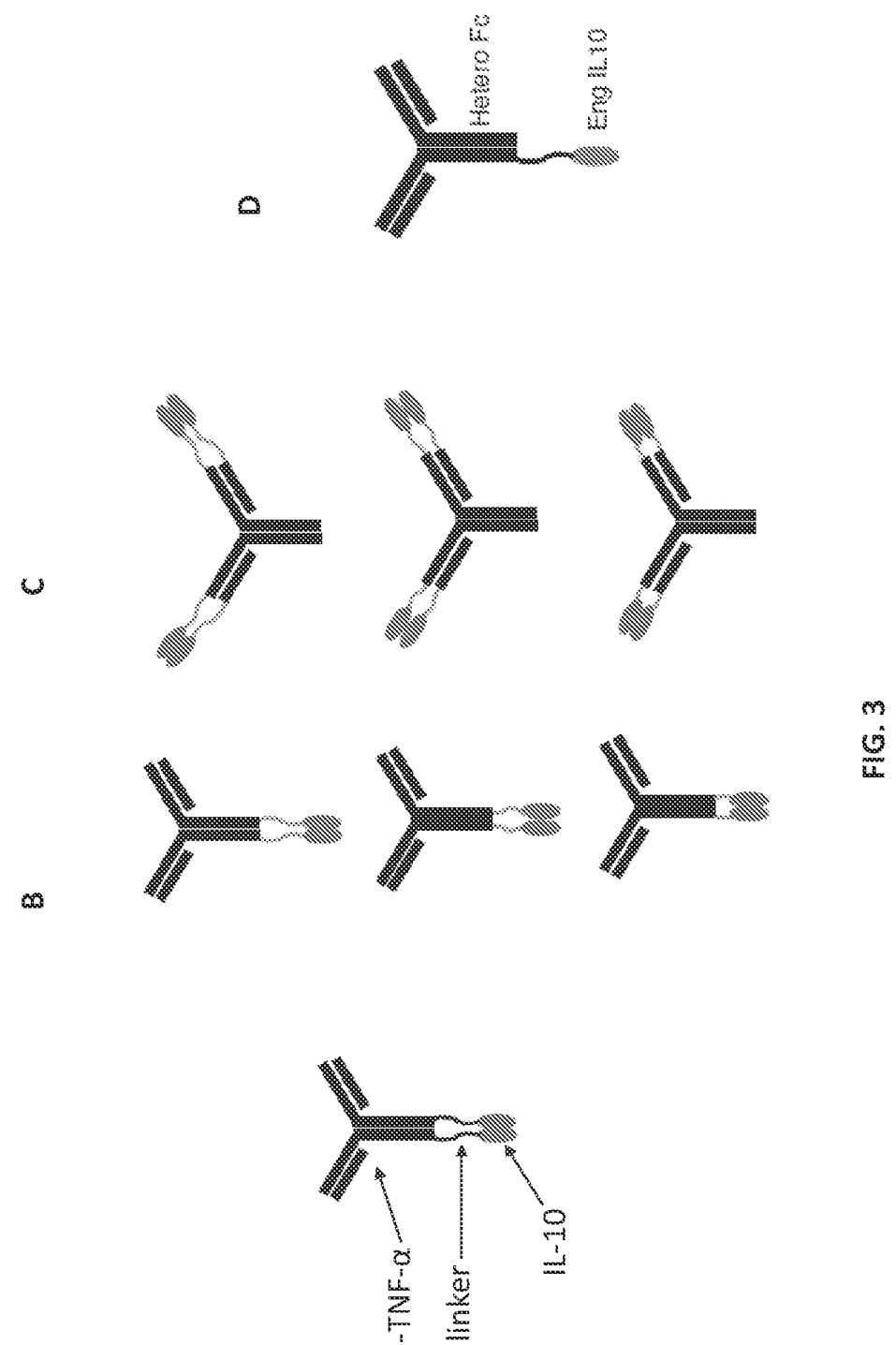
FIG. 3A-FIG. 3D depict exemplary fusion protein constructs of the disclosure.

For purposes of explanation, specific nomenclature is set forth to provide a thorough understanding of the present disclosure. However, it will be apparent to one skilled in the art that these specific details are not required to practice the aspects of the present disclosure. Descriptions of specific applications are provided only as representative examples. The aspects of the present disclosure are not intended to be limited to the embodims shown, but are to be accorded the widest possible scope consistent with the principles and features disclosed herein.

As used herein, the singular forms "a", "an" and "the" are intended to include the plural forms as well, unless the context clearly indicates otherwise. For example, "a fusion protein" is understood to represent one or more fusion proteins. As such, the terms "a" (or "an"), "one or more," and "at least one" can be used interchangeably herein.

Furthermore, to the extent that the terms "including", "includes", "having", "has", "with", or variants thereof are used in either the detailed description and/or the claims, such terms are intended to be inclusive in a manner similar to the term "comprising."

Ranges can be expressed herein as from "about" one particular value, and/or to "about" another particular value. When such a range is expressed, another case includes from the one particular value and/or to the other particular value. Similarly, when values are expressed as approximations, by use of the antecedent "about," it will be understood that the particular value forms another case. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5. The term "about" also accounts for typical error or imprecision in measurement of values.

The compositions and methods of this disclosure as described herein may employ, unless otherwise indicated, conventional techniques and descriptions of molecular biology (including recombinant techniques), cell biology, biochemistry, immunochemistry and ophthalmic techniques, which are within the skill of those who practice in the art. Such conventional techniques include methods for observing and analyzing the retina, or vision in a subject, cloning and propagation of recombinant virus, formulation of a pharmaceutical composition, and biochemical purification and immunochemistry. Specific illustrations of suitable techniques are provided in the examples herein. However, equivalent conventional procedures can also be used. Such conventional techniques and descriptions can be found in standard laboratory manuals such as Green, et al., Eds., Genome Analysis: A Laboratory Manual Series (Vols. I-IV) (1999); Weiner, et al., Eds., Genetic Variation: A Laboratory Manual (2007); Dieffenbach, Dveksler, Eds., PCR Primer: A Laboratory Manual (2003); Bowtell and Sambrook, DNA Microarrays: A Molecular Cloning Manual (2003); Mount, Bioinformatics: Sequence and Genome Analysis (2004); Sambrook and Russell, Condensed Protocols from Molecular Cloning: A Laboratory Manual (2006); and Sambrook and Russell, Molecular Cloning: A Laboratory Manual (2002) (all from Cold Spring Harbor Laboratory Press); Stryer, L., Biochemistry (4th Ed.) W.H. Freeman, N.Y. (1995); Gait, "Oligonucleotide Synthesis: A Practical Approach" IRL Press, London (1984); Nelson and Cox, Lehninger, Principles of Biochemistry, 3rd Ed., W.H. Freeman Pub., New York (2000); and Berg et al., Biochemistry, 5th Ed., W.H. Freeman Pub., New York (2002), all of which are herein incorporated by reference in their entirety for all purposes.

Overview

In certain embodiments, the disclosure provides fusion proteins comprising a molecule that binds an immunostimulatory mediator fused to an immunosuppressive cytokine molecule. In some embodiments, the binding molecule is an antagonist of the immunostimulatory mediator. In some aspects, the binding molecule is a protein or fragment thereof. In certain aspects, the binding protein is a Tumor Necrosis Factor α (TNFα) binding protein or fragment thereof. In some aspects, the immunosuppressive cytokine molecule is interleukin-10 (IL-10) or a fragment thereof. In various aspects, the disclosure provides fusion proteins comprising a TNFα binding protein or fragment thereof and an IL-10 molecule or fragment thereof. In certain embodiments, the fusion proteins of the disclosure comprise the amino acid sequence of SEQ ID NO: 4. In some embodiments, the fusion proteins of the disclosure comprise the amino acid sequence of SEQ ID NO: 24. In other embodiments, the fusion proteins of the disclosure comprise the amino acid sequence of SEQ ID NO: 36. In yet other embodiments, the fusion proteins of the disclosure comprise the amino acid sequence of SEQ ID NO: 37. In still other embodiments, the fusion proteins of the disclosure comprise the amino acid sequence of SEQ ID NO: 26. In further embodiments, the fusion proteins of the disclosure comprise the amino acid sequence of SEQ ID NO: 27. In additional embodiments, the fusion proteins of the disclosure comprise the amino acid sequence of SEQ ID NO: 39. In certain aspects, the fusion proteins of the disclosure are encoded by a nucleic acid sequence comprising the sequence of SEQ ID NO: 19. In other aspects, the fusion proteins of the disclosure are encoded by a nucleic acid sequence comprising the sequence of SEQ ID NO: 31. In further aspects, the fusion proteins of the disclosure are encoded by a nucleic acid sequence comprising the sequence of SEQ ID NO: 38. In some embodiments, the nucleic acid coding sequences encoding the fusion proteins of the disclosure are codon optimized for expression in particular cells, such as eukaryotic cells. The eukaryotic cells may be those of or derived from a particular organism, such as a mammal, including but not limited to human, mouse, rat, rabbit, dog, or non-human primate. In general, "codon optimization" refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.). In some embodiments, one or more codons (e.g. 1, 2, 3, 4, 5, 10, 15, 20, 25, 50, or more, or all codons) are optimized in a nucleic acid sequence encoding a fusion protein of the disclosure corresponding to the most frequently used codon for a particular amino acid.

The terms "protein" and "polypeptide" are used interchangeably. As used herein, the term "protein" is intended to encompass a singular protein as well as plural proteins, and refers to a molecule composed of monomers (amino acids) linearly linked by amide bonds (also known as peptide bonds). The term "protein" refers to any chain or chains of two or more amino acids, and does not refer to a specific length of the product. Thus, peptides, dipeptides, tripeptides, oligopeptides, polypeptide, amino acid chain, "fusion protein," or any other term used to refer to a chain or chains of two or more amino acids, are included within the definition of "protein," and the term "protein" can be used instead of, or interchangeably with any of these terms. The term "protein" is also intended to refer to the products of post-expression modifications of the protein, including without limitation glycosylation, acetylation, phosphorylation, amidation, derivatization by known protecting/blocking groups, proteolytic cleavage, or modification by non-naturally occurring amino acids. A protein can be derived from a natural biological source or produced by recombinant technology, but is not necessarily translated from a designated nucleic acid sequence. It can be generated in any manner, including by chemical synthesis.

In certain embodiments, the IL-10 or a fragment thereof comprises a sequence having at least about or at most about 50%, 55%, 60%, 65%, 70%, 75%, 80%, 85%, 90%, 95%, or 99% identity with any one of: SEQ ID NO: 1, SEQ ID NO: 25, SEQ ID NO: 30, and any combination thereof. In embodiments, the IL-10 comprises the amino acid sequence of SEQ ID NO: 1. In other embodiments, the IL-10 comprises the amino acid sequence of SEQ ID NO: 25. In yet other embodiments, the IL-10 comprises the amino acid sequence of SEQ ID NO: 30.

In embodiments, the TNFα binding protein or a fragment thereof comprises a sequence having at least about or at most about 50%, 55%, 60%, 65%, 70%, 75%, 80%, 85%, 90%, 95%, or 99% identity with any one of: SEQ ID NO: 5, SEQ ID NO: 29, SEQ ID NO: 16, SEQ ID NO: 7, SEQ ID NO: 8, SEQ ID NO: 9, SEQ ID NO: 6, SEQ ID NO: 17, SEQ ID NO: 10, SEQ ID NO: 11, SEQ ID NO: 12, and any combination thereof. In embodiments, the TNFα binding protein comprises the amino acid sequence of SEQ ID NO: 5. In some aspects, the TNFα binding protein comprises the amino acid sequence of SEQ ID NO: 29. In some embodiments, the TNFα binding protein comprises the amino acid sequence of SEQ ID NO: 16. In further embodiments, the TNFα binding protein comprises the amino acid sequence of SEQ ID NO: 7. In even further embodiments, the TNFα binding protein comprises the amino acid sequence of SEQ ID NO: 8. In additional embodiments, the TNFα binding protein comprises the amino acid sequence of SEQ ID NO: 9. In other embodiments, the TNFα binding protein comprises the amino acid sequence of SEQ ID NO: 6. In still other embodiments, the TNFα binding protein comprises the amino acid sequence of SEQ ID NO: 17. In further embodiments, the TNFα binding protein comprises the amino acid sequence of SEQ ID NO: 10. In still further embodiments, the TNFα binding protein comprises the amino acid sequence of SEQ ID NO: 11. In additional embodiments, the TNFα binding protein comprises the amino acid sequence of SEQ ID NO: 12. In yet other embodiments, the TNFα binding protein comprises the amino acid sequence of SEQ ID NO: 5 and the amino acid sequence of SEQ ID NO: 6. In still other embodiments, the TNFα binding protein comprises the amino acid sequence of SEQ ID NO: 29 and the amino acid sequence of SEQ ID NO: 6. In further embodiments, the TNFα binding protein comprises the amino acid sequence of SEQ ID NO: 16 and the amino acid sequence of SEQ ID NO: 6. In additional embodiments, the TNFα binding protein comprises the amino acid sequence of SEQ ID NO: 16 and the amino acid sequence of SEQ ID NO: 17.

In the context of proteins, a "linear sequence" or a "sequence" is an order of amino acids in a protein in an amino to carboxyl terminal direction in which residues that neighbor each other in the sequence are contiguous in the primary structure of the protein.

In certain embodiments, the TNFα binding protein is linked via its C-terminus end to the N-terminus end of the IL-10 molecule. In other embodiments, the TNFα binding protein is linked via its N-terminus end to the C-terminus end of the IL-10 molecule. In certain aspects, the TNFα binding protein is directly linked to the IL-10 molecule. In other aspects, the TNFα binding protein is linked to the IL-10 molecule via a linker. In additional aspects, the TNFα binding protein is linked to the IL-10 molecule via one or more linkers. In certain aspects, the one or more linkers comprise the same amino acid sequence. In other aspects, the one or more linkers comprise different amino acid sequences. In certain embodiments, at least one linker comprises a different amino acid sequence as compared to the amino acid sequence of the other linkers. In embodiments, the linker comprises a sequence having at least about or at most about 50%, 55%, 60%, 65%, 70%, 75%, 80%, 85%, 90%, 95%, 99%, or 100% identity to any one of: SEQ ID NO: 2, 3, 13, 14, 15, 32, 33, 34, and 35. In embodiments, the linker comprises an amino acid sequence including, but not limited to, the amino acid sequences of SEQ ID NO: 2, 3, 13, 14, 15, 32, 33, 34, and 35. In specific aspects, the linker comprises the amino acid sequence of SEQ ID NO: 34. In other aspects, the linker comprises the amino acid sequence of SEQ ID NO: 14.

As used herein, the terms "attached," "linked," "fused," or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant "fusion protein" is a single protein containing two or more segments that correspond to polypeptides encoded by the original ORFs (which segments are not normally so joined in nature). Although the reading frame is thus made continuous throughout the fused segments, the segments can be physically or spatially separated by, for example, one or more in-frame linker sequences. For example, in certain embodiments, polynucleotides encoding a TNFα binding protein can be fused, in-frame, but be separated from a polynucleotide encoding an IL-10 molecule, as long as the "fused" polynucleotides are co-translated as part of a continuous protein.

Also included as fusion proteins of the present disclosure are fragments, derivatives, analogs, or variants of the foregoing fusion proteins, and any combination thereof. The terms "fragment," "variant," "derivative," and "analog" when referring to fusion proteins of the present disclosure include any portion of a fusion protein that retain at least some of the pro-inflammatory cytokine inhibiting properties of the corresponding fusion protein of the disclosure. Fragments of fusion proteins of the present disclosure include proteolytic fragments, as well as deletion fragments. Variants of fusion proteins of the present disclosure include fragments as described above, and also fusion proteins with altered amino acid sequences due to amino acid substitutions, deletions, or insertions. Variants can occur naturally or be non-naturally occurring. Non-naturally occurring variants can be produced using art-known mutagenesis techniques. Variant polypeptides can comprise conservative or non-conservative amino acid substitutions, deletions, or additions. Variant polypeptides can also be referred to herein as "fusion protein analogs." As used herein a "derivative" of a fusion protein of the disclosure refers to a subject fusion protein having one or more residues chemically derivatized by reaction of a functional side group. Also included as "derivatives" are those fusion proteins that contain one or more non-naturally occurring amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine. Derivatives of fusion proteins of the present disclosure can include fusion proteins that have been altered so as to exhibit additional features not found on the reference fusion proteins of the disclosure.

The fusion proteins of the disclosure can be of a size of about 3 or more, 5 or more, 10 or more, 20 or more, 25 or more, 50 or more, 75 or more, 100 or more, 200 or more, 500 or more, 1,000 or more, or 2,000 or more amino acids. Fusion proteins of the disclosure can have a defined three-dimensional structure, although they do not necessarily have such structure. Fusion proteins with a defined three-dimensional structure are referred to as folded, and polypeptides that do not possess a defined three-dimensional structure, but rather can adopt a large number of different conformations, are referred to as unfolded. As used herein, the term glycoprotein refers to a protein coupled to at least one carbohydrate moiety that is linked to the protein via an oxygen-containing or a nitrogen-containing side chain of an amino acid residue, e.g., a serine residue or an asparagine residue.

In certain embodiments, the TNFα binding protein is positioned at the N-terminus of the IL-10 molecule. In other embodiments, the TNFα binding protein is positioned at the C-terminus of the IL-10 molecule. In certain aspects, the TNFα binding protein is linked via its C-terminus end to the N-terminus end of the IL-10 molecule. In other aspects, the TNFα binding protein is linked via its N-terminus end to the C-terminus end of the IL-10 molecule. In certain embodiments, the fusion proteins of the disclosure comprise the amino acid sequence of SEQ ID NO: 30. In other embodiments, the fusion proteins of the disclosure comprise the amino acid sequence of SEQ ID NO: 25. In additional embodiments, the fusion proteins of the disclosure comprise the amino acid sequence of SEQ ID NO: 1. In some embodiments, the fusion proteins of the disclosure comprise the amino acid sequence of SEQ ID NO: 5. In other embodiments, the fusion proteins of the disclosure comprise the amino acid sequence of SEQ ID NO: 29. In some embodiments, the fusion proteins of the disclosure comprise the amino acid sequence of SEQ ID NO: 16. In further embodiments, the fusion proteins of the disclosure comprise the amino acid sequence of SEQ ID NO: 7. In even further embodiments, the fusion proteins of the disclosure comprise the amino acid sequence of SEQ ID NO: 8. In additional embodiments, the fusion proteins of the disclosure comprise the amino acid sequence of SEQ ID NO: 9. In other embodiments, the fusion proteins of the disclosure comprise the amino acid sequence of SEQ ID NO: 6. In still other embodiments, the fusion proteins of the disclosure comprise the amino acid sequence of SEQ ID NO: 17. In further embodiments, the fusion proteins of the disclosure comprise the amino acid sequence of SEQ ID NO: 10. In even further embodiments, the fusion proteins of the disclosure comprise the amino acid sequence of SEQ ID NO: 11. In additional embodiments, the fusion proteins of the disclosure comprise the amino acid sequence of SEQ ID NO: 12. In yet other embodiments, the fusion proteins of the disclosure comprise the amino acid sequence of SEQ ID NO: 5 and the amino acid sequence of SEQ ID NO: 6. In additional embodiments, the fusion proteins of the disclosure comprise the amino acid sequence of SEQ ID NO: 29 and the amino acid sequence of SEQ ID NO:6. In further embodiments, the fusion proteins of the disclosure comprise the amino acid sequence of SEQ ID NO: 16 and the amino acid sequence of SEQ ID NO: 6. In additional embodiments, the fusion proteins of the disclosure comprise the amino acid sequence of SEQ ID NO: 16 and the amino acid sequence of SEQ ID NO: 17. In certain embodiments, the fusion proteins of the disclosure comprise the amino acid sequence of SEQ ID NO: 4. In specific embodiments, the fusion proteins of the disclosure comprise the amino acid sequence of SEQ ID NO: 24. In additional embodiments, the fusion proteins of the disclosure comprise the amino acid sequence of SEQ ID NO: 36. In yet other embodiments, the fusion proteins of the disclosure comprise the amino acid sequence of SEQ ID NO: 37. In still other embodiments, the fusion proteins of the disclosure comprise the amino acid sequence of SEQ ID NO: 39. In further embodiments, the fusion proteins of the disclosure comprise the amino acid sequence of SEQ ID NO: 26. In yet further embodiments, the fusion proteins of the disclosure comprise the amino acid sequence of SEQ ID NO: 27.

In certain aspects, the fusion proteins of the disclosure comprise a TNFα binding protein and at least one IL-10 molecule. In some aspects, the fusion proteins of the disclosure comprise two, three, four, five, or six IL-10 molecules. In specific aspects, the fusion proteins of the disclosure consist of two IL-10 molecules. In certain embodiments, the IL-10 molecule binds to an IL-10 receptor. In other embodiments, the IL-10 molecule binds to a cell expressing an IL-10 receptor. In specific embodiments, the fusion proteins of the disclosure consist of a TNFα binding protein linked by a linker to an IL-10 molecule.

In certain aspects, the fusion proteins of the disclosure are bifunctional. By "bifunctional" it is meant that the fusion proteins are capable of acting on two different target molecules in a cell. In certain aspects, the fusion proteins of the disclosure act on the target molecules by inhibiting the activities and/or production of two different target molecules.

As described in detail below, nucleic acids encoding the fusion proteins of the disclosure, vectors comprising such nucleic acids, and host cells comprising such nucleic acids or vectors are also provided.

As used herein, the term "cytokine" refers to small proteins involved in cell signaling as they engage with their corresponding receptor sites. Cytokines include, without limitations, Chemokine, Interferon (IFN), Interleukin (IL-), TNF family, CSF (colony stimulating factor) and TGF (Transforming Growth Factor) molecules. In particular embodiments, cytokines include Interleukin-1β (IL-1β), Interleukin-2 (IL-2), Interleukin-4 (IL-4), Interleukin-6 (IL-6), Interleukin-10 (IL-10), Interleukin-17 (IL-17), Interleukin-12p70 (IL-12p70), Interleukin-1 receptor antagonist (IL-1ra), Macrophage Inflammatory Protein-1 beta (MIP-1 beta), Macrophage Inflammatory Protein-1 alpha (MIP-1 alpha), Tumor Necrosis factor-alpha (TNF-α), Tumor Necrosis factor-beta (TNF-β), Interferon-gamma (IFN-γ), Chemokine ligand 2 (CCL2), also called Monocyte Chemoattractant Protein 1 (MCP1), Brain-Derived Neurotrophic Factor (BDNF) and Eotaxin-1.

Cytokines produced during acute inflammation can be divided into two group: pro-inflammatory cytokines (e.g., IL-1 and TNF-α) and anti-inflammatory cytokines (e.g., IL-10). Inflammation also draws phagocytes to the site of pathogen invasion, where the phagocytes generally efficiently recognize, ingest, and kill the extracellular pathogens. Cytokines are essentially pro-inflammatory, and thus typically termed "inflammatory cytokines." Inflammatory cytokines are produced predominantly by activated macrophages and are involved in the up regulation of inflammatory reactions. Macrophages maintain sufficient supply of iron for erythropoiesis and an increase of IL-1β promotes efficient iron storage within macrophages or monocytes by increasing the expression of ferritin, both at the transcriptional and posttranscriptional level. Inflammatory cytokines include, among others, tumor necrosis factor (TNF-α, cachexin, or cachectin), Interleukin-1 (IL-1, α and β), IL-2, IL-4, IL-5, IL-6, IL-12, IL-13, IL-17A, IL-22, IL-31, IL-33, and Interferon-γ and GM-CSF (granulocyte-macrophage colony-stimulating factor, that functions as a cytokine). In some aspects, inflammatory cytokines include, but are not limited to, IL-1α, IL-1β, IL-6, TNFα, INF-γ, chemokines, IL-12, IL-12/23p40, IL-17, IL-17A, IL-18, IL-20 and IL-23, LIF; and GM-CSF. In specific embodiments, inflammatory cytokines are TNFα, IL-17A, IL-12, IL-12/23p40, IL-6, IFN-γ, GM-CSF, or IL-1β.

Cytokines also include "anti-inflammatory cytokines." The anti-inflammatory cytokines are a series of immunoregulatory molecules that control the pro-inflammatory cytokine response. Cytokines act in concert with specific cytokine inhibitors and soluble cytokine receptors to regulate the human immune response. Their physiologic role in inflammation and pathologic role in systemic inflammatory states are increasingly recognized. Major anti-inflammatory cytokines include, but are not limited to, interleukin (IL)-1 receptor antagonist, IL-10, IL-1ra, sTNF-RI, sTNF-RII, IL-4, and IL-13. Leukemia inhibitory factor, interferon-alpha, IL-6, and transforming growth factor (TGF)-β are categorized as either anti-inflammatory or pro-inflammatory cytokines, under various circumstances. Specific cytokine receptors for IL-1, TNF-α, and IL-18 also function as inhibitors for pro-inflammatory cytokines. In specific aspects, an anti-inflammatory cytokine is IL-10.

The overexpression and/or dysregulation of the inflammatory cytokines are a part of the pathophysiology that is found in many inflammatory conditions. This further pertains to inflammation in wound healing, including, but not limited to, traumatic, surgical, chronic stasis and burn wounds. Dysregulation of cytokine or growth factor expression hinders acute healing of wounds, and blocking the excessive production of specific pro-inflammatory cytokines can lead to a path toward mitigating their effects. This can be done by administering agents that bind to their signal receptor sites, so as to reduce the over-expression of the corresponding pro-inflammatory proteins. Many of such antagonists are produced using recombinant antibody techniques.

In certain embodiments, the fusion proteins of the disclosure are capable of inhibiting the production of one or more cytokines in a cell. In some aspects, the one or more cytokines are inflammatory cytokines. Thus, in certain aspects, the fusion proteins of the disclosure are capable of inhibiting the production of one or more pro-inflammatory cytokines in a cell.

In certain embodiments, the fusion proteins of the disclosure show an increased inhibitory effect on pro-inflammatory cytokine production than the molar equivalent of IL-10 (mIL10), a TNFα binding protein, or the codelivery of the molar equivalent of IL-10 molecule and a TNFα binding protein (mIL10+anti-TNFα). In certain cases, the fusion proteins of the disclosure show a greater than additive, i.e. synergistic, inhibitory effect on pro-inflammatory cytokine production than the molar equivalent of IL-10 (mIL10), a TNFα binding protein, or the codelivery of the molar equivalent of IL-10 molecule and a TNFα binding protein (mIL10+anti-TNFα). In certain aspects, the fusion proteins of the disclosure show an at least 10 fold, 20 fold, 30 fold, 40 fold, 50 fold, 70 fold, 100 fold, 150 fold, 200 fold, 300 fold, 500 fold, 700 fold, 900 fold, 1,000 fold, or at least 10,000 fold increased inhibitory effect on pro-inflammatory cytokine production than the codelivery of the molar equivalent of IL-10 molecule and a TNFα binding protein (mIL10+anti-TNFα).

In other embodiments, the fusion proteins of the disclosure show an increased inhibitory effect on pro-inflammatory cytokine production than at least the molar equivalent of IL-10, a TNFα binding protein, or the codelivery of at least the molar equivalent of IL-10 and a TNFα binding protein. In certain cases, the fusion proteins of the disclosure show a greater than additive, i.e. synergistic, inhibitory effect on pro-inflammatory cytokine production than at least one molar equivalent of IL-10, a TNFα binding protein, or the codelivery of at least the molar equivalent of IL-10 molecule and a TNFα binding protein. In certain aspects, the fusion proteins of the disclosure show an at least: 10 fold, 20 fold, 30 fold, 40 fold, 50 fold, 70 fold, 100 fold, 150 fold, 200 fold, 300 fold, 500 fold, 700 fold, 900 fold, 1,000 fold, or at least 10,000 fold increased inhibitory effect on pro-inflammatory cytokine production than the codelivery of at least the molar equivalent of IL-10 molecule and a TNFα binding protein.

In specific embodiments, the fusion proteins of the disclosure show an increased inhibitory effect on pro-inflammatory cytokine production than the molar equivalents (2 moles of IL10 per mole of the fusion protein) of IL-10 (2mIL10), a TNFα binding protein, or the codelivery of the molar equivalents of the IL-10 molecule and a TNFα binding protein (2mIL10+anti-TNFα). In certain cases, the fusion proteins of the disclosure show a greater than additive, i.e. synergistic, inhibitory effect on pro-inflammatory cytokine production than the molar equivalents of IL-10 (2mIL10), a TNFα binding protein, or the codelivery of the molar equivalents of IL-10 molecule and a TNFα binding protein (2mIL10+anti-TNFα)n. In certain aspects, the fusion proteins of the disclosure show an at least 10 fold, 20 fold, 30 fold, 40 fold, 50 fold, 70 fold, 100 fold, 150 fold, 200 fold, 300 fold, 500 fold, 700 fold, 900 fold, 1,000 fold, or at least 10,000 fold increased inhibitory effect on pro-inflammatory cytokine production than the codelivery of molar equivalents of IL-10 molecule and a TNFα binding protein (2mIL10+anti-TNFα).

In some embodiments, the one or more pro-inflammatory cytokines include, without limitations, TNFα, IL-17A, IL-12, IL-12/23p40, IL-6, IFN-γ, GM-CSF, or IL-1β.

TNF-α is a pro-inflammatory cytokine that is involved with systemic inflammation, as well as being a regulator of immune cells. In embodiments, a fusion protein of the disclosure can comprise TNF-α or a fragment thereof. TNF-α comprises multiple domains, including but not limited to a cytoplasmic domain, a transmembrane domain, and an extracellular domain. In embodiments, provided is a fusion protein that comprises a TNF-α extracellular domain. A TNF-α extracellular domain can comprise a binding portion of the TNF-α. In embodiments, a fusion protein comprises a fragment of TNF-α capable of binding TNFR1 and/or TNFR2. In embodiments, a fusion protein comprises a fragment of TNF-α capable of preferentially binding TNFR1 over TNFR2 or TNFR2 over TNFR1. Dysregulation of TNF-α is related to many disease states including but not limited to: autoimmune disease, inflammatory bowel disease, cancer, Alzheimer's disease, inflammatory skin disorders, such as psoriasis and eczema, as well as numerous other conditions.

The terms "TNF-α", "TNF-α molecule(s)," "TNF-α protein(s)," "TNF-α polypeptide(s)," and the like are intended to be construed broadly and include, for example, human and non-human TNF-α-related polypeptides, including homologs, variants (including muteins), and fragments thereof, as well as TNF-α polypeptides having, for example, a leader sequence (e.g., the signal peptide), and modified versions of the foregoing. In certain embodiments, TNF-α is full-length. In other embodiments, TNF-α is mature TNF-α. In yet other embodiments, TNF-α can include a full-length TNF-α, a fragment thereof, or a TNF-α variant polypeptide, wherein the fragment of TNF-α or TNF-α variant polypeptide retains some or all functional properties of active TNF-α. A fragment of TNF-α can retain comparable activity to a WT or full-length TNF-α protein as determined by an in vitro or in vivo assay. For example, a fragment of TNF-α can refer to the binding portion of TNF-α that retains binding capacity as determined by a binding assay selected from the group consisting of: ELISA, Electro-chemiluminescence method (ELC), Radioimmunoassay (RIA), Fluorescence immunoassay (FIA), Thermal shift assay, LC-MS detection, Surface plasmon resonance (SPR), and Bio-layer interferometry (BLI). In embodiments, the binding capacity is at least about 80%, 85%, 90%, 95%, 96%, 97%, 98%, 99%, or 100% comparable to the WT TNF-α.

In certain aspects, the fusion proteins of the disclosure completely or fully inhibit the production of one or more inflammatory cytokines in a cell. In other aspects, the fusion proteins of the disclosure partially inhibit the production of one or more inflammatory cytokines in a cell. In certain embodiments, the complete or partial inhibition of the production of one or more inflammatory cytokines in a cell by the fusion proteins of the disclosure is sufficient to treat an inflammatory condition or autoimmune condition in a subject. In methods provided herein, administration of a fusion protein of the disclosure is sufficient to reduce or eliminate production of one or more inflammatory cytokines in a subject in need thereof, thereby treating a disease or condition in the subject. In methods provided herein, administration of a fusion protein of the disclosure is sufficient to reduce or eliminate a symptom of a disease or condition in a subject in need thereof as compared to an otherwise comparable subject lacking the administering. In embodiments, the symptom of the disease or condition comprises inflammation. In embodiments, a reduction in inflammation is determined by at least one of: reduced level of a pro-inflammatory cytokine, reduction in the presence of immune cells at a site of inflammation, reduction in cellular apoptosis, reduction in cellular necrosis, reduction in vasodilation, or any combination thereof.

In other embodiments, the fusion proteins of the disclosure are capable of inhibiting the activity of one or more inflammatory cytokines in a cell. In certain aspects, the fusion proteins of the disclosure completely or fully inhibit the activity of one or more inflammatory cytokines in a cell. In other aspects, the fusion proteins of the disclosure partially inhibit the activity of one or more inflammatory cytokines in a cell. In certain embodiments, the complete or partial inhibition of the activity of one or more inflammatory cytokines in a cell by the fusion proteins of the disclosure is sufficient to treat an inflammatory condition or autoimmune condition in a subject.

In yet other embodiments, the fusion proteins of the disclosure are capable of inhibiting both the activity and the production of one or more inflammatory cytokines in a cell. In certain aspects, the fusion proteins of the disclosure completely or fully inhibit the activity and production of one or more inflammatory cytokines in a cell. In other aspects, the fusion proteins of the disclosure partially inhibit the activity and production of one or more inflammatory cytokines in a cell. In certain embodiments, the complete or partial inhibition of the activity and production of one or more inflammatory cytokines in a cell by the fusion proteins of the disclosure is sufficient to treat an inflammatory condition or autoimmune condition in a subject.

Figure 30:
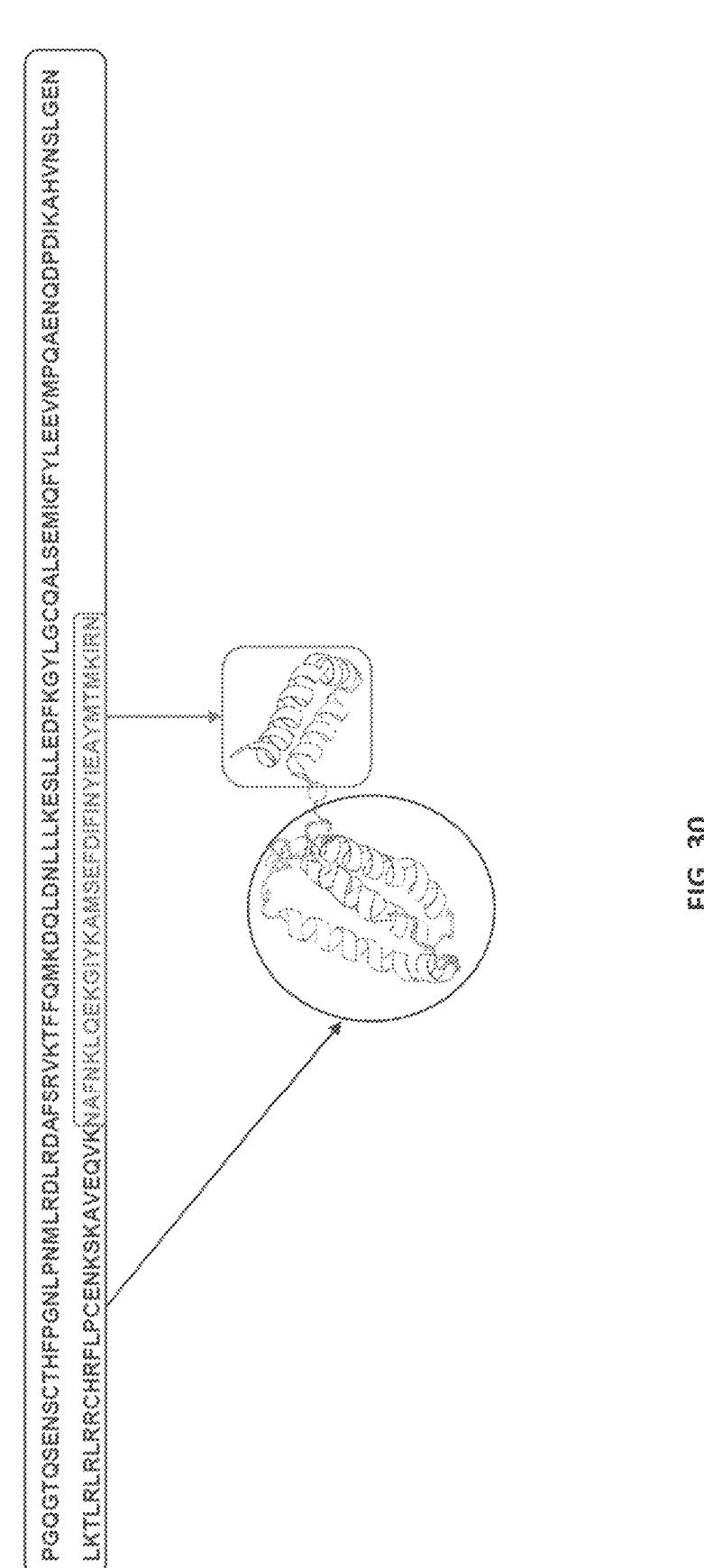
FIG. 30 shows the domain structure of full-length human IL-10 molecule having an amino acid sequence of SEQ ID NO: 1. The Carboxy-terminal (C-terminal) "tail domain" (shown in the rectangle) having an amino acid sequence of SEQ ID NO: 30 can be removed to create an active truncated human IL-10 molecule (shown in the circle) having an amino acid sequence of SEQ ID NO: 25.

In certain aspects, the fusion proteins of the disclosure also comprise one or more immunosuppressive cytokines, e.g., IL-10. In certain embodiments, the IL-10 molecule is a human IL-10 molecule. In other embodiments, the IL-10 molecule is a non-human, e.g., viral, murine or primate IL-10 molecule. In specific embodiments, the IL-10 molecule is a human IL-10 molecule that comprises an amino acid sequence of SEQ ID NO: 1. In certain cases, the IL-10 molecule is a wild type protein. In other cases, the IL-10 molecule is a variant of the wild type 11-10 protein. In some cases, the IL-10 molecule is a mutated protein comprising an amino acid sequence in which one or more acid residues are mutated, substituted, or deleted amino compared to the wild-type amino acid sequence. In certain aspects, the IL-10 molecule is a full-length protein. In some aspects, the full-length IL-10 molecule has a domain structure as shown in FIG. 30. In other aspects, the IL-10 molecule is a truncated protein. In certain embodiments, the truncated IL-10 molecule retains its biological activity. In certain embodiments, the IL-10 molecule contains a truncation of one or more amino acid residues at its C-terminal end. In embodiments, the IL-10 molecule contains a truncation of 1, 2, 3, 4, 5, 6, 7, 8, 9, 10, 11, 12, 13, 14, 15, 16, 17, 18, 19, or 20 amino acid residues at its C-terminal end. In embodiments, the IL-10 molecule contains a truncation of 1-3, 1-5, 2-5, 3-5, 2-8, 3-8, 5-10, or 1-10 amino acid residues at its C-terminal end. In embodiments, the IL-10 molecule contains a truncation of one or more amino acid residues at its N-terminal end. In embodiments, the IL-10 molecule contains a truncation of 1, 2, 3, 4, 5, 6, 7, 8, 9, 10, 11, 12, 13, 14, 15, 16, 17, 18, 19, or 20 amino acid residues at its N-terminal end. In embodiments, the IL-10 molecule contains a truncation of 1-3, 1-5, 2-5, 3-5, 2-8, 3-8, 5-10, or 1-10 amino acid residues at its N-terminal end. In embodiments, the C-terminal "tail domain" portion (FIG. 30) of the full-length IL-10 molecule can be removed to create an active truncated human IL-10 molecule. In certain aspects, the removable C-terminal portion of IL-10 comprises the amino acid sequence of SEQ ID NO: 30. In some embodiments, the active truncated IL-10 molecule comprises the amino acid sequence of SEQ ID NO: 25. In embodiments, a fusion protein comprises a fragment of IL-10. In embodiments, a fragment of IL-10 comprises any one of an A-F helice of IL-10 or combinations thereof. In embodiments, a fragment of IL-10 comprises a fragment of IL-10 capable of binding the IL-10 receptor. In embodiments, a fragment of an IL-10 molecule contains a truncation of 1, 2, 3, 4, 5, 6, 7, 8, 9, 10, 11, 12, 13, 14, 15, 16, 17, 18, 19, or 20 amino acid residues at its C-terminal end or N-terminal end as compared to a WT IL-10 molecule. In embodiments, the fragment of an IL-10 molecule contains a truncation of 1-3, 1-5, 2-5, 3-5, 2-8, 3-8, 5-10, or 1-10 amino acid residues at its C-terminal end and N-terminal end as compared to a WT IL-10 molecule.

IL-10 is a pleiotropic cytokine that regulates multiple immune responses through actions on T cells, B cells, macrophages, and antigen presenting cells (APC). IL-10 may suppress immune responses by inhibiting expression of IL-1α, IL-1β, IL-6, IL-8, TNF-α, GM-CSF and G-CSF in activated monocytes and activated macrophages, and it also suppresses IFN-γ production by NK cells. Although IL-10 is predominantly expressed in macrophages, expression has also been detected in activated T cells, B cells, mast cells, and monocytes. In addition to suppressing immune responses, IL-10 exhibits immuno-stimulatory properties, including stimulating the proliferation of IL-2- and IL-4-treated thymocytes, enhancing the viability of B cells, and stimulating the expression of MHC class II.

The terms "IL-10", "IL-10 molecule(s)," "IL-10 protein(s)," "IL-10 polypeptide(s)," "IL-10 moiety" and the like are intended to be construed broadly and include, for example, human and non-human IL-10-related polypeptides, including homologs, variants (including muteins), and fragments thereof, as well as IL-10 polypeptides having, for example, a leader sequence (e.g., the signal peptide), and modified versions of the foregoing. In certain embodiments, the IL-10 molecule is a full-length polypeptide. In some embodiments, the IL-10 molecule is a truncated polypeptide. In other embodiments, the IL-10 molecule is a mature IL-10 molecule. In yet other embodiments, the IL-10 molecule can include a full-length IL-10 polypeptide, a fragment thereof, or an IL-10 variant polypeptide, wherein the fragment of IL-10 or IL-10 variant polypeptide retains some or all functional properties of active IL-10. A fragment of IL-10 can refer to a fragment that retains comparable activity to IL-10 protein as determined by an in vitro or in vivo assay. For example, a fragment of IL-10 can refer to the binding portion of IL-10 that retains binding capacity as determined by a binding assay selected from the group consisting of: ELISA, Electro-chemiluminescence method (ELC), Radio-immunoassay (RIA), Fluorescence immunoassay (FIA), Thermal shift assay, LC-MS detection, Surface plasmon resonance (SPR), and Bio-layer interferometry (BLI). In embodiments, the binding capacity is at least about 80%, 85%, 90%, 95%, 96%, 97%, 98%, 99%, or 100% comparable to the WT IL-10.

As a result of its pleiotropic activity, IL-10 has been linked to a broad range of diseases, disorders and conditions, including inflammatory conditions, immune-related disorders, fibrotic disorders and cancer. Clinical and pre-clinical evaluations with IL-10 for a number of such diseases, disorders and conditions have solidified its therapeutic potential. Moreover, pegylated IL-10 has been shown to be more efficacious than non-pegylated IL-10 in certain therapeutic settings.

Human IL-10 is a homodimer that becomes biologically inactive upon disruption of the non-covalent interactions between the two monomer subunits. Data obtained from the published crystal structure of IL-10 indicates that the functional dimer exhibits certain similarities to IFN-γ (Zdanov et al., (1995) Structure (Lond) 3:591-601).

In certain aspects, the fusion proteins of the disclosure are capable of reducing T cell proliferation. In certain embodiments, the fusion proteins of the disclosure show an increased inhibitory effect on T cell proliferation over molar equivalents of IL-10 (mIL10), a TNFα binding protein, or the codelivery of a molar equivalent of IL-10 molecule and a TNFα binding protein (mIL10+anti-TNFα). In certain cases, the fusion proteins of the disclosure show a greater than additive, i.e. synergistic, inhibitory effect on pro-inflammatory cytokine production than a molar equivalent of IL-10 molecule and a TNFα binding protein (mIL10+anti-TNFα), a TNFα binding protein, or the codelivery of a molar equivalents of IL-10 molecule and a TNFα binding protein (mIL10+anti-TNFα). In certain aspects, the fusion proteins of the disclosure show an at least 10 fold, 20 fold, 30 fold, 40 fold, 50 fold, 70 fold, 100 fold, 150 fold, 200 fold, 300 fold, 500 fold, 700 fold, 900 fold, 1,000 fold, or at least 10,000 fold increased inhibitory effect on T cell proliferation than the codelivery of a molar equivalent of IL-10 molecule and a TNFα binding protein (mIL10+anti-TNFα).

In other embodiments, the fusion proteins of the disclosure show an increased inhibitory effect on T cell proliferation than at least one IL-10 molecule alone, a TNFα binding protein alone, or a combination of at least one IL-10 molecule and a TNFα binding protein. In certain cases, the fusion proteins of the disclosure show a greater than additive, i.e. synergistic, inhibitory effect on pro-inflammatory cytokine production than at least one IL-10 molecule alone, a TNFα binding protein alone, or a combination of at least one IL-10 molecule and a TNFα binding protein. In certain aspects, the fusion proteins of the disclosure show an at least 10 fold, 20 fold, 30 fold, 40 fold, 50 fold, 70 fold, 100 fold, 150 fold, 200 fold, 300 fold, 500 fold, 700 fold, 900 fold, 1,000 fold, or at least 10,000 fold increased inhibitory effect on T cell proliferation than a combination of at least one IL-10 molecule and a TNFα binding protein.

In yet other embodiments, the fusion proteins of the disclosure show an increased inhibitory effect on T cell proliferation over molar equivalents of IL-10 (mIL10), a TNFα binding protein, or the codelivery of molar equivalents of IL-10 molecule and a TNFα binding protein (mIL10+anti-TNFα). In certain cases, the fusion proteins of the disclosure show a greater than additive, i.e. synergistic, inhibitory effect on pro-inflammatory cytokine production than molar equivalents of IL-10 (mIL10), a TNFα binding protein, or the codelivery of molar equivalents of IL-10 molecule and a TNFα binding protein (mIL10+anti-TNFα). In certain aspects, the fusion proteins of the disclosure show an at least 10 fold, 20 fold, 30 fold, 40 fold, 50 fold, 70 fold, 100 fold, 150 fold, 200 fold, 300 fold, 500 fold, 700 fold, 900 fold, 1,000 fold, or at least 10,000 fold increased inhibitory effect on T cell proliferation than a combination of molar equivalents of IL-10 molecule and a TNFα binding protein (mIL10+anti-TNFα).

In certain embodiments, the TNFα binding molecule or TNFα binding moiety provided herein is a TNFα binding protein. Thus, in certain embodiments, the fusion proteins of the disclosure comprise a TNFα binding protein. In some embodiments, the TNFα binding protein specifically or preferentially binds TNFα. In some aspects, the TNFα is a full-length protein. In other aspects, the TNFα is a variant or a fragment of the full-length protein.

A "binding protein," "antigen binding protein," "binding molecule" or "antigen binding molecule" of the present disclosure refers in its broadest sense to a protein or molecule that specifically binds an antigenic determinant. In certain embodiments, the binding protein specifically binds to TNFα, e.g., full-length TNFα or mature TNFα. In certain embodiments, the TNFα binding protein is a human protein. In other embodiments, the TNFα binding protein is a non-human, e.g., viral, murine or primate protein. In some cases, the TNFα binding protein is a wild type protein. In other cases, the TNFα binding protein is a variant of the wild type TNFα binding protein. In certain cases, the TNFα binding protein is a mutated protein comprising an amino acid sequence in which one or more acid residues are mutated, substituted, or deleted amino compared to the wild-type amino acid sequence. In some aspects, the TNFα binding protein is a full-length protein. In other aspects, the TNFα binding protein is a truncated protein. In embodiments, the TNFα binding protein contains a truncation of one or more amino acid residues at its C-terminal end. In embodiments, the TNFα binding protein contains a truncation of one or more amino acid residues at its N-terminal end.

In some embodiments, a binding protein of the disclosure is an antibody or an antigen-binding fragment thereof. In other embodiments, a binding molecule of the disclosure comprises at least one heavy or light chain CDR of a reference antibody molecule. In other embodiments, a binding protein of the disclosure comprises at least two CDRs from one or more reference antibody molecules. In other embodiments, a binding protein of the disclosure comprises at least three CDRs from one or more reference antibody molecules. In other embodiments, a binding protein of the disclosure comprises at least four CDRs from one or more reference antibody molecules. In other embodiments, a binding protein of the disclosure comprises at least five CDRs from one or more reference antibody molecules. In other embodiments, a binding protein of the disclosure comprises at least six CDRs from one or more reference antibody molecules.

In certain aspects, the TNFα binding proteins are antibodies or antigen-binding fragments thereof. In certain embodiments, the TNFα binding protein of the disclosure, binds specifically or preferentially to TNFα. In some aspects, the TNFα is a full-length protein. In other aspects, the TNFα is a variant or a fragment of the full-length protein. In some aspects, the TNFα binding protein specifically binds to the same epitope of TNFα as a reference anti-TNFα antibody molecule. In other aspects, the TNFα binding protein competitively inhibits the binding of a reference anti-TNFα antibody molecule to one or more epitopes of TNFα. In certain embodiments, the TNFα binding protein competitively inhibits the binding of a reference anti-TNFα antibody molecule to the same epitope of TNFα.

In certain embodiments, the anti-TNFα antibody comprises a heavy chain comprising the amino acid sequence of SEQ ID NO:5. In certain embodiments, the anti-TNFα antibody comprises a heavy chain comprising the amino acid sequence of SEQ ID NO:29. In certain aspects, the anti-TNFα antibody comprises a heavy chain comprising the amino acid sequence of SEQ ID NO:16. In other aspects, the anti-TNFα antibody comprises a heavy chain comprising the amino acid sequence of SEQ ID NO:7. In yet other aspects, the anti-TNFα antibody comprises a heavy chain comprising the amino acid sequence of SEQ ID NO:8. In further aspects, the anti-TNFα antibody comprises a heavy chain comprising the amino acid sequence of SEQ ID NO:9. In additional aspects, the anti-TNFα antibody comprises a heavy chain comprising the amino acid sequences of SEQ ID NOs:7, 8, and 9. In certain embodiments, the anti-TNFα antibody comprises a light chain comprising the amino acid sequence of SEQ ID NO: 6. In some aspects, the anti-TNFα antibody comprises a light chain comprising the amino acid sequence of SEQ ID NO:17. In other aspects, the anti-TNFα antibody comprises a light chain comprising the amino acid sequence of SEQ ID NO:10. In yet other aspects, the anti-TNFα antibody comprises a light chain comprising the amino acid sequence of SEQ ID NO:11. In further aspects, the anti-TNFα antibody comprises a light chain comprising the amino acid sequence of SEQ ID NO:12. In additional aspects, the anti-TNFα antibody comprises a heavy chain comprising the amino acid sequences of SEQ ID NOs:10, 11, and 12. In certain embodiments, the anti-TNFα antibody comprises a heavy chain comprising the amino acid sequence of SEQ ID NO: 5 and a light chain comprising the amino acid sequence of SEQ ID NO:6. In yet other embodiments, the anti-TNFα antibody comprises a heavy chain comprising the amino acid sequence of SEQ ID NO: 29 and a light chain comprising the amino acid sequence of SEQ ID NO:6. In further embodiments, the anti-TNFα antibody comprises the amino acid sequence of SEQ ID NO: 16 and the amino acid sequence of SEQ ID NO: 6. In certain other embodiments, the anti-TNFα antibody comprises a heavy chain comprising the amino acid sequence of SEQ ID NO: 21. In other embodiments, the anti-TNFα antibody comprises a heavy chain comprising the amino acid sequence of SEQ ID NO: 23. In further embodiments, the anti-TNFα antibody comprises a light chain comprising the amino acid sequence of SEQ ID NO: 20. In yet further embodiments, the anti-TNFα antibody comprises a light chain comprising the amino acid sequence of SEQ ID NO: 22. In still other embodiments, the anti-TNFα antibody comprises a heavy chain comprising the amino acid sequence of SEQ ID NO: 21 and a light chain comprising the amino acid sequence of SEQ ID NO: 20. In certain embodiments, the anti-TNFα antibody of the disclosure comprises a heavy chain comprising an amino acid sequence that has at least 80%, 85%, 88%, 89%, 90%, 91%, 92%, 93%, 94%, 95%, 96%, 97%, 98%, or 99% sequence identity to the amino acid sequence of SEQ ID NO: 5, 7, 8, 9, 16, 21, 23, or 29. In other embodiments, the anti-TNFα antibody of the disclosure comprises a light chain comprising an amino acid sequence that has at least 80%, 85%, 88%, 89%, 90%, 91%, 92%, 93%, 94%, 95%, 96%, 97%, 98%, or 99% sequence identity to the amino acid sequence of SEQ ID NO: 6, 10, 11, 12, 17, 20, or 22. In yet other embodiments, the anti-TNFα antibody of the disclosure comprises a heavy chain comprising an amino acid sequence that has at least 80%, 85%, 88%, 89%, 90%, 91%, 92%, 93%, 94%, 95%, 96%, 97%, 98%, or 99% sequence identity to the amino acid sequence of SEQ ID NO:5, 7, 8, 9, 16, 21, 23, or 29, and a light chain comprising an amino acid sequence that has at least 80%, 85%, 88%, 89%, 90%, 91%, 92%, 93%, 94%, 95%, 96%, 97%, 98%, or 99% sequence identity to the amino acid sequence of SEQ ID NO:6, 10, 11, 12, 17, 20, or 22.

In certain embodiments, the anti-TNFα antibody comprises a heavy chain variable region ($V_H$) comprising the amino acid sequence of SEQ ID NO: 16. In some embodiments, the anti-TNFα antibody comprises a light chain variable region ($V_L$) comprising the amino acid sequence of SEQ ID NO: 17. In other embodiments, the anti-TNFα antibody comprises a $V_H$ comprising the amino acid sequence of SEQ ID NO: 16 and a $V_L$ comprising the amino acid sequence of SEQ ID NO: 17. In certain other embodiments, the anti-TNFα antibody comprises a $V_H$ comprising the amino acid sequence of SEQ ID NO: 23. In other embodiments, the anti-TNFα antibody comprises a $V_L$ comprising the amino acid sequence of SEQ ID NO: 22. In still other embodiments, the anti-TNFα antibody comprises a $V_H$ comprising the amino acid sequence of SEQ ID NO: 23 and a $V_L$ comprising the amino acid sequence of SEQ ID NO: 22. In certain aspects, the anti-TNFα antibody comprises a $V_L$ comprising an amino acid sequence that has at least 80%, 85%, 88%, 89%, 90%, 91%, 92%, 93%, 94%, 95%, 96%, 97%, 98%, or 99% sequence identity to the amino acid sequence of SEQ ID NO:17 or 22. In other aspects, the anti-TNFα antibody comprises a $V_H$ comprising an amino acid sequence that has at least 80%, 85%, 88%, 89%, 90%, 91%, 92%, 93%, 94%, 95%, 96%, 97%, 98%, or 99% sequence identity to the amino acid sequence of SEQ ID NO:16 or 23. In additional aspects, the anti-TNFα antibody comprises a $V_L$ comprising an amino acid sequence that has at least 80%, 85%, 88%, 89%, 90%, 91%, 92%, 93%, 94%, 95%, 96%, 97%, 98%, or 99% sequence identity to the amino acid sequence of SEQ ID NO:17 or 22, and a $V_H$ comprising an amino acid sequence that has at least 80%, 85%, 88%, 89%, 90%, 91%, 92%, 93%, 94%, 95%, 96%, 97%, 98%, or 99% sequence identity to the amino acid sequence of SEQ ID NO:16 or 23.

In certain aspects, the TNFα binding protein binds to the same epitope of TNFα as an antibody comprising a $V_H$ of SEQ ID NO: 16 and a $V_L$ of SEQ ID NO: 17. In some aspects, the TNFα binding protein specifically binds to TNFα and competitively inhibits binding of a reference anti-TNFα antibody molecule. Thus, in some embodiments, the fusion proteins of the disclosure competitively inhibit the binding to TNFα of an anti-TNFα antibody. In certain aspects, the anti-TNFα antibody comprises a $V_H$ of SEQ ID NO: 16. In some aspects, the anti-TNFα antibody comprises a $V_L$ of SEQ ID NO: 17. In other aspects, the anti-TNFα antibody comprises a $V_H$ of SEQ ID NO: 16 and a $V_L$ of SEQ ID NO: 17. In other embodiments, the fusion proteins of the disclosure competitively inhibit the binding to TNFα of an antibody comprising a $V_H$ of SEQ ID NO: 16 and a $V_L$ of SEQ ID NO: 17.

In certain aspects, the TNFα binding protein binds to the same epitope of TNFα as an antibody comprising a $V_H$ of SEQ ID NO: 23 and a $V_L$ of SEQ ID NO: 22. In some aspects, the TNFα binding protein specifically binds to TNFα and competitively inhibits binding of a reference anti-TNFα antibody molecule. Thus, in some embodiments, the fusion proteins of the disclosure competitively inhibit the binding to TNFα of an anti-TNFα antibody. In certain aspects, the anti-TNFα antibody comprises a $V_H$ of SEQ ID NO: 23. In some aspects, the anti-TNFα antibody comprises a $V_L$ of SEQ ID NO: 22. In other aspects, the anti-TNFα antibody comprises a $V_H$ of SEQ ID NO: 23 and a $V_L$ of SEQ ID NO: 22. In other embodiments, the fusion proteins of the disclosure competitively inhibits the binding to TNFα of an antibody comprising a $V_H$ of SEQ ID NO: 23 and a $V_L$ of SEQ ID NO: 22. In certain aspects, the TNFα binding protein binds to the same epitope of TNFα as an antibody comprising a $V_L$ comprising an amino acid sequence that has at least 80%, 85%, 88%, 89%, 90%, 91%, 92%, 93%, 94%, 95%, 96%, 97%, 98%, or 99% sequence identity to the amino acid sequence of SEQ ID NO:17 or 22. In other aspects, the TNFα binding protein binds to the same epitope of TNFα as an antibody comprising a $V_H$ comprising an amino acid sequence that has at least 80%, 85%, 88%, 89%, 90%, 91%, 92%, 93%, 94%, 95%, 96%, 97%, 98%, or 99% sequence identity to the amino acid sequence of SEQ ID NO:16 or 23. In additional aspects, the TNFα binding protein binds to the same epitope of TNFα as an antibody comprising a $V_L$ comprising an amino acid sequence that has at least 80%, 85%, 88%, 89%, 90%, 91%, 92%, 93%, 94%, 95%, 96%, 97%, 98%, or 99% sequence identity to the amino acid sequence of SEQ ID NO:17 or 22, and a $V_H$ comprising an amino acid sequence that has at least 80%, 85%, 88%, 89%, 90%, 91%, 92%, 93%, 94%, 95%, 96%, 97%, 98%, or 99% sequence identity to the amino acid sequence of SEQ ID NO:16 or 23.

In certain embodiments, the TNFα binding proteins of the disclosure comprise sequences and/or properties of anti-TNFα antibodies provided herein. Exemplary amino acid sequences and nucleic acid sequences of the TNFα binding proteins, the IL-10 moieties, and the fusion proteins of the disclosure are provided in Table 1.

TABLE 1

Sequences of TNFα Binding Proteins, IL-10, linkers, and fusion proteins
of the disclosure:

| SEQ ID NO: | Molecule | SEQUENCE |
|---|---|---|
| 1 | Full-length hIL-10 | PGQGTQSENSCTHFPGNLPNMLRDLRDAFSRVKTFFQMKDQLD NLLLKESLLEDFKGYLGCQALSEMIQFYLEEVMPQAENQDPDIK AHVNSLGENLKTLRLRLRRCHRFLPCENKSKAVEQVKNAFNKL QEKGIYKAMSEFDIFINYIEAYMTMKIRN |
| 2 | G4SS linker | GGGGSS |
| 3 | (G4S)₂S linker | GGGGSGGGGSS |
| 4 | Full-length K fusion protein-3X Linker (CDRs are underlined; linker is double underlined) | QVQLVESGGGVVQPGRSLRLSCAASGFIFSSYAMHWVRQAPG NGLEWVAFMSYDGSNKKYADSVKGRFTISRDNSKNTLYLQMN SLRAEDTAVYYCARDRGISAGGNYYYYGMDVWGQGTTVTVS SASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKRVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNKALPAPIE KTISKAKGQPREPQVYTLPPSREEMTKNQVSLTCLVKGFYPSDI AVEWESNGQPENNYKTTPPVLDSDGSFFLYSKLTVDKSRWQQ GNVFSCSVMHEALHNHYTQKSLSLSPGKGGGGSGGGGSGGGG SSPGQGTQSENSCTHFPGNLPNMLRDLRDAFSRVKTFFQMKDQ LDNLLLKESLLEDFKGYLGCQALSEMIQFYLEEVMPQAENQDP DIKAHVNSLGENLKTLRLRLRRCHRFLPCENKSKAVEQVKNAF NKLQEKGIYKAMSEFDIFINYIEAYMTMKIRN |
| 5 | Heavy chain of the K fusion protein (CDRS are underlined) | QVQLVESGGGVVQPGRSLRLSCAASGFIFSSYAMHWVRQAPG NGLEWVAFMSYDGSNKKYADSVKGRFTISRDNSKNTLYLQMN SLRAEDTAVYYCARDRGISAGGNYYYYGMDVWGQGTTVTVS SASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKRVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNKALPAPIE KTISKAKGQPREPQVYTLPPSREEMTKNQVSLTCLVKGFYPSDI AVEWESNGQPENNYKTTPPVLDSDGSFFLYSKLTVDKSRWQQ GNVFSCSVMHEALHNHYTQKSLSLSPGK |
| 6 | Light chain (K and A fusion proteins) (CDRs are underlined) | EIVLTQSPATLSLSPGERATLSCRASQSVYSYLAWYQQKPGQAP RLLIYDASNRAIGIPARFSGSGSGTDFTLTISSLEPEDFAVYYCQQ RSNWPPFTFGPGTKVDIKRTVAAPSVFIFPPSDEQLKSGTASVVC LLNNFYPREAKVQWKVDNALQSGNSQESVTEQDSKDSTYSLSS TLTLSKADYEKHKVYACEVTHQGLSSPVTKSFNRGEC |
| 7 | V_H-CDR1 | SYAMH |
| 8 | V_H-CDR2 | FMSYDGSNKKYADSVKG |
| 9 | V_H CDR3 | DRGISAGGNYYYYGMDV |
| 10 | V_L-CDR1 | RASQSVYSYLA |
| 11 | V_L-CDR2 | DASNRAI |
| 12 | V_L-CDR3 | QQRSNWPPFT |
| 13 | (S4G)3-linker | SSSSGSSSSGSSSSG |
| 14 | (G4S)₃S-linker | GGGGSGGGGSGGGGSS |
| 15 | (G4S)₄S-linker | GGGGSGGGGSGGGGSGGGGSS |
| 16 | V_H (K and A fusion proteins) | QVQLVESGGGVVQPGRSLRLSCAASGFIFSSYAMHWVRQAPG NGLEWVAFMSYDGSNKKYADSVKGRFTISRDNSKNTLYLQMN SLRAEDTAVYYCARDRGISAGGNYYYYGMDVWGQGTTVTVS S |

TABLE 1-continued

Sequences of TNFα Binding Proteins, IL-10, linkers, and fusion proteins of the disclosure:

| SEQ ID NO: | Molecule | SEQUENCE |
|---|---|---|
| 17 | $V_L$ (K and A fusion proteins) | EIVLTQSPATLSLSPGERATLSCRASQSVYSYLAWYQQKPGQAP RLLIYDASNRAIGIPARFSGSGSGTDFTLTISSLEPEDFAVYYCQQ RSNWPPFTFGPGTKVDIKR |
| 18 | DNA sequence of the light chain (K and A fusion proteins) | GAAATCGTGCTGACCCAGAGCCCCGCCACCCTGTCTCTGAGC CCTGGCGAGAGAGCCACCCTGAGCTGCAGAGCCAGCCAGAG CGTGTACTCCTACCTGGCTTGGTATCAGCAGAAGCCCGGCCA GGCCCCCAGACTGCTGATCTACGACGCCAGCAACCGGGCCA TCGGCATCCCTGCCAGATTTTCTGGCAGCGGCAGCGGCACCG ACTTCACCCTGACCATCAGCAGCCTGGAACCCGAGGACTTCG CCGTGTACTACTGCCAGCAGCGGAGCAACTGGCCCCCCTTCA CCTTCGGCCCTGGCACCAAGGTGGACATCAAGCGTACGGTG GCTGCACCATCTGTCTTCATCTTCCCGCCATCTGATGAGCAG TTGAAATCTGGAACTGCCTCTGTTGTGTGCCTGCTGAATAAC TTCTATCCCAGAGAGGCCAAAGTACAGTGGAAGGTGGATAA CGCCCTCCAATCGGGTAACTCCCAGGAGAGTGTCACAGAGC AGGACAGCAAGGACAGCACCTACAGCCTCAGCAGCACCCTG ACGCTGAGCAAAGCAGACTACGAGAAACACAAAGTCTACGC CTGCGAAGTCACCCATCAGGGCCTGAGCTCGCCCGTCACAA AGAGCTTCAACAGGGGAGAGTGT |
| 19 | DNA sequence of full-length K fusion protein with 2X linker | CAGGTGCAGCTGGTGGAAAGCGGCGGAGGCGTGGTGCAGCC CGGCAGAAGCCTGAGACTGAGCTGCGCTGCCAGCGGCTTCA TCTTCAGCAGCTACGCCATGCACTGGGTCCGCCAGGCCCCTG GCAACGGACTGGAATGGGTGGCCTTCATGAGCTACGACGGC AGCAACAAGAAGTACGCCGACAGCGTGAAGGGCCGGTTCAC CATCAGCCGGGACAACAGCAAGAACACCCTGTACCTGCAGA TGAACAGCCTGCGGGCTGAGGACACCGCCGTGTACTACTGC GCCAGAGACCGAGGCATCAGTGCTGGCGGCAACTACTACTA CTACGGCATGGACGTGTGGGGCCAGGGCACCACCGTGACCG TGTCTAGCGCGTCGACCAAGGGCCCATCCGTCTTCCCCCTGG CACCCTCCTCCAAGAGCACCTCTGGGGGCACAGCGGCCCTG GGCTGCCTGGTCAAGGACTACTTCCCCGAACCGGTGACGGTG TCCTGGAACTCAGGCGCTCTGACCAGCGGCGTGCACACCTTC CCGGCTGTCCTACAGTCCTCAGGACTCTACTCCCTCAGCAGC GTGGTGACCGTGCCCTCCAGCAGCTTGGGCACCCAGACCTAC ATCTGCAACGTGAATCACAAGCCCAGCAACACCAAGGTGGA CAAGAGAGTTGAGCCCAAATCTTGTGACAAAACTCACACAT GCCCACCGTGCCCAGCACCTGAACTCCTGGGGGGACCGTCA GTCTTCCTCTTCCCCCCAAAACCCAAGGACACCCTCATGATC TCCCGGACCCCTGAGGTCACATGCGTGGTGGTGGACGTGAG CCACGAAGACCCTGAGGTCAAGTTCAACTGGTACGTGGACG GCGTGGAGGTGCATAATGCCAAGACAAAGCCGCGGGAGGAG CAGTACAACAGCACGTACCGTGTGGTCAGCGTCCTCACCGTC CTGCACCAGGACTGGCTGAATGGCAAGGAGTACAAGTGCAA GGTCTCCAACAAAGCCCTCCCAGCCCCCATCGAGAAAACCA TCTCCAAAGCCAAAGGGCAGCCCCGAGAACCACAGGTCTAC ACCCTGCCCCCATCCCGGGAGGAGATGACCAAGAACCAGGT CAGCCTGACCTGCCTGGTCAAAGGCTTCTATCCCAGCGACAT CGCCGTGGAGTGGGAGAGCAATGGGCAGCCGGAGAACAACT ACAAGACCACGCCTCCCGTGCTGGACTCCGACGGCTCCTTCT TCCTCTATAGCAAGCTCACCGTGGACAAGAGCAGGTGGCAG CAGGGGAACGTCTTCTCATGCTCCGTGATGCATGAGGCTCTG CACAACCACTACACGCAGAAGAGCTTAAGCCTGTCTCCGGG TAAAGGAGGAGGAGGAAGCGGAGGAGGAGGAAGCCCAGGC CAGGGCACCCAGTCTGAGAACAGCTGCACCCACTTCCCAGG CAACCTGCCTAACATGCTTCGAGATCTCCGAGATGCCTTCAG CAGAGTGAAGACTTTCTTTCAAATGAAGGATCAGCTGGACA ACTTGTTGTTAAAGGAGTCCTTGCTGGAGGACTTTAAGGGTT ACCTGGGTTGCCAAGCCTTGTCTGAGATGATCCAGTTTTACC TGGAGGAGGTGATGCCCCAAGCTGAGAACCAAGACCCAGAC ATCAAGGCGCATGTGAACTCCCTGGGGGAGAACCTGAAGAC CCTCAGGCTGAGGCTACGGCGCTGTCATCGATTTCTTCCCTG TGAAAACAAGAGCAAGGCCGTGGAGCAGGTGAAGAATGCCT TTAATAAGCTCCAAGAGAAAGGCATCTACAAAGCCATGAGT GAGTTTGACATCTTCATCAACTACATAGAAGCCTACATGACA ATGAAGATACGAAAC |
| 20 | Light chain-WT-Goli | EIVLTQSPATLSLSPGERATLSCRASQSVYSYLAWYQQKPGQAP RLLIYDASNRATGIPARFSGSGSGTDFTLTISSLEPEDFAVYYCQ QRSNWPPFTFGPGTKVDIKRTVAAPSVFIFPPSDEQLKSGTASVV CLLNNFYPREAKVQWKVDNALQSGNSQESVTEQDSKDSTYSLS STLTLSKADYEKHKVYACEVTHQGLSSPVTKSFNRGEC |

TABLE 1-continued

Sequences of TNFα Binding Proteins, IL-10, linkers, and fusion proteins
of the disclosure:

| SEQ ID NO: | Molecule | SEQUENCE |
|---|---|---|
| 21 | Heavy chain-WT-Goli | QVQLVESGGGVVQPGRSLRLSCAASGFIFSSYAMHWVRQAPG<br>NGLEWVAFMSYDGSNKKYADSVKGRFTISRDNSKNTLYLQMN<br>SLRAEDTAVYYCARDRGIAAGGNYYYYGMDVWGQGTTVTVS<br>SASTKGPSVFPLAPSSKSTSGGTAALGCLVKDYFPEPVTVSWNS<br>GALTSGVHTFPAVLQSSGLYSLSSVVTVPSSSLGTQTYICNVNH<br>KPSNTKVDKRVEPKSCDKTHTCPPCPAPELLGGPSVFLFPPKPK<br>DTLMISRTPEVTCVVVDVSHEDPEVKFNWYVDGVEVHNAKTK<br>PREEQYNSTYRVVSVLTVLHQDWLNGKEYKCKVSNKALPAPIE<br>KTISKAKGQPREPQVYTLPPSREEMTKNQVSLTCLVKGFYPSDI<br>AVEWESNGQPENNYKTTPPVLDSDGSFFLYSKLTVDKSRWQQ<br>GNVFSCSVMHEALHNHYTQKSLSLSPGK |
| 22 | V_L-WT-Goli | EIVLTQSPATLSLSPGERATLSCRASQSVYSYLAWYQQKPGQAP<br>RLLIYDASNRATGIPARFSGSGSGTDFTLTISSLEPEDFAVYYCQ<br>QRSNWPPFTFGPGTKVDIKR |
| 23 | V_H-WTGoli | QVQLVESGGGVVQPGRSLRLSCAASGFIFSSYAMHWVRQAPG<br>NGLEWVAFMSYDGSNKKYADSVKGRFTISRDNSKNTLYLQMN<br>SLRAEDTAVYYCARDRGIAAGGNYYYYGMDVWGQGTTVTVS<br>S |
| 24 | Full-length A fusion protein-3X Linker | QVQLVESGGGVVQPGRSLRLSCAASGFIFSSYAMHWVRQAPG<br>NGLEWVAFMSYDGSNKKYADSVKGRFTISRDNSKNTLYLQMN<br>SLRAEDTAVYYCARDRGISAGGNYYYYGMDVWGQGTTVTVS<br>SASTKGPSVFPLAPSSKSTSGGTAALGCLVKDYFPEPVTVSWNS<br>GALTSGVHTFPAVLQSSGLYSLSSVVTVPSSSLGTQTYICNVNH<br>KPSNTKVDKRVEPKSCDKTHTCPPCPAPELLGGPSVFLFPPKPK<br>DTLMISRTPEVTCVVVDVSHEDPEVKFNWYVDGVEVHNAKTK<br>PREEQYNSTYRVVSVLTVLHQDWLNGKEYKCKVSNKALPAPIE<br>KTISKAKGQPREPQVYTLPPSREEMTKNQVSLTCLVKGFYPSDI<br>AVEWESNGQPENNYKTTPPVLDSDGSFFLYSKLTVDKSRWQQ<br>GNVFSCSVMHEALHNHYTQKSLSLSPGAGGGGSGGGGSGGGG<br>SSPGQGTQSENSCTHFPGNLPNMLRDLRDAFSRVKTFFQMKDQ<br>LDNLLLKESLLEDFKGYLGCQALSEMIQFYLEEVMPQAENQDP<br>DIKAHVNSLGENLKTLRLRLRRCHRFLPCENKSKAVEQVKNAF<br>NKLQEKGIYKAMSEFDIFINYIEAYMTMKIRN |
| 25 | Truncated hIL-10 (N-terminal) | PGQGTQSENSCTHFPGNLPNMLRDLRDAFSRVKTFFQMKDQLD<br>NLLLKESLLEDFKGYLGCQALSEMIQFYLEEVMPQAENQDPDIK<br>AHVNSLGENLKTLRLRLRRCHRFLPCENKSKAVEQVK |
| 26 | Anti-TNFα(K)-Linker3X-Truncated-hIL10 | QVQLVESGGGVVQPGRSLRLSCAASGFIFSSYAMHWVRQAPG<br>NGLEWVAFMSYDGSNKKYADSVKGRFTISRDNSKNTLYLQMN<br>SLRAEDTAVYYCARDRGISAGGNYYYYGMDVWGQGTTVTVS<br>SASTKGPSVFPLAPSSKSTSGGTAALGCLVKDYFPEPVTVSWNS<br>GALTSGVHTFPAVLQSSGLYSLSSVVTVPSSSLGTQTYICNVNH<br>KPSNTKVDKRVEPKSCDKTHTCPPCPAPELLGGPSVFLFPPKPK<br>DTLMISRTPEVTCVVVDVSHEDPEVKFNWYVDGVEVHNAKTK<br>PREEQYNSTYRVVSVLTVLHQDWLNGKEYKCKVSNKALPAPIE<br>KTISKAKGQPREPQVYTLPPSREEMTKNQVSLTCLVKGFYPSDI<br>AVEWESNGQPENNYKTTPPVLDSDGSFFLYSKLTVDKSRWQQ<br>GNVFSCSVMHEALHNHYTQKSLSLSPGKGGGGSGGGGSGGGG<br>SPGQGTQSENSCTHFPGNLPNMLRDLRDAFSRVKTFFQMKDQL<br>DNLLLKESLLEDFKGYLGCQALSEMIQFYLEEVMPQAENQDPDI<br>KAHVNSLGENLKTLRLRLRRCHRFLPCENKSKAVEQVK |
| 27 | Anti-TNFα(A)-Linker3X-Truncated-hIL10 | QVQLVESGGGVVQPGRSLRLSCAASGFIFSSYAMHWVRQAPG<br>NGLEWVAFMSYDGSNKKYADSVKGRFTISRDNSKNTLYLQMN<br>SLRAEDTAVYYCARDRGISAGGNYYYYGMDVWGQGTTVTVS<br>SASTKGPSVFPLAPSSKSTSGGTAALGCLVKDYFPEPVTVSWNS<br>GALTSGVHTFPAVLQSSGLYSLSSVVTVPSSSLGTQTYICNVNH<br>KPSNTKVDKRVEPKSCDKTHTCPPCPAPELLGGPSVFLFPPKPK<br>DTLMISRTPEVTCVVVDVSHEDPEVKFNWYVDGVEVHNAKTK<br>PREEQYNSTYRVVSVLTVLHQDWLNGKEYKCKVSNKALPAPIE<br>KTISKAKGQPREPQVYTLPPSREEMTKNQVSLTCLVKGFYPSDI<br>AVEWESNGQPENNYKTTPPVLDSDGSFFLYSKLTVDKSRWQQ<br>GNVFSCSVMHEALHNHYTQKSLSLSPGAGGGGSGGGGSGGGG<br>SPGQGTQSENSCTHFPGNLPNMLRDLRDAFSRVKTFFQMKDQL<br>DNLLLKESLLEDFKGYLGCQALSEMIQFYLEEVMPQAENQDPDI<br>KAHVNSLGENLKTLRLRLRRCHRFLPCENKSKAVEQVK |
| 28 | Alternative DNA | GAGATTGTGCTGACCCAGTCTCCTGCCACACTGTCTTTGAGC<br>CCTGGCGAGAGAGCTACCCTGTCCTGTAGAGCCTCTCAGTCC |

TABLE 1-continued

Sequences of TNFα Binding Proteins, IL-10, linkers, and fusion proteins
of the disclosure:

| SEQ ID NO: | Molecule | SEQUENCE |
|---|---|---|
| | sequence of the light chain (K + A fusion proteins) | GTGTACTCCTACCTGGCCTGGTATCAGCAGAAGCCTGGACAG GCTCCCCGGCTGCTGATCTACGATGCCTCTAACAGAGCCATC GGCATCCCCGCCAGATTCTCCGGATCTGGCTCTGGCACAGAC TTTACCCTGACCATCTCCAGCCTGGAACCTGAGGACTTCGCC GTGTACTACTGCCAGCAGCGGTCTAACTGGCCTCCTTTCACC TTTGGACCCGGCACCAAGGTGGACATCAAGAGAACAGTGGC CGCTCCTTCCGTGTTCATCTTCCCACCTTCCGACGAGCAGCTG AAGTCTGGCACCGCTTCTGTCGTGTGCCTGCTGAACAACTTC TACCCTCGGGAAGCCAAGGTGCAGTGGAAAGTGGATAACGC CCTGCAGTCCGGCAACTCCCAAGAGTCTGTGACCGAGCAGG ACTCCAAGGACAGCACCTACAGCCTGTCCTCCACACTGACCC TGTCCAAGGCCGACTACGAGAAGCACAAGGTGTACGCCTGC GAAGTGACCCATCAGGGCCTGTCTAGCCCTGTGACCAAGTCT TTCAACCGGGGCGAGTGC |
| 29 | Heavy chain of the A fusion protein | QVQLVESGGGVVQPGRSLRLSCAASGFIFSSYAMHWVRQAPG NGLEWVAFMSYDGSNKKYADSVKGRFTISRDNSKNTLYLQMN SLRAEDTAVYYCARDRGISAGGNYYYYGMDVWGQGTTVTVS SASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKRVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNKALPAPIE KTISKAKGQPREPQVYTLPPSREEMTKNQVSLTCLVKGFYPSDI AVEWESNGQPENNYKTTPPVLDSDGSFFLYSKLTVDKSRWQQ GNVFSCSVMHEALHNHYTQKSLSLSPGA |
| 30 | Truncated hIL-10 (C-terminal) | NAFNKLQEKGIYKAMSEFDIFINYIEAYMTMKIRN |
| 31 | DNA sequence of full-length A fusion protein | CAGGTGCAGCTGGTGGAAAGCGGCGGAGGCGTGGTGCAGCC CGGCAGAAGCCTGAGACTGAGCTGCGCTGCCAGCGGCTTCA TCTTCAGCAGCTACGCCATGCACTGGGTCCGCCAGGCCCCTG GCAACGGACTGGAATGGGTGGCCTTCATGAGCTACGACGGC AGCAACAAGAAGTACGCCGACAGCGTGAAGGGCCGGTTCAC CATCAGCCGGGACAACAGCAAGAACACCCTGTACCTGCAGA TGAACAGCCTGCGGGCTGAGGACACCGCCGTGTACTACTGC GCCAGAGACCGAGGCATCAGTGCTGGCGGCAACTACTACTA CTACGGCATGGACGTGTGGGGCCAGGGCACCACCGTGACCG TGTCTAGCGCGTCGACCAAGGGCCCATCCGTCTTCCCCCTGG CACCCTCCTCCAAGAGCACCTCTGGGGGCACAGCGGCCCTG GGCTGCCTGGTCAAGGACTACTTCCCCGAACCGGTGACGGTG TCCTGGAACTCAGGCGCTCTGACCAGCGGCGTGCACACCTTC CCGGCTGTCCTACAGTCCTCAGGACTCTACTCCCTCAGCAGC GTGGTGACCGTGCCCTCCAGCAGCTTGGGCACCCAGACCTAC ATCTGCAACGTGAATCACAAGCCCAGCAACACCAAGGTGGA CAAGAGAGTTGAGCCCAAATCTTGTGACAAAACTCACACAT GCCCACCGTGCCCAGCACCTGAACTCCTGGGGGGACCGTCA GTCTTCCTCTTCCCCCCAAAACCCAAGGACACCCTCATGATC TCCCGGACCCCTGAGGTCACATGCGTGGTGGTGGACGTGAG CCACGAAGACCCTGAGGTCAAGTTCAACTGGTACGTGGACG GCGTGGAGGTGCATAATGCCAAGACAAAGCCGCGGGAGGAG CAGTACAACAGCACGTACCGTGTGGTCAGCGTCCTCACCGTC CTGCACCAGGACTGGCTGAATGGCAAGGAGTACAAGTGCAA GGTCTCCAACAAAGCCCTCCCAGCCCCCATCGAGAAAACCA TCTCCAAAGCCAAAGGGCAGCCCCGAGAACCACAGGTCTAC ACCCTGCCCCCATCCCGGGAGGAGATGACCAAGAACCAGGT CAGCCTGACCTGCCTGGTCAAAGGCTTCTATCCCAGCGACAT CGCCGTGGAGTGGGAGAGCAATGGGCAGCCGGAGAACAACT ACAAGACCACGCCTCCCGTGCTGGACTCCGACGGCTCCTTCT TCCTCTATAGCAAGCTCACCGTGGACAAGAGCAGGTGGCAG CAGGGGAACGTCTTCTCATGCTCCGTGATGCATGAGGCTCTG CACAACCACTACACGCAGAAGAGCTTAAGCCTGTCTCCGGG TGCAGGAGGCGGCGGTTCAGGCGGAGGTGGCTCTGGCGGTG GCGGAAGTAGCCCAGGCCAGGGCACCCAGTCTGAGAACAGC TGCACCCACTTCCCAGGCAACCTGCCTAACATGCTTCGAGAT CTCCGAGATGCCTTCAGCAGAGTGAAGACTTTCTTTCAAATG AAGGATCAGCTGGACAACTTGTTGTTAAAGGAGTCCTTGCTG GAGGACTTTAAGGGTTACCTGGGTTGCCAAGCCTTGTCTGAG ATGATCCAGTTTTACCTGGAGGAGGTGATGCCCCAAGCTGAG AACCAAGACCCAGACATCAAGGCGCATGTGAACTCCCTGGG GGAGAACCTGAAGACCCTCAGGCTGAGGCTACGGCGCTGTC |

TABLE 1-continued

Sequences of TNFα Binding Proteins, IL-10, linkers, and fusion proteins
of the disclosure:

| SEQ ID NO: | Molecule | SEQUENCE |
|---|---|---|
| | | ATCGATTTCTTCCCTGTGAAAACAAGAGCAAGGCCGTGGAG CAGGTGAAGAATGCCTTTAATAAGCTCCAAGAGAAAGGCAT CTACAAAGCCATGAGTGAGTTTGACATCTTCATCAACTACAT AGAAGCCTACATGACAATGAAGATACGAAAC |
| 32 | G4S linker | GGGGS |
| 33 | (G4S)₂ linker | GGGGSGGGGS |
| 34 | (G4S)₃- linker | GGGGSGGGGSGGGGS |
| 35 | (G4S)₄- linker | GGGGSGGGGSGGGGSGGGGS |
| 36 | Alternative full- lengthK fusion protein-3X Linker | QVQLVESGGGVVQPGRSLRLSCAASGFIFSSYAMHWVRQAPG NGLEWVAFMSYDGSNKKYADSVKGRFTISRDNSKNTLYLQMN SLRAEDTAVYYCARDRGISAGGNYYYYGMDVWGQGTTVTVS SASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKRVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNKALPAPIE KTISKAKGQPREPQVYTLPPSREEMTKNQVSLTCLVKGFYPSDI AVEWESNGQPENNYKTTPPVLDSDGSFFLYSKLTVDKSRWQQ GNVFSCSVMHEALHNHYTQKSLSLSPGKGGGGSGGGGSGGGG SPGQGTQSENSCTHFPGNLPNMLRDLRDAFSRVKTFFQMKDQL DNLLLKESLLEDFKGYLGCQALSEMIQFYLEEVMPQAENQDPDI KAHVNSLGENLKTLRLRLRRCHRFLPCENKSKAVEQVKNAFNK LQEKGIYKAMSEFDIFINYIEAYMTMKIRN |
| 37 | Alternative full-length A fusion protein-3X Linker | QVQLVESGGGVVQPGRSLRLSCAASGFIFSSYAMHWVRQAPG NGLEWVAFMSYDGSNKKYADSVKGRFTISRDNSKNTLYLQMN SLRAEDTAVYYCARDRGISAGGNYYYYGMDVWGQGTTVTVS SASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKRVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNKALPAPIE KTISKAKGQPREPQVYTLPPSREEMTKNQVSLTCLVKGFYPSDI AVEWESNGQPENNYKTTPPVLDSDGSFFLYSKLTVDKSRWQQ GNVFSCSVMHEALHNHYTQKSLSLSPGAGGGGSGGGGSGGGG SPGQGTQSENSCTHFPGNLPNMLRDLRDAFSRVKTFFQMKDQL DNLLLKESLLEDFKGYLGCQALSEMIQFYLEEVMPQAENQDPDI KAHVNSLGENLKTLRLRLRRCHRFLPCENKSKAVEQVKNAFNK LQEKGIYKAMSEFDIFINYIEAYMTMKIRN |
| 38 | DNA sequence of full- length alternative A fusion protein | CAGGTTCAGCTGGTTGAATCTGGCGGCGGAGTGGTGCAGCCT GGCAGATCTCTGAGACTGTCTTGTGCCGCCTCCGGCTTCATC TTCTCCAGCTACGCTATGCACTGGGTCCGACAGGCCCCTGGC AATGGATTGGAGTGGGTCGCCTTCATGTCCTACGACGGCTCC AACAAGAAATACGCCGACTCCGTGAAGGGCAGATTCACCAT CTCTCGGGACAACTCCAAGAACACCCTGTACCTGCAGATGA ACTCCCTGAGAGCCGAGGACACCGCCGTGTACTACTGCGCTA GAGACAGAGGCATCTCCGCTGGCGGCAATTACTACTACTAC GGCATGGACGTGTGGGGCCAGGGCACAACAGTGACAGTGTC CTCCGCTTCCACCAAGGGACCCTCTGTGTTTCCTCTGGCTCCC TCCAGCAAGTCTACCTCTGGTGGAACAGCTGCCCTGGGCTGC CTGGTCAAGGATTACTTTCCTGAGCCTGTGACCGTGTCCTGG AACTCTGGCGCTCTGACATCTGGCGTGCACACCTTTCCAGCT GTGCTGCAGTCCTCCGGCCTGTACTCTCTGTCCTCTGTCGTGA CCGTGCCTTCCAGCTCTCTGGGCACCCAGACCTACATCTGCA ATGTGAACCACAAGCCTTCCAACACCAAGGTGGACAAGAGA GTGGAACCCAAGTCCTGCGACAAGACCCACACCTGTCCTCC ATGTCCTGCTCCAGAACTGCTCGGCGGACCTTCCGTGTTCCT GTTTCCTCCAAAGCCTAAGGACACCCTGATGATCTCTCGGAC CCCTGAAGTGACCTGCGTGGTGGTGGATGTGTCTCACGAGGA TCCCGAAGTGAAGTTCAATTGGTACGTGGACGGCGTGGAAG TGCACAACGCCAAGACCAAGCCTAGAGAGGAACAGTACAAC TCCACCTACAGAGTGGTGTCCGTGCTGACCGTGCTGCACCAG GATTGGCTGAACGGCAAAGAGTACAAGTGCAAGGTGTCCAA CAAGGCCCTGCCTGCTCCTATCGAAAAGACCATCTCCAAGGC |

TABLE 1-continued

Sequences of TNFα Binding Proteins, IL-10, linkers, and fusion proteins
of the disclosure:

| SEQ ID NO: | Molecule | SEQUENCE |
|---|---|---|
| | | CAAGGGCCAGCCTAGGGAACCCCAGGTTTACACCCTGCCTC |
| | | CAAGCCGGGAAGAGATGACCAAGAACCAGGTGTCCCTGACC |
| | | TGCCTCGTGAAGGGATTCTACCCCTCCGATATCGCCGTGGAA |
| | | TGGGAGTCTAATGGCCAGCCTGAGAACAACTACAAGACAAC |
| | | CCCTCCTGTGCTGGACTCCGACGGCTCATTCTTCCTGTACTCC |
| | | AAGCTGACAGTGGACAAGTCCAGATGGCAGCAGGGCAACGT |
| | | GTTCTCCTGCTCCGTGATGCACGAGGCCCTGCACAATCACTA |
| | | CACCCAGAAGTCCCTGTCTCTGTCTCCTGGTGCTGGTGGCGG |
| | | AGGATCTGGCGGAGGCGGATCAGGCGGTGGTGGTTCTCCTG |
| | | GACAGGGAACCCAGTCCGAGAACTCCTGCACACACTTCCCT |
| | | GGCAACCTGCCTAACATGCTGCGGGACCTGAGAGATGCCTTC |
| | | TCCAGAGTGAAAACATTCTTCCAGATGAAGGATCAGCTGGA |
| | | CAACCTGCTGCTGAAAGAGTCCCTGCTGGAAGATTTCAAGG |
| | | GCTACCTGGGCTGTCAGGCCCTGTCCGAGATGATCCAGTTCT |
| | | ACCTGGAAGAAGTGATGCCCCAGGCCGAGAATCAGGACCCT |
| | | GATATCAAGGCCCACGTGAACAGCCTGGGCGAGAACCTGAA |
| | | AACCCTGCGGCTGAGACTGCGGCGGTGCCACAGATTTCTGCC |
| | | CTGCGAGAACAAGTCCAAGGCCGTGGAACAAGTGAAGAACG |
| | | CCTTCAACAAGCTGCAAGAGAAGGGCATCTACAAGGCTATG |
| | | TCCGAGTTCGACATCTTCATCAACTACATCGAGGCCTACATG |
| | | ACCATGAAGATCCGGAAC |
| 39 | Alternative full-length K fusion protein-2X Linker | QVQLVESGGGVVQPGRSLRLSCAASGFIFSSYAMHWVRQAPG<br>NGLEWVAFMSYDGSNKKYADSVKGRFTISRDNSKNTLYLQMN<br>SLRAEDTAVYYCARDRGISAGGNYYYYGMDVWGQGTTVTVS<br>SASTKGPSVFPLAPSSKSTSGGTAALGCLVKDYFPEPVTVSWNS<br>GALTSGVHTFPAVLQSSGLYSLSSVVTVPSSSLGTQTYICNVNH<br>KPSNTKVDKRVEPKSCDKTHTCPPCPAPELLGGPSVFLFPPKPK<br>DTLMISRTPEVTCVVVDVSHEDPEVKFNWYVDGVEVHNAKTK<br>PREEQYNSTYRVVSVLTVLHQDWLNGKEYKCKVSNKALPAPIE<br>KTISKAKGQPREPQVYTLPPSREEMTKNQVSLTCLVKGFYPSDI<br>AVEWESNGQPENNYKTTPPVLDSDGSFFLYSKLTVDKSRWQQ<br>GNVFSCSVMHEALHNHYTQKSLSLSPGKGGGGSGGGGSPGQG<br>TQSENSCTHFPGNLPNMLRDLRDAFSRVKTFFQMKDQLDNLLL<br>KESLLEDFKGYLGCQALSEMIQFYLEEVMPQAENQDPDIKAHV<br>NSLGENLKTLRLRLRRCHRFLPCENKSKAVEQVKNAFNKLQEK<br>GIYKAMSEFDIFINYIEAYMTMKIRN |

In some aspects, the TNFα binding protein is an anti-TNFα antibody, antibody fragments thereof, or antigen-binding fragments, variants, or derivatives thereof. In certain embodiments, the anti-TNFα antibody is a human antibody. In some embodiments, the anti-TNFα antibody is an engineered antibody. In other embodiments, the anti-TNFα antibody is a humanized antibody. In some aspects, the anti-TNFα antibody is a monoclonal antibody. In other aspects, the anti-TNFα antibody is a polyclonal antibody. In certain cases, the anti-TNFα antibody is a mouse antibody. IN other case, the anti-TNFα antibody is a primatized antibody. In yet other aspects, the anti-TNFα antibody is a single-chain antibody. In some embodiments, the anti-TNFα antibody is a chimeric antibody.

Antibodies or antigen-binding fragments, variants, or derivatives thereof of the disclosure include, but are not limited to, polyclonal, monoclonal, mouse, human, humanized, primatized, or chimeric antibodies, single-chain antibodies, epitope-binding fragments, e.g., Fab, Fab' and F(ab')2, Fd, Fvs, single-chain Fvs (scFv), disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to TNFα disclosed herein). ScFv molecules are known in the art and are described, e.g., in U.S. Pat. No. 5,892,019. Immunoglobulin or antibody molecules of the disclosure can be of any type (e.g., IgG, IgE, IgM, IgD, IgA, and IgY), class (e.g., IgGl, IgG2, IgG3, IgG4, IgA1, and IgA2, etc.), or subclass of immunoglobulin molecule.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgGl, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules such as toxins, radioisotopes, etc.

The term "antibody fragment" or "antibody fragment thereof" refers to a portion of an intact antibody. An "antigen-binding fragment" or "antigen-binding fragment thereof" refers to a portion of an intact antibody that binds to an antigen. An antigen-binding fragment can contain the antigenic determining variable regions of an intact antibody. Examples of antibody fragments include, but are not limited to Fab, Fab', F(ab')2, and Fv fragments, linear antibodies, scFvs, VHH antibodies, Camelid antibodies, and single chain antibodies.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example, in U.S. Pat. No. 5,939,598 by Kucherlapati et al. Completely human antibodies are particularly desirable for therapeutic treatment of human patients.

Human antibodies can be made by variety of methods known in the art including phage display methods using antibody libraries derived from human immunoglobulin sequences as described in Vaughan et al., Nat. Biotech. i4:309-314 (1996), Sheets et al., Proc. Nat'l. Acad. Sci. 95:6157-6162 (1998), Hoogenboom and Winter, J. Mol. Biol. 227:381 (1992), and Marks et al., J. Mol. Biol. 222:581 (1991)). Additional examples of phage display methods that can be used to make and use antibodies include those disclosed in Rothe et al., J. Mol. Biol, 376: 1182 (2008), Brinkman et al., J. Immunol Methods 182:41-50 (1995); Ames et al., J. Immunol. Methods 184: 177-186 (1995); Kettleborough et al., Eur. J. Immunol. 24:952-958 (1994); Persic et al., Gene 787:9-18 (1997); Burton et al., Advances in Immunology 57:191-280 (1994): PCT Application No. PCT/GB 1/01 1 4: PCT publications WO 90/02809; WO 91/10737; WO 92/01047; WO 92/18619; WO 93/11236; WO 95/15982; WO 95/20401; and U.S. Pat. Nos. 6,172,197; 5,885,793, 6,521,404; 6,544,731; 6,555,313; 6,582,915; 6,593,081; 6,300,064; 6,653,068; 6,706,484; 7,264,963; 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

In addition, as known in the art, human antibodies can be produced using transgenic mice which are incapable of expressing functional endogenous immunoglobulins, but which can express human immunoglobulin genes. For an overview of this technology, see Lonberg and Huszar, Int. Rev. Immunol. 13:65-93 (1995).

Further techniques available in the art of antibody engineering have made it possible to isolate human antibodies or fragments thereof. For example, human hybridomas can be made as described by Kontermann and Sefan, Antibody Engineering, Springer Laboratory Manuals (2001). Fully human antibodies can likewise be produced by various display technologies, e.g., phage display or other viral display systems. In phage display methods, functional antibody domains are displayed on the surface of phage particles, which carry the polynucleotide sequences encoding them. For example, DNA sequences encoding $V_H$ and $V_L$ regions are amplified from animal cDNA libraries (e.g., human or murine cDNA libraries of lymphoid tissues) or synthetic cDNA libraries. In certain embodiments, the DNA encoding the $V_H$ and $V_L$ regions are joined together by an scFv linker by PGR and cloned into a phagemid vector (e.g., p CANTAB 6 or pComb 3 HSS). The vector is electroporated in E. coli and the E. coli is infected with helper phage. Phage used in these methods are typically filamentous phage including fd and M13, and the $V_H$ or $V_L$ regions are usually recombinantly fused to either the phage gene III or gene VIII. Phage expressing an antigen binding domain that binds to an antigen of interest (i.e., TNFα) can be selected or identified with antigen, e.g., using labeled antigen or antigen bound or captured to a solid surface or bead.

"Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s).

"Human" or "fully human" antibodies also include "human" or "fully human" antibodies, as described above, that comprise, consist essentially of, or consist of, variants (including derivatives) of antibody molecules (e.g., the $V_H$ regions and/or $V_L$ regions) described herein, which antibodies or antigen-binding fragments, variants, or derivatives thereof specifically bind to a TNFα polypeptide or fragment or variant thereof. Standard techniques known to those of skill in the art can be used to introduce mutations in the nucleotide sequence encoding a human anti-TNFα antibody, including, but not limited to, site-directed mutagenesis and PCR-mediated mutagenesis which result in amino acid substitutions. The variants (including derivatives) can encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$CDRl, $V_H$CDR2, $V_H$CDR3, $V_L$ region, $V_L$CDR1, $V_L$CDR2, or $V_L$CDR3.

In certain embodiments, the amino acid substitutions are conservative amino acid substitutions. Alternatively, mutations can be introduced randomly along all or part of the coding sequence, such as by saturation mutagenesis, and the resultant mutants can be screened for biological activity to identify mutants that retain activity (e.g., the ability to bind a TNFα polypeptide, e.g., human, primate, murine, or any combination of human, primate and murine TNFα). Such variants (or derivatives thereof) of "human" or "fully human" antibodies can also be referred to as human or fully human antibodies that are "optimized" or "optimized for antigen binding," and include antibodies that have improved affinity to antigen.

Basic immunoglobulin structures in vertebrate systems are relatively well understood. See, e.g., Harlow et al. (1988) Antibodies: A Laboratory Manual (2nd ed.; Cold Spring Harbor Laboratory Press).

The term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgGl, IgG2, IgG3, IgG4, IgAl, etc. are well characterized and are known to confer functional specialization. Modified versions of each of these classes and isotypes are readily discernable to the skilled artisan in view of the instant disclosure and, accordingly, are within the scope of the instant disclosure. While the following discussion will generally be directed to the IgG class of immunoglobulin molecules, all immunoglobulin classes are clearly within the scope of the present disclosure.

With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

The base of the antibody "Y" is called the $F_c$ (Fragment, crystallizable) region, and is composed of two heavy chains that contribute two or three constant domains depending on the class of the antibody. Thus, the $F_c$ region binds to a specific class of $F_c$ receptors, and other immune molecules, such as complement proteins. Both the light and heavy chains are divided into regions of structural and functional homology. The terms "constant" and "variable" are used functionally. In this regard, it will be appreciated that the variable domains of both the light ($V_L$ or $V_K$) and heavy ($V_H$) chain portions determine antigen recognition and specificity. Conversely, the constant domains of the light chain ($C_L$) and the heavy chain ($C_H1$, $C_H2$ or $C_H3$) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the $C_H3$ and $C_L$ domains comprise the carboxy-terminus of the heavy and light chain, respectively.

The "variable domain" (variable domain of a light chain ($V_L$), variable region of a heavy chain ($V_H$)) as used herein denotes the light and heavy chain which is involved directly in binding the antibody to the target. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the target binding site. The antibody heavy and light chain CDR3 regions play a particularly important role in the binding specificity/affinity of the fusion proteins according to the disclosure and therefore provide a further object of the disclosure.

As indicated above, the "variable region" or "hypervariable region" or "target-binding portion of an antibody" allows the antibody to selectively recognize and specifically bind epitopes on antigens. That is, the $V_L$ domain and $V_H$ domain, or subset of the complementarity determining regions (CDRs) within these variable domains, of an antibody combine to form the variable region that defines a three-dimensional antigen binding site. This quaternary antibody structure forms the antigen binding site present at the end of each arm of the Y. More specifically, the antigen binding site is defined by three CDRs on each of the $V_H$ and $V_L$ chains. In some instances, e.g., certain immunoglobulin molecules derived from camelid species or engineered based on camelid immunoglobulins, a complete immunoglobulin molecule can consist of heavy chains only, with no light chains. See, e.g., Hamers-Casterman et al., Nature 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment.

The remainder of the amino acids in the antigen binding domains, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see below).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest," and by Chothia and Lesk, J. Mol. Biol. 9(5):901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. IMGT (ImMunoGeneTics) also provides a numbering system for the immunoglobulin variable regions, including the CDRs. See, e.g., Lefranc, M. P. et al., Dev. Comp. Immunol. 27: 55-77(2003), which is herein incorporated by reference. The IMGT numbering system was based on an alignment of more than 5,000 sequences, structural data, and characterization of hypervariable loops and allows for easy comparison of the variable and CDR regions for all species. The appropriate amino acid residues that encompass the CDRs as defined by each of the above cited references are set forth below in Table 2 as a comparison. The exact residue numbers that encompass a particular CDR can vary depending on the sequence and size of the CDR. Those skilled in the art can routinely determine which residues comprise a particular CDR given the variable region amino acid sequence of the antibody.

TABLE 2

| | CDR Definitions[1] | | | |
|---|---|---|---|---|
| SEQ ID NO: | Sequence | Kabat | Chothia | IMGT |
| 7 | $V_H$CDR1 | 31-35 | 26-32 | 26-35 |
| 8 | $V_H$CDR2 | 50-56 | 52-58 | 51-57 |
| 9 | $V_H$CDR3 | 95-102 | 95-102 | 93-102 |
| 10 | $V_L$CDR1 | 24-34 | 26-32 | 27-32 |
| 11 | $V_L$CDR2 | 50-56 | 50-52 | 50-52 |
| 12 | $V_L$CDR3 | 89-97 | 91-96 | 89-97 |

[1]Numbering of all CDR definitions in Table 2 is according to the numbering convention set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest."

As used herein, the term "heavy chain portion" includes amino acid sequences derived from an immunoglobulin heavy chain. A polypeptide comprising a heavy chain portion comprises at least one of: a $C_H1$ domain, a hinge (e.g., upper, middle, and/or lower hinge region) domain, a $C_H2$ domain, a $C_H3$ domain, or a variant or fragment thereof. For example, a binding polypeptide for use in the disclosure can comprise a polypeptide chain comprising a $C_H1$ domain; a polypeptide chain comprising a $C_H1$ domain, at least a portion of a hinge domain, and a $C_H2$ domain; a polypeptide chain comprising a $C_H1$ domain and a $C_H3$ domain; a polypeptide chain comprising a CHI domain, at least a portion of a hinge domain, and a $C_H3$ domain, or a polypeptide chain comprising a $C_H1$ domain, at least a portion of a hinge domain, a $C_H2$ domain, and a $C_H3$ domain. In another embodiment, a polypeptide of the disclosure comprises a polypeptide chain comprising a $C_H3$ domain. Further, a binding polypeptide for use in the disclosure can lack at least a portion of a $C_H2$ domain (e.g., all or part of a $C_H2$ domain). As set forth above, it will be understood by one of ordinary skill in the art that these domains (e.g., the heavy chain portions) can be modified such that they vary in amino acid sequence from the naturally occurring immunoglobulin molecule.

In certain embodiments, anti-TNFα antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the disclosure are not identical.

The heavy chain portions of a binding molecule for use in the diagnostic and treatment methods disclosed herein can be derived from different immunoglobulin molecules. For example, a heavy chain portion of a polypeptide can comprise a $C_H1$ domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain, e.g., a kappa or lambda light chain. The light chain portion can comprise at least one of a $V_L$ or $C_L$ domain.

Anti-TNFα antibodies, or antigen-binding fragments, variants, or derivatives thereof disclosed herein can be described or specified in terms of the epitope(s) or portion(s) of an antigen, e.g., a target polypeptide disclosed herein (e.g., full-length or mature TNFα) that they recognize, have affinity for, preferentially bind, or specifically bind. The portion of a target polypeptide that specifically interacts with the antigen binding domain of an antibody is an "epitope," or an "antigenic determinant." A target polypeptide can comprise a single epitope, but typically comprises at least two epitopes, and can include any number of epitopes, depending on the size, conformation, and type of antigen. Furthermore, it should be noted that an "epitope" on a target polypeptide can be or can include non-polypeptide elements, e.g., an epitope can include a carbohydrate side chain.

The minimum size of a peptide or polypeptide epitope for an antibody is thought to be about four to five amino acids. Peptide or polypeptide epitopes can contain at least seven, at least nine, or at least about 15 to about 30 amino acids. Since a CDR can recognize an antigenic peptide or polypeptide in its tertiary form, the amino acids comprising an epitope need not be contiguous, and in some cases, may not even be on the same peptide chain. A peptide or polypeptide epitope recognized by anti-TNFα antibodies of the present disclosure can contain a sequence of at least 4, at least 5, at least 6, at least 7, at least 8, at least 9, at least 10, at least 15, at least 20, at least 25, or between about 15 to about 30 contiguous or non-contiguous amino acids of TNFα.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" can be deemed to have a higher specificity for a given epitope than antibody "B," or antibody "A" can be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody can cross-react with the related epitope.

By way of non-limiting example, an antibody can be considered to bind a first epitope preferentially if it binds said first epitope with a dissociation constant ($K_D$) that is less than the antibody's $K_D$ for the second epitope. In another non-limiting example, an antibody can be considered to bind a first antigen preferentially if it binds the first epitope with an affinity that is at least one order of magnitude less than the antibody's $K_D$ for the second epitope. In another non-limiting example, an antibody can be considered to bind a first epitope preferentially if it binds the first epitope with an affinity that is at least two orders of magnitude less than the antibody's $K_D$ for the second epitope.

In another non-limiting example, an antibody can be considered to bind a first epitope preferentially if it binds the first epitope with an off rate (k(off)) that is less than the antibody's k(off) for the second epitope. In another non-limiting example, an antibody can be considered to bind a first epitope preferentially if it binds the first epitope with an affinity that is at least one order of magnitude less than the antibody's k(off) for the second epitope. In another non-limiting example, an antibody can be considered to bind a first epitope preferentially if it binds the first epitope with an affinity that is at least two orders of magnitude less than the antibody's k(off) for the second epitope. An antibody or antigen-binding fragment, variant, or derivative thereof disclosed herein can be said to bind a target polypeptide disclosed herein (e.g., TNFα, e.g., human, primate, murine, or any combination of human, primate and murine TNFα) or a fragment or variant thereof with an off rate (k(off)) of less than or equal to $5 \times 10^{-2}$ sec$^{-1}$, $10^{-2}$ sec$^{-1}$, $5 \times 10^{-3}$ sec$^{-1}$, or $10^{-3}$ sec$^{-1}$. An antibody of the disclosure can be said to bind a target polypeptide disclosed herein (e.g., TNFα, e.g., human, primate, murine, or any combination of human, primate and murine TNFα) or a fragment or variant thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{5}$ sec$^{-1}$, $5 \times 10^{-6}$ sec$^{-1}$, $10^{-6}$ sec$^{-1}$, $5 \times 10^{-7}$ sec$^{-1}$, or $10^{7}$ sec$^{-1}$.

An antibody or antigen-binding fragment, variant, or derivative thereof disclosed herein can be said to bind a target polypeptide disclosed herein (e.g., TNFα, e.g., human, primate, murine, or any combination of human, primate and murine TNFα) or a fragment or variant thereof with an on rate (k(on)) of greater than or equal to $10^{3}$ M$^{-1}$sec$^{-1}$, $5 \times 10^{3}$ M$^{-1}$sec$^{-1}$, $10^{4}$ M$^{-1}$sec$^{-1}$, or $5 \times 10^{4}$ M$^{-1}$ sec$^{-1}$. An antibody of the disclosure can bind a target polypeptide disclosed herein (e.g., TNFα, e.g., human, primate, murine, or any combination of human, primate and murine TNFα) or a fragment or variant thereof with an on rate (k(on)) greater than or equal to $10^{5}$ M$^{-1}$sec$^{-1}$, $5 \times 10^{5}$ M$^{-1}$sec$^{-1}$, $10^{6}$ M$^{-1}$sec$^{-1}$, or $5 \times 10^{6}$ M$^{-1}$sec$^{-1}$, or $10^{7}$ M$^{-1}$ sec$^{-1}$.

An antibody is said to "competitively inhibit" binding of a reference antibody to a given epitope if it preferentially binds to that epitope or an overlapping epitope to the extent that it blocks, to some degree, binding of the reference antibody to the epitope. Competitive inhibition can be determined by any method known in the art, for example, competition ELISA assays. An antibody can be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al. (1988) Antibodies: A Laboratory Manual (Cold Spring Harbor Laboratory Press, 2nd ed.) pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-TNFα antibodies or antigen-binding fragments, variants, or derivatives thereof of the disclosure can also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross-reactive epitope generally contains many of the same complementary structural features as the inducing epitope, and in some cases, can fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody can be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody can be deemed "highly specific" for a certain epitope, if it does not bind any other analog, ortholog, or homolog of that epitope.

As intended herein, two amino acid sequences or nucleic acid sequences are "identical," "homologous," or "similar" when greater than 80%, preferably greater than 85%, preferably greater than 90% of the amino acids or nucleic acid sequences are identical, or greater than about 90%, preferably greater than 95%, are similar (functionally identical). To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences. In one embodiment, the two sequences are the same length. The determination of percent identity between two sequences can be accomplished using a mathematical algorithm. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

In certain embodiments, anti-TNFα binding proteins, e.g., antibodies or antigen-binding fragments, variants or derivatives thereof of the disclosure can also be described or specified in terms of their binding affinity to a polypeptide of the disclosure, e.g., TNFα, e.g., human, primate, murine, or any combination of human, primate and murine TNFα. Useful binding affinities include those with a dissociation constant or $K_D$ less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In some embodiments, the anti-TNFα binding proteins bind to human TNFα with a dissociation constant or $K_D$ less than 1 nM. In some embodiments, the anti-TNFα binding protein binds to cynomolgus TNFα with a dissociation constant or $K_D$ less than 5 nM. In some embodiments, the anti-TNFα binding protein binds to human TNFα with a dissociation constant or Kd less than 1 nM and binds to cynomolgus TNFα with a dissociation constant or $K_D$ less than 5 nM.

As previously indicated, the subunit structures and three-dimensional configuration of the constant regions of the various immunoglobulin classes are well known. As used herein, the term "$V_H$ domain" includes the amino terminal variable domain of an immunoglobulin heavy chain and the term "$C_H1$ domain" includes the first (most amino terminal) constant region domain of an immunoglobulin heavy chain. The $C_H1$ domain is adjacent to the $V_H$ domain and is amino terminal to the hinge region of an immunoglobulin heavy chain molecule.

As used herein the term "$C_H2$ domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E. A. et al.). The $C_H2$ domain is unique in that it is not closely paired with another domain. Rather, two N-linked branched carbohydrate chains are interposed between the two $C_H2$ domains of an intact native IgG molecule. It is also well documented that the $C_H3$ domain extends from the $C_H2$ domain to the C-terminal of the IgG molecule and comprises approximately 108 residues.

As used herein, the term "hinge region" includes the portion of a heavy chain molecule that joins the $C_H1$ domain to the $C_H2$ domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., J. Immunol., 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the $C_H1$ and $C_L$ regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which can be intact, partial or modified in accordance with the instant disclosure) is obtained from a second species. In certain embodiments the target binding region or site will be from a non-human source (e.g., mouse or primate) and the constant region is human.

As used herein, the term "engineered antibody" refers to an antibody in which the variable domain in either the heavy or light chain or both is altered by at least partial replacement of one or more CDRs from an antibody of known specificity and, if necessary, by partial framework region replacement and sequence changing. Although the CDRs can be derived from an antibody of the same class or even subclass as the antibody from which the framework regions are derived, it is envisaged that the CDRs will be derived from an antibody of different class or from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable domain to transfer the antigen binding capacity of one variable domain to another. Rather, it may only be necessary to transfer those residues that are necessary to maintain the activity of the target binding site.

For example, in certain embodiments, humanization of an anti-TNFα antibody can be essentially performed following the method of Winter and co-workers (Jones et al., Nature 321:522-525 (1986); Riechmann et al., Nature 332:323-321 (1988); Verhoeyen et al., Science 239: 1534-1536 (1988)), by substituting rodent or mutant rodent anti-TNFα CDRs or CDR sequences into the corresponding sequences of a human antibody. See also U.S. Pat. Nos. 5,225,539; 5,585,089; 5,693,761; 5,693,762; 5,859,205; herein incorporated by reference. The resulting humanized anti-TNFα antibody would comprise at least one rodent or mutant rodent CDR within the fully human framework regions of the variable domain of the heavy and/or light chain of the humanized antibody. In some instances, residues within the framework regions of one or more variable domains of the humanized anti-TNFα antibody are replaced by corresponding non-human (for example, rodent) residues (see, e.g., U.S. Pat. Nos. 5,585,089; 5,693,761; 5,693,762; and 6,180,370), in which case the resulting humanized anti-TNFα antibody would comprise partially human framework regions within the variable domain of the heavy and/or light chain.

Furthermore, in some embodiments, humanized antibodies can comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the CDRs correspond to those of a non-human immunoglobulin and all or substantially all of the framework regions are those of a human immunoglobulin sequence. In some instances, the humanized antibody optionally also will comprise at least a portion of an immunoglobulin constant region ($F_c$), typically that of a human immunoglobulin. For further details see Jones et al., Nature 331:522-525 (1986); Riechmann et al., Nature 332:323-329 (1988); and Presta, Curr. Op. Struct. Biol. 2:593-596 (1992); herein incorporated by reference. Accordingly, such "humanized" antibodies can include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, e.g., U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

In certain embodiments, the fusion proteins of the disclosure have an amino acid sequence that has at least 80%, 85%, 88%, 89%, 90%, 91%, 92%, 93%, 94%, or 95% sequence identity to the amino acid sequence of SEQ ID NO: 4. In other embodiments, the fusion proteins of the disclosure share at least 96%, 97%, 98%, 99%, or 100% sequence identity to the amino acid sequence of SEQ ID NO: 4. In additional embodiments, the fusion proteins of the disclosure have an amino acid sequence that has at least 80%, 85%, 88%, 89%, 90%, 91%, 92%, 93%, 94%, or 95% sequence identity to the amino acid sequence of SEQ ID NO: 24. In other embodiments, the fusion proteins of the disclosure share at least 96%, 97%, 98%, 99%, or 100% sequence identity to the amino acid sequence of SEQ ID NO: 24. In additional embodiments, the fusion proteins of the disclosure have an amino acid sequence that has at least 80%, 85%, 88%, 89%, 90%, 91%, 92%, 93%, 94%, or 95% sequence identity to the amino acid sequence of SEQ ID NO: 36. In other embodiments, the fusion proteins of the disclosure share at least 96%, 97%, 98%, 99%, or 100% sequence identity to the amino acid sequence of SEQ ID NO: 36. In additional embodiments, the fusion proteins of the disclosure have an amino acid sequence that has at least 80%, 85%, 88%, 89%, 90%, 91%, 92%, 93%, 94%, or 95% sequence identity to the amino acid sequence of SEQ ID NO: 37. In other embodiments, the fusion proteins of the disclosure share at least 96%, 97%, 98%, 99%, or 100% sequence identity to the amino acid sequence of SEQ ID NO: 37. In further embodiments, the fusion proteins of the disclosure have an amino acid sequence that has at least 80%, 85%, 88%, 89%, 90%, 91%, 92%, 93%, 94%, or 95% sequence identity to the amino acid sequence of SEQ ID NO: 26. In other embodiments, the fusion proteins of the disclosure share at least 96%, 97%, 98%, 99%, or 100% sequence identity to the amino acid sequence of SEQ ID NO: 26. In further embodiments, the fusion proteins of the disclosure have an amino acid sequence that has at least 80%, 85%, 88%, 89%, 90%, 91%, 92%, 93%, 94%, or 95% sequence identity to the amino acid sequence of SEQ ID NO: 27. In other embodiments, the fusion proteins of the disclosure share at least 96%, 97%, 98%, 99%, or 100% sequence identity to the amino acid sequence of SEQ ID NO: 27. In yet additional embodiments, the fusion proteins of the disclosure have an amino acid sequence that has at least 80%, 85%, 88%, 89%, 90%, 91%, 92%, 93%, 94%, or 95% sequence identity to the amino acid sequence of SEQ ID NO: 39. In other embodiments, the fusion proteins of the disclosure share at least 96%, 97%, 98%, 99%, or 100% sequence identity to the amino acid sequence of SEQ ID NO: 39.

In certain embodiments, the TNFα binding molecules of the disclosure share at least 96%, 97%, 98%, 99%, or 100% sequence identity to the amino acid sequence of SEQ ID NO: 5. In further embodiments, the TNFα binding molecules of the disclosure share at least 96%, 97%, 98%, 99%, or 100% sequence identity to the amino acid sequence of SEQ ID NO: 21. In additional embodiments, the TNFα binding molecules of the disclosure share at least 96%, 97%, 98%, 99%, or 100% sequence identity to the amino acid sequence of SEQ ID NO: 29. In certain embodiments, the TNFα binding molecules of the disclosure have an amino acid sequence that has at least 80%, 85%, 88%, 89%, 90%, 91%, 92%, 93%, 94%, or 95% sequence identity to the amino acid sequence for a reference anti-TNFα antibody molecule. The reference anti-TNFα antibody includes, but is not limited to, Golimumab, Etanercept, Adalimumab, Infliximab, Certolizumab pegol, or a modified version, derivative, or variant of these antibodies. In specific embodiments, the reference anti-TNFα antibody is a variant of Golimumab. In further embodiments, the TNFα binding molecules of the disclosure share at least 96%, 97%, 98%, 99%, or 100% sequence identity to the reference antibody.

In certain aspects, a threonine in the light chain CDR2 at position 56 (Kabat numbering) of Golimumab is mutated to isoleucine in the TNFα binding molecule of the disclosure (FIG. 29). In other aspects, an alanine in the heavy chain CDR3 at position 99 (Kabat numbering) of Golimumab is mutated to serine in the TNFα binding molecule of the disclosure (FIG. 29). In yet other aspects, a threonine in the light chain CDR2 at position 56 (Kabat numbering) of Golimumab is mutated to isoleucine or an alanine in the heavy chain CDR3 at position 99 (Kabat numbering) of Golimumab is mutated to seine in the TNFα binding molecule of the disclosure. In still other aspects, a threonine in the light chain CDR2 at position 56 (Kabat numbering) of Golimumab is mutated to isoleucine and an alanine in the heavy chain CDR3 at position 99 (Kabat numbering) of Golimumab is mutated to serine in the TNFα binding molecule of the disclosure. In certain embodiments, the fusion proteins of the disclosure comprise an additional mutation at position 478 (Kabat numbering) of Golimumab. In some aspects, the lysine at position 478 (Kabat numbering) of Golimumab is mutated to alanine (K478A) in the fusion proteins of the disclosure (FIG. 1).

In certain embodiments, the TNFα binding molecule of the disclosure is an isolated antibody or antigen-binding fragment, variant, or derivative thereof comprising, consisting essentially of, or consisting of a heavy chain that has an amino acid sequence that is at least 80%, 85%, 90%, 91%, 92%, 93%, 94%, 95%, 96%, 97%, 98%, 99%, or 100% identical to a heavy chain amino acid sequence of SEQ ID NO: 5, wherein the antibody or antigen binding fragment, variant, or derivative thereof comprises the V$_H$ amino acid sequence of SEQ ID NO: 16 and specifically or preferentially binds to TNFα.

In other embodiments, the TNFα binding molecule of the disclosure is an isolated antibody or antigen-binding fragment, variant, or derivative thereof comprising, consisting essentially of, or consisting of a heavy chain that has an amino acid sequence that is at least 80%, 85%, 90%, 91%, 92%, 93%, 94%, 95%, 96%, 97%, 98%, 99%, or 100% identical to a heavy chain amino acid sequence of SEQ ID NO: 29, wherein the antibody or antigen binding fragment, variant, or derivative thereof comprises the V$_H$ amino acid sequence of SEQ ID NO: 16 and specifically or preferentially binds to TNFα. In yet other embodiments, the TNFα binding molecule of the disclosure is an isolated antibody or antigen-binding fragment, variant, or derivative thereof comprising, consisting essentially of, or consisting of a heavy chain that has an amino acid sequence that is at least 80%, 85%, 90%, 91%, 92%, 93%, 94%, 95%, 96%, 97%, 98%, 99%, or 100% identical to a heavy chain amino acid sequence of SEQ ID NO: 21, wherein the antibody or antigen binding fragment, variant, or derivative thereof comprises the V$_H$ amino acid sequence of SEQ ID NO: 23 and specifically or preferentially binds to TNFα.

In other embodiments, the TNFα binding molecule of the disclosure is an isolated antibody or antigen-binding fragment, variant, or derivative thereof comprising, consisting essentially of, or consisting of a light chain that has an amino acid sequence that is at least 80%, 85%, 90%, 91%, 92%, 93%, 94%, 95%, 96%, 97%, 98%, 99%, or 100% identical to a light chain amino acid sequence of SEQ ID NO: 6, wherein the antibody or antigen binding fragment, variant, or derivative thereof comprises the V$_L$ amino acid sequence of SEQ ID NO: 17 and specifically or preferentially binds to TNFα.

In certain embodiments, the TNFα binding molecule of the disclosure is an isolated antibody or antigen-binding fragment, variant, or derivative thereof comprising, consisting essentially of, or consisting of a V$_H$ domain that has an amino acid sequence that is at least 80%, 85%, 90%, 91%, 92%, 93%, 94%, 95%, 96%, 97%, 98%, 99%, or 100% identical to a V$_H$ amino acid sequence of SEQ ID NO: 16, wherein the antibody or antigen binding fragment, variant, or derivative thereof comprising the $V_H$ domain specifically or preferentially binds to TNFα.

In other embodiments, the TNFα binding molecule of the disclosure is an isolated antibody or antigen-binding fragment, variant, or derivative thereof comprising, consisting essentially of, or consisting of a $V_L$ domain that has an amino acid sequence that is at least 80%, 85%, 90%, 91%, 92%, 93%, 94%, 95%, 96%, 97%, 98%, 99%, or 100% identical to a $V_L$ amino acid sequence of SEQ ID NO: 17, wherein the antibody or antigen binding fragment, variant, or derivative thereof comprising the $V_L$ domain specifically or preferentially binds to TNFα.

In yet other embodiments, the TNFα binding molecule of the disclosure is an isolated antibody or antigen-binding fragment, variant, or derivative thereof comprising, consisting essentially of, or consisting of a heavy chain region and a light chain region that have an amino acid sequence that is at least 80%, 85%, 90%, 91%, 92%, 93%, 94%, 95%, 96%, 97%, 98%, 99%, or 100% identical to the heavy chain and light chain amino acid sequence of SEQ ID NO: 5 and 6, respectively, wherein the antibody or antigen binding fragment, variant, or derivative thereof comprises the $V_H$ amino acid sequence of SEQ ID NO: 16 and $V_L$ amino acid sequence of SEQ ID NO: 17, respectively and specifically or preferentially binds to TNFα.

In other embodiments, the TNFα binding molecule of the disclosure is an isolated antibody or antigen-binding fragment, variant, or derivative thereof comprising, consisting essentially of, or consisting of a heavy chain region and a light chain region that have an amino acid sequence that is at least 80%, 85%, 90%, 91%, 92%, 93%, 94%, 95%, 96%, 97%, 98%, 99%, or 100% identical to the heavy chain and light chain amino acid sequence of SEQ ID NO: 29 and 6, respectively, wherein the antibody or antigen binding fragment, variant, or derivative thereof comprises the $V_H$ amino acid sequence of SEQ ID NO: 16 and $V_L$ amino acid sequence of SEQ ID NO: 17, respectively and specifically or preferentially binds to TNFα.

In additional embodiments, the TNFα binding molecule of the disclosure is an isolated antibody or antigen-binding fragment, variant, or derivative thereof comprising, consisting essentially of, or consisting of a heavy chain region and a light chain region that have an amino acid sequence that is at least 80%, 85%, 90%, 91%, 92%, 93%, 94%, 95%, 96%, 97%, 98%, 99%, or 100% identical to the heavy chain and light chain amino acid sequence of SEQ ID NO: 36 and 6, respectively, wherein the antibody or antigen binding fragment, variant, or derivative thereof comprises the $V_H$ amino acid sequence of SEQ ID NO: 16 and $V_L$ amino acid sequence of SEQ ID NO: 17, respectively and specifically or preferentially binds to TNFα.

In yet other embodiments, the TNFα binding molecule of the disclosure is an isolated antibody or antigen-binding fragment, variant, or derivative thereof comprising, consisting essentially of, or consisting of a heavy chain region and a light chain region that have an amino acid sequence that is at least 80%, 85%, 90%, 91%, 92%, 93%, 94%, 95%, 96%, 97%, 98%, 99%, or 100% identical to the heavy chain and light chain amino acid sequence of SEQ ID NO: 37 and 6, respectively, wherein the antibody or antigen binding fragment, variant, or derivative thereof comprises the $V_H$ amino acid sequence of SEQ ID NO: 16 and $V_L$ amino acid sequence of SEQ ID NO: 17, respectively and specifically or preferentially binds to TNFα.

In yet other embodiments, the TNFα binding molecule of the disclosure is an isolated antibody or antigen-binding fragment, variant, or derivative thereof comprising, consisting essentially of, or consisting of a $V_H$ domain and a $V_L$ domain that have an amino acid sequence that is at least 80%, 85%, 90%, 91%, 92%, 93%, 94%, 95%, 96%, 97%, 98%, 99%, or 100% identical to the $V_H$ and $V_L$ amino acid sequence of SEQ ID NO: 16 and 17, respectively, wherein the antibody or antigen binding fragment, variant, or derivative thereof comprising the $V_H$ and $V_L$ domains specifically or preferentially binds to TNFα.

In certain embodiments, the TNFα binding molecule of the disclosure is an isolated antibody or antigen-binding fragment, variant, or derivative thereof comprising, consisting essentially of, or consisting of a $V_H$ domain that comprises, consists essentially of, or consists of one or more of the $V_H$-CDR1, $V_H$-CDR2, and $V_H$-CDR3 sequences of SEQ ID NOs: 7, 8, and 9, respectively, wherein the antibody or antigen binding fragment, variant, or derivative thereof comprising the $V_H$ and $V_L$ domains specifically or preferentially binds to TNFα. In certain aspects, the TNFα binding molecule of the disclosure is an isolated antibody or antigen-binding fragment, variant, or derivative thereof comprising, consisting essentially of, or consisting of a $V_H$ domain that has an amino acid sequence that is at least 80%, 85%, 90%, 91%, 92%, 93%, 94%, 95%, 96%, 97%, 98%, 99%, or 100% identical to one or more of the $V_H$-CDR1, $V_H$-CDR2, and $V_H$-CDR3 sequences of SEQ ID NOs: 7, 8, and 9, respectively, wherein the antibody or antigen binding fragment, variant, or derivative thereof comprising the $V_H$ and $V_L$ domains specifically or preferentially binds to TNFα. In some embodiments, the TNFα binding molecule of the disclosure is an isolated antibody or antigen-binding fragment, variant, or derivative thereof comprising, consisting essentially of, or consisting of a $V_L$ domain that comprises, consists essentially of, or consists of one or more of the $V_L$-CDR1, $V_L$-CDR2, and $V_L$-CDR3 sequences of SEQ ID NOs: 10, 11, and 12, respectively, wherein the antibody or antigen binding fragment, variant, or derivative thereof comprising the $V_H$ and $V_L$ domains specifically or preferentially binds to TNFα. In some aspects, the TNFα binding molecule of the disclosure is an isolated antibody or antigen-binding fragment, variant, or derivative thereof comprising, consisting essentially of, or consisting of a $V_L$ domain that has an amino acid sequence that is at least 80%, 85%, 90%, 91%, 92%, 93%, 94%, 95%, 96%, 97%, 98%, 99%, or 100% identical to one or more of the $V_L$-CDR1, $V_L$-CDR2, and $V_L$-CDR3 sequences of SEQ ID NOs: 10, 11, and 12, respectively, wherein the antibody or antigen binding fragment, variant, or derivative thereof comprising the $V_H$ and $V_L$ domains specifically or preferentially binds to TNFα. In other embodiments, the TNFα binding molecule of the disclosure is an isolated antibody or antigen-binding fragment, variant, or derivative thereof comprising, consisting essentially of, or consisting of a $V_H$ domain and a $V_L$ domain that comprise, consist essentially of, or consist of one or more of the $V_H$-CDR1, $V_H$-CDR2, $V_H$CDR3, $V_L$-CDR1, $V_L$-CDR2, and $V_L$-CDR3 sequences of SEQ ID NOs: 7, 8, 9, 10, 11, and 12, respectively, wherein the antibody or antigen binding fragment, variant, or derivative thereof comprising the $V_H$ and $V_L$ domains specifically or preferentially binds to TNFα. In yet other embodiments, the TNFα binding molecule of the disclosure is an isolated antibody or antigen-binding fragment, variant, or derivative thereof comprising, consisting essentially of, or consisting of a $V_H$ domain and a $V_L$ domain that comprise, consist essentially of, or consist of, or consist of the $V_H$-CDR1, $V_H$-CDR2, $V_H$CDR3, $V_L$-CDR1, $V_L$-CDR2, and $V_L$-CDR3 sequences of SEQ ID NOs: 7, 8, 9, 10, 11, and 12, respectively, wherein the antibody or antigen binding fragment, variant, or derivative thereof comprising the $V_H$ and $V_L$ domains specifically or preferentially binds to TNFα.

In some embodiments, suitable biologically active variants of the fusion proteins of the disclosure can be used in the methods of the present disclosure. In certain aspects, such variants will retain the IL-10-inhibiting and TNFα-binding properties of the parent fusion protein. Methods for making protein variants are generally available in the art.

Methods for mutagenesis and nucleotide sequence alterations are well known in the art. See, for example, Walker and Gaastra, eds. (1983) Techniques in Molecular Biology (MacMillan Publishing Company, New York): Kunkel, Proc. Natl. Acad. Sci. USA 82:488-492 (1985); Kunkel e al., Methods Enzymol. 154:367-382 (1987); Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest can be found in the model of Dayhoff et al. (1978) in Atlas of Protein Sequence and Structure (Natl. Biomed. Res. Found., Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. Conservative substitutions, such as exchanging one amino acid with another having similar properties, can be beneficial. Examples of conservative amino acid substitutions as taught by the PAM 250 matrix of the Dayhoff et al. model include, but are not limited to, Gly4↔Ala, Val4↔Ile4↔Leu, Asp4↔Glu, Lys4↔Arg, Asn4↔Gln, and Phe4↔Trp4↔Tyr.

Methods for measuring the binding specificity of the TNFα binding molecule, e.g., an antibody or antigen-binding fragment, variant, or derivative thereof, include, but are not limited to, standard competitive binding assays, cytotoxicity assays, ELISA assays, and the like.

When discussed herein whether any particular polypeptide, including the constant regions, CDRs, $V_H$ domains, or $V_L$ domains disclosed herein, is at least 65%, 70%, 75%, 80%, 85%, 90%, 91%, 92%, 93%, 94%, 95%, 96%, 97%, 98%, 99%, or even 100% identical to another polypeptide, the % identity can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) Adv. Appl. Math. 2:482-489, to find the best segment of homology between two sequences. When using BESTFIT or any other sequence alignment program to determine whether a particular sequence is, for example, 95% identical to a reference sequence according to the present disclosure, the parameters are set, of course, such that the percentage of identity is calculated over the full-length of the reference polypeptide sequence and that gaps in homology of up to 5% of the total number of amino acids in the reference sequence are allowed.

For purposes of the present disclosure, percent sequence identity can be determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) Adv. Appl. Math. 2:482-489. A variant can, for example, differ from a reference IL-10 molecule or a reference anti-TNFα antibody by as few as 1 to 15 amino acid residues, as few as 1 to 10 amino acid residues, such as 6-10, as few as 5, as few as 4, 3, 2, or even 1 amino acid residue.

In certain embodiments, the primary amino acid sequence of the fusion proteins, or the antigen-binding moiety thereof, of the disclosure can be augmented by derivatization using sugar moieties (glycosylation) or by other supplementary molecules such as lipids, phosphate, acetyl groups and the like. In other embodiments, it can also be augmented by conjugation with saccharides. Certain aspects of such augmentation can be accomplished through post-translational processing systems of the producing host; other such modifications can be introduced in vitro. Such modifications are included in the definition of a fusion protein used herein so long as the desired properties of the fusion protein are not destroyed. It is expected that such modifications can quantitatively or qualitatively affect the activity, either by enhancing or diminishing the activity of the fusion protein, or the antigen-binding moiety thereof, in the various assays. In further embodiments, individual amino acid residues of the fusion proteins of the disclosure can be modified by oxidation, reduction, or other derivatization, and the fusion proteins can be cleaved to obtain fragments that retain activity. Such alterations that do not destroy the desired properties (e.g., inhibition of IL-10 production and/or activity, binding specificity for TNFα, binding affinity, and associated activity, inhibition of TNFα activity, etc.) do not remove the protein sequence from the definition of fusion proteins of the disclosure as used herein.

The art provides substantial guidance regarding the preparation and use of polypeptide variants. In preparing variants of the fusion proteins of the disclosure, one of skill in the art can readily determine which modifications to the native protein's nucleotide or amino acid sequence will result in a variant that is suitable for use as a therapeutically active component of a pharmaceutical composition used in the methods of the present disclosure.

The constant region of an anti-TNFα antibody can be mutated to alter effector function in a number of ways. For example, see U.S. Pat. No. 6,737,056B1 and U.S. Patent Application Publication No. 2004/0132101A1, which disclose $F_c$ mutations that optimize antibody binding to $F_c$ receptors.

In certain embodiments, the $F_c$ portion of an anti-TNFα antibody can be mutated to decrease effector function using techniques known in the art. For example, the deletion or inactivation (through point mutations or other means) of a constant region domain can reduce $F_c$ receptor binding of the circulating modified antibody. Yet other modifications of the constant region can be used to modify disulfide linkages or oligosaccharide moieties that allow for enhanced localization due to increased antigen specificity or antibody flexibility. The resulting physiological profile, bioavailability and other biochemical effects of the modifications, such as biodistribution and serum half-life, can easily be measured and quantified using well known immunological techniques without undue experimentation.

In certain aspects, fusion proteins of the disclosure also include derivatives that are modified, e.g., by the covalent attachment of any type of molecule to the fusion proteins such that the covalent attachment does not prevent the fusion proteins from retaining their activities (e.g., the ability to inhibit IL-10, and bind TNFα). For example, but not by way of limitation, fusion protein derivatives include proteins that have been modified, e.g., by glycosylation, acetylation, PEGylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, etc. Additionally, the derivative can contain one or more nonclassical amino acids.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to inhibit IL-10, and bind a TNFα molecule).

For example, it is possible to introduce mutations only in framework regions or only in CDR regions of the antibody moiety of the fusion proteins of the disclosure. Introduced mutations can be silent or neutral missense mutations, i.e., have no, or little, effect on the antibody moiety's ability to bind antigen. These types of mutations can be useful to optimize codon usage, or improve a hybridoma's antibody production. Alternatively, non-neutral missense mutations can alter the antibody moiety's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein can routinely be expressed and the functional and/or biological activity of the encoded protein, (e.g., ability to specifically bind at least one epitope of a TNFα molecule) can be determined using techniques described herein or by routinely modifying techniques known in the art.

In certain embodiments, the anti-TNFα antibody moiety of the fusion proteins disclosure comprise at least one optimized complementarity-determining region (CDR). By "optimized CDR" is intended that the CDR has been modified and optimized sequences selected based on the sustained or improved binding affinity and/or anti-TNFα activity that is imparted to an anti-TNFα antibody comprising the optimized CDR. "Anti-TNFα activity" can include, e.g., activity which modulates one or more of the activities associated with TNFα. Anti-TNFα activity can also be attributed to a decrease in incidence or severity of diseases associated with TNFα expression, including, but not limited to, certain types of inflammatory and/or autoimmune conditions. The modifications can involve replacement of amino acid residues within the CDR such that the anti-TNFα antibody moiety retains specificity for the TNFα antigen and has improved binding affinity and/or improved anti-TNFα activity.

In certain embodiments, the present disclosure provides for polynucleotides or nucleic acid molecules encoding the fusion proteins of the disclosure, or fragments, variants, or derivatives thereof.

In certain embodiments are provided one or more polynucleotides that encode the fusion proteins of the disclosure, or fragments, variants, or derivatives thereof. In certain aspects, the polynucleotides are isolated polynucleotides. The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)).

In certain aspects are provided one or more nucleic acids encoding the fusion proteins of the disclosure, or fragments, variants, or derivatives thereof. In certain aspects, the nucleic acids are isolated nucleic acids. The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, that has been removed from its native environment. For example, a recombinant polynucleotide encoding a fusion protein of the disclosure or a fragment thereof, contained in a vector is considered isolated for the purposes of the present disclosure. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present disclosure. Isolated polynucleotides or nucleic acids according to the present disclosure further include such molecules produced synthetically. In addition, a polynucleotide or a nucleic acid can be or can include a regulatory element such as a promoter, ribosome binding site, or a transcription terminator.

As intended herein the term "isolated nucleic acid" or "isolated polynucleotide" refers to any type of isolated nucleic acid or polynucleotide, it can notably be natural or synthetic, DNA or RNA, single or double stranded. In particular, where the nucleic acid is synthetic, it can comprise non-natural modifications of the bases or bonds, in particular for increasing the resistance to degradation of the nucleic acid. Where the nucleic acid is RNA, the modifications notably encompass capping its ends or modifying the 2' position of the ribose backbone so as to decrease the reactivity of the hydroxyl moiety, for instance by suppressing the hydroxyl moiety (to yield a 2'-deoxyribose or a 2'-deoxyribose-2'-fluororibose), or substituting the hydroxyl moiety with an alkyl group, such as a methyl group (to yield a 2'-O-methyl-ribose).

In certain embodiments, a polynucleotide or nucleic acid of the disclosure is a RNA, for example, in the form of a messenger RNA (mRNA).

In certain embodiments, the polynucleotide or nucleic acid is DNA. In the case of DNA, a polynucleotide comprising a nucleic acid that encodes a polypeptide normally can include a promoter and/or other transcription or translation control elements operably associated with one or more coding regions. An operable association is when a coding region for a gene product, e.g., a polypeptide or protein, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

In some embodiments, the nucleic acid molecules of the disclosure comprise, consist essentially of, or consist of a nucleic acid sequence that is at least 70%, 75%, 80%, 85%, 90%, 91%, 92%, 93%, 94%, 95%, 96%, 97%, 98%, 99%, or 100% identical to the amino acid sequence of a reference nucleic acid sequence comprising SEQ ID NO: 18. In other embodiments, the nucleic acid molecules of the disclosure comprise, consist essentially of, or consist of a nucleic acid sequence that is at least 70%, 75%, 80%, 85%, 90%, 91%, 92%, 93%, 94%, 95%, 96%, 97%, 98%, 99%, or 100% identical to the amino acid sequence of a reference nucleic acid sequence comprising SEQ ID NO: 19. In yet other embodiments, the nucleic acid molecules of the disclosure comprise, consist essentially of, or consist of a nucleic acid sequence that is at least 70%, 75%, 80%, 85%, 90%, 91%, 92%, 93%, 94%, 95%, 96%, 97%, 98%, 99%, or 100% identical to the amino acid sequence of a reference nucleic acid sequence comprising SEQ ID NO:28. In additional embodiments, the nucleic acid molecules of the disclosure comprise, consist essentially of, or consist of a nucleic acid sequence that is at least 70%, 75%, 80%, 85%, 90%, 91%, 92%, 93%, 94%, 95%, 96%, 97%, 98%, 99%, or 100% identical to the amino acid sequence of a reference nucleic acid sequence comprising SEQ ID NO: 31. In further embodiments, the nucleic acid molecules of the disclosure comprise, consist essentially of, or consist of a nucleic acid sequence that is at least 70%, 75%, 80%, 85%, 90%, 91%, 92%, 93%, 94%, 95%, 96%, 97%, 98%, 99%, or 100% identical to the amino acid sequence of a reference nucleic acid sequence comprising SEQ ID NO:38. In some embodiments, the nucleic acid coding sequences encoding the fusion proteins of the disclosure are codon optimized for expression in particular cells, such as eukaryotic cells. The eukaryotic cells may be those of or derived from a particular organism, such as a mammal, including but not limited to human, mouse, rat, rabbit, dog, or non-human primate.

In certain embodiments, the nucleic acid molecules encode fusion proteins of the disclosure that comprise a light chain comprising an amino acid sequence that is at least 70%, 75%, 80%, 85%, 90%, 91%, 92%, 93%, 94%, 95%, 96%, 97%, 98%, 99%, or 100% identical to the amino acid sequence of a reference polypeptide sequence comprising the amino acid sequence of SEQ ID NO: 6. In other embodiments, the nucleic acid molecules encoding the fusion proteins of the disclosure comprise an amino acid sequence that is at least 70%, 75%, 80%, 85%, 90%, 91%, 92%, 93%, 94%, 95%, 96%, 97%, 98%, 99%, or 100% identical to the amino acid sequence of a reference polypeptide sequence comprising the amino acid sequence of SEQ ID NO: 20. In yet other embodiments, the nucleic acid molecules encode fusion proteins of the disclosure that comprise a heavy chain comprising an amino acid sequence that is at least 70%, 75%, 80%, 85%, 90%, 91%, 92%, 93%, 94%, 95%, 96%, 97%, 98%, 99%, or 100% identical to the amino acid sequence of a reference polypeptide sequence comprising the amino acid sequence of SEQ ID NO: 5. In still other embodiments, the nucleic acid molecules encode fusion proteins of the disclosure that comprise a heavy chain comprising an amino acid sequence that is at least 80%, 85%, 90%, 91%, 92%, 93%, 94%, 95%, 96%, 97%, 98%, 99%, or 100% identical to the amino acid sequence of a reference polypeptide sequence comprising the amino acid sequence of SEQ ID NO: 29. In further embodiments, the nucleic acid molecules encode fusion proteins of the disclosure that comprise, consist essentially of, or consist of an amino acid sequence that is at least 80%, 85%, 90%, 91%, 92%, 93%, 94%, 95%, 96%, 97%, 98%, 99%, or 100% identical to the amino acid sequence of a reference polypeptide sequence comprising the amino acid sequence of SEQ ID NO: 4. In additional embodiments, the nucleic acid molecules encode fusion proteins of the disclosure that comprise, consist essentially of, or consist of an amino acid sequence that is at least 80%, 85%, 90%, 91%, 92%, 93%, 94%, 95%, 96%, 97%, 98%, 99%, or 100% identical to the amino acid sequence of a reference polypeptide sequence comprising the amino acid sequence of SEQ ID NO: 24. In other embodiments, the nucleic acid molecules encode fusion proteins of the disclosure that comprise, consist essentially of, or consist of an amino acid sequence that is at least 80%, 85%, 90%, 91%, 92%, 93%, 94%, 95%, 96%, 97%, 98%, 99%, or 100% identical to the amino acid sequence of a reference polypeptide sequence comprising the amino acid sequence of SEQ ID NO: 26, 27, 36, 37, or 39. In yet other embodiments, the nucleic acid molecules encode fusion proteins of the disclosure that comprise an amino acid sequence that is at least 80%, 85%, 90%, 91%, 92%, 93%, 94%, 95%, 96%, 97%, 98%, 99%, or 100% identical to the amino acid sequence of a reference polypeptide sequence comprising the amino acid sequence of SEQ ID NO: 6 or 20 and the amino acid sequence of SEQ ID NO: 5 or 29. In certain embodiments, the nucleic acid molecules encode fusion proteins, or fragments, variants, or derivatives thereof that inhibit the production and/or activity of IL-10 and additionally inhibit TNFα activity.

In certain aspects, any of the nucleic acid molecules described above can further include additional nucleic acids, encoding, e.g., a signal peptide to direct secretion of the encoded fusion proteins of the disclosure. In other aspects, the present disclosure includes compositions comprising one or more of the nucleic acid molecules described above.

The nucleic acid molecules of the disclosure can be produced or manufactured by any method known in the art. For example, if the nucleotide sequence of a fusion protein of the disclosure is known, a nucleic acid molecule encoding the fusion protein can be assembled from chemically synthesized oligonucleotides (e.g., as described in Kutmeier et al., Bio Techniques 17:242 (1994)), which, briefly, involves the synthesis of overlapping oligonucleotides containing portions of the sequence encoding the fusion protein, annealing and ligating of those oligonucleotides, and then amplification of the ligated oligonucleotides by PCR.

In other embodiments, a nucleic acid molecule encoding a fusion protein of the disclosure or fragment, variant, or derivative thereof, can be generated from a nucleic acid from a suitable source. In certain embodiments a nucleic acid encoding a fusion protein of the disclosure can be chemically synthesized or obtained from a suitable source (e.g., a cDNA library, or a cDNA library generated from, or nucleic acid, e.g., poly A+ RNA, isolated from, any tissue or cells expressing fusion protein, such as recombinant cells selected to express a protein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes a fusion protein of the disclosure. Amplified nucleic acids generated by PCR can then be cloned into replicable cloning vectors using any method well known in the art.

Once the nucleotide sequence and corresponding amino acid sequence of the fusion protein, or fragment, variant, or derivative thereof is determined, its nucleotide sequence can be manipulated using methods well known in the art for the manipulation of nucleotide sequences, e.g., recombinant DNA techniques, site directed mutagenesis, PCR, etc. (see, for example, the techniques described in Sambrook et al. (1990) Molecular Cloning, A Laboratory Manual (2nd ed.; Cold Spring Harbor Laboratory, Cold Spring Harbor, N.Y.) and Ausubel et al., eds. (1998) Current Protocols in Molecular Biology (John Wiley & Sons, NY), which are both incorporated by reference herein in their entireties), to generate active fusion proteins having a different amino acid sequence, for example to create amino acid substitutions, deletions, and/or insertions.

A nucleic acid molecule encoding a fusion protein of the disclosure, or fragment, variant, or derivative thereof, can be composed of any polyribonucleotide or polydeoxyribonucleotide, which can be unmodified RNA or DNA or modified RNA or DNA. In certain aspects, a nucleic acid molecule encoding a fusion protein, or antigen-binding fragment, variant, or derivative thereof can be composed of single- and double-stranded DNA, DNA that is a mixture of single- and double-stranded regions, single and double-stranded RNA, and RNA that is mixture of single- and double-stranded regions, hybrid molecules comprising DNA and RNA that can be single-stranded or, double-stranded or a mixture of single- and double-stranded regions. In other aspects, a nucleic acid molecule encoding a fusion protein of the disclosure, or fragment, variant, or derivative thereof can be composed of triple-stranded regions comprising RNA or DNA or both RNA and DNA. In other embodiments, a nucleic acid molecule encoding a fusion protein of the disclosure, or fragment, variant, or derivative thereof, can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" or "nucleic acid molecule" embraces chemically, enzymatically, or metabolically modified forms.

A nucleic acid molecule encoding a non-natural variant of a fusion protein of the disclosure, or fragment or derivative thereof can be created by introducing one or more nucleotide substitutions, additions or deletions into the nucleotide sequence of the parent nucleic acid molecule such that one or more amino acid substitutions, additions or deletions are introduced into the encoded protein. In some embodiments, mutations can be introduced by standard techniques, such as site-directed mutagenesis and PCR-mediated mutagenesis. In certain aspects, conservative amino acid substitutions can be made at one or more non-essential amino acid residues.

DNA sequences that encode the fusion proteins of the disclosure, or fragments, variants, or derivatives thereof can be made using reverse transcriptase and DNA polymerase in accordance with well-known methods.

DNA, typically plasmid DNA, can be isolated from the cells using techniques known in the art, restriction mapped and sequenced in accordance with standard, well known techniques set forth in detail, e.g., in the foregoing references relating to recombinant DNA techniques.

Following manipulation of the isolated genetic material to provide fusion proteins of the disclosure, or fragments, variants, or derivatives thereof, the nucleic acid molecules encoding the fusion proteins of the disclosure are typically inserted in an expression vector for introduction into host cells that can be used to produce the desired quantity of the fusion protein.

Recombinant expression of the fusion proteins of the disclosure, or fragments, variants, or derivatives thereof requires construction of an expression vector containing a polynucleotide that encodes the fusion protein. Once a polynucleotide encoding a fusion protein of the disclosure has been obtained, the vector for the production of the fusion protein can be produced by recombinant DNA technology using techniques well known in the art. Thus, methods for preparing a fusion protein by expressing a polynucleotide containing the protein encoding nucleotide sequence are described herein. Methods that are well known to those skilled in the art can be used to construct expression vectors containing fusion protein coding sequences and appropriate transcriptional and translational control signals. These methods include, for example, in vitro recombinant DNA techniques, synthetic techniques, and in vivo genetic recombination. The disclosure, thus, provides replicable vectors comprising a nucleotide sequence encoding a fusion protein of the disclosure, or fragments, variants, or derivatives thereof, operably linked to a promoter.

The term "vector" or "expression vector" is used herein to mean vectors used in accordance with the present disclosure as a vehicle for introducing into and expressing a desired gene in a host cell. As known to those skilled in the art, such vectors can easily be selected from the group consisting of plasmids, phages, viruses and retroviruses. In general, vectors compatible with the instant disclosure will comprise a selection marker, appropriate restriction sites to facilitate cloning of the desired gene and the ability to enter and/or replicate in eukaryotic or prokaryotic cells.

The term "expression" or "expressing" as used herein refers to a process by which a gene produces a biochemical product, for example, a protein. The process includes any manifestation of the functional presence of the gene within the cell including, without limitation, gene knockdown as well as both transient expression and stable expression. It includes without limitation transcription of the gene into messenger RNA (mRNA), and the translation of such mRNA into protein(s). If the final desired product is a biochemical product, expression includes the creation of that biochemical product and any precursors. Expression of a gene produces a "gene product." As used herein, a gene product can be either a nucleic acid, e.g., a messenger RNA produced by transcription of a gene, or a protein, which is translated from a transcript. Gene products described herein further include nucleic acids with "post transcriptional modifications," e.g., polyadenylation, or proteins with "post translational modifications," e.g., methylation, glycosylation, the addition of lipids, association with other protein subunits, proteolytic cleavage, and the like.

In certain embodiments, the disclosure provides vectors comprising the nucleic acid molecules or of the disclosure. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked.

The coding region of the nucleic acids or polynucleotides of the disclosure is cloned into an expression vector. As used herein, a "coding region" is a portion of nucleic acid that consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions of the present disclosure can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode TNFα binding protein and an IL-10 molecule. In addition, a vector, polynucleotide, or nucleic acid of the disclosure can encode heterologous coding regions, either fused or unfused to a nucleic acid encoding a fusion protein of the disclosure, or fragment, variant, or derivative thereof. Heterologous coding regions include without limitation specialized elements or motifs, such as a secretory signal peptide or a heterologous functional domain.

For the purposes of this disclosure, numerous expression vector systems can be employed. For example, one class of vector utilizes DNA elements that are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells that have integrated the DNA into their chromosomes can be selected by introducing one or more markers which allow selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements can also be needed for optimal synthesis of mRNA. These elements can include signal sequences, splice signals, as well as transcriptional promoters, enhancers, and termination signals.

In certain aspects, any expression vector that is capable of eliciting expression in eukaryotic cells can be used in the present disclosure. Examples of suitable vectors include, but are not limited to plasmids pcDNA3, pHCMV/Zeo, pCR3.1, pEF 1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those that express suitably high levels of recombinant proteins is routine experimentation that can be carried out, for example, by robotic systems.

In some embodiments, the expression vectors of the disclosure comprise one or more transcription control regions. A variety of transcription control regions are known to those skilled in the art. These include, without limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to, ribosome binding sites, translation initiation and termination codons, and elements derived from picornaviruses (particularly an internal ribosome entry site, or IRES, also referred to as a CITE sequence).

Nucleic acid coding regions of the present disclosure can be associated with additional coding regions that encode secretory or signal peptides, which direct the secretion of a fusion protein encoded by a polynucleotide of the present disclosure. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that proteins secreted by vertebrate cells generally have a signal peptide fused to the N-terminus of the protein, which is cleaved from the complete or "full-length" protein to produce a secreted or "mature" form of the protein. In certain embodiments, the native signal peptide, e.g., an immunoglobulin heavy chain or light chain signal peptide is used, or a functional derivative of that sequence that retains the ability to direct the secretion of the protein that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse β-glucuronidase.

Once the vector or DNA sequence encoding a fusion protein of the disclosure has been prepared, the expression vector can be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway (1988) "Mammalian Expression Vectors" in Vectors, ed. Rodriguez and Denhardt (Butterworths, Boston, Mass.), Chapter 24.2, pp. 470-472. In certain embodiments, plasmid introduction into the host is via electroporation. The host cells harboring the expression construct are grown under conditions appropriate to the production of the fusion protein, and assayed for fusion protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques, and the transfected cells are then cultured by conventional techniques to produce a fusion protein for use in the methods described herein. Thus, the disclosure includes host cells containing a polynucleotide encoding a fusion protein of the disclosure, operably linked to a heterologous promoter.

The disclosure also provides host cells comprising the nucleic acid molecules or the vectors of the disclosure. As used herein, "host cells" refers to cells that harbor vectors constructed using recombinant DNA techniques and encoding at least one heterologous gene. In descriptions of processes for isolation of recombinant proteins from recombinant hosts, the terms "cell" and "cell culture" are used interchangeably to denote the source of the protein unless it is clearly specified otherwise. In other words, recovery of fusion proteins of the disclosure from the "cells" can mean either from spun down whole cells, or from the cell culture containing both the medium and the suspended cells.

A variety of host-expression vector systems can be utilized to express fusion proteins of the disclosure for use in the methods described herein. Such host-expression systems represent vehicles by which the coding sequences of interest can be produced and subsequently purified, but also represent cells that can, when transformed or transfected with the appropriate nucleotide coding sequences, express a fusion protein of the disclosure in situ. These include, but are not limited to, microorganisms such as bacteria (e.g., *E. coli, B. subtilis*) transformed with recombinant bacteriophage DNA, plasmid DNA or cosmid DNA expression vectors containing fusion protein coding sequences; yeast (e.g., *Saccharomyces, Pichia*) transformed with recombinant yeast expression vectors containing fusion protein coding sequences; insect cell systems infected with recombinant virus expression vectors (e.g., baculovirus) containing fusion protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing fusion protein coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli* or eukaryotic cells, are routinely used for the expression of recombinant fusion proteins. For example, mammalian cells such as Chinese hamster ovary cells (CHO), in conjunction with vectors comprising, e.g., the major intermediate early gene promoter element from human cytomegalovirus are an effective expression system for recombinant proteins (Foecking et al., Gene 45:101 (1986); Cockett et al., Bio/ Technology 8:2 (1990)).

In certain embodiments, the host cell line used for protein expression is of mammalian origin; those skilled in the art are credited with ability to determine particular host cell lines that are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, WI38, R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

In addition, a host cell strain can be chosen that modulates the expression of the inserted nucleic acid sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used.

For long-term, high-yield production of recombinant proteins, stable expression is useful. For example, cell lines that stably express the antibody molecule can be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which stably express the fusion proteins of the disclosure.

A number of selection systems can be used, including, but not limited to, the herpes simplex virus thymidine kinase (Wigler et al., Cell 11:223 (1977)), hypoxanthine-guanine phosphoribosyltransferase (Szybalska and Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan and Berg, Proc. Natl. Acad. Sci. USA 78:2072 (1981)); neo, which confers resistance to the aminoglycoside G-418 (Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260: 926-932 (1993); and Morgan and Anderson, Ann. Rev. Biochem. 62:191-217 (1993); TIB TECH 11(5):155-215 (May, 1993)); and hygro, which confers resistance to hygromycin (Santerre et al., Gene 30:147 (1984). Methods commonly known in the art of recombinant DNA technology which can be used are described in Ausubel et al. (1993) Current Protocols in Molecular Biology (John Wiley & Sons, NY); Kriegler (1990) "Gene Transfer and Expression" in A Laboratory Manual (Stockton Press, NY); Dracopoli et al. (eds) (1994) Current Protocols in Human Genetics (John Wiley & Sons, NY) Chapters 12 and 13; Colberre-Garapin et al. (1981) J. Mol. Biol. 150:1, which are incorporated by reference herein in their entireties.

In vitro production allows scale-up to give large amounts of the desired proteins. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. In certain embodiments, the solutions of proteins can be purified by the customary chromatography methods, for example gel filtration, ion-exchange chromatography, chromatography over DEAE-cellulose or (immuno-) affinity chromatography.

In other embodiments, genes encoding fusion proteins of the disclosure, or fragments, variants, or derivatives thereof are expressed in non-mammalian cells including, without limitations, insect, bacteria or yeast or plant cells. Bacteria that readily take up nucleic acids include members of the Enterobacteriaceae, such as strains of *Escherichia coli* or *Salmonella*; Bacillaceae, such as *Bacillus subtilis*; Pneumococcus; *Streptococcus*, and *Haemophilus influenzae*. In certain aspects, when expressed in bacteria, the heterologous polypeptides typically become part of inclusion bodies. In certain embodiments, heterologous polypeptides are isolated, purified and then assembled into functional molecules.

In bacterial systems, a number of expression vectors can be advantageously selected depending upon the use intended for the recombinant protein molecule being expressed. For example, when a large quantity of the protein proteins of the disclosure is to be produced, for the generation of pharmaceutical compositions, vectors which direct the expression of high levels of fusion protein products that are readily purified can be desirable. Such vectors include, but are not limited, to the *E. coli* expression vector pUR278 (Ruther et al., EMBO J. 2:1791 (1983)), in which the protein coding sequence can be ligated individually into the vector in frame with the lacZ coding region so that a fusion protein is produced; pIN vectors (Inouye and Inouye, Nucleic Acids Res. 13:3101-3109 (1985): Van Heeke and Schuster, J. Biol. Chem. 24:5503-5509 (1989)); and the like. pGEX vectors can also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes can also be used. *Saccharomyces cerevisiae*, or common baker's yeast, is the most commonly used among eukaryotic microorganisms although a number of other strains are commonly available, e.g., *Pichia pastoris.*

For expression in *Saccharomyces*, the plasmid YRp7, for example, (Stinchcomb et al., Nature 282:39 (1979); Kingsman et al., Gene 7:141 (1979); Tschemper et al., Gene 10:157 (1980)) is commonly used. This plasmid already contains the TRP1 gene, which provides a selection marker for a mutant strain of yeast lacking the ability to grow in tryptophan, for example ATCC No. 44076 or PEP4-1 (Jones, Genetics 85:12 (1977)). The presence of the trp 1 lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The protein coding sequence can be cloned individually into non-essential regions (for example the polyhedrin gene) of the virus and placed under control of an AcNPV promoter (for example the polyhedrin promoter).

In certain specific embodiments, the host cell is a bacterial cell. In other embodiments, the host cell is a mammalian cell. In yet other embodiments, the host cell is an insect cell.

In certain embodiments, the recombinant fusion proteins of the disclosure are expressed at a level of at least about 100 ng/ml, least about 1 µg/ml, at least about 10 µg/ml, at least about 20 µg/ml, at least about 25 µg/ml, at least about 50 µg/ml, at least about 100 µg/ml, at least about 1 mg/ml, at least about 10 mg/ml, at least about 100 µg/ml, or at least about 1 g/ml of the host cell. In some embodiments, the fusion proteins of the disclosure are expressed at a level of at least about 25 µg/ml of the host cell. In specific embodiments, the recombinant fusion proteins of the disclosure are expressed at a level of about 25 µg/ml of the host cell.

Once the fusion proteins of the disclosure have been recombinantly expressed, the proteins can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins.

This, in certain aspects the disclosure provides methods for producing the fusion proteins of the disclosure comprising expressing the fusion proteins in a host cell and purifying the fusion protein.

In certain embodiments, a fusion protein of the disclosure is an isolated fusion protein. In other embodiments, a fusion protein is a purified fusion protein. In some embodiments, the disclosure provides a method of producing the fusion proteins of the disclosure comprising expressing the fusion proteins in a host cell and purifying the fusion proteins. By an "isolated" or "purified" fusion protein, or a fragment, variant, or derivative thereof is intended a fusion protein that is not in its natural milieu. No particular level of purification is required. For example, an isolated fusion protein can be removed from its native or natural environment. Recombinantly produced fusion proteins and fusion proteins expressed in host cells are considered isolated for purpose of the disclosure, as are native or recombinant fusion proteins that have been separated, fractionated, or partially or substantially purified by any suitable technique.

In certain embodiments, fusion proteins of the disclosure can include derivatives that are modified, i.e., by the covalent attachment of any type of molecule to the fusion proteins such that covalent attachment does not prevent the activity of the fusion proteins. For example, but not by way of limitation, the fusion protein derivatives include fusion proteins that have been modified, e.g., by glycosylation, acetylation, PEGylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, etc. In certain aspects, the derivative can contain one or more non-classical amino acids.

In some embodiments, the fusion proteins of the disclosure, or fragments, variants, or derivatives thereof can be composed of amino acids joined to each other by peptide bonds or modified peptide bonds, i.e., peptide isosteres, and can contain amino acids other than the 20 gene-encoded amino acids. In certain aspects, for example, the fusion proteins of the disclosure, or fragments, variants, or derivatives thereof can be modified by natural processes, such as posttranslational processing, or by chemical modification techniques that are well known in the art. Such modifications are well described in basic texts and in more detailed monographs, as well as in a voluminous research literature. In certain embodiments, modifications can occur anywhere in the fusion protein molecules, including the peptide backbone, the amino acid sidechains and the amino or carboxyl termini, or on moieties such as carbohydrates. It will be appreciated that the same type of modification can be present in the same or varying degrees at several sites in a given fusion protein of the disclosure. Also, a given fusion protein can contain many types of modifications. In certain aspects, fusion proteins of the disclosure can be branched, for example, as a result of ubiquitination. In other aspects, fusion proteins of the disclosure can be cyclic, with or without branching. Cyclic, branched, and branched cyclic fusion proteins can result from posttranslational natural processes or can be made by synthetic methods. Modifications include, without limitations, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, crosslinking, cyclization, disulfide bond formation, demethylation, formation of covalent crosslinks, formation of cysteine, formation of pyroglutamate, formylation, gamma-carboxylation, glycosylation, GPI anchor formation, hydroxylation, iodination, methylation, myristoylation, oxidation, PEGylation, proteolytic processing, phosphorylation, prenylation, racemization, selenoylation, sulfation, transfer-RNA mediated addition of amino acids to proteins such as arginylation, and ubiquitination. (See, for instance, Proteins—Structure and Molecular Properties, T. E. Creighton, W. H. Freeman and Company, NY; 2nd ed. (1993); Johnson, ed. (1983) Posttranslational Covalent Modification of Proteins (Academic Press, NY), pgs. 1-12; Seifter et al., Meth. Enzymol. 182:626-646 (1990); Rattan et al., Ann. NY Acad. Sci. 663:48-62 (1992)).

In other embodiments, fusion proteins of the disclosure, or fragments, variants, or derivatives thereof can be fused to marker sequences, such as a peptide to facilitate their purification or detection. In some embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

Fusion proteins of the disclosure, or fragments, variants, or derivatives thereof can be prepared using methods that are well known in the art (see for example U.S. Pat. Nos. 5,116,964 and 5,225,538). In some aspects, the precise site at which the fusion is made can be selected empirically to optimize the activity and/or binding characteristics of the fusion proteins. DNA encoding a fusion protein of the disclosure is then transfected into a host cell for expression.

In certain embodiments, fusion proteins of the disclosure, or fragments, variants, or derivatives thereof can be used in non-conjugated form or can be conjugated to at least one of a variety of molecules, e.g., to improve the therapeutic properties of the molecule, to facilitate target detection, or for imaging or therapy of the patient. In some aspects, fusion proteins of the disclosure, or fragments, variants, or derivatives thereof can be labeled or conjugated either before or after purification, or when purification is performed.

Fusion proteins of the disclosure, or fragments, variants, or derivatives thereof can be conjugated to therapeutic agents, prodrugs, peptides, proteins, enzymes, viruses, lipids, biological response modifiers, pharmaceutical agents, or PEG.

Those skilled in the art will appreciate that conjugates can also be assembled using a variety of techniques depending on the selected agent to be conjugated. For example, conjugates with biotin are prepared, e.g., by reacting a binding polypeptide with an activated ester of biotin such as the biotin N-hydroxysuccinimide ester. Similarly, conjugates with a fluorescent marker can be prepared in the presence of a coupling agent, or by reaction with an isothiocyanate, such as fluorescein-isothiocyanate. Conjugates of the fusion proteins of the disclosure, or fragments, variants, or derivatives thereof are prepared in an analogous manner.

The present disclosure further encompasses fusion proteins, or fragments, variants, or derivatives thereof conjugated to a diagnostic or therapeutic agent. In certain aspects, the fusion proteins of the disclosure, or fragments, variants, or derivatives thereof can be used diagnostically to, for example, monitor the development or progression of a disease as part of a clinical testing procedure to, e.g., determine the efficacy of a given treatment and/or prevention regimen. For example, detection can be facilitated by coupling the fusion proteins of the disclosure, or fragments, variants, or derivatives thereof to a detectable substance. Examples of detectable substances include, without limitation, various enzymes, prosthetic groups, fluorescent materials, luminescent materials, bioluminescent materials, radioactive materials, positron emitting metals using various positron emission tomographies, and nonradioactive paramagnetic metal ions. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{111}In$, $^{90}Y$, or $^{99}Tc$.

Fusion proteins of the disclosure, or fragments, variants, or derivatives thereof can be detectably labeled by coupling the fusion proteins, or fragments, variants, or derivatives thereof to a chemiluminescent compound. The presence of the chemiluminescent-tagged fusion protein molecules is determined by detecting the presence of luminescence that arises during the course of a chemical reaction. Examples of particularly useful chemiluminescent labeling compounds include, but are not limited to, luminol, isoluminol, theromatic acridinium ester, imidazole, acridinium salt and oxalate ester.

Fusion proteins of the disclosure, or fragments, variants, or derivatives thereof can be detectably labeled by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md.; Diagnostic Horizons 2:1-7 (1978); Voller et al, J. OM. Pathol. 31:507-520 (1978); Butler, Meth. Enzymol. 73:482-523 (1981); Maggio, ed. (1980) Enzyme Immunoassay, CRC Press, Boca Raton, Fla.; Ishikawa et al., eds. (1981) Enzyme Immunoassay (Kgaku Shoin, Tokyo). The enzyme, which is bound to the fusion protein will react with an appropriate substrate, such as a chromogenic substrate, in such a manner as to produce a chemical moiety which can be detected, for example, by spectrophotometric, fluorimetric or by visual means. Enzymes which can be used to detectably label the fusion proteins of the disclosure include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. In certain aspects, the detection can be accomplished by colorimetric methods which employ a chromogenic substrate for the enzyme. In other aspects, detection can be accomplished by visual comparison of the extent of enzymatic reaction of a substrate in comparison with similarly prepared standards. In some embodiments, the TNFα-binding moiety of the fusion proteins of the disclosure is detectably labeled is by linking the same to an enzyme. In other embodiments, the IL-10 molecule of the fusion proteins of the disclosure is detectably labeled is by linking the same to an enzyme.

In certain aspects, detection is accomplished using any of a variety of other immunoassays. For example, by radioactively labeling the fusion proteins of the disclosure, or fragments, variants, or derivatives thereof, it is possible to detect the fusion proteins through the use of a radioimmunoassay (RIA) (see, for example, Weintraub (March, 1986) Principles of Radioimmunoassays, Seventh Training Course on Radioligand Assay Techniques (The Endocrine Society), which is incorporated by reference herein). In some aspects, the radioactive isotope can be detected by means including, but not limited to, a gamma counter, a scintillation counter, or autoradiography.

In some embodiments, the fusion proteins of the disclosure, or fragments, variants, or derivatives thereof is detectably labeled using fluorescence emitting metals such as [152]Eu, or others of the lanthanide series. These metals can be linked to the binding molecule using such metal chelating groups as diethylenetriaminepentacetic acid (DTPA) or ethylenediaminetetraacetic acid (EDTA).

Techniques for conjugating various moieties to an antibody moiety (e.g., an anti-TNFα antibody) are well known, see, e.g., Amon et al. (1985) "Monoclonal Antibodies for Immunotargeting of Drugs in Cancer Therapy" in Monoclonal Antibodies and Cancer Therapy, ed. Reisfeld et al. (Alan R. Liss, Inc.), pp. 243-56; Hellstrom et al. (1987) "Antibodies for Drug Delivery," in Controlled Drug Delivery, ed. Robinson et al. (2nd ed., Marcel Dekker, Inc.), pp. 623-53); Thorpe (1985) "Antibody Carriers of Cytotoxic Agents in Cancer Therapy: A Review," in Monoclonal Antibodies '84: Biological and Clinical Applications, ed. Pinchera et al., pp. 475-506; "Analysis, Results, and Future Prospective of the Therapeutic Use of Radiolabeled Antibody in Cancer Therapy," in Monoclonal Antibodies for Cancer Detection and Therapy, ed. Baldwin et al., Academic Press, pp. 303-16 (1985); and Thorpe et al. (1982) "The Preparation and Cytotoxic Properties of Antibody-Toxin Conjugates," Immunol. Rev. 62:119-58.

Methods of the disclosure are directed to the use of isolated or purified fusion proteins of the disclosure, including fragments, variants, and derivatives thereof, to treat or prevent an inflammatory or autoimmune disease.

In certain embodiments, the disclosure provides a method of increasing half-life of an IL-10 protein comprising producing the fusion proteins of the disclosure.

In certain aspects, the stability and half-life of the IL-10 moiety is not affected by attaching it with the TNFα binding protein in the fusion proteins of the disclosure. In other aspects, the stability of the IL-10 moiety is increased by attaching it with the TNFα binding protein in the fusion proteins of the disclosure. In some cases, the half-life of the IL-10 moiety is increased by attaching it with the TNFα binding protein in the fusion proteins of the disclosure.

In certain embodiments, the fusion proteins of the disclosure persist for up to a maximum of about 1 day, about 2 days, 5 days, about 7 days, about 10 days, about 14 days, about 21 days, about 28 days, about 1 month, about 2 months, about 3 months, or about 6 months following administration in a subject. In embodiments, the fusion proteins of the disclosure persist for up to a maximum of about 5 days, 7 days, 10 days, 12 days, 14 days, 20 days, or 30 days following an administration to a subject. In embodiments, the fusion proteins of the disclosure persist for up to a maximum of about 14 day following a single intravenous dose in a subject.

In certain aspects, the activity of the TNFα binding protein is not affected by attaching it with the IL-10 moiety in the fusion proteins of the disclosure. In some aspects, the activity of the TNFα binding protein is increased by attaching it with the IL-10 moiety in the fusion proteins of the disclosure. Thus, in some embodiments, the disclosure provides a method of increasing the activity of the TNFα binding protein comprising producing the fusion proteins of the disclosure.

In other embodiments, the fusion proteins of the disclosure are capable of preventing an autoimmune disease or inflammatory disease when administered to a subject in need thereof. In some embodiments, the disclosure provides methods of preventing an autoimmune disease or inflammatory disease in a subject comprising administering to the subject an effective amount of a fusion protein of the disclosure. In other embodiments, the fusion proteins of the disclosure are capable of reducing an autoimmune response or inflammatory response when administered to a subject in need thereof. In addition, the disclosure provides methods of reducing or eliminating an autoimmune response or inflammatory response in a subject comprising administering to the subject an effective amount of a fusion protein of the disclosure. In certain embodiments, the effective amount of the fusion proteins of the disclosure is at least about 0.1 mg/kg of the subject, at least about 0.3 mg/kg of the subject, at least about 0.5 mg/kg of the subject, at least about 1 mg/kg of the subject, at least about 3 mg/kg of the subject, at least about 5 mg/kg of the subject, or at least about 10 mg/kg of the subject. In specific embodiments, the effective amount of the fusion proteins of the disclosure is about 10 mg/kg of the subject.

In certain embodiments, the dose volume of the fusion proteins of the disclosure is at least about 0.1 mL/kg, at least about 1 mL/kg, or at least about 10 mL/kg of the subject. In some embodiments, the dose volume of a fusion protein of the disclosure is at least about 1 mL/kg of the subject. In specific embodiments, the dose volume of a fusion protein of the disclosure is about 1 mL/kg of the subject.

In other embodiments, the fusion proteins of the disclosure are capable of treating an autoimmune disease or inflammatory disease when administered to a subject in need thereof. In some embodiments, the disclosure provides methods of treating an autoimmune disease or inflammatory disease in a subject comprising administering to the subject an effective amount of a fusion protein of the disclosure. In certain embodiments, the effective amount of the fusion proteins of the disclosure is at least about 0.1 mg/kg of the subject, at least about 0.3 mg/kg of the subject, at least about 1 mg/kg of the subject, or at least about 10 mg/kg of the subject. In specific embodiments, the effective amount of the fusion proteins of the disclosure is about 10 mg/kg of the subject.

As used herein, the term "treat" or "treatment" refers to both therapeutic treatment and prophylactic or preventative measures, wherein the object is to prevent or slow down (lessen) an undesired physiological change or condition or disorder, such as the progression of an autoimmune condition. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. In certain embodiments, the term "treating" or "treatment", as used herein, means reversing, alleviating, inhibiting the progress of, or preventing the disorder or condition to which such term applies, or one or more symptoms of such disorder or condition (e.g., autoimmune diseases).

The term "autoimmune condition" or "autoimmune disease" is a disease that can affect any part of the body and encompasses all diseases associated with the immune system attacking the body's own cells and tissue, resulting in chronic inflammation and tissue damage. It is a Type III hypersensitivity reaction in which antibody-immune complexes precipitate and cause a further immune response (Inaki & Lee, Nat Rev Rheumatol, 2010; 6: 326-337).

"Inflammation" or is a complex cellular and biochemical process that occurs in the affected blood vessels and adjacent tissues in response to an injury or abnormal stimulation caused by a physical, chemical, or biologic agent, such as a pathogen, allergen or irritant. The inflammatory process includes local reactions and resulting morphologic changes in tissue; the destruction or removal of the causative agent; and the responses that lead to repair and healing. In most instances, inflammation is a beneficial and transient process, which subsides as the body attacks and overcomes an infectious or other harmful agent. However, in some instances, inflammation can be chronic self-perpetuating process, for example, as part of an ongoing degenerative process (such as arthritis) or autoimmune disease, leading to destruction of tissue. Chronic inflammation is associated with a variety of disorders, including rheumatoid arthritis, atherosclerosis, ischemic heart disease, periodontitis, colitis, and some cancers.

An "inflammatory response" or "inflammatory condition" consists of a cascade of biochemical events, involving the local vascular system and immune system, and various cells within the injured tissue. The process involves the release of numerous cell-derived mediators, including histamine, interferon-gamma, interleukin-8, leukotriene, nitric oxide, prostaglandins, tumor necrosis factor-alpha, and interleukin-1. In particular, interleukin-1 (IL-1) includes a family of cytokines that can stimulate lymphocytes and macrophages, activate phagocytes, increase prostaglandin production, contribute to degeneration of bone joints, increase bone marrow cell proliferation, and are involved in many chronic inflammatory conditions. IL-1 can be generated by macrophages, monocytes, and dendritic cells, and can be part of the inflammatory response against infection.

By "subject" or "patient" or "individual" or "animal" or "mammal," is meant any subject, particularly a mammalian subject, for whom diagnosis, prognosis, or therapy is desired. Mammalian subjects include, without limitations, humans, domestic animals, farm animals, and zoo, sports, or pet animals such as dogs, cats, guinea pigs, rabbits, rats, mice, horses, cattle, and cows. In certain embodiments, the term "patient," "subject," "subject in need thereof," or "patient in need thereof" is intended to mean a human or non-human mammal affected, likely to be affected, or suspected to be affected with an inflammatory condition or disease, or an autoimmune condition or disease.

As used herein, phrases such as "subject in need thereof," "a subject that would benefit from administration the fusion proteins of the disclosure" and "an animal in need of treatment" includes subjects, such as mammalian subjects, that would benefit from administration of the fusion proteins of the disclosure, e.g., for treatment, i.e., palliation or prevention of a disease, with the fusion proteins of the disclosure.

The terms "administration," "administer," and the like, as they apply to, for example, a subject, cell, tissue, organ, or biological sample, refer to contact of, for example, the fusion proteins of the disclosure; a pharmaceutical composition comprising the foregoing, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

By "biological sample" is intended any biological sample obtained from an individual, cell line, tissue culture, or other source of cells potentially expressing a fusion protein of the disclosure, or fragments, variants, or derivatives thereof. Methods for obtaining tissue biopsies and body fluids from mammals are well known in the art.

In certain embodiments, the route of administration of the fusion proteins of the disclosure includes, but is not limited to, oral, intraperitoneal, transdermal, subcutaneous, by intravenous or intramuscular injection, by inhalation, topical, intralesional, infusion; liposome-mediated delivery; topical, intrathecal, gingival pocket, rectal, intrabronchial, nasal, transmucosal, intestinal, ocular or optic delivery, or any other methods known in the art.

Though the present disclosure refers to diagnostic methods and treatment of various diseases and disorders with the fusion proteins of the disclosure, the methods described herein are also applicable to fragments, variants, and derivatives of these fusion proteins that retain the desired properties of the fusion proteins of the disclosure, e.g., capable of treating inflammatory or autoimmune diseases by specifically binding and neutralizing TNFα and additionally inhibiting activity/production of IL-10.

In some embodiments, treatment includes the application or administration of the fusion proteins of the disclosure, or fragments, variants, or derivatives thereof to a subject or patient, or application or administration of the fusion proteins of the disclosure to an isolated tissue or cell line from a subject or patient, where the subject or patient has a disease, a symptom of a disease, or a predisposition toward a disease. In other embodiments, treatment is also intended to include the application or administration of a pharmaceutical composition comprising a fusion protein of the disclosure, or a fragment, variant, or derivative thereof to a subject or patient, or application, or administration of a pharmaceutical composition comprising a fusion protein of the disclosure to an isolated tissue or cell line from a subject or patient, who has a disease, a symptom of a disease, or a predisposition toward a disease. In embodiments, the application or administration of the pharmaceutical is sufficient to treat a disease or a condition. In embodiments, the administering is sufficient to reduce or eliminate at least one symptom of a disease or condition in a subject in need thereof. In embodiments, a disease or condition comprises inflammation. In embodiments, a disease or condition is autoimmune.

In embodiments, the fusion proteins of the disclosure, including fragments, variants, and derivatives thereof are useful for the treatment or prevention of various autoimmune conditions or various inflammatory conditions. For example, therapy with at least one fusion protein of the disclosure causes a physiological response, for example, a reduction in any one of: TNFα, IL-17A, IL-12, IL-12/23p40, IL-6, IFN-γ, GM-CSF, and/or IL-1β that is beneficial with respect to treatment of disease states associated with TNFα-expressing cells in a subject. In embodiments, the reduction is of IFN-γ.

In embodiments, the fusion proteins of the disclosure are formulated as a pharmaceutical composition. In some embodiments, a pharmaceutical composition incorporates particulate forms, protective coatings, protease inhibitors, or permeation enhancers for various routes of administration, including parenteral, pulmonary, nasal and oral. The pharmaceutical compositions can be administered in a variety of unit dosage forms depending upon the method/mode of administration. Suitable unit dosage forms include, but are not limited to, powders, tablets, pills, capsules, lozenges, suppositories, patches, nasal sprays, injectables, implantable sustained-release formulations, etc.

In some embodiments, a pharmaceutical composition comprises an acceptable carrier and/or excipient. A pharmaceutically acceptable carrier includes any solvents, dispersion media, or coatings that are physiologically compatible and that preferably does not interfere with or otherwise inhibit the activity of the therapeutic agent. Preferably, the carrier is suitable for intravenous, intramuscular, oral, intraperitoneal, transdermal, topical, or subcutaneous administration. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers. Other pharmaceutically acceptable carriers and their formulations are well-known and generally described in, for example, Remington: The Science and Practice of Pharmacy, 21$^{st}$ Edition, Philadelphia, PA. Lippincott Williams & Wilkins, 2005. Various pharmaceutically acceptable excipients are well-known in the art and can be found in, for example, Handbook of Pharmaceutical Excipients (5th ed., Ed. Rowe et al., Pharmaceutical Press, Washington, D.C.).

In certain embodiments, the fusion proteins of the disclosure, including fragments, variants, and derivatives thereof are useful for the treatment or prevention of various autoimmune conditions or various inflammatory conditions. For example, therapy with at least one fusion protein of the disclosure causes a physiological response, for example, a reduction in interferon that is beneficial with respect to treatment of disease states associated with TNFα-expressing cells in a subject.

In certain embodiments, the disclosure relates to fusion proteins of the disclosure, or fragments, variants, and derivatives thereof for use as a medicament, in particular for use in the treatment or prophylaxis of an autoimmune condition or disease. In certain aspects, the autoimmune diseases or inflammatory diseases include, but are not limited to, Addison's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune pancreatitis, Autoimmune retinopathy, Autoimmune urticarial, Axonal & neuronal neuropathy (AMAN), Baló disease, Behçet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss, Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Graft vs host disease (GVHD), Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hypogammaglobulinemia, IgA Nephropathy, IgG4-related sclerosing disease, Immune thrombocytopenic purpura (ITP), Inclusion body myositis (IBM), Inflammatory bowel disease (IBD), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multiple sclerosis, Myasthenia gravis, Myositis, Narcolepsy, Neuromyelitis optica, Neutropenia, Non-alcoholic Fatty Liver Disease (NAFLD), Non-alcoholic Steatohepatitis (NASH), Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatic, Polymyositis, Post myocardial infarction syndrome, Post pericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, and Wegener's granulomatosis (or Granulomatosis with Polyangiitis (GPA)). In embodiments, the inflammatory disease is Non-alcoholic Steatohepatitis (NASH). In embodiments, administration of a pharmaceutical composition described herein is sufficient to reduce or eliminate at least one symptom of any of the aforementioned diseases. In embodiments, the at least one symptom comprises inflammation. In embodiments, the disease is NASH and the at least one symptom is selected from the group consisting of: fatigue, abdominal pain, abdominal swelling, enlarged spleen, enlarged blood vessel, red palms, and jaundice. In embodiments, administration of a pharmaceutical composition described herein is sufficient to prevent, reduce, or eliminate a complication of NASH. Complications of NASH comprise: cirrhosis, liver fibrosis, ascites, esophageal varices, hepatic encephalopathy, liver cancer, and/or end-stage liver failure. In embodiments, administration of a pharmaceutical composition described herein is sufficient to prevent liver cancer in a subject having NASH. In embodiments, administration of a pharmaceutical composition described herein is sufficient to prevent liver failure in a subject having NASH. In embodiments, administration of a pharmaceutical composition described herein is sufficient to reduce or prevent liver fibrosis in a subject having NASH. In embodiments, administration of a pharmaceutical composition described herein is sufficient to reduce or prevent ascites in a subject having NASH.

In some aspects, in accordance with the methods of the present disclosure, at least one fusion protein of the disclosure, or fragments, variants, and derivatives thereof is used to promote a positive therapeutic response with respect to an autoimmune response. By "positive therapeutic response" with respect to autoimmune treatment is intended an improvement in the disease in association with the activity of these fusion proteins, or fragments, variants, or derivatives thereof, and/or an improvement in the symptoms associated with the disease. In certain embodiments, a reduction in T cell proliferation is observed with fusion protein treatment. In other embodiments, a decrease in one or more pro-inflammatory cytokines including, but not limited to, IL-17A, IL-12, IL-12/23p40, IL-6, IL-1beta, IFN-γ, TNFα, and/or GM-CSF is observed, or a decrease in one or more symptoms associated with the autoimmune or inflammatory disease is observed with fusion protein treatment. In some aspects, an improvement in the disease can be characterized as a complete response. By "complete response" is intended an absence of clinically detectable disease with normalization of any previously test results. Such a response must persist for at least one month following treatment according to the methods of the disclosure. In other aspects, an improvement in the disease can be categorized as being a partial response.

In certain embodiments is provided method of inhibiting production of one or more pro-inflammatory cytokines in a cell by the fusion proteins of the disclosure. In certain aspects, is provided a method of inhibiting production of one or more pro-inflammatory cytokines comprising incubating a cell secreting the one or more pro-inflammatory cytokines with an effective amount of a fusion protein of the disclosure. The terms "inhibit," "inhibition," and the like include partial as well as complete inhibition.

In certain embodiments, the fusion proteins of the disclosure show an increased inhibitory effect on pro-inflammatory cytokine production than a molar equivalent of IL-10 (mIL10), a TNFα binding protein, or the codelivery of a molar equivalent of IL-10 molecule and a TNFα binding protein (mIL10+anti-TNFα). In certain cases, the fusion proteins of the disclosure show a greater than additive, i.e. synergistic, inhibitory effect on pro-inflammatory cytokine production than a molar equivalent of IL-10 (mIL10), a TNFα binding protein, or the codelivery of a molar equivalent of IL-10 molecule and a TNFα binding protein (mIL10+anti-TNFα). In certain aspects, the fusion proteins of the disclosure show an at least 10 fold, at least 100 fold, at least 1,000 fold, or at least 10,000 fold increased inhibitory effect on pro-inflammatory cytokine production than the codelivery of a molar equivalent of IL-10 molecule and a TNFα binding protein (mIL10+anti-TNFα).

In other embodiments, the fusion proteins of the disclosure show an increased inhibitory effect on pro-inflammatory cytokine production than at least the molar equivalent of IL-10, a TNFα binding protein, or the codelivery of at least the molar equivalent of IL-10 molecule and a TNFα binding protein. In certain cases, the fusion proteins of the disclosure show a greater than additive, i.e. synergistic, inhibitory effect on pro-inflammatory cytokine production than at least the molar equivalent of IL-10 molecule, a TNFα binding protein, or the codelivery of at least the molar equivalent of IL-10 molecule and a TNFα binding protein. In embodiments, the fusion proteins of the disclosure show an at least 10 fold, 20 fold, 30 fold, 40 fold, 50 fold, 70 fold, 100 fold, 150 fold, 200 fold, 300 fold, 500 fold, 700 fold, 900 fold, 1,000 fold, or at least 10,000 fold increased inhibitory effect on pro-inflammatory cytokine production than the codelivery of at least the molar equivalent of IL-10 and a TNFα binding protein.

In yet other embodiments, the fusion proteins of the disclosure show an increased inhibitory effect on pro-inflammatory cytokine production than a molar equivalent of IL-10 (mIL10), a TNFα binding protein, or the codelivery of a molar equivalent of IL-10 molecule and a TNFα binding protein (mIL10+anti-TNFα). In certain cases, the fusion proteins of the disclosure show a greater than additive, i.e. synergistic, inhibitory effect on pro-inflammatory cytokine production than a molar equivalent of IL-10 (mIL10), a TNFα binding protein, or the codelivery of a molar equivalent of IL-10 molecule and a TNFα binding protein (mIL10+anti-TNFα). In certain aspects, the fusion proteins of the disclosure show an at least 10 fold, 20 fold, 30 fold, 40 fold, 50 fold, 70 fold, 100 fold, 150 fold, 200 fold, 300 fold, 500 fold, 700 fold, 900 fold, 1,000 fold, or at least 10,000 fold increased inhibitory effect on pro-inflammatory cytokine production than the codelivery of a molar equivalent of IL-10 molecule and a TNFα binding protein (mIL10+anti-TNFα).

In yet other embodiments, the fusion proteins of the disclosure show an increased inhibitory effect on pro-inflammatory cytokine production than a molar equivalent of IL-10 (mIL10), a TNFα binding protein, or the codelivery of a molar equivalent of IL-10 molecule and a TNFα binding protein (mIL10+anti-TNFα). In certain cases, the fusion proteins of the disclosure show a greater than additive, i.e. synergistic, inhibitory effect on pro-inflammatory cytokine production than molar equivalents of IL-10 (mIL10), a TNFα binding protein, or the codelivery of molar equivalents of IL-10 molecule and a TNFα binding protein (mIL10+anti-TNFα). In certain aspects, the fusion proteins of the disclosure show an at least 10 fold, 20 fold, 30 fold, 40 fold, 50 fold, 70 fold, 100 fold, 150 fold, 200 fold, 300 fold, 500 fold, 700 fold, 900 fold, 1,000 fold, or at least 10,000 fold increased inhibitory effect on pro-inflammatory cytokine production than the codelivery of molar equivalents of IL-10 molecule and a TNFα binding protein (mIL10+anti-TNFα).

In certain embodiments, the present disclosure provides methods for inhibiting one or more pro-inflammatory cytokine production in a subject comprising administering to the subject an effective amount of one or more fusion proteins of the disclosure, or one or more of the pharmaceutical compositions of the disclosure. In some embodiments, the one or more inflammatory cytokines include, but are not limited to, TNFα, IL-17A, IL-12, IL-12/23p40, IL-6, IFN-γ, GM-CSF, or IL-1β.

In other aspects, the fusion proteins of the disclosure are capable of reducing T cell proliferation in a subject. Thus, in certain embodiments the present disclosure provides methods for inhibiting T cell proliferation in a subject comprising administering to the subject an effective amount of one or more fusion proteins of the disclosure, or one or more of the pharmaceutical compositions of the disclosure.

In certain embodiments, the fusion proteins of the disclosure show an increased inhibitory effect on T cell proliferation over molar equivalents of IL-10 (mIL10), a TNFα binding protein, or the codelivery of molar equivalents of IL-10 molecule and a TNFα binding protein (mIL10+anti-TNFα). In certain cases, the fusion proteins of the disclosure show a greater than additive, i.e. synergistic, inhibitory effect on pro-inflammatory cytokine production over molar equivalents of IL-10 (mIL10), a TNFα binding protein, or the codelivery of molar equivalents of IL-10 molecule and a TNFα binding protein (mIL10+anti-TNFα). In certain aspects, the fusion proteins of the disclosure show an at least 10 fold, at least 100 fold, at least 1,000 fold, or at least 10,000 fold increased inhibitory effect on T cell proliferation than the codelivery of molar equivalents of IL-10 molecule and a TNFα binding protein (mIL10+anti-TNFα).

In other embodiments, the fusion proteins of the disclosure show an increased inhibitory effect on T cell proliferation than at least the molar equivalent of IL-10, a TNFα binding protein, or the codelivery of at least the molar equivalent of IL-10 molecule and a TNFα binding protein. In certain cases, the fusion proteins of the disclosure show a greater than additive, i.e. synergistic, inhibitory effect on pro-inflammatory cytokine production than at least the molar equivalent of IL-10 molecule, a TNFα binding protein, or the codelivery of at least the molar equivalent of IL-10 molecule and a TNFα binding protein. In certain aspects, the fusion proteins of the disclosure show an at least 10 fold, 20 fold, 30 fold, 40 fold, 50 fold, 70 fold, 100 fold, 150 fold, 200 fold, 300 fold, 500 fold, 700 fold, 900 fold, 1,000 fold, or at least 10,000 fold increased inhibitory effect on T cell proliferation than the codelivery of at least one molar equivalent of IL-10 and a TNFα binding protein.

In yet other embodiments, the fusion proteins of the disclosure show an increased inhibitory effect on T cell proliferation over molar equivalents of IL-10 (mIL10), a TNFα binding protein, or the codelivery of molar equivalents of IL-10 molecule and a TNFα binding protein (mIL10+anti-TNFα). In certain cases, the fusion proteins of the disclosure show a greater than additive, i.e. synergistic, inhibitory effect on pro-inflammatory cytokine production than molar equivalents of IL-10 (mIL10), a TNFα binding protein, or the codelivery of molar equivalents of IL-10 molecule and a TNFα binding protein (mIL10+anti-TNFα). In certain aspects, the fusion proteins of the disclosure show an at least 10 fold, 20 fold, 30 fold, 40 fold, 50 fold, 70 fold, 100 fold, 150 fold, 200 fold, 300 fold, 500 fold, 700 fold, 900 fold, 1,000 fold, or at least 10,000 fold increased inhibitory effect on T cell proliferation than the codelivery of molar equivalents of IL-10 molecule and a TNFα binding protein (mIL10+anti-TNFα).

In some embodiments, the fusion proteins of the disclosure, or fragments, variants, and derivatives thereof also find use in the treatment of inflammatory diseases, autoimmune diseases, and deficiencies and/or disorders of the immune system.

In certain aspects, clinical response can be assessed using screening techniques such as magnetic resonance imaging (MRI) scan, X-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, a subject undergoing therapy with the fusion proteins of the disclosure, or fragments, variants, and derivatives thereof can experience the beneficial effect of an improvement in one or more symptoms associated with the disease.

In further embodiments, the fusion proteins of the disclosure, or fragments, variants, and derivatives thereof are used for diagnostic monitoring of protein levels in tissue as part of a clinical testing procedure, e.g., to determine the efficacy of a given treatment regimen. In some aspects, detection is facilitated by coupling the fusion proteins of the disclosure to a detectable substance. Examples of detectable substances include, without limitation, various enzymes, prosthetic groups, fluorescent materials, luminescent materials, bioluminescent materials, and radioactive materials. Examples of suitable enzymes include, but are not limited to, horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

Methods of preparing and administering the fusion proteins of the disclosure, or fragments, variants, and derivatives thereof to a subject in need thereof are well known to or are readily determined by those skilled in the art.

In some aspects, the disclosure provides a pharmaceutical composition comprising a fusion protein of the disclosure and one or more pharmaceutically acceptable excipients. In certain embodiments, the fusion proteins of the disclosure, or fragments, variants, and derivatives thereof can be administered in a pharmaceutically effective amount for the in vivo treatment of diseases such as inflammatory or autoimmune diseases. In this regard, it will be appreciated that the fusion proteins of the disclosure will be formulated so as to facilitate administration and promote stability of the active agent. In certain aspects, pharmaceutical compositions in accordance with the present disclosure can comprise a pharmaceutically acceptable, nontoxic, sterile carrier.

For the purposes of the instant application, a "pharmaceutically effective amount" or "effective amount" of a fusion protein of the disclosure, or fragments, variants, and derivatives thereof shall be held to mean an amount sufficient to achieve effective binding to a target and to achieve a benefit, e.g., to ameliorate symptoms of a disease or condition or to detect a substance or a cell.

Pharmaceutical compositions suitable for injectable should be sterile and should be fluid to the extent that easy syringability exists. It should be stable under the conditions of manufacture and storage and will beneficially be preserved against the contaminating action of microorganisms, such as bacteria and fungi. In some aspects, prevention of the action of microorganisms can be achieved by various antibacterial and antifungal agents. Suitable formulations for use in the therapeutic methods disclosed herein are described in Remington's Pharmaceutical Sciences (Mack Publishing Co.) 16th ed. (1980).

In keeping with the scope of the present disclosure, the fusion proteins of the disclosure, or fragments, variants, and derivatives thereof can be administered to a human or other animal in accordance with the aforementioned methods of treatment in an amount sufficient to produce a therapeutic effect. In certain aspects, the fusion proteins of the disclosure, or fragments, variants, and derivatives thereof can be administered to such human or other animal in a conventional dosage form prepared by combining the antibody or antigen-binding fragment, variant, or derivative thereof of the disclosure with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables.

By "therapeutically effective dose or amount" or "effective amount" is intended an amount of a fusion protein of the disclosure, or fragments, variants, and derivatives thereof that when administered brings about a positive therapeutic response with respect to treatment of a patient with a disease or condition to be treated.

Therapeutically effective doses of the compositions of the present disclosure, for treatment of, e.g., autoimmune diseases vary depending upon many different factors, including means of administration, target site, physiological state of the patient, whether the patient is human or an animal, other medications administered, and whether treatment is prophylactic or therapeutic. In certain aspects, the subject is a human. In embodiments, a subject has NASH. In embodiments, a subject has NASH and at least one additional disease or condition (e.g. diabetes, advanced age, and/or abdominal fatty deposits). In embodiments, non-human mammals including transgenic mammals can also be treated. In some embodiments, treatment dosages are titrated to optimize safety and efficacy.

The present disclosure also provides for the use of the fusion proteins of the disclosure, or fragments, variants, and derivatives thereof in the manufacture of a medicament for treating an inflammatory disease or autoimmune disease.

The disclosure further provides diagnostic methods useful during diagnosis of certain types of autoimmune diseases, which involves measuring the expression level of TNFα protein or transcript in tissue or other cells or body fluid from an individual and comparing the measured expression level with a standard TNFα expression level in normal tissue or body fluid, whereby an increase in the expression level compared to the standard is indicative of a disorder.

The fusion proteins of the disclosure, or fragments, variants, and derivatives thereof can be assayed for immunospecific binding by any method known in the art. In certain embodiments, the immunoassays that are used include, but are not limited to, competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. Such assays are routine and well known in the art (see, e.g., Ausubel et al., eds, (1994) Current Protocols in Molecular Biology (John Wiley & Sons, Inc., NY) Vol. 1, which is incorporated by reference herein in its entirety). Exemplary immunoassays are described briefly below (but are not intended by way of limitation).

The fusion proteins of the disclosure, or fragments, variants, and derivatives thereof, additionally, can be employed histologically, as in immunofluorescence, immunoelectron microscopy or non-immunological assays, for in situ detection of ILT7 protein or conserved variants or peptide fragments thereof. In situ detection can be accomplished by removing a histological specimen from a patient, and applying thereto a labeled fusion protein of the disclosure, or fragments, variants, and derivatives thereof applied by overlaying the labeled fusion protein (or fragment) onto a biological sample. Through the use of such a procedure, it is possible to determine not only the presence of TNFα, or conserved variants or peptide fragments, but also its distribution in the examined tissue. Using the present disclosure, those of ordinary skill will readily perceive that any of a wide variety of histological methods (such as staining procedures) can be modified in order to achieve such in situ detection.

Immunoassays and non-immunoassays for TNFα gene products or conserved variants or peptide fragments thereof typically comprise incubating a sample, such as a biological fluid, a tissue extract, freshly harvested cells, or lysates of cells which have been incubated in cell culture, in the presence of a detectably labeled fusion protein of the disclosure, or fragments, variants, and derivatives thereof capable of binding to TNFα or conserved variants or peptide fragments thereof, and detecting the bound fusion protein of the disclosure, or fragments, variants, and derivatives thereof by any of a number of techniques well known in the art.

In certain embodiments, the biological sample can be brought in contact with and immobilized onto a solid phase support or carrier such as nitrocellulose, or other solid support which is capable of immobilizing cells, cell particles or soluble proteins. In some aspects, the support can then be washed with suitable buffers followed by treatment with the detectably labeled fusion protein of the disclosure, or fragment, variant, or derivative thereof. In certain aspects, the solid phase support can then be washed with the buffer a second time to remove unbound antibody. In some embodiments, the fusion proteins of the disclosure are optionally subsequently labeled. The amount of bound label on solid support can then be detected by conventional means.

By "solid phase support or carrier" is intended any support capable of binding a fusion protein of the disclosure, or fragment, variant, or derivative thereof. Well-known supports or carriers include, but are not limited to, glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present disclosure. The support material can have virtually any possible structural configuration so long as the coupled molecule is capable of binding to an antigen or an antibody. Thus, the support configuration can be spherical, as in a bead, or cylindrical, as in the inside surface of a test tube, or the external surface of a rod. Alternatively, the surface can be flat such as a sheet, test strip, etc. Exemplary supports include polystyrene beads. Those skilled in the art will know many other suitable carriers for binding antibody or antigen, or will be able to ascertain the same by use of routine experimentation.

The binding activity of the fusion proteins of the disclosure, or fragments, variants, or derivatives thereof can be determined according to well-known methods. Those skilled in the art will be able to determine operative and optimal assay conditions for each determination by employing routine experimentation.

The binding affinity of the proteins of the disclosure, or fragments, variants, or derivatives thereof to an antigen and the off-rate of such an interaction can be determined by competitive binding assays. One example of a competitive binding assay is a radioimmunoassay comprising the incubation of labeled antigen (e.g., $^3$H or $^{125}$I) with the fusion proteins of the disclosure in the presence of increasing amounts of unlabeled antigen, and the detection of the fusion protein bound to the labeled antigen. The affinity of the fusion proteins of the disclosure for a particular antigen and the binding off-rates can be determined from the data by scatchard plot analysis. Competition with a second binding protein can also be determined using radioimmunoassays. In this case, the antigen is incubated with a fusion protein of the disclosure that is conjugated to a labeled compound (e.g., $^3$H or $^{125}$I) in the presence of increasing amounts of an unlabeled second binding protein.

There are a variety of methods available for measuring the affinity of a binding protein-antigen interaction, but relatively few for determining rate constants. Most of the methods rely on either labeling the binding protein or antigen, which inevitably complicates routine measurements and introduces uncertainties in the measured quantities.

Surface plasmon resonance (SPR) as performed on BIACORE® offers a number of advantages over conventional methods of measuring the affinity of binding protein-antigen interactions: (i) no requirement to label either binding protein or antigen; (ii) binding proteins do not need to be purified in advance, cell culture supernatant can be used directly; (iii) real-time measurements, allowing rapid semi-quantitative comparison of different binding protein interactions, are enabled and are sufficient for many evaluation purposes; (iv) biospecific surface can be regenerated so that a series of different binding proteins can easily be compared under identical conditions; (v) analytical procedures are fully automated, and extensive series of measurements can be performed without user intervention. BIA applications Handbook, version AB (reprinted 1998), BIACORE® code No. BR-1001-86, BIAtechnology Handbook, version AB (reprinted 1998), BIACORE® code No. BR-1001-84. SPR based binding studies require that one member of a binding pair be immobilized on a sensor surface. The binding partner immobilized is referred to as the ligand. The binding partner in solution is referred to as the analyte. In some cases, the ligand is attached indirectly to the surface through binding to another immobilized molecule, which is referred as the capturing molecule. SPR response reflects a change in mass concentration at the detector surface as analytes bind or dissociate.

Based on SPR, real-time BIACORE® measurements monitor interactions directly as they happen. The technique is well suited to determination of kinetic parameters. Comparative affinity ranking is simple to perform, and both kinetic and affinity constants can be derived from the sensorgram data.

When analyte is injected in a discrete pulse across a ligand surface, the resulting sensorgram can be divided into three essential phases: (i) Association of analyte with ligand during sample injection; (ii) Equilibrium or steady state during sample injection, where the rate of analyte binding is balanced by dissociation from the complex; (iii) Dissociation of analyte from the surface during buffer flow.

The association and dissociation phases provide information on the kinetics of analyte-ligand interaction ($k_a$ and $k_d$, the rates of complex formation and dissociation, $k_d/k_a=K_D$). The equilibrium phase provides information on the affinity of the analyte-ligand interaction ($K_D$).

BIA evaluation software provides comprehensive facilities for curve fitting using both numerical integration and global fitting algorithms. With suitable analysis of the data, separate rate and affinity constants for interaction can be obtained from simple BIACORE® investigations. The range of affinities measurable by this technique is very broad ranging from mM to pM.

Epitope mapping with BIACORE®, in contrast to conventional techniques using radioimmunoassay, ELISA or other surface adsorption methods, does not require labeling or purified antibodies, and allows multi-site specificity tests using a sequence of several monoclonal antibodies. Additionally, large numbers of analyses can be processed automatically.

Pair-wise binding experiments test the ability of two binding proteins to bind simultaneously to the same antigen. Binding proteins directed against separate epitopes will bind independently, whereas binding proteins directed against identical or closely related epitopes will interfere with each other's binding. These binding experiments with BIACORE® are straightforward to carry out.

Peptide inhibition is another technique used for epitope mapping. This method can complement pair-wise protein binding studies, and can relate functional epitopes to structural features when the primary sequence of the antigen is known. Peptides or antigen fragments are tested for inhibition of binding of different binding proteins to immobilized antigen. Peptides that interfere with binding of a given binding protein are assumed to be structurally related to the epitope defined by that binding protein.

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press)

(1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

NUMBERED EMBODIMENTS

Notwithstanding the appended claims, the following numbered embodiments are also contemplated by the instant disclosure.

1. A fusion protein comprising a first and second domain, with the first domain comprising a Tumor Necrosis Factor α (TNFα) binding protein and the second domain comprising an interleukin-10 (IL-10) molecule.

2. The fusion protein of embodiment 1, wherein the TNFα binding protein is positioned at N-terminus of the IL-10 molecule.

3. The fusion protein of embodiment 2, wherein the TNFα binding protein is linked via its C-terminus end to N-terminus end of the IL-10 molecule.

4. The fusion protein of embodiment 1, wherein the TNFα binding protein is directly linked to the IL-10 molecule.

5. The fusion protein of embodiment 1, wherein the TNFα binding protein is linked to the IL-10 molecule via a linker.

6. The fusion protein of embodiment 1, wherein the IL-10 molecule comprises an amino acid sequence selected from the group consisting of the amino acid sequences of SEQ ID NOs: 1 and 25.

7. The fusion protein of embodiment 6, wherein the IL-10 molecule comprises the amino acid sequence of SEQ ID NO: 1.

8. The fusion protein of embodiment 1, wherein the TNFα binding protein comprises an amino acid sequence selected from the group consisting of the amino acid sequences of SEQ ID NOs: 5 and 29.

9. The fusion protein of embodiment 8, wherein the TNFα binding protein comprises the amino acid sequence of SEQ ID NO: 29.

10. The fusion protein of embodiment 5, wherein the linker comprises an amino acid sequence selected from the group consisting of the amino acid sequences of SEQ ID NOs: 2, 3, 13, 14, 15, 32, 33, 34, and 35.

11. The fusion protein of embodiment 10, wherein the linker comprises the amino acid sequence of SEQ ID NO: 34.

12. The fusion protein of embodiment 5, wherein the fusion protein comprises an amino acid sequence selected from the group consisting of the amino acid sequences of SEQ ID NOs: 4, 24, 26, 27, 36, 37, and 39.

13. The fusion protein of embodiment 12, wherein the fusion protein comprises the amino acid sequence of SEQ ID NO: 24.

14. The fusion protein of embodiment 12, wherein the fusion protein comprises the amino acid sequence of SEQ ID NO: 37.

15. The fusion protein of embodiment 1, wherein the TNFα binding protein binds to the same epitope of TNFα as an antibody comprising a heavy chain variable region (VH) of SEQ ID NO: 16 and a light chain variable region (VL) of SEQ ID NO: 17.

16. The fusion protein of embodiment 1, wherein the fusion protein competitively inhibits the binding to TNFα of an antibody comprising a VH of SEQ ID NO: 16 and a VL of SEQ ID NO: 17.

17. The fusion protein of embodiment 1, wherein the IL-10 molecule binds to an IL-10 receptor.

18. The fusion protein of embodiment 1, wherein the IL-10 molecule binds to a cell expressing an IL-10 receptor.

19. The fusion protein of embodiment 1, wherein the fusion protein consists of the TNFα binding protein and one IL-10 molecule.

20. The fusion protein of embodiment 1, wherein the fusion protein further comprises at least one additional IL-10 molecule.

21. The fusion protein of embodiment 20, wherein the fusion protein comprises two IL-10 molecules.

22. A nucleic acid encoding the fusion protein of embodiment 1.

23. A vector comprising the nucleic acid of embodiment 22.

24. A host cell comprising the nucleic acid of embodiment 20 or the vector of embodiment 23.

25. The host cell of embodiment 24, wherein the host cell is a bacterial cell.

26. The host cell of embodiment 24, wherein the host cell is a mammalian cell.

27. A pharmaceutical composition comprising: a) the fusion protein of embodiment 1; and b) one or more pharmaceutically acceptable excipients.

28. A method of treating a subject with an autoimmune disease or inflammatory disease comprising administering to the subject an effective amount of the fusion protein of embodiment 1.

29. The method of embodiment 28, wherein the autoimmune disease or inflammatory disease is selected from a group consisting of Addison's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune pancreatitis, Autoimmune retinopathy, Autoimmune urticarial, Axonal & neuronal neuropathy (AMAN), Baló disease, Behçet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss, Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Graft vs host disease (GVHD), Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hypogammalglobulinemia, IgA Nephropathy, IgG4-related sclerosing disease, Immune thrombocytopenic purpura (ITP), Inclusion body myositis (IBM), Inflammatory bowel disease (IBD), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multiple sclerosis, Myasthenia gravis, Myositis, Narcolepsy, Neuromyelitis optica, Neutropenia, Non-alcoholic Fatty Liver Disease (NAFLD), Non-alcoholic Steatohepatitis (NASH), Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatic, Polymyositis, Post myocardial infarction syndrome, Post pericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, and Wegener's granulomatosis (or Granulomatosis with Polyangiitis (GPA)).

30. The method of embodiment 29, wherein the inflammatory disease is NASH.

31. A method of reducing an autoimmune response or inflammatory response in a subject comprising administering to the subject an effective amount of the fusion protein of embodiment 1.

32. A method of producing the fusion protein of embodiment 1 comprising expressing the fusion protein in a host cell and purifying the fusion protein.

33. A method of inhibiting T cell proliferation comprising incubating a peripheral blood mononuclear cell (PBMC) with an effective amount of the fusion protein of embodiment 1.

34. A method of inhibiting T cell proliferation in a subject comprising administering to the subject an effective amount of the fusion protein of embodiment 1 or the pharmaceutical composition of embodiment 27.

35. The method of embodiment 34, wherein the fusion protein shows an increased inhibitory effect on T cell proliferation than at least one molar equivalent of IL-10 (mIL10), a TNFα binding protein, or codelivery of at least one molar equivalent of IL-10 molecule and a TNFα binding protein (mIL10+anti-TNFα).

36. The fusion protein of embodiment 34, wherein the fusion protein shows an at least 10 fold, at least 100 fold, at least 1,000 fold, or at least 10,000 fold better inhibitory effect on T cell proliferation than a codelivery of at least one molar equivalent of IL-10 molecule and a TNFα binding protein (mIL10+anti-TNFα).

37. A method of inhibiting production of one or more pro-inflammatory cytokines comprising incubating a cell secreting one or more pro-inflammatory cytokines with an effective amount of the fusion protein of embodiment 1.

38. A method of inhibiting production of one or more pro-inflammatory cytokines in a subject comprising administering to the subject an effective amount of the fusion protein of embodiment 1.

39. The method of embodiment 37, wherein the fusion protein shows an increased inhibitory effect on pro-inflammatory cytokine production than at least one molar equivalent of IL-10 (mIL10), a TNFα binding protein, or codelivery of at least one molar equivalent of IL-10 molecule and a TNFα binding protein (mIL10+anti-TNFα).

40. The method of embodiment 39, wherein the fusion protein shows an at least 10 fold, at least 100 fold, at least 1,000 fold, or at least 10,000 fold increased inhibitory effect on pro-inflammatory cytokine production than codelivery of at least one molar equivalent of IL-10 molecule and a TNFα binding protein (mIL10+anti-TNFα).

41. The method of embodiment 40, wherein the one or more pro-inflammatory cytokines are selected from a group consisting of TNFα, IL-17A, IL-12, IL-12/23p40, IL-6, IFN-γ, GM-CSF, and IL-1β.

42. The method of embodiment 28, wherein the effective amount of the fusion protein is at least about 0.1 mg/kg of the subject.

43. The method of embodiment 28, wherein the effective amount of the fusion protein is at least about 0.3 mg/kg of the subject.

44. The method of embodiment 28, wherein the effective amount of the fusion protein is at least about 1 mg/kg of the subject.

45. The method of embodiment 28, wherein the effective amount of the fusion protein is at least about 3 mg/kg of the subject.

46. The method of embodiment 28, wherein the effective amount of the fusion protein is at least about 10 mg/kg of the subject.

47. A fusion protein comprising a first and second domain, wherein the first domain comprises a Tumor Necrosis Factor $\alpha$ (TNF$\alpha$) binding protein, and wherein the second domain comprises interleukin-10 (IL-10).

48. The fusion protein of embodiment 47, wherein the TNF$\alpha$ binding protein is positioned at an N-terminus of the IL-10.

49. The fusion protein of embodiment 48, wherein the TNF$\alpha$ binding protein is linked via its C-terminus end to the N-terminus of the IL-10.

50. The fusion protein of any one of embodiments 47-49, wherein the TNF$\alpha$ binding protein is directly linked to the IL-10.

51. The fusion protein of any one of embodiments 47-49, wherein the TNF$\alpha$ binding protein is linked to the IL-10 via a linker.

52. The fusion protein of any one of embodiments 47-51, wherein the IL-10 comprises an amino acid sequence comprising at least 80% identity to a sequence selected from the group consisting of SEQ ID NOs: 1 and 25.

53. The fusion protein of embodiment 52, wherein the IL-10 comprises an amino acid sequence comprising at least 85%, 90%, 95%, 97%, 98%, 99%, or 100% identity to a sequence selected from the group consisting of SEQ ID NOs: 1 and 25.

54. The fusion protein of embodiment 53, wherein the IL-10 comprises the sequence of SEQ ID NO: 1.

55. The fusion protein of any one of embodiments 47-54, wherein the TNF$\alpha$ binding protein comprises an amino acid sequence comprising at least 80% identity to a sequence selected from the group consisting of SEQ ID NOs: 5 and 29.

56. The fusion protein of embodiment 55, wherein the TNF$\alpha$ binding protein comprises an amino acid sequence comprising at least 85%, 90%, 95%, 97%, 98%, 99%, or 100% identity to a sequence selected from the group consisting of SEQ ID NOs: 5 and 29.

57. The fusion protein of embodiment 56, wherein the TNF$\alpha$ binding protein comprises the sequence of SEQ ID NO: 29.

58. The fusion protein of any one of embodiments 51-57, wherein the linker comprises an amino acid sequence comprising at least 80% identity to a sequence selected from the group consisting of SEQ ID NOs: 2, 3, 13, 14, 15, 32, 33, 34, and 35.

59. The fusion protein of embodiment 58, wherein the linker comprises an amino acid sequence comprising at least 85%, 90%, 95%, 97%, 98%, 99%, or 100% identity to a sequence selected from the group consisting of SEQ ID NOs: 2, 3, 13, 14, 15, 32, 33, 34, and 35.

60. The fusion protein of embodiment 59, wherein the linker comprises the amino acid sequence of SEQ ID NO: 34.

61. The fusion protein of any one of embodiments 51-60, wherein the fusion protein comprises an amino acid sequence comprising at least 80% identity to a sequence selected from the group consisting of SEQ ID NOs: 4, 24, 26, 27, 36, 37, and 39.

62. The fusion protein of embodiment 61, wherein the fusion protein comprises an amino acid sequence comprising at least 85%, 90%, 95%, 97%, 98%, 99%, or 100% identity to a sequence selected from the group consisting of SEQ ID NOs: 4, 24, 26, 27, 36, 37, and 39.

63. The fusion protein of embodiment 62, wherein the fusion protein comprises the amino acid sequence of SEQ ID NO: 24.

64. The fusion protein of embodiment 62, wherein the fusion protein comprises the amino acid sequence of SEQ ID NO: 37.

65. The fusion protein of any one of embodiments 47-64, wherein the TNF$\alpha$ binding protein binds to the same epitope of TNF$\alpha$ as an antibody comprising a heavy chain variable region ($V_H$) of SEQ ID NO: 16 and a light chain variable region ($V_L$) of SEQ ID NO: 17.

66. The fusion protein of any one of embodiments 47-65, wherein the fusion protein competitively inhibits the binding to TNF$\alpha$ of an antibody comprising a $V_H$ of SEQ ID NO: 16 and a $V_L$ of SEQ ID NO: 17.

67. The fusion protein of any one of embodiments 47-66, wherein the IL-10 binds to an IL-10 receptor.

68. The fusion protein of any one of embodiments 47-66, wherein the IL-10 binds to a cell expressing an IL-10 receptor.

69. The fusion protein of any one of embodiments 47-68, wherein the fusion protein consists of the TNF$\alpha$ binding protein and the IL-10.

70. The fusion protein of any one of embodiments 47-68, wherein the fusion protein further comprises at least one additional IL-10.

71. The fusion protein of any one of embodiments 47-68, wherein the fusion protein comprises two IL-10.

72. The fusion protein of any one of embodiments 47-71, wherein the TNF$\alpha$ binding protein is a TNF$\alpha$ binding protein fragment.

73. The fusion protein of any one of embodiments 47-71, wherein the IL-10 is an IL-10 fragment.

74. A nucleic acid that comprises a sequence that encodes the fusion protein of any one of embodiments 47-73.

75. A vector comprising the nucleic acid of embodiment 74.

76. A host cell comprising the nucleic acid of embodiment 74 or the vector of embodiment 75.

77. The host cell of embodiment 76, wherein the host cell is a bacterial cell.

78. The host cell of embodiment 76, wherein the host cell is a mammalian cell.

79. A pharmaceutical composition comprising: (a) the fusion protein of any one of embodiments 47-73; and (b) one or more pharmaceutically acceptable excipients.

80. The pharmaceutical composition of embodiment 79, wherein the pharmaceutical composition is in unit dose form.

81. A method of treating a disease or condition, the method comprising administering the pharmaceutical composition of any one of embodiments 79-80 to a subject in need thereof thereby treating the disease or condition.

82. The method of embodiment 81, wherein the administering is sufficient to reduce or eliminate at least one symptom of the disease or condition in the subject in need thereof.

83. The method of any one of embodiments 81-82, wherein the disease or condition comprises inflammation.

84. The method of any one of embodiments 81-82, wherein the disease or condition is autoimmune.

85. A method of treating a subject with an autoimmune disease or inflammatory disease comprising administering to the subject an effective amount of the fusion protein of any one of embodiments 47-73; or the pharmaceutical composition of any one of embodiments 79-80, thereby treating the autoimmune disease or inflammatory disease.

86. The method of embodiment 85, wherein the autoimmune disease or inflammatory disease is selected from a group consisting of: Addison's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune pancreatitis, Autoimmune retinopathy, Autoimmune urticarial, Axonal & neuronal neuropathy (AMAN), Baló disease, Behçet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss, Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Graft vs host disease (GVHD), Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hypogammaglobulinemia, IgA Nephropathy, IgG4-related sclerosing disease, Immune thrombocytopenic purpura (ITP), Inclusion body myositis (IBM), Inflammatory bowel disease (IBD), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multiple sclerosis, Myasthenia gravis, Myositis, Narcolepsy, Neuromyelitis optica, Neutropenia, Non-alcoholic Fatty Liver Disease (NAFLD), Non-alcoholic Steatohepatitis (NASH), Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatic, Polymyositis, Post myocardial infarction syndrome, Post pericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, and Wegener's granulomatosis (or Granulomatosis with Polyangiitis (GPA)).

87. The method of embodiment 86, wherein the subject has an inflammatory disease, and wherein the inflammatory disease is NASH.

88. A method of reducing an autoimmune response or inflammatory response in a subject in need thereof comprising administering to the subject in need thereof an effective amount of: the fusion protein of any one of embodiments 47-73; or the pharmaceutical composition of any one of embodiments 79-80.

89. A method of producing the fusion protein of any one of embodiments 47-73, the method comprising: expressing the fusion protein in a host cell; and purifying the fusion protein.

90. A method of isolating a fusion protein, the method comprising: contacting a host cell with the nucleic acid of embodiment 74 or the vector of embodiment 75 thereby transforming the host cell; and purifying the fusion protein encoded by the nucleic acid or the vector, thereby isolating the fusion protein.

91. A method of inhibiting T cell proliferation comprising contacting a peripheral blood mononuclear cell (PBMC) with an effective amount of the fusion protein of any one of embodiments 47-73.

92. A method of inhibiting T cell proliferation in a subject in need thereof comprising administering to the subject in need thereof an effective amount of: the fusion protein of any one of embodiments 47-73; or the pharmaceutical composition of any one of embodiments 79-80, thereby inhibiting the T cell proliferation in the subject in need thereof.

93. The method of embodiment 92, wherein the fusion protein shows an increased inhibitory effect on T cell proliferation as compared to: a) at least one molar equivalent of IL-10 (mIL10); b) a TNFα binding protein; or c) codelivery of at least one molar equivalent of IL-10 or a fragment thereof and a TNFα binding protein (mIL10+anti-TNFα).

94. The method of embodiment 93, comprising c), wherein the increased inhibitory effect comprises at least 10 fold, at least 100 fold, at least 1,000 fold, or at least 10,000 fold increased inhibition on T cell proliferation as compared to the codelivery of the at least one molar equivalent of the mIL10+anti-TNFα.

95. A method of inhibiting production of one or more pro-inflammatory cytokines comprising contacting a cell secreting one or more pro-inflammatory cytokines with an effective amount of the fusion protein of any one of embodiments 47-73.

96. A method of inhibiting production of one or more pro-inflammatory cytokines in a subject in need thereof comprising administering to the subject in need thereof an effective amount of: the fusion protein of any one of embodiments 47-73; or the pharmaceutical composition of any one of embodiments 79-80, thereby inhibiting production of the one or more pro-inflammatory cytokines in the subject in need thereof.

97. The method of embodiment 96, wherein the fusion protein shows an increased inhibitory effect on pro-inflammatory cytokine production as compared to: a) at least one molar equivalent of IL-10 (mIL10); b) a TNFα binding protein; or c) codelivery of at least one molar equivalent of IL-10 and a TNFα binding protein (mIL10+anti-TNFα).

98. The method of embodiment 97, comprising c), wherein the fusion protein shows an at least 10 fold, at least 100 fold, at least 1,000 fold, or at least 10,000 fold increased inhibitory effect on pro-inflammatory cytokine production as compared to the codelivery of the at least one molar equivalent of the mIL10+anti-TNFα.

99. The method of embodiment 98, wherein the one or more pro-inflammatory cytokines are selected from a group consisting of TNFα, IL-17A, IL-12, IL-12/23p40, IL-6, IFN-γ, GM-CSF, and IL-1β.

100. The method of any one of embodiments 96-99, wherein the effective amount of the fusion protein is at least about 0.1 mg/kg of the subject in need thereof.

101. The method of any one of embodiments 96-100, wherein the effective amount of the fusion protein is at least about 0.3 mg/kg of the subject in need thereof.

102. The method of any one of embodiments 96-101, wherein the effective amount of the fusion protein is at least about 1 mg/kg of the subject in need thereof.

103. The method of any one of embodiments 96-102, wherein the effective amount of the fusion protein is at least about 3 mg/kg of the subject in need thereof.

104. The method of any one of embodiments 96-103, wherein the effective amount of the fusion protein is at least about 10 mg/kg of the subject in need thereof.

The following examples are offered by way of illustration and not by way of limitation.

EXAMPLES

Example 1: Preparation and Cloning of the Anti-TNFα-Antibody-IL-10 Fusion Construct Anti-TNFα-Antibody Cloning The variable genes of anti-TNFα-antibody with double mutation of T56I (CDR2, VL) and A99S (CDR3, VH) were synthesized from GeneArt, Thermo Fisher Scientific. The VH and VL gene were digested by BsrGI/SalI and BssHII/BsiWI, respectively, and cloned sequentially (VH first and then VL) into an expression vector bearing the constant region of IgG1/kappa that was digested with the same restriction enzymes. Both heavy and light chains are under the control of respective CMV immediate/early enhancer/promoter. Recombinant clones were identified by colony PCR using primers complementary to the 5′ and 3′ends of the recombinant gene inserts and further verified by DNA sequencing.

Construction of Anti-TNFα-Antibody-IL-10Fusion

The gene for the C-terminal 7 amino acids (LSLSPGA) of Fc, (G4S)₃S linker or the (G4S)₃linker, and human IL-10 was synthesized by GeneArt. The last amino acid of Fc was changed from K to A (K478A, Fc). The gene was digested by AflII/EcoRI and ligated into the pOE vector containing the anti-TNFα-antibody. The construct was confirmed by colony PCR and further validated by DNA sequencing with the IL-10 gene fused to the C-terminus of the anti-TNFα-antibody heavy chain.

Example 2: Expression of the Anti-TNFα-Antibody-IL-10 Fusion Protein

Two different fusion protein constructs ("K" fusion construct and "A" fusion construct) were synthesized and their expression levels were determined. Each construct comprised an IL-10 moiety linked to each heavy chain carboxy-terminus of an anti-TNFα antibody via a linker molecule. The linker molecule comprised the amino acid sequence: GGGGSGGGGSGGGGSS (SEQ ID NO:14) or GGGGSGGGGSGGGGS (SEQ ID NO:34). The K fusion construct has the amino acid sequence of SEQ ID NO:4 or 36, and the A fusion construct has the amino acid sequence of SEQ ID NO:24 or 37. The heavy chain of the K fusion construct has the amino acid sequence of SEQ ID NO:5. The heavy chain of the A fusion construct has the amino acid sequence of SEQ ID NO:29. As such, the A fusion protein has an additional lysine to alanine substitution at position 478 (K478A) in the heavy chain as compared to the K fusion protein (FIG. 1A).

Expression of the K fusion protein construct yielded 88% of the protein monomer with a concomitant loss of 45% of the protein (FIG. 1B). In contrast, expression of the A fusion protein construct yields 99% of the protein monomer, with 0% loss (FIG. 1C). The protein expression level of the A fusion protein construct was determined to be μ25 μg/ml. The A fusion protein was used in the cynomolgus monkey studies described below.

Example 3: Binding Specificity of the Anti-TNFα-Antibody-IL-10 Fusion Proteins The binding specificity for TNFα and IL-10 receptor of the K fusion protein and the A fusion protein was determined. Anti-TNFα antibody and IgG1 molecules were used as controls in these binding studies. The K fusion protein, the A fusion protein, and the anti-TNFα antibody all showed comparable binding to TNFα. No TNFα binding was observed for the IgG1 molecule (FIG. 2A). The K fusion protein and the A fusion protein, but not the anti-TNFα antibody and the IgG1 molecule showed binding to the IL-10 receptor (FIG. 2B). Therefore, the K fusion protein and the A fusion protein both exhibited binding specificity to TNFα as well as the IL-10receptor.

Example 4: Purification of the Anti-TNFα-Antibody-IL-10 Fusion Protein

The pOE plasmid containing the anti-TNFα-antibody-IL-10 fusion construct from Example 1 was transfected in CHO-G22 cells. CHO-G22 cells were cultured with 25 μM L-methionine sulfoximine and 100 μg/mL hygromycin in proprietary CHO medium at 37° C., 5% CO2, and 80% humidity. One day prior to transfection, CHO-G22 cells were diluted to 1×10⁶ cells/mL in proprietary CHO medium without hygromycin and L-methionine sulfoximine and grown overnight. 500 μg of plasmid were diluted into 7.5 mL of 150 mM NaCl, and 2.5 mL of 1 mg/mL PEI-max was mixed with 5 mL of the 150 mM NaCl solution. The DNA and PEI-max solutions were combined and incubated for 1 min at room temperature before adding to 500 mL of 2×10⁶ CHO-G22 cells. The transfected cells were grown for 24 hr. as described above. Thereafter the temperature was changed to 34° C. and supplemented with 500 mL of proprietary CHO medium. The culture medium was collected 14 days after transfection. The anti-TNFα-antibody-IL-10 fusion protein was purified from the culture medium using protein A affinity chromatography. The purified anti-TNFα-antibody-IL-10 fusion protein was subsequently buffer exchanged using dialysis in PBS pH 7.2.

Figure 4:
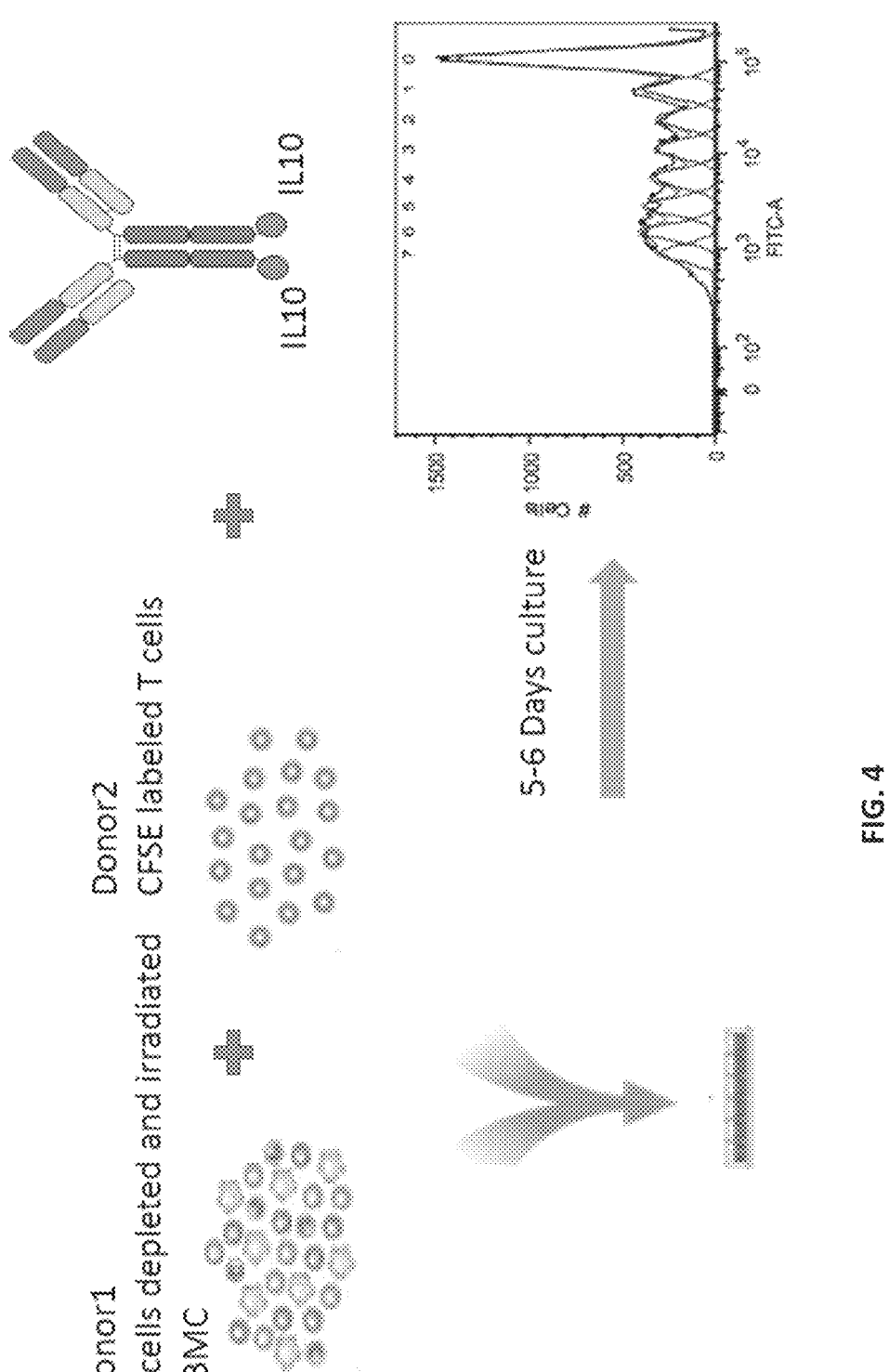
FIG. 4 shows an allogenic mixed lymphocyte reaction (MLR) assay design to study the effect of an anti-TNFα-antibody-IL-10 fusion protein on T cell proliferation. In brief, in an MLR assay, T cells from one donor will proliferate in the presence of antigen presenting cells (APCs) from a different or allogenic donor. This is caused by the recognition of an HLA mismatch between two unrelated donors, which provokes an immune response from the T cells. MLR can be used as a means of inducing generalized stimulation/activation of T cells in culture.

Example 5: Effect of the Fusion Protein on T Cell Proliferation in an Allogenic Mixed Lymphocyte Reaction (MLR) Assay Allogenic Mixed Lymphocyte Reaction Assay Design Allogenic Mixed Lymphocyte Reaction (MLR) is an in vitro cellular immune assay that occurs between two allogeneic lymphocyte populations (same species but genetically distinct) (FIG. 4). A one-way allogenic MLR was used to test whether T cell proliferation is increased or inhibited in response to the anti-TNFα-antibody-IL-10 fusion protein of the disclosure. Therefore, the proliferative response is a functional test, which demonstrates how T-cells are affected by the fusion protein. T cells in the assay were tested for proliferation in the presence of an isotype control antibody, molar equivalents of an anti-TNFα antibody, or molar equivalents of IL-10 (2IL10), the codelivery of molar equivalents of IL-10 and an anti-TNFα antibody (2IL10+anti-TNFα), or the anti-TNFα-antibody-IL-10 protein (FIGS. 5 and 6).

To perform the allogenic MLR, peripheral blood mononuclear cells (PBMCs) from one individual (Donor 1) were isolated using a standard protocol (see, e.g., WO2011068896 A1). The isolated PBMCs were depleted of T cells using T cell specific magnetic beads and irradiated to inhibit proliferation of cells from donor 1. The T cell-depleted PBMCs from Donor 1 were then mixed with carboxyfluorescein succinimidyl ester (CFSE)-labeled T cells from another individual (Donor 2), and the mixed lymphocytes were cultured for 5-6 days. CFSE is an effective and popular means to monitor lymphocyte division (Quah, B J, et at, 2007, Nature Protocols, 2:2049-2056). CFSE covalently labels intracellular molecules with the fluorescent dye, carboxyfluorescein. Thus, when a CFSE-labeled cell divides, its progeny are endowed with half the number of carboxyfluorescein-tagged molecules and thus each cell division can be assessed by measuring the corresponding decrease in cell fluorescence via Flow cytometry (Quah and Parish, 2010, J. Vis. Exp., 44:2259). The capacity of CFSE to label lymphocyte populations with a high fluorescent intensity of exceptionally low variance, coupled with its low cell toxicity, make it an ideal dye to measure cell division. The MLR cultures were incubated in the presence of an isotype control antibody, molar equivalents of an anti-TNFα antibody, molar equivalents of IL-10 (2IL10), the codelivery of molar equivalents of IL-10 and the anti-TNFα antibody (2IL10+anti-TNFα), or the anti-TNFα-antibody-IL-10 fusion protein, and then analyzed by flow cytometry to determine the percentage of proliferating T cells. The results are shown in FIGS. 5 and 6.

Figure 5:
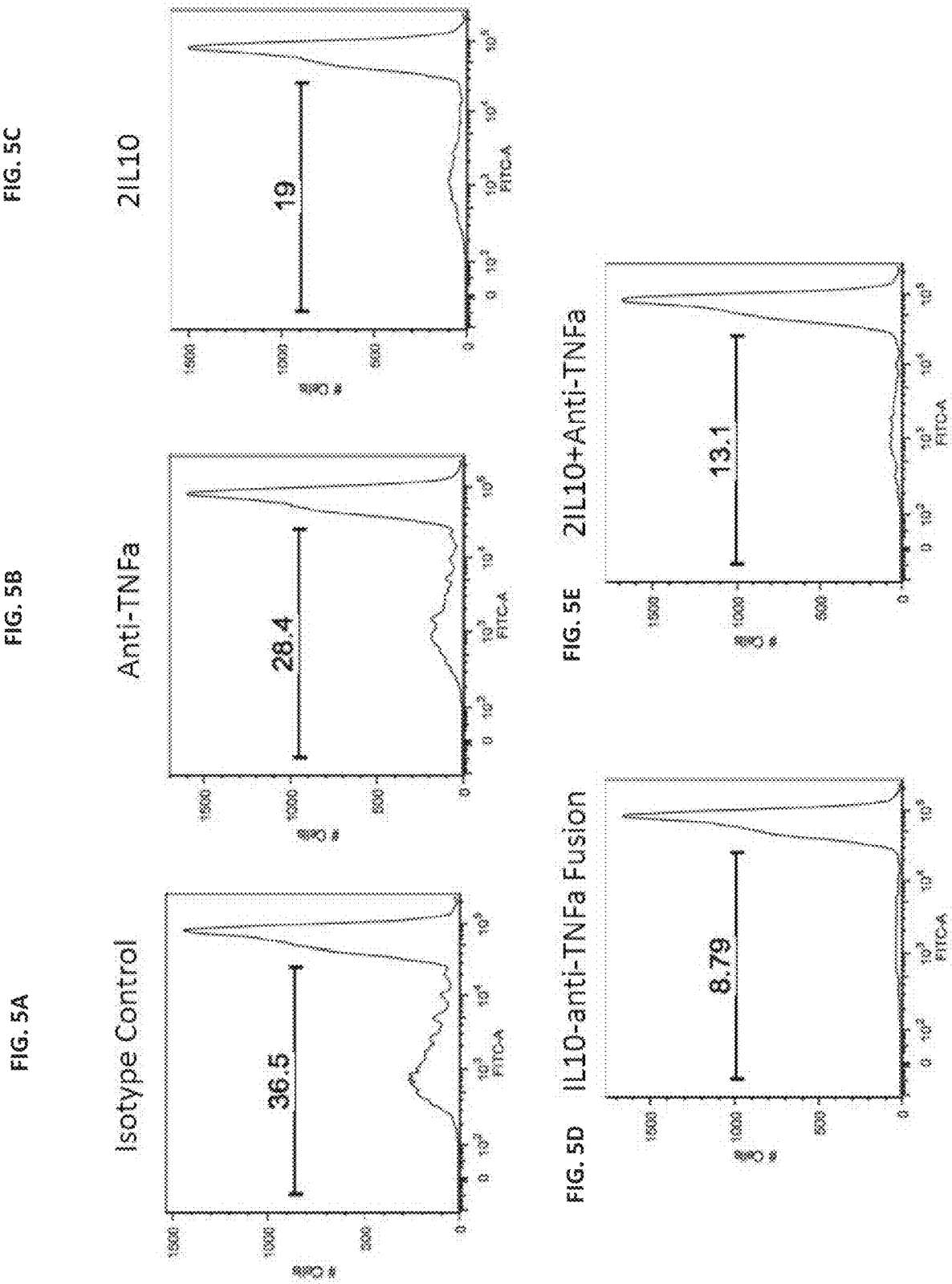
FIG. 5A-FIG. 5E show flow cytometry plots depicting the effect of an anti-TNFα-antibody-IL-10 fusion protein on T cell proliferation in an allogenic MLR assay. Data shows that T cell proliferation is markedly reduced with fusion protein treatment.

T cell proliferation was markedly reduced with the anti-TNFα-antibody-IL-10 fusion protein in comparison to the isotype control antibody, the anti-TNFα antibody alone, 2IL10 alone, or the 2IL10+anti-TNFα (FIG. 5).

Figure 6:
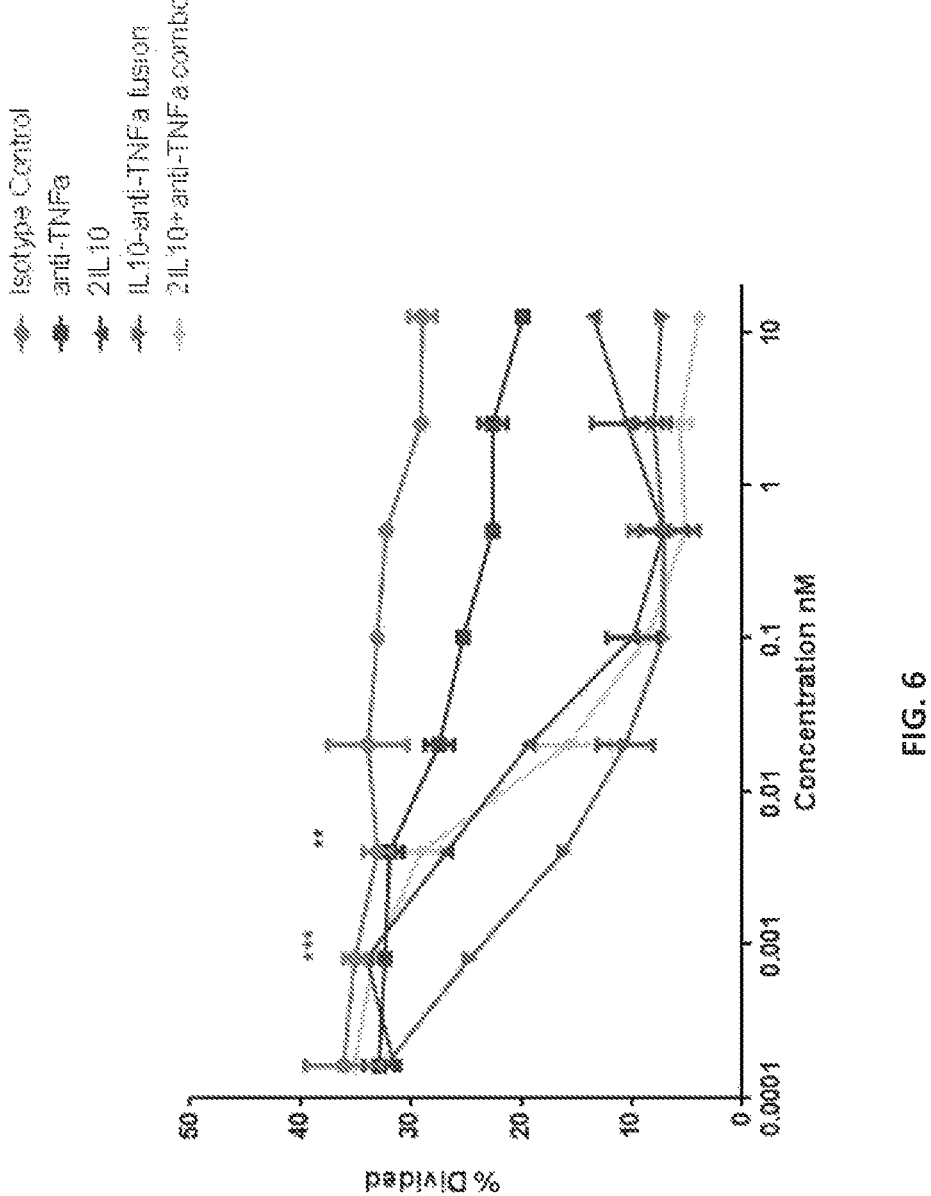
FIG. 6 shows the effect of increasing concentrations (0.00016 nM, 0.0008 nM, 0.004 nM, 0.02 nM, 0.1 nM, 0.5 nM, 2.5 nM, and 12.5 nM) of the anti-TNFα-antibody-IL-10 fusion protein on T cell proliferation in an allogenic MLR assay.

The effect of different concentrations of the anti-TNFα-antibody-IL-10 fusion protein on T cell proliferation was also studied (FIG. 6). As shown in FIG. 6, especially at very low concentrations (e.g., at 0.0008 nM, 0.004 nM, and 0.02 nM), the IL-10-anti-TNFα fusion protein had an about 10-fold increased inhibitory effect on T cell proliferation than IL-10 alone and an about 10,000-fold increased inhibitory effect on T cell proliferation than the anti-TNFα antibody alone. Surprisingly, the anti-TNFα-antibody-IL-10 fusion protein showed a greater than additive, i.e. synergistic, inhibitory effect on T cell proliferation in comparison to the codelivery of molar equivalents of IL-10 and the anti-TNFα antibody (2IL10+anti-TNFα) over the concentration range of 0.0008 nM to 0.04 nM (see FIG. 6).

Example 6: Inhibitory Effect of the Fusion Protein on T Cell Proliferation in Pro-Inflammatory Conditions The MLR described above was also used to study the effect of the anti-TNFα-antibody-IL-10 fusion protein on T cell proliferation in proinflammatory conditions (FIG. 7). The MLR cultures were stimulated with 5 μg/mL of polyinosinic:polycytidylic acid (poly I:C) (FIG. 7A), 20 ng/ml thymic stromal lymphopoietin (TSLP) (FIG. 7B), or 1 μg/mL lipopolysaccharide (LPS) (FIG. 7C). Poly I:C, TSLP, and LPS are pro-inflammatory molecules that induce proliferation of the CFSE-labeled T cells. The cultures were treated with 0.00016 nM, 0.0008 nM, 0.004 nM, 0.02 nM, 0.1 nM, 0.5 nM, 2.5 nM, or 12.5 nM concentrations of either an isotype control antibody, an anti-TNFα antibody, 2IL10, 2IL10+anti-TNFα, or the anti-TNFα-antibody-IL-10 fusion protein, and the level of T cell proliferation was measured by flow cytometry.

As shown in FIG. 7, the anti-TNFα-antibody-IL-10 fusion protein inhibits T cell proliferation at all concentrations of 0.0008 nM and above, but especially at very low concentrations of the fusion protein (0.0008 nM, 0.004 nM, and 0.02 nM). The fusion protein markedly inhibited T cell proliferation compared to the isotype control antibody, the anti-TNFα antibody, 2IL10, or 2IL10+anti-TNFα. Unexpectedly, the anti-TNFα-antibody-IL-10 fusion protein showed a greater than additive, i.e. synergistic, inhibitory effect on T cell proliferation in pro-inflammatory conditions in comparison to the codelivery of 2IL10+anti-TNFα over the concentration range of 0.0008 nM to 0.02 nM.

FIGS. 8, 9, and 10 provide representative flow plots showing that the anti-TNFα-antibody-IL-10 fusion protein markedly inhibits T cell proliferation in response to poly I:C, TSLP, and LPS stimulation. As seen in FIGS. 8, 9, and 10, at each pro-inflammatory condition, anti-TNFα-antibody-IL-10 fusion protein unexpectedly showed a greater than additive, i.e. synergistic, inhibitory effect on T cell proliferation in comparison to 2IL10+anti-TNFα combination treatment.

Figures 12A, 12B, 12C, 12D:
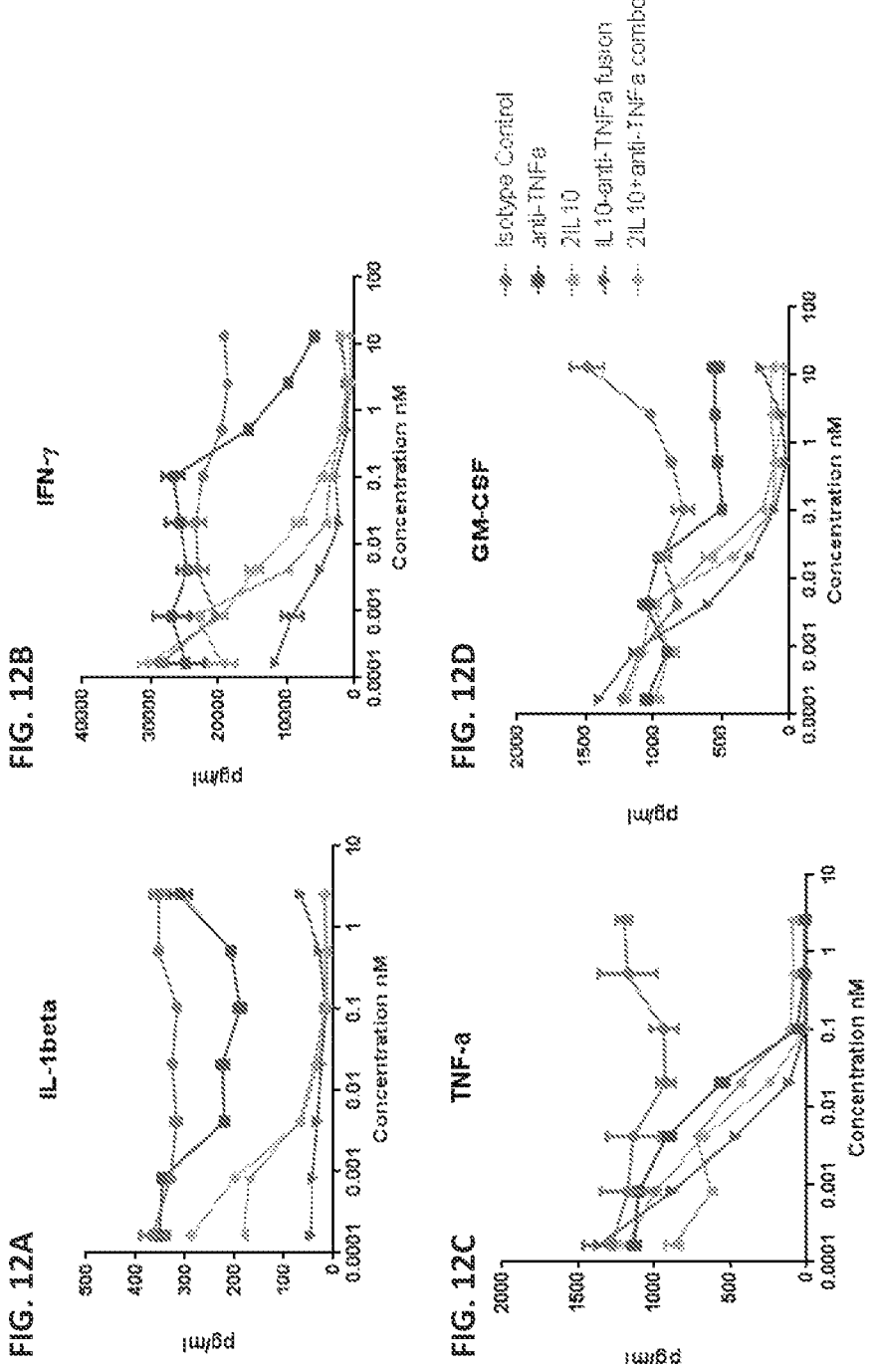
FIG. 12A-FIG. 12D show the effect of increasing concentrations (0.00016 nM, 0.0008 nM, 0.004 nM, 0.02 nM, 0.1 nM, 0.5 nM, and 2.5 nM) of the anti-TNFα-antibody-IL-10 fusion protein on the production of pro-inflammatory cytokines using an allogenic MLR assay.

Example 7: Inhibitory Effect of the Fusion Protein on the Production of Th1-, Th17-, and Th2-Type Cytokines The MLR was also used to study the effect of the anti-TNFα-antibody-IL-10 fusion protein on the production of Th1-, Th2-, and Th17-type pro-inflammatory cytokines (FIGS. 11 and 12). The MLR cultures were treated with 0.00016 nM, 0.0008 nM, 0.004 nM, 0.02 nM, 0.5 nM, 2.5 nM, or 12.5 nM concentrations of either an isotype control antibody, an anti-TNFα antibody, 2IL10, 2IL10+anti-TNFα antibody combination, or the anti-TNFα-antibody-IL-10 fusion protein. Production of the pro-inflammatory cytokines IL-17A (FIG. 11A), IL-1α (FIG. 11B), IL-12/23p40 (FIG. 11C), IL-6 (FIG. 11D), IL-1β (FIG. 12A), IFN-γ (FIG. 12B), TNFα (FIG. 12C), and GM-CSF (FIG. 12D) was measured.

As shown in FIGS. 11 and 12, the anti-TNFα-antibody-IL-10 fusion protein markedly inhibited production of the pro-inflammatory cytokines. Further, at the very low treatment concentrations of 0.00016 nM, 0.0008 nM, 0.004 nM, and 0.02 nM, the fusion protein had an increased inhibitory effect on the production of IL-17A, IL-1α, IL-12/23p40, IL-6, IL-1β, and IFNγ compared to the isotype control antibody, the anti-TNFα antibody, 2IL10, or the 2IL10+anti-TNFα antibody treatment combination. Surprisingly, the anti-TNFα-antibody-IL-10 fusion protein showed a greater than additive, i.e. synergistic, inhibitory effect on the pro-inflammatory cytokine production compared to the codelivery of 2IL10+anti-TNFα antibody over the concentration range of 0.00016 nM to 0.02 nM.

Therefore, the anti-TNFα-antibody-IL-10 fusion protein markedly inhibits the production of pro-inflammatory cytokines.

Figures 13, 13A, 13B:
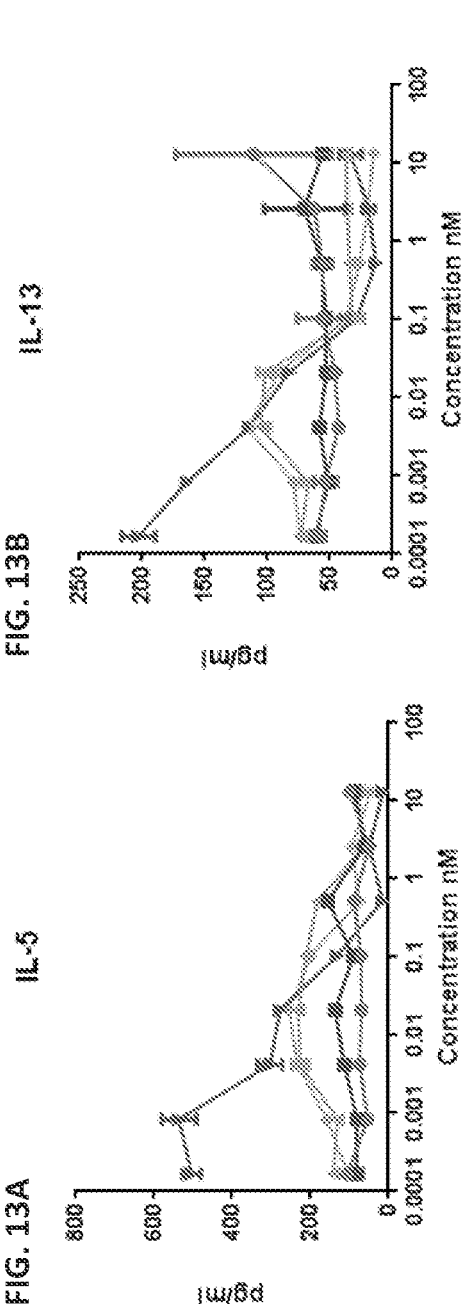
FIG. 13A-FIG. 13B show the effect of increasing concentrations (0.00016 nM, 0.0008 nM, 0.004 nM, 0.02 nM, 0.1 nM, 0.5 nM, 2.5 nM and 12.5 nM) of the anti-TNFα-antibody-IL-10 fusion protein on the production of the Th2-type cytokines, IL-5 and IL-13. The anti-TNFα-antibody-IL-10 fusion protein does not inhibit production of the Th2-type cytokines, IL-5 (FIG. 13A) and IL-13 (FIG. 13B).

In keeping with the above results, FIG. 13 shows that the anti-TNFα-antibody-IL-10 fusion protein did not inhibit production of the Th2-type cytokines, IL-5 (FIG. 13A) and IL-13 (FIG. 13B).

Example 8: Stability and Activity Studies on Anti-TNFα-Antibody-IL-10 Fusion Protein The stability of the IL-10 moiety of the anti-TNFα-antibody-IL-10 fusion protein was determined throughout the course of an MLR assay treated with the fusion protein at concentrations of 0.00016 nM, 0.0008 nM, 0.004 nM, 0.02 nM, 0.1 nM, and 0.5 nM by quantifying IL-10 concentrations in the supernatant. In brief, total T cells were enriched from human healthy donor PBMCs using EasySep Human T cell enrichment kit (STEMCELL) and then the T cells were labeled with CFSE. T cell-depleted PBMCs (APCs) were prepared by depleting T cells from allogenic PBMCs using Dynabeads CD3 (Thermo). The allogenic APCs were irradiated at 30Gy prior to coculture. The CFSE-labeled T cells were co-cultured with irradiated allogeneic APCs at T cell: APC ratios of 1:1 or 2:1 in the presence or absence of various concentrations of Isotype control, anti-TNF-α antibody, IL-10, anti-TNFα-antibody-IL-10 fusion protein, and IL-10+anti-TNFα antibody treatment combination. After 5-6 days of culture, the IL-10 concentration in culture supernatant was quantified by Meso Scale Discovery (MSD) assay. As shown in FIG. 14, the IL-10 moiety on the anti-TNFα-antibody-IL-10 fusion protein was found to be more stable that recombinant IL-10.

As shown in FIG. 15, the anti-TNFα antibody had a similar effect on TNF production whether in combination with IL10 (2IL10+anti-TNFα antibody) or else as part of the anti-TNFα-antibody-IL-10 fusion protein, suggesting that the activity of the anti-TNFα-antibody moiety was not affected by fusion to two IL-10 molecules.

Example 9: Efficacy Study for the Anti-TNFα-Antibody-IL-10 Fusion Protein 15 cynomolgus monkeys were divided into 5 groups (3 monkey/group). A single intravenous dose of the anti-TNFα-antibody-IL-10 fusion protein was administered to each monkey at target doses of 0.1 mg/kg to 10 mg/kg, as shown in Table 3 below. The dose volume was 1 mL/kg.

TABLE 3

Groups and doses used in monkey studies.

| Group | Test Article | Dose |
|---|---|---|
| 1 | Anti-TNFα-antibody-IL-10 fusion protein | 0.1 mg/kg |
| 2 | Anti-TNFα-antibody-IL-10 fusion protein | 0.3 mg/kg |
| 3 | Anti-TNFα-antibody-IL-10 fusion protein | 1 mg/kg |
| 4 | Anti-TNFα-antibody-IL-10 fusion protein | 3 mg/kg |
| 5 | Anti-TNFα-antibody-IL-10 fusion protein | 10 mg/kg |

Clinical observations were made twice daily, pre-dose on the day of dosing, and at least 1 and 4 hours post dose. Bodyweight was monitored at least twice (one week apart) pre-treatment, prior to dosing on day 1, day 4 and day 8, and once weekly thereafter. Food consumption was monitored once daily (visual assessment only). Serum concentrations were monitored over 1 month. Blood samples for pharmacokinetic (PK) analysis were prepared on the following days: day 1 (pre-dose, 2 hour, 6 hour, 12 hour post dose), day 2 (24 hour), day 3 (48 hour), day 4 (72 hour), day 8 (168 hour), day 15, day 22 and day 29. Blood samples for pharmacodynamics (PD) analysis were prepared on the following days: day −7, predose and approximately 12 hours postdose on study day 1, on study days 2 (24 hour), day 3 (48 hour), day 4 (72 hour), day 8 (168 hour), and days 15, 22, and 29.

As shown in FIG. 16, following a single intravenous dose of the anti-TNFα-antibody-IL-10 fusion protein, blood from each cynomolgus monkey was collected at day 1 through day 28 and the presence of total and intact forms of the anti-TNFα-antibody-IL-10 fusion protein in the circulation was measured. ELISA was performed to measure all forms of the anti-TNFα-antibody-IL-10 fusion protein in circulation (FIG. 16A). The ELISA used sh-ahIgG as the immobilized antibody and HRP-labeled gt-ahIgG as the detection antibody in a sandwich assay format. ECL and MSD assays were performed to measure only the intact form of the anti-TNFα-antibody-IL-10 fusion protein in circulation (FIG. 16B). The ECL/MSD assays used a-hIL10 monoclonal antibody as the immobilized antibody and a labeled anti-ID (anti-TNFα) as the detection antibody in a sandwich assay format. Both assays showed that the total form (FIG. 16C) and intact form (FIG. 16D) of the anti-TNFα-antibody-IL-10 fusion protein persisted for up to a maximum of 14 days in the circulation following a single intravenous dose. Therefore, the half-life of IL-10 increased from several hours to several days when fused to an anti-TNFα antibody.

Example 10: Pharmacokinetic Studies

The Anti-TNFα Activity of the TNFα Binding Moiety in the Anti-TNFα-Antibody-IL-10Fusion Protein is not Affected by IL-10 Fusion In a competition assay, TNFα binding of the anti-TNFα-antibody-IL-10 fusion protein of the disclosure was compared to a reference anti-TNFα-antibody to determine if the anti-TNFα activity of the TNFα binding moiety in the anti-TNFα-antibody-IL-10 fusion protein was affected by IL-10 fusion. Binding of the fusion protein and the reference antibody to TNFα molecules was determined in the presence of increasing concentrations of a competing biotin-labeled anti-TNFα antibody. The anti-TNFα beads were spun down and the amount of the fusion protein and reference antibody in the pulled-down beads was measured as a function of increasing concentrations of the competing labeled antibody. As shown in FIG. 17, the binding profile of both the fusion protein and the reference anti-TNFα-antibody was identical, indicating that the anti-TNFα activity of the TNFα binding moiety in the anti-TNFα-antibody-IL-10 fusion protein was not affected by fusion to IL-10 molecules. A control IgG molecule did not bind the beads at any concentration (FIG. 17).

Test cynomolgus monkeys were injected subcutaneously with a single dose of the anti-TNFα-antibody-IL-10 fusion protein at 3 mg/kg or 10 mg/kg. Whole blood from each monkey was collected at times of PK assessment, as detailed above. For comparison, control data from the Golimumab (anti-TNFα antibody) Biologics License Application (www.fda.gov) is shown. In the Golimumab PK assessment, monkeys were similarly injected subcutaneously with a single dose of an anti-TNFα antibody at 3 mg/kg or 10 mg/kg. As shown in FIG. 18, the half-life of the anti-TNFα-antibody-IL-10 fusion protein was 1.98±0.763 for the 3 mg/kg dose, and 3.23±0.342 for the 10 mg/kg dose. In comparison, the half-life of the anti-TNFα antibody was 1.08 (0.45 to 1.65) for the 3 mg/kg dose, and 0.46±0.14 for the 10 mg/kg dose. Additionally, the clearance rate of the anti-TNFα-antibody-IL-10 fusion protein was determined to be 22.5±4.23 mL/day/kg for the 3 mg/kg dose, and 14.9±1.2 mL/day/kg for the 10 mg/kg dose. In comparison, the clearance rate of the anti-TNFα antibody was 19.84±10.16 9 mL/day/kg for the 3 mg/kg dose, and 20.74±9.79 mL/day/kg for the 10 mg/kg dose. Therefore, the attachment of IL-10 to the TNFα binding moiety does not adversely impact the half-life or clearance of the anti-TNFα-antibody-IL-10 fusion protein.

Example 11: Ex-Vivo Pharmacodynamics Studies

Figure 19:
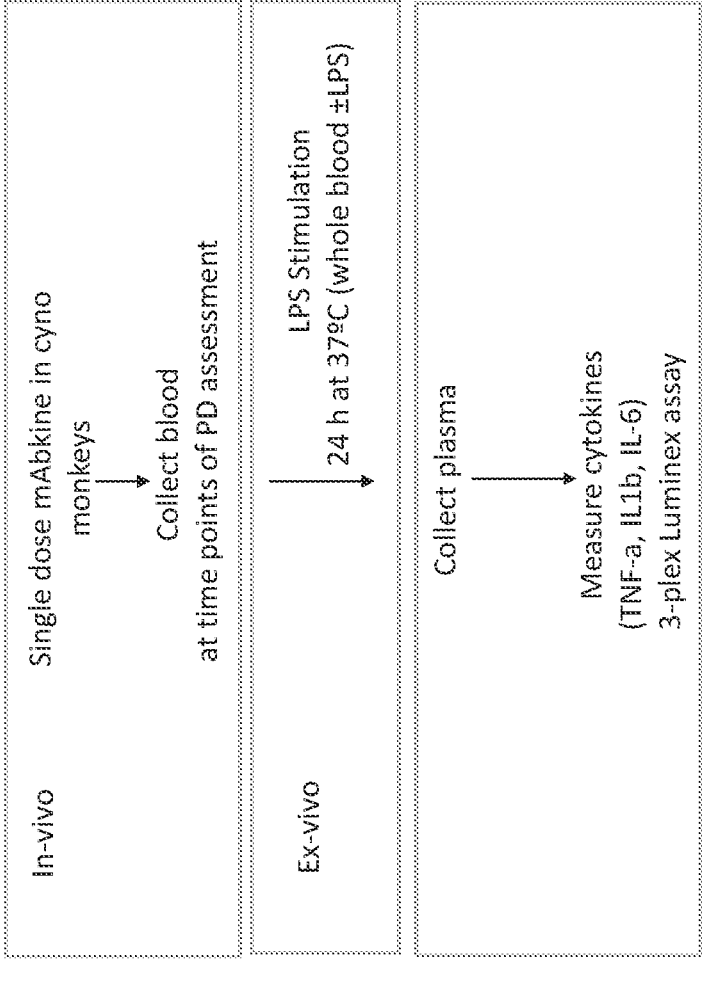
FIG. 19 shows the design of a pharmacodynamic assay to study the role of the anti-TNFα-antibody-IL-10 fusion protein on ex-vivo LPS-stimulated cytokine production in whole blood of cynomolgus monkeys treated with increasing doses of the anti-TNFα-antibody-IL-10 fusion protein (0.1 mg/kg, 0.3 mg/kg, 1 mg/kg, 3 mg/kg, and 10 mg/kg).

FIG. 19 shows the design of a PD assay to study the role of the anti-TNFα-antibody-IL-10 fusion protein in an ex-vivo LPS-stimulated cytokine production in cynomolgus monkey whole blood. In short, a single dose of the anti-TNFα-antibody-IL-10 fusion protein was administered i.v. to cynomolgus monkeys as described above, and whole blood from each monkey was collected at times of PD assessment, as detailed above. Whole blood was then incubated with LPS for 24 hours at 37° C. to induce LPS-stimulated cytokine production. At the end of the 24-hour period, whole blood was spun down and the plasma was collected and measured for cytokine production (TNFα, IL-1β, and IL-6) using a 3-plex Luminex assay.

Figure 20:
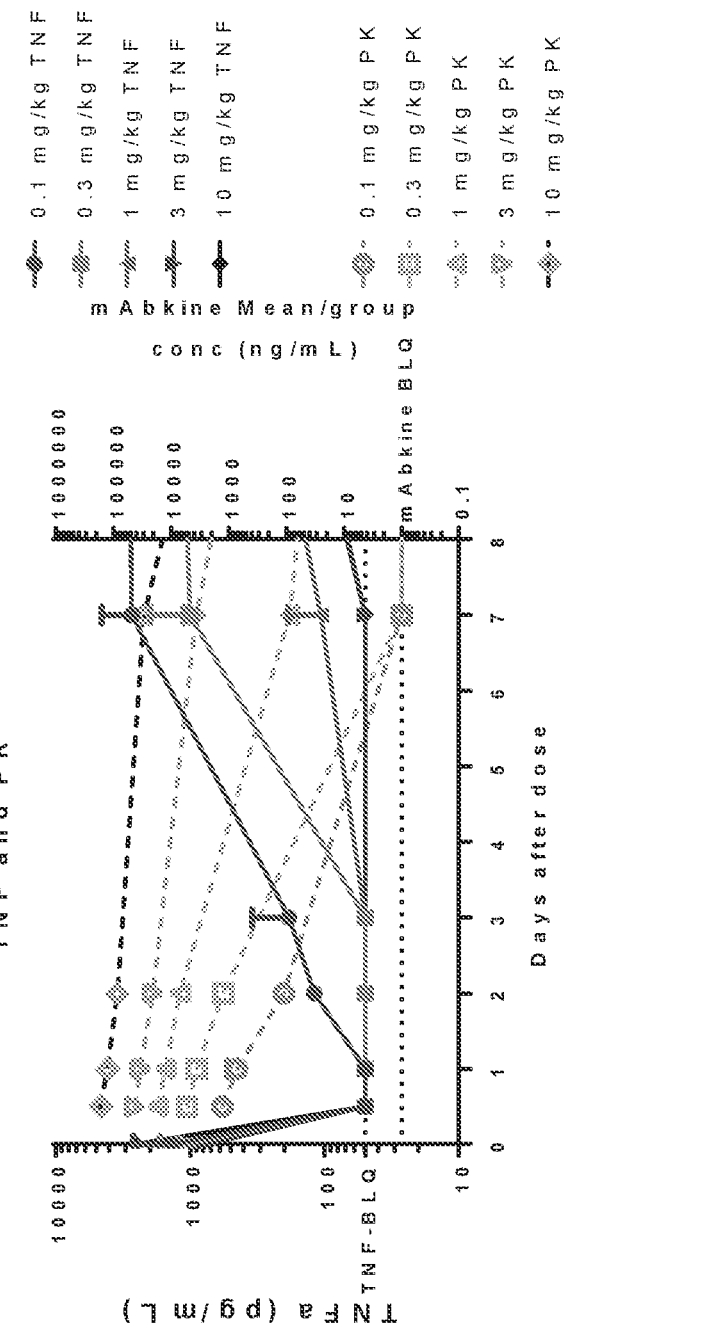
FIG. 20 shows the results of the pharmacodynamic assay to study the role of the anti-TNFα-antibody-IL-10 fusion protein (mAbkine) in an ex-vivo LPS-stimulated cytokine production in cynomolgus monkey whole blood. Persistent suppression of LPS-induced TNFα production by the anti-TNFα-antibody-IL-10 fusion protein was observed in a dose-dependent manner (FIG. 20, solid lines). The dose-dependent suppression of TNFα production showed a direct correlation with the concentration of the fusion protein measured at each day (FIG. 20, dotted lines). The inhibition of TNFα production was maximal between day 0.5 to day 3 post-dosing, depending on the dose.

Suppression of LPS-induced TNFα production by the anti-TNFα-antibody-IL-10 fusion protein was observed in a dose-dependent manner (FIG. 20, solid lines) with nearly complete suppression of TNFα production at the 3 mg/kg and 10 mg/kg doses up to day 7 post-injection. The dose-dependent suppression of TNFα production showed a direct correlation with the concentration of the fusion protein measured at each day (FIG. 20, dotted lines). The inhibition of TNFα production was maximal between day 0.5 to day 3 after dosing.

Figure 21:
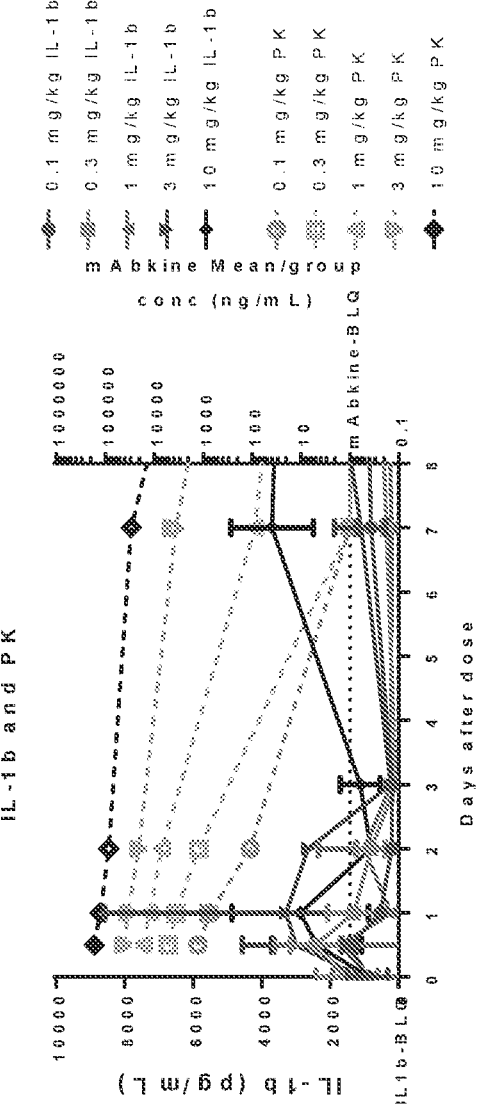
FIG. 21 shows additional results of the pharmacodynamic assay to study the role of the anti-TNFα-antibody-IL-10 fusion protein in an ex-vivo LPS-stimulated cytokine production in cynomolgus monkey whole blood. IL-10 dependent suppression of LPS-induced IL-1β production following treatment with the anti-TNFα-antibody-IL-10 fusion protein was also observed (FIG. 21, solid lines). Maximal inhibition for IL-1β occurred at day 3 after dosing. However, no evident dose-dependency was observed for the inhibition of IL-1β production (FIG. 21, compare solid lines to dotted lines).

Suppression of LPS-induced IL-1β production by the anti-TNFα-antibody-IL-10 fusion protein was also observed (FIG. 21, solid lines). Maximal inhibition for IL-1β occurred between day 2-3 after dosing. However, no evident dose-dependency was observed for the inhibition of IL-1β production (FIG. 21, compare solid lines to dotted lines). IL-1β production recovered as the concentration of the anti-TNFα-antibody-IL-10 fusion protein declined in vivo (not shown).

Additionally, suppression of LPS-induced IL-6 production by the anti-TNFα-antibody-IL-10 fusion protein was observed (FIG. 22, solid lines). The inhibition of IL-6 production was maximal at day 2 after dosing. However, no evident dose-dependency was observed for the inhibition of IL-6 production (FIG. 22, compare solid lines to dotted lines). IL-6 production recovered as the concentration of the anti-TNFα-antibody-IL-10 fusion protein declined in vivo (not shown).

Identical PK profiles of intact and total anti-TNFα-antibody-IL-10 fusion protein following administration of a single intravenous dose in cynomolgus monkeys demonstrate that the fusion protein molecule contained both anti-TNFα-antibody and IL-10 moieties.

The anti-TNFα-antibody-IL-10 fusion protein exhibited nonlinear PK, $t^{1/2}$=0.45 days (0.1 mg/kg)-3.2 days (10 mg/kg).

The TNFα detection assays showed binding of the anti-TNFα-antibody moiety of the anti-TNFα-antibody-IL-10 fusion protein to the TNFα ligand. The duration of fusion protein inhibition of ex-vivo LPS-induced TNFα production was dose-dependent.

The in vivo presence of the anti-TNFα-antibody-IL-10 fusion protein reduces IL-6 and IL-1β production in the ex vivo stimulation of cyno whole blood with LPS. Ex-vivo LPS-induced IL-1β and IL-6 production was inhibited upon fusion protein treatment and recovered when the fusion protein levels declined in vivo. Maximal inhibition for TNFα and IL-1β occurred at day 3 and for IL-6 at day 2 after dosing. The dose-dependent suppression of TNFα production showed a direct correlation with the concentration of the fusion protein. No clear dose-dependency was observed for either IL-1β or IL-6.

Figure 23:
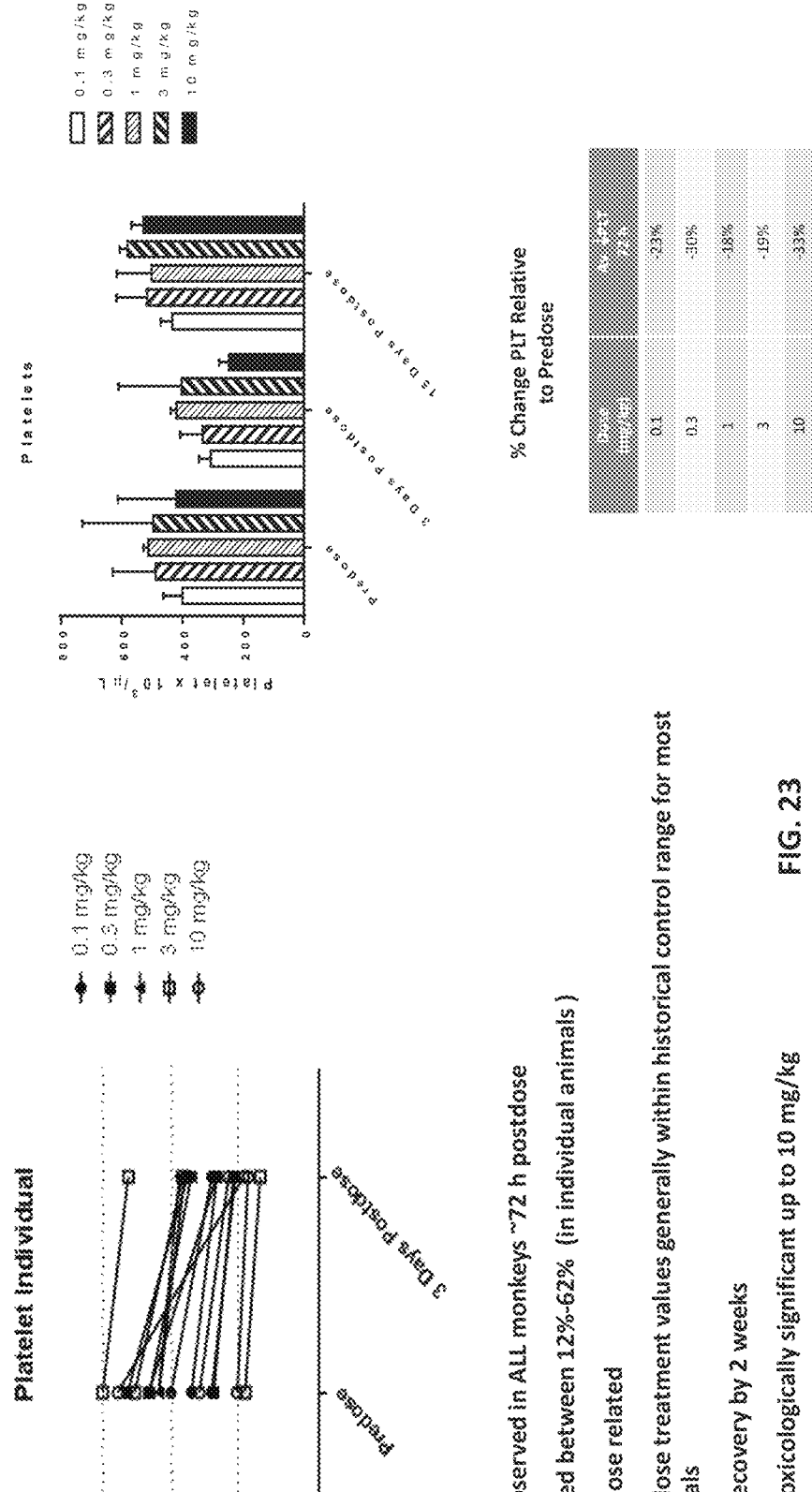
FIG. 23 shows the changes in hematology parameters (platelets) following intravenous administration of the anti-TNFα-antibody-IL-10 fusion protein in cynomolgus monkeys. Reversible decreases were noted in platelets following single intravenous injection of the anti-TNFα-antibody-IL-10 fusion protein at all doses ranging from 0.1 mg/kg to 10 mg/kg. The decrease in platelets was observed in all monkeys ~72 hours post-dose. The decrease in platelets ranged between ~12%-62% in individual animals. Full recovery was observed by 2 weeks post-dose. The decrease in platelets was not toxicologically significant in all tested doses.

Example 12: Reported Hematological Changes in Cynomolgus Monkeys Following Single Administration of Anti-TNFα-Antibody-IL-10 Fusion Protein As shown in FIG. 23, reversible decreases were noted in platelets following single IV injection of the anti-TNFα-antibody-IL-10 fusion protein at all doses ranging from 0.1 mg/kg to 10 mg/kg. The decrease in platelets was observed in all monkeys ~72 hours post-dose. The decrease in platelets ranged between ~12%-62% in individual animals. The post-dose treatment values were generally within the historical control range for most animals. Full recovery was observed by 2 weeks post-dose. The decrease in platelets was not toxicologically significant up to doses of 10 mg/kg. Table 4 shows the percentage change in platelets relative to predose.

TABLE 4

| Decrease in platelets in monkeys at various doses of the fusion protein. | |
| --- | --- |
| Dose (mg/kg) | Average Decrease in platelets 72 hours post-dose |
| 0.1 | −23% |
| 0.3 | −30% |
| 1 | −18% |
| 3 | −19% |
| 10 | −33% |

Decreases in RBC parameters observed following single IV injection of the anti-TNFα-antibody-IL-10 fusion protein at all doses ranging from 0.1 mg/kg to 10 mg/kg (FIG. 24). The decrease in RBC were observed in all monkeys ~72 hours post-dose. The decrease in RBC ranged between ~6%-19% in individual animals. The post-dose treatment values were within historical control range for the majority of treated animals. Two weeks post-dose, a trend towards recovery was observed at doses≤1 mg/kg, with more persistent reduction in RBC noted at doses≥3 mg/kg. The decrease in RBC was not toxicologically significant up to doses of 10 mg/kg. The possibility of the hematological changes being solely caused by procedural effects (e.g., impact of frequent blood sampling) was excluded. Table 5 shows the percentage change in RBC relative to predose.

TABLE 5

Decrease in RBCs in monkeys at various doses of the fusion protein.
Average Decrease in RBC 15

| Dose (mg/kg) | Average Decrease in RBCs 72 hours post-dose | Average Decrease in RBC 15 days post-dose |
|---|---|---|
| 0.1 | −17.6% | −6.8% |
| 0.3 | −16.6% | −8.8% |
| 1 | −18.4% | −10.7% |
| 3 | −13% | −12% |
| 10 | −13% | −18% |

Figure 25:
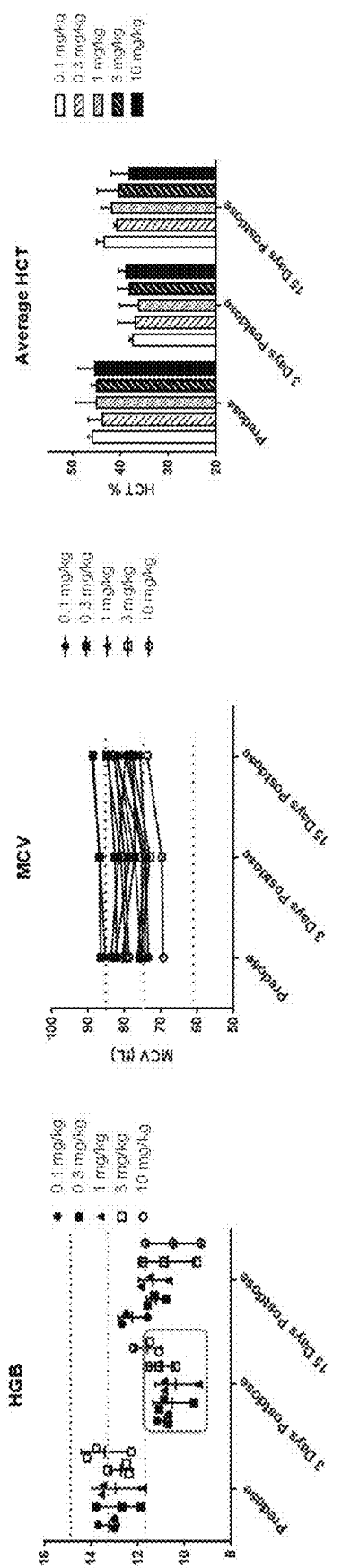
FIG. 25 shows that anemia is exhibited in cynomolgus monkeys following single intravenous injection of the anti-TNFα-antibody-IL-10 fusion protein at all doses ranging from 0.1 mg/kg to 10 mg/kg. The decrease in hemoglobin was observed in all monkeys ~72 hours post-dose. The decrease in hemoglobin ranged between ~7%-21% in 4 monkeys. Slight anemia (HGB<11.8 g/dL) was present in all but 1 monkey correlated with decreases in RBC and HCT. MCV values relatively unchanged indicating normocytic anemia. Anemia persisted at doses>0.1 mg/kg up to 2 weeks post dosing.

Anemia was observed in cynomolgus monkeys following single IV injection of the anti-TNFα-antibody-IL-10 fusion protein at all doses ranging from 0.1 mg/kg to 10 mg/kg (FIG. 25). The decrease in hemoglobin was observed in all monkeys µ72 hours post-dose. The decrease in hemoglobin ranged between ~7%-21% in 4 monkeys. Slight anemia (HGB<11.8 g/dL) present in all but 1 monkey correlated with decrease in RBC and HCT. MCV values were stable throughout the study, indicating normocytic anemia. Anemia persisted at doses>0.1 mg/kg up to 2 weeks post dosing. Table 6 shows the percentage change in hemoglobin relative to predose.

TABLE 6

Decrease in hemoglobin (HGB) in monkeys at various doses of the fusion protein.

| Dose (mg/kg) | Average Decrease in HGB 72 hours post-dose | Average Decrease in HGB 15 days post-dose |
|---|---|---|
| 0.1 | −18% | −7.3% |
| 0.3 | −18% | −12% |
| 1 | −20% | −12% |
| 3 | −13% | −15% |
| 10 | −13% | −21% |

Figure 26:
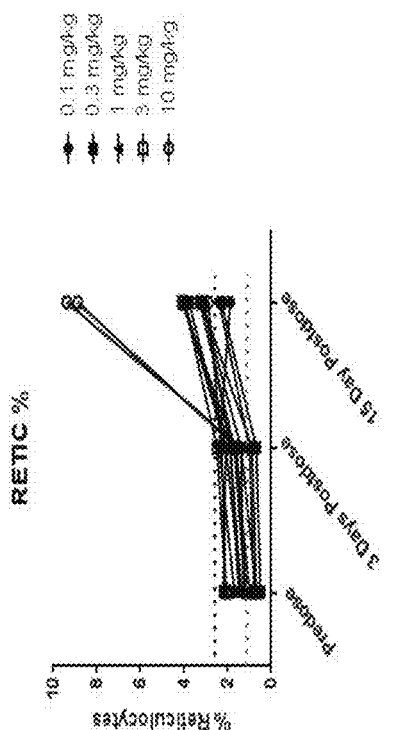
FIG. 26 shows that compensatory reticulocytosis is exhibited in cynomolgus monkeys following single intravenous injection of the anti-TNFα-antibody-IL-10 fusion protein at all doses ranging from 0.1 mg/kg to 10 mg/kg, and repeated blood sampling. The increase in reticulocytes was observed in all monkeys 15 days post-dose. Relatively unchanged reticulocytes were observed at 72 h with increases up to 9.8-fold by day 15 in individual monkeys. This was consistent with a compensatory response to normocytic anemia.

Compensatory reticulocytosis was observed in cynomolgus monkeys following single IV injection of the anti-TNFα-antibody-IL-10 fusion protein at all doses ranging from 0.1 mg/kg to 10 mg/kg, and repeated blood sampling (FIG. 26). The increase in reticulocytes was observed in all monkeys 15 days post-dose. Relatively unchanged reticulocytes were observed at 72 h with increases up to 9.8-fold by Day 15 in individual monkeys. This was consistent with a compensatory response to normocytic anemia. Table 7 shows the percentage change in hemoglobin relative to predose.

TABLE 7

Increase in reticulocytes in monkeys at various doses of the fusion protein.

| Dose (mg/kg) | Average Increase in Reticulocytes 72 hours post-dose | Average Increase in Reticulocytes 15 days post-dose |
|---|---|---|
| 0.1 | 17% | 2.1-fold |
| 0.3 | 9% | 2.9-fold |
| 1 | 27% | 3.0-fold |
| 3 | 21% | 5.1-fold |
| 10 | 7.3% | 4.3-fold |

Decreases in RBC parameters and platelets were not dose-related, which suggested a possible procedural effect (e.g., repeated blood sampling). Therefore, the impact of repeated blood sampling was evaluated in cynomolgus monkeys (FIG. 27). In the study, 10 mL blood was sampled over 72 hours. In the study, 10 mL of blood was sampled over 72 hours. Based on the average bodyweight of a cynomolgus monkey of 2.6 kg (2.2-3.3 kg) and the blood volume of approximately 60 ml/kg, it is estimated that the blood volume of a cynomolgus monkey is approximately 156 ml (132-198 ml). Therefore, the amount of blood sampled in the study was approximately 6.4% (5.1-7.6%) of the total blood volume of a cynomolgus monkey. The decrease in platelets, RBCs, and HGB parameters in the monkeys (FIG. 23-25) treated with various doses of the fusion protein was compared to this theoretically calculated parameter. The decreases in platelets, RBCs and HGB parameters exceed the expected effect of repeated blood sampling.

Average bodyweight of the cynomolgus monkeys was 2.6 kg (range 2.2-3.3 kg). Blood volume of cynomolgus monkey is ~60 mL/kg. Therefore, estimated blood volume 2.6 kg monkey was ~156 mL (range 132-198 mL). The sampled blood was ~6.4% of total blood volume on average (range 5.1-7.6%).

Thus, decreases in Platelets and RBC parameters exceed expected effect of repeated blood sampling.

The effect of the anti-TNFα-antibody-IL-10 fusion protein at all doses ranging from 0.1 mg/kg to 10 mg/kg on WBC Parameters was also studied (FIG. 28). Post dosing increases in WBC, PMN and/or LYM was observed in all monkeys ~72 hours post-dose. Increases in PMN primarily drove increases in WBC at 72 hours. A trend to baseline values observed 2 weeks post dosing. Table 8 shows the average percentage change in WBC, PMN, and LYM relative to predose.

TABLE 8

Average percentage change in WBC, PMN, and LYM
in monkeys at various doses of the fusion protein.

| Dose (mg/kg) | Average Increase in WBC 72 hours | Average Increase in PMN 72 hours | Average Increase in LYM 72 hours |
|---|---|---|---|
| 0.1 | 21% | 74% | 19% |
| 0.3 | 50% | 94% | 11% |
| 1 | 44% | 43% | 51% |
| 3 | 41% | 54% | 26% |
| 10 | 58% | 106% | 52% |

OTHER EMBODIMENTS

While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A fusion protein comprising a first and second domain, wherein the first domain comprises a Tumor Necrosis Factor α (TNFα) binding antibody, and wherein the second domain comprises interleukin-10 (IL-10), wherein the TNFα binding antibody comprises a heavy chain variable region ($V_H$) comprising SEQ ID NO: 16 and a light chain variable region ($V_L$) comprising SEQ ID NO: 17, and wherein the IL-10 comprises the sequence of SEQ ID NO: 1.

2. The fusion protein of claim 1, wherein the TNFα binding antibody is positioned at an N-terminus of the IL-10.

3. The fusion protein of claim 2, wherein the TNFα binding antibody is linked via its C-terminus end to the N-terminus of the IL-10.

4. The fusion protein of claim 1, wherein the TNFα binding antibody is directly linked to the IL-10.

5. The fusion protein of claim 1, wherein the TNFα binding antibody is linked to the IL-10 via a linker.

6. The fusion protein of claim 1, wherein the TNFα binding antibody comprises an amino acid sequence comprising SEQ ID NO: 5 or 29.

7. The fusion protein of claim 6, wherein the TNFα binding antibody comprises the sequence of SEQ ID NO: 29.

8. The fusion protein of claim 5, wherein the linker comprises an amino acid sequence comprising SEQ ID NO: 2, 3, 13, 14, 15, 32, 33, 34, or 35.

9. The fusion protein of claim 8, wherein the linker comprises the amino acid sequence of SEQ ID NO: 34.

10. The fusion protein of claim 1, wherein the fusion protein comprises an amino acid sequence comprising SEQ ID NO: 4, 24, 26, 27, 36, 37, or 39.

11. The fusion protein of claim 10, wherein the fusion protein comprises the amino acid sequence of SEQ ID NO: 24.

12. The fusion protein of claim 10, wherein the fusion protein comprises the amino acid sequence of SEQ ID NO: 37.

13. The fusion protein of claim 1, wherein the fusion protein consists of the TNFα binding antibody and the IL-10.

14. The fusion protein of claim 1, wherein the fusion protein comprises at least two IL-10.

15. A pharmaceutical composition comprising:
a) the fusion protein of claim 1; and
b) one or more pharmaceutically acceptable excipients.

* * * * *